United States Patent
Alexander et al.

(10) Patent No.: US 8,324,204 B2
(45) Date of Patent: Dec. 4, 2012

(54) FUSED THIOPHENE DERIVATIVES AS KINASE INHIBITORS

(75) Inventors: Rikki Peter Alexander, Slough (GB); Stuart Bailey, Slough (GB); Stephen Brand, Dundee (GB); Daniel Christopher Brookings, Slough (GB); Julien Alistair Brown, Slough (GB); Alan Findlay Haughan, Slough (GB); Natasha Kinsella, Slough (GB); Christopher Lowe, Slough (GB); Stephen Robert Mack, Slough (GB); William Ross Pitt, Slough (GB); Marianna Dilani Richard, Slough (GB); Andrew Sharpe, Slough (GB); Laura Jane Tait, Slough (GB)

(73) Assignee: UCB Pharma SA, Brussels (BE)

( * ) Notice: Subject to any disclaimer, the term of this patent is extended or adjusted under 35 U.S.C. 154(b) by 411 days.

(21) Appl. No.: 12/303,713

(22) PCT Filed: Jun. 4, 2007

(86) PCT No.: PCT/GB2007/002051
§ 371 (c)(1),
(2), (4) Date: Aug. 20, 2010

(87) PCT Pub. No.: WO2007/141504
PCT Pub. Date: Dec. 13, 2007

(65) Prior Publication Data
US 2010/0305066 A1 Dec. 2, 2010

(30) Foreign Application Priority Data

Jun. 6, 2006 (GB) .................................. 0611152.0

(51) Int. Cl.
*A61K 31/535* (2006.01)

(52) U.S. Cl. ............... 514/233.5; 514/233.8; 514/235.5; 514/212.06; 544/143; 544/69; 544/122; 544/127; 544/146

(58) Field of Classification Search ............... 514/233.5, 514/235.2, 212.06, 233.8; 544/143, 69, 122, 544/127, 146, 131
See application file for complete search history.

(56) References Cited

U.S. PATENT DOCUMENTS
2005/0227959 A1 * 10/2005 Yoshida et al. .......... 514/210.19

FOREIGN PATENT DOCUMENTS
WO 2006046031 5/2006

OTHER PUBLICATIONS

Thompson et al., Current Medicinal Chemistry, Oct. 2002, 9(19), pp. 1751-1762.*
Fickentscher K et al., Farbreaktionen Von 2, 3-Dicyan-1, 4-Dithiaanthrachinon, Archiv Der Pharmazie, 1968, pp. 588-592, vol. 301, No. 8.
International Search Report dated Sep. 18, 2007.

* cited by examiner

*Primary Examiner* — Andrew D Kosar
*Assistant Examiner* — Valerie Rodriguez-Garcia
(74) *Attorney, Agent, or Firm* — McDonnell Boehnen Hulbert & Berghoff LLP

(57) ABSTRACT

A series of 5,6-dihydro-1-benzothiophen-7(4H)-one derivatives, and analogues thereof, which are substituted in the 2-position by an optionally substituted morpholin-4-yl moiety, being selective inhibitors of PI3 kinase enzymes, are accordingly of benefit in medicine, for example in the treatment of inflammatory, autoimmune, cardiovascular, neurodegenerative, metabolic, oncological, nociceptive or ophthalmic conditions.

6 Claims, No Drawings

FUSED THIOPHENE DERIVATIVES AS KINASE INHIBITORS

This is a National Stage of International Application No. PCT/GB2007/002051, filed Jun. 4, 2007.

The present invention relates to a class of fused thiophene derivatives, and to their use in therapy. More particularly, the invention provides a family of 5,6-dihydro-1-benzothiophen-7(4H)-one derivatives, and analogues thereof, which are substituted in the 2-position by an optionally substituted morpholin-4-yl moiety. These compounds are selective inhibitors of phosphoinositide 3-kinase (PI3K) enzymes, and are accordingly of benefit as pharmaceutical agents, especially in the treatment of adverse inflammatory, autoimmune, cardiovascular, neurodegenerative, metabolic, oncological, nociceptive and ophthalmic conditions.

The PI3K pathway is implicated in a variety of physiological and pathological functions that are believed to be operative in a range of human diseases. Thus, PI3Ks provide a critical signal for cell proliferation, cell survival, membrane trafficking, glucose transport, neurite outgrowth, membrane ruffling, superoxide production, actin reorganization and chemotaxis (cf. S. Ward et al., *Chemistry & Biology*, 2003, 10, 207-213; and S. G. Ward & P. Finan, *Current Opinion in Pharmacology*, 2003, 3, 426-434); and are known to be involved in the pathology of cancer, and metabolic, inflammatory and cardiovascular diseases (cf. M. P. Wymann et al., *Trends in Pharmacol. Sci.*, 2003, 24, 366-376). Aberrant upregulation of the PI3K pathway is implicated in a wide variety of human cancers (cf. S. Brader & S. A. Eccles, *Tumori*, 2004, 90, 2-8).

The compounds of use in the present invention, being potent and selective PI3K inhibitors, are therefore beneficial in the treatment and/or prevention of various human ailments. These include autoimmune and inflammatory disorders such as rheumatoid arthritis, multiple sclerosis, asthma, inflammatory bowel disease, psoriasis and transplant rejection; cardiovascular disorders including thrombosis, cardiac hypertrophy, hypertension, and irregular contractility of the heart (e.g. during heart failure); neurodegenerative disorders such as Alzheimer's disease, Parkinson's disease, Huntington's disease, stroke, amyotrophic lateral sclerosis, spinal cord injury, head trauma and seizures; metabolic disorders such as obesity and type 2 diabetes; oncological conditions including leukaemia, glioblastoma, lymphoma, melanoma, and human cancers of the liver, bone, skin, brain, pancreas, lung, breast, stomach, colon, rectum, prostate, ovary and cervix; pain and nociceptive disorders; and ophthalmic disorders including age-related macular degeneration (ARMD).

In addition, the compounds of use in the present invention may be beneficial as pharmacological standards for use in the development of new biological tests and in the search for new pharmacological agents. Thus, the compounds of use in this invention may be useful as radioligands in assays for detecting compounds capable of binding to human PI3K enzymes.

The compounds of use in the present invention are potent and selective PI3K inhibitors having a binding affinity ($IC_{50}$) for the human PI3Kα and/or PI3Kβ and/or PI3Kγ and/or PI3Kδ isoform of 50 μM or less, generally of 20 μM or less, usually of 5 μM or less, typically of 1 μM or less, suitably of 500 nM or less, ideally of 100 nM or less, and preferably of 20 nM or less (the skilled person will appreciate that a lower $IC_{50}$ figure denotes a more active compound). The compounds of the invention may possess at least a 10-fold selective affinity, typically at least a 20-fold selective affinity, suitably at least a 50-fold selective affinity, and ideally at least a 100-fold selective affinity, for the human PI3Kα and/or PI3Kβ and/or PI3Kγ and/or PI3Kδ isoform relative to other human kinases.

The present invention provides a compound of formula (I), or a pharmaceutically acceptable salt or solvate thereof:

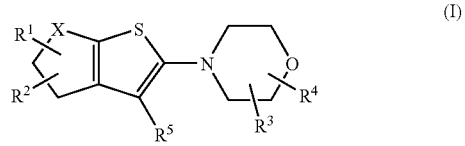

wherein

—X— represents a group of formula (a), (b), (c), (d), (e), (f) or (g):

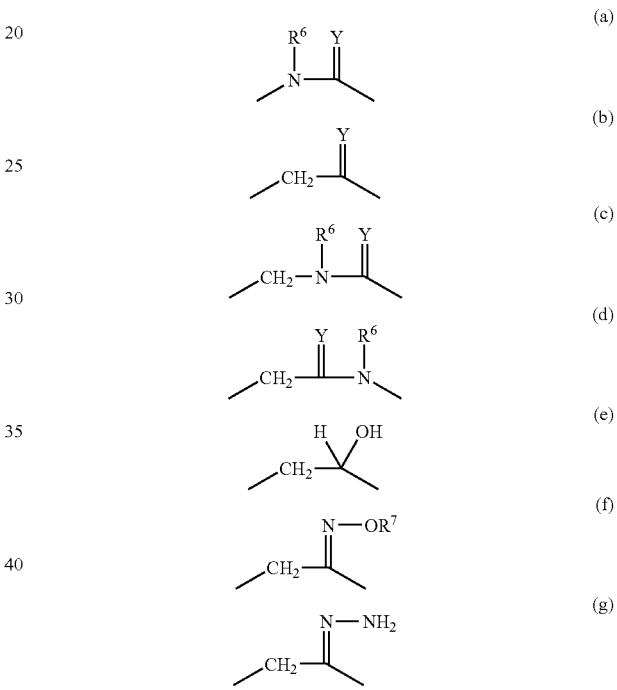

Y represents oxygen or sulphur;

$R^1$ and $R^2$ independently represent hydrogen; or $C_{1-6}$ alkyl, $C_{3-7}$ cycloalkyl, $C_{3-7}$ cycloalkyl($C_{1-6}$)alkyl, aryl, aryl($C_{1-6}$) alkyl, $C_{3-7}$ heterocycloalkyl, $C_{3-7}$ heterocycloalkyl-($C_{1-6}$) alkyl, heteroaryl or heteroaryl($C_{1-4}$)alkyl, any of which groups may be optionally substituted by one or more substituents; or $R^1$ and $R^2$, when both are attached to the same carbon atom, represent, when taken together with the carbon atom to which they are both attached, $C_{3-7}$ cycloalkyl or $C_{3-7}$ heterocycloalkyl, either of which groups may be optionally substituted by one or more substituents; or $R^1$ and $R^2$, when attached to adjacent carbon atoms, represent, when taken together with the carbon atoms to which they are attached, $C_{5-7}$ cycloalkyl, phenyl or heteroaryl, any of which groups may be optionally benzo-fused and/or substituted by one or more substituents;

$R^3$ and $R^4$ independently represent hydrogen; or $C_{1-6}$ alkyl, $C_{3-7}$ cycloalkyl, $C_{3-7}$ cycloalkyl($C_{1-6}$)alkyl, aryl, aryl($C_{1-6}$) alkyl, aryl($C_{2-6}$)alkenyl, aryl($C_{2-6}$)alkynyl, biaryl($C_{1-6}$)alkyl, $C_{3-7}$ heterocycloalkyl, $C_{3-7}$ heterocycloalkyl($C_{1-6}$)alkyl, $C_{3-7}$ heterocycloalkylcarbonyl, heteroaryl, heteroaryl($C_{1-6}$)alkyl, heteroaryl-aryl($C_{1-6}$)alkyl or aryl-heteroaryl($C_{1-6}$)alkyl, any of which groups may be optionally substituted by one or more substituents; or $R^3$ and $R^4$, when both are attached to the same carbon atom, represent, when taken together with the carbon atom to which they are both attached, $C_{3-7}$ cycloalkyl or $C_{3-7}$ heterocycloalkyl, either of which groups may be optionally substituted by one or more substituents; or $R^3$ and $R^4$, when attached to adjacent carbon atoms, represent, when taken together with the carbon atoms to which they are attached, $C_{5-7}$ cycloalkyl, phenyl or heteroaryl, any of which groups may be optionally benzo-fused and/or substituted by one or more substituents;

$R^5$ represents hydrogen, halogen, cyano, —$SR^a$, —$COR^e$, —$CO_2R^b$ or —$CONR^cR^d$; or $R^5$ represents $C_{1-6}$ alkyl, $C_{2-6}$ alkenyl, $C_{2-6}$ alkenylcarbonyl, $C_{2-6}$ alkynyl, cycloalkyl, $C_{3-7}$ cycloalkyl($C_{1-6}$)alkyl, $C_{3-7}$ cycloalkyl($C_{2-6}$)alkenyl, $C_{3-7}$ cycloalkyl($C_{2-6}$)alkynyl, aryl, aryl($C_{1-6}$)alkyl, aryl($C_{2-6}$)alkenyl, aryl($C_{2-6}$)alkynyl, biaryl, $C_{3-7}$ heterocycloalkyl, $C_{3-7}$ heterocycloalkyl($C_{1-6}$)alkyl, $C_{3-7}$ heterocycloalkyl($C_{2-6}$)alkenyl, $C_{3-7}$ heterocycloalkyl-($C_{2-6}$)alkynyl, $C_{3-7}$ heterocycloalkylcarbonyl($C_{2-6}$)alkenyl, $C_{5-9}$ heterobicycloalkyl-($C_{2-6}$)alkynyl, $C_{3-7}$ heterocycloalkyl-aryl, $C_{3-7}$ heterocycloalkyl($C_{1-6}$)alkyl-aryl, $C_{3-7}$ heterocycloalkyl-biaryl, heteroaryl, heteroaryl($C_{1-6}$)alkyl, heteroaryl($C_{1-6}$)alkylcarbonyl, heteroaryl($C_{2-6}$)alkenyl, heteroaryl($C_{2-6}$)alkynyl, heteroaroylcarbonyl, $C_{3-7}$ heterocycloalkyl-heteroaryl, $C_{3-7}$ heterocycloalkyl-heteroaryl($C_{2-6}$)alkynyl, heteroaryl-aryl, heteroaryl-aryl($C_{1-6}$)alkyl, aryl-heteroaryl, aryl-heteroaryl($C_{1-6}$)alkyl, $C_{3-7}$ heterocycloalkyl-aryl-heteroaryl, $C_{3-7}$ heterocycloalkyl($C_{1-6}$)alkyl-aryl-heteroaryl, $C_{5-9}$ heterobicycloalkyl($C_{1-6}$)alkyl-aryl-heteroaryl, heteroaryl-aryl-heteroaryl, bi(heteroaryl), $C_{3-7}$ heterocycloalkylcarbonyl-bi(heteroaryl), aryloxyaryl, aryl($C_{1-6}$)alkoxyaryl, heteroaryl($C_{1-6}$)alkoxyaryl, aryl($C_{1-6}$)alkylaminoaryl, heteroaryl($C_{1-6}$)alkylaminoaryl, $C_{3-7}$ cycloalkylcarbonylaminoaryl, arylcarbonylaminoaryl, aryl($C_{1-6}$)alkylcarbonylaminoaryl, $C_{3-7}$ heterocycloalkylcarbonylaminoaryl, heteroarylcarbonylaminoaryl, aryl-($C_{3-7}$)heterocycloalkylcarbonylaminoaryl, arylsulphonylaminoaryl, aryl($C_{1-6}$)alkyl-sulphonylaminoaryl, heteroaryl($C_{1-6}$)alkylsulphonylaminoaryl, $C_{3-7}$ cycloalkylamino-carbonylaminoaryl, arylaminocarbonylaminoaryl, $C_{3-7}$ heterocycloalkylaminocarbonyl-aminoaryl, $C_{3-7}$ heterocycloalkylaminocarbonylaminoaryl, heteroaryl($C_{1-6}$)alkyl-aminocarbonylaminoaryl, $C_{3-7}$ heterocycloalkylcarbonylcarbonylaminoaryl, $C_{3-7}$ heterocycloalkyl($C_{1-6}$)alkylaminocarbonylcarbonylaminoaryl, arylcarbonylaryl, $C_{3-7}$ heterocycloalkylcarbonylaryl, $C_{3-7}$ heterocycloalkylcarbonyl($C_{1-6}$)alkylaryl, aryl($C_{1-6}$)-alkylaminocarbonylaryl, $C_{3-7}$ heterocycloalkyl($C_{1-6}$)alkylaminocarbonylaryl, heteroaryl-aminocarbonylaryl, heteroaryl($C_{1-6}$)alkylaminocarbonylaryl, $C_{3-7}$ heterocycloalkylamino-carbonyl($C_{1-6}$)alkylaryl, $C_{3-7}$ heterocycloalkyl($C_{1-6}$)alkylaminocarbonyl($C_{1-6}$)alkylaryl, heteroarylaminocarbonyl($C_{1-6}$)alkylaryl, heteroaryl($C_{1-6}$)alkylaminocarbonyl($C_{1-6}$)alkyl-aryl, arylaminoheteroaryl, $C_{3-7}$ heterocycloalkylamino-aryl-heteroaryl, $C_{3-7}$ heterocycloalkylcarbonylamino-aryl-heteroaryl, $C_{3-7}$ heterocycloalkylaminocarbonyl-amino-aryl-heteroaryl, $C_{3-7}$ heterocycloalkylcarbonyl-aryl-heteroaryl, $C_{3-7}$ heterocycloalkyl($C_{1-6}$)alkylcarbonyl-aryl-heteroaryl, $C_{5-9}$ heterobicycloalkylcarbonyl-aryl-heteroaryl, $C_{3-7}$ heterocycloalkyl($C_{1-6}$)alkyl-aryl-heteroaryl, $C_{3-7}$ heterocycloalkyl-aminocarbonyl-aryl-heteroaryl, $C_{3-7}$ heterocycloalkyl($C_{1-6}$)alkylaminocarbonyl-aryl-heteroaryl or $C_{3-7}$ heterocycloalkylaminocarbonyl($C_{1-6}$)alkyl-aryl-heteroaryl, any of which groups may be optionally substituted by one or more substituents;

$R^a$ represents $C_{1-6}$ alkyl, aryl or heteroaryl, any of which groups may be optionally substituted by one or more substituents;

$R^b$ represents hydrogen; or optionally substituted $C_{1-6}$ alkyl;

$R^c$ represents hydrogen; or $C_{1-6}$ alkyl, aryl, aryl($C_{1-6}$)alkyl, heteroaryl, heteroaryl($C_{1-6}$)alkyl or (aryl)(heteroaryl)($C_{1-6}$)alkyl, any of which groups may be optionally substituted by one or more substituents;

$R^d$ represents hydrogen or $C_{1-6}$ alkyl;

$R^e$ represents $C_{1-6}$ alkyl; and $R^6$ and $R^7$ independently represent hydrogen or $C_{1-6}$ alkyl.

The present invention also provides a compound of formula (I) as depicted above, or a pharmaceutically acceptable salt or solvate thereof, wherein —X—, $R^1$, $R^2$, $R^3$ and $R^4$ are as defined above;

$R^5$ represents hydrogen, halogen, cyano, —$SR^a$, —$CO_2R^b$ or —$CONR^cR^d$; or $R^5$ represents $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, $C_{3-7}$ cycloalkyl($C_{2-6}$)alkenyl, $C_{3-7}$ cycloalkyl($C_{2-6}$)alkynyl, aryl, aryl($C_{1-6}$)alkyl, aryl-($C_{2-6}$)alkenyl, aryl($C_{2-6}$)alkynyl, biaryl, $C_{3-7}$ heterocycloalkyl, $C_{3-7}$ heterocycloalkyl-($C_{1-6}$)alkyl, $C_{3-7}$ heterocycloalkyl($C_{2-6}$)alkenyl, $C_{3-7}$ heterocycloalkyl($C_{2-6}$)alkynyl, $C_{5-9}$ heterobicycloalkyl($C_{2-6}$)alkynyl, $C_{3-7}$ heterocycloalkyl-aryl, $C_{3-7}$ heterocycloalkyl-($C_{1-6}$)alkyl-aryl, heteroaryl, heteroaryl($C_{1-6}$)alkyl, heteroaryl($C_{2-6}$)alkenyl, heteroaryl-($C_{2-6}$)alkynyl, $C_{3-7}$ heterocycloalkyl-heteroaryl($C_{2-6}$)alkynyl, heteroaryl-aryl, heteroaryl-aryl($C_{1-6}$)alkyl, aryl-heteroaryl, aryl-heteroaryl($C_{1-6}$)alkyl or bi(heteroaryl), any of which groups may be optionally substituted by one or more substituents; and $R^a$, $R^b$, $R^c$ and $R^d$ are as defined above.

Where $R^1$ and/or $R^2$ and/or $R^3$ and/or $R^4$ in the compounds of formula (I) above is other than hydrogen, and/or where $R^5$ is other than hydrogen, halogen or cyano, this group may be unsubstituted, or substituted by one or more substituents. Typically, $R^1$ and/or $R^2$ and/or $R^3$ and/or $R^4$ and/or $R^5$ will be unsubstituted, or substituted by one or two substitutents. Suitably, $R^1$ and/or $R^2$ and/or $R^3$ and/or $R^4$ and/or $R^5$ will be unsubstituted or monosubstituted.

For use in medicine, the salts of the compounds of formula (I) will be pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example, be formed by mixing a solution of the compound of the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

Suitable alkyl groups which may be present on the compounds of use in the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tent-butyl and 2,2-dimethylpropyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

Typical $C_{2-6}$ alkenyl groups include vinyl and allyl.

Typical $C_{2-6}$ alkynyl groups include ethynyl, prop-1-yn-1-yl, but-1-yn-1-yl and 3-methylbut-1-yn-1-yl.

Specific $C_{3-7}$ cycloalkyl groups are cyclopropyl, cyclobutyl, cyclopentyl, cyclohexyl and cycloheptyl.

Suitable aryl groups include phenyl and naphthyl, preferably phenyl. Suitable aryl($C_{1-6}$)alkyl groups include benzyl, phenylethyl, phenylpropyl and naphthylmethyl.

Specific aryl($C_{2-6}$)alkenyl groups include 2-phenylethenyl and 3-phenylprop-2-en-1-yl.

Specific aryl($C_{2-6}$)alkynyl groups include phenylethynyl, 3-phenylprop-1-yn-1-yl and 3-phenylprop-2-yn-1-yl.

Particular biaryl groups include biphenyl and naphthylphenyl.

Suitable heterocycloalkyl groups, which may comprise benzo-fused analogues thereof, include azetidinyl, tetrahydrofuranyl, pyrrolidinyl, indolinyl, imidazolidinyl, tetrahydropyranyl, piperidinyl, 1,2,3,4-tetrahydroquinolinyl, 1,2,3,4-tetrahydro-isoquinolinyl, piperazinyl, 1,2,3,4-tetrahydroquinoxalinyl, homopiperazinyl, morpholinyl, benzomorpholinyl and thiomorpholinyl.

Typical heterobicycloalkyl groups include quinuclidinyl, 8-azabicyclo[3.2.1]octyl and 3,8-diazabicyclo[3.2.1]octyl.

Suitable heteroaryl groups include furyl, benzofuryl, dibenzofuryl, thienyl, benzothienyl, dibenzothienyl, pyrrolyl, indolyl, pyrrolo[2,3-b]pyridinyl, pyrazolyl, indazolyl, oxazolyl, isoxazolyl, thiazolyl, isothiazolyl, imidazolyl, imidazo[1,2-a]-pyridinyl, benzimidazolyl, oxadiazolyl, thiadiazolyl, triazolyl, benzotriazolyl, tetrazolyl, pyridinyl, quinolinyl, isoquinolinyl, pyridazinyl, pyrimidinyl and pyrazinyl groups.

Typical bi(heteroaryl) groups include benzofuryl-pyridinyl, benzothienyl-pyridinyl, indolyl-pyridinyl, isoxazolyl-pyridinyl, bipyridinyl and isoquinolinyl-pyridinyl.

The term "halogen" as used herein is intended to include fluorine, chlorine, bromine and iodine atoms, especially fluoro or chloro.

Where the compounds of formula (I) have one or more asymmetric centres, they may accordingly exist as enantiomers. Where the compounds of the invention possess two or more asymmetric centres, they may additionally exist as diastereomers. The invention is to be understood to extend to all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C$=$O$)-enol ($CH$=$CHOH$) tautomers. Formula (I) and the formulae depicted hereinafter are intended to represent all individual tautomers and all possible mixtures thereof, unless stated or shown otherwise.

Specific sub-classes of compounds in accordance with the present invention are represented by the compounds of formula (IA), (IB), (IC), (ID), (IE), (IF) and (IG):

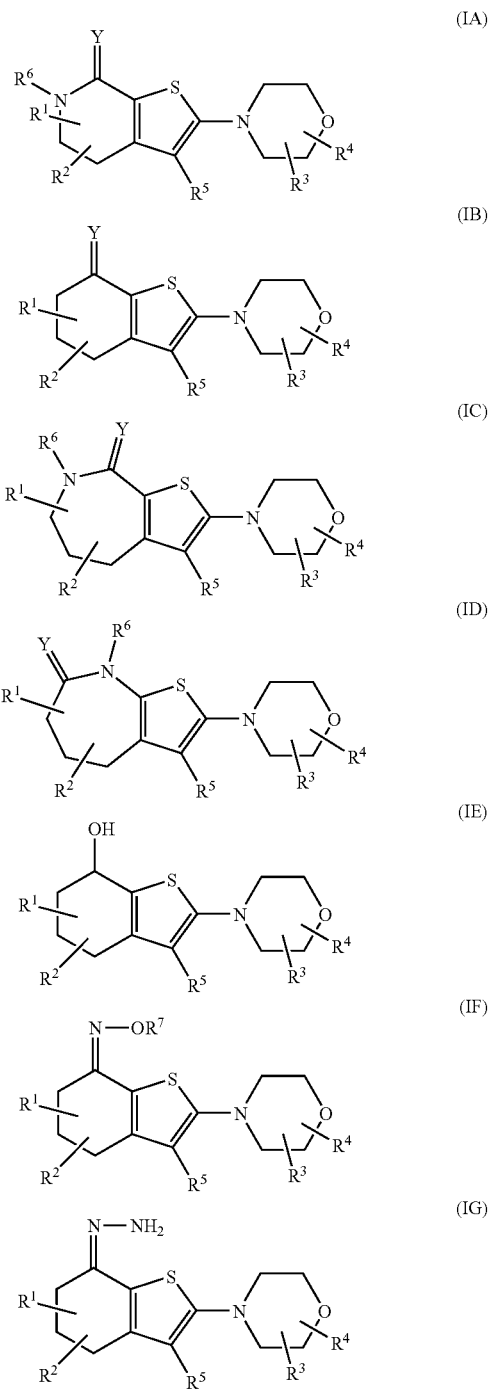

wherein Y, $R^1$, $R^2$, $R^3$, $R^4$, $R^5$, $R^6$ and $R^7$ are as defined above.

Particular sub-classes of compounds in accordance with the present invention are represented by the compounds of formula (IA), (IB) and (IC) as depicted above.

In the compounds of formula (I), —X— suitably represents a group of formula (a), (b) or (c) as depicted above. In one embodiment, —X— represents a group of formula (a). In another embodiment, —X— represents a group of formula (b). In a further embodiment, —X-represents a group of formula (c).

In one embodiment, Y is oxygen. In another embodiment, Y is sulphur.

Suitably, $R^1$ represents hydrogen; or $C_{1-6}$ alkyl, aryl or heteroaryl, any of which groups may be optionally substituted by one or more substituents.

Suitably, $R^2$ represents hydrogen or optionally substituted $C_{1-6}$ alkyl.

Examples of typical substituents on $R^1$ and/or $R^2$ include halogen, cyano, nitro, $C_{1-6}$ alkyl, trifluoromethyl, hydroxy, $C_{1-6}$ alkoxy, difluoromethoxy, trifluoromethoxy, aryloxy, $C_{1-6}$ alkylthio, $C_{1-6}$ alkylsulphonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulphonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulphonyl, $C_{1-6}$ alkylaminosulphonyl and di($C_{1-6}$)alkylaminosulphonyl; especially halogen, $C_{1-6}$ alkoxy or $C_{1-6}$ alkylthio.

Examples of particular substituents on $R^1$ and/or $R^2$ include fluoro, chloro, bromo, cyano, nitro, methyl, trifluoromethyl, hydroxy, methoxy, difluoromethoxy, trifluoromethoxy, phenoxy, methylthio, methylsulphonyl, amino, methylamino, dimethylamino, acetylamino, methoxycarbonylamino, methylsulphonylamino, formyl, acetyl, carboxy, methoxycarbonyl, aminocarbonyl, methylaminocarbonyl, dimethylaminocarbonyl, aminosulphonyl, methylaminosulphonyl and dimethylaminosulphonyl; especially chloro, methoxy or methylthio.

Typical values of $R^1$ include hydrogen, methyl, n-propyl, isopropyl, phenyl, chlorophenyl, methoxyphenyl, methylthiophenyl and furyl. In one embodiment, $R^1$ is hydrogen. A particular value of $R^1$ is methyl.

Typical values of $R^2$ include hydrogen and methyl. In one embodiment, $R^2$ is hydrogen. In another embodiment, $R^2$ is $C_{1-6}$ alkyl, especially methyl.

Alternatively, $R^1$ and $R^2$, when both are attached to the same carbon atom, may together form an optionally substituted spiro linkage. Thus, $R^1$ and $R^2$, when both are attached to the same carbon atom, may represent, when taken together with the carbon atom to which they are both attached, $C_{3-7}$ cycloalkyl or $C_{3-7}$ heterocycloalkyl, either of which groups may be unsubstituted, or substituted by one or more, typically by one or two, substituents. In this context, $R^1$ and $R^2$, when taken together with the carbon atom to which they are both attached, may suitably represent an optionally substituted cyclopentyl, cyclohexyl, pyrrolidine or piperidine ring, especially cyclopentyl or cyclohexyl.

Alternatively, $R^1$ and $R^2$, when attached to adjacent carbon atoms, may together form an optionally benzo-fused and/or substituted cycloalkyl, phenyl or heteroaryl (e.g. pyridinyl) ring fused to the ring containing the variable X. Thus, $R^1$ and $R^2$, when attached to adjacent carbon atoms, may represent, when taken together with the carbon atoms to which they are attached, $C_{5-7}$ cycloalkyl, phenyl or heteroaryl (e.g. pyridinyl), any of which groups may be benzo-fused and/or unsubstituted, or substituted by one or more, typically by one or two, substituents. In this context, in one embodiment, $R^1$ and $R^2$, when taken together with the adjacent carbon atoms to which they are attached, suitably represent a phenyl ring fused to the ring containing the variable X. Also in this context, in another embodiment, $R^1$ and $R^2$, when taken together with the adjacent carbon atoms to which they are attached, suitably represent a benzo-fused cyclopentyl ring, i.e. an indanyl moiety fused to the ring containing the variable X.

Typically, $R^3$ represents hydrogen; or $C_{1-6}$ alkyl, aryl, aryl($C_{1-6}$)alkyl, aryl-($C_{2-6}$)alkynyl, biaryl($C_{1-6}$)alkyl, $C_{3-7}$ heterocycloalkyl($C_{1-6}$)alkyl, $C_{3-7}$ heterocycloalkyl-carbonyl, heteroaryl($C_{1-6}$)alkyl, heteroaryl-aryl($C_{1-6}$)alkyl or aryl-heteroaryl($C_{1-6}$)alkyl, any of which groups may be optionally substituted by one or more substituents.

In a representative embodiment, $R^3$ represents $C_{1-6}$ alkyl, aryl($C_{1-6}$)alkyl, biaryl-($C_{1-6}$)alkyl, heteroaryl($C_{1-6}$)alkyl or heteroaryl-aryl($C_{1-6}$)alkyl, any of which groups may be optionally substituted by one or more substituents. Preferably, $R^3$ represents methyl, arylmethyl, biarylmethyl, heteroarylmethyl or heteroaryl-arylmethyl, any of which groups may be optionally substituted by one or more substituents.

In a particular embodiment, $R^3$ represents substituted or unsubstituted indolyl-($C_{1-6}$)alkyl. Advantageously, $R^3$ represents substituted or unsubstituted indolylmethyl.

Illustratively, $R^3$ represents hydrogen; or methyl, phenyl, benzyl, phenylethyl, naphthylmethyl, phenylpropynyl, biphenylmethyl, naphthylphenylmethyl, indolinylmethyl, 1,2,3,4-tetrahydroquinolinylmethyl, 1,2,3,4-tetrahydroisoquinolinyl-methyl, piperidinylcarbonyl, 1,2,3,4-tetrahydroquinolinylcarbonyl, 1,2,3,4-tetrahydroisoquinolinylcarbonyl, 1,2,3,4-tetrahydroquinoxalinylcarbonyl, benzothienylmethyl, indolylmethyl, pyrrolo[2,3-b]pyridinylmethyl, benzimidazolylmethyl, benzotriazolylmethyl, pyridinylmethyl, quinolinylmethyl, isoquinolinylmethyl, benzofurylbenzyl, thienylbenzyl, benzothienylbenzyl, indolylbenzyl, isoxazolylbenzyl, pyrazolylbenzyl, pyridinylbenzyl, pyrimidinylbenzyl or phenylpyridinylmethyl, any of which groups may be optionally substituted by one or more substituents.

Suitably, $R^4$ represents hydrogen or optionally substituted $C_{1-6}$ alkyl.

Examples of suitable substituents on $R^3$ and/or $R^4$ include halogen, cyano, nitro, $C_{1-6}$ alkyl, hydroxy($C_{1-6}$)alkyl, trifluoromethyl, aryl($C_{1-6}$)alkyl, hydroxy, $C_{1-6}$ alkoxy, difluoromethoxy, trifluoromethoxy, aryloxy, aryl($C_{1-6}$)alkoxy, methylenedioxy, $C_{1-6}$ alkylthio, arylthio, $C_{1-6}$ alkylsulphonyl, arylsulphonyl, $C_{1-6}$ alkylsulphonyloxy, amino, $C_{1-6}$ alkylamino, di($C_{1-6}$)alkylamino, phenylamino, [($C_{1-6}$)alkyl](phenyl)amino, pyridinylamino, pyrrolidinyl, morpholinyl, $C_{2-6}$ alkylcarbonylamino, benzofurylcarbonylamino, $C_{2-6}$ alkoxycarbonylamino, $C_{1-6}$ alkylsulphonylamino, arylsulphonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, benzothienylmethylaminocarbonyl, aminosulphonyl, $C_{1-6}$ alkylaminosulphonyl and di($C_{1-6}$)alkylaminosulphonyl.

Examples of representative substituents on $R^3$ and/or $R^4$ include fluoro, chloro, bromo, cyano, nitro, methyl, hydroxymethyl, trifluoromethyl, benzyl, hydroxy, methoxy, ethoxy, difluoromethoxy, trifluoromethoxy, phenoxy, benzyloxy, methylenedioxy, methylthio, phenylthio, methylsulphonyl, phenylsulphonyl, methylsulphonyloxy, amino, methylamino, dimethylamino, phenylamino, N-methyl-N-phenylamino, pyridinylamino, pyrrolidinyl, morpholinyl, acetylamino, benzofurylcarbonylamino, methoxycarbonylamino, methylsulphonylamino, phenylsulphonylamino, formyl, acetyl, carboxy, methoxycarbonyl, aminocarbonyl, methylaminocarbonyl, dimethylaminocarbonyl, benzothienylmethylaminocarbonyl, aminosulphonyl, methylaminosulphonyl and dimethylaminosulphonyl.

Specific values of $R^3$ include hydrogen, methyl, phenoxymethyl, phenylthiomethyl, aminomethyl, phenylaminomethyl, N-methyl-N-phenylaminomethyl, pyridinylamino-methyl, benzofurylcarbonylaminomethyl, phenylsulphonylaminomethyl, benzothienyl-methylaminocarbonylmethyl, phenyl, benzyl, chlorobenzyl, bromobenzyl, pyrrolidinyl-benzyl, morpholinyl-benzyl, phenylethyl, naphthylmethyl, phenylpropynyl, biphenylmethyl, fluorobiphenylmethyl, difluorobiphenylmethyl, chlorobiphenylmethyl, dichlorobiphenylmethyl, bromobiphenylmethyl, cyanobiphenylmethyl, methylbiphenyl-methyl, (fluoro)(methyl)biphenylmethyl, dimethylbiphenylmethyl, hydroxymethyl-biphenylmethyl, trifluoromethylbiphenylmethyl, bis(trifluoromethyl)biphenylmethyl, methoxybiphenylmethyl, dimethoxybiphenylmethyl, ethoxybiphenylmethyl, methylenedioxybiphenylmethyl, trifluoromethoxybiphenylmethyl, phenoxy-biphenylmethyl, methylthiobiphenylmethyl, aminobiphenylmethyl, acetylamino-biphenylmethyl, methylsulphonylaminobiphenylmethyl, acetylbiphenylmethyl, aminocarbonylbiphenylmethyl, naphthylphenylmethyl, indolinylmethyl, 1,2,3,4-tetrahydroquinolinylmethyl, 1,2,3,4-tetrahydroisoquinolinylmethyl, piperidinylcarbonyl, 1,2,3,4-tetrahydroquinolinylcarbonyl, methyl-1,2,3,4-tetrahydroquinolinylcarbonyl, methoxy-1,2,3,4-tetrahydroquinolinylcarbonyl, 1,2,3,4-tetrahydroisoquinolinylcarbonyl, 1,2,3,4-tetrahydroquinoxalinylcarbonyl, benzothienylmethyl, indolylmethyl, methyl-indolylmethyl, hydroxyindolylmethyl, benzyloxyindolylmethyl, acetylindolylmethyl, methylsulphonyloxyindolylmethyl, pyrrolo[2,3-b]pyridinylmethyl, benzimidazolylmethyl, benzotriazolylmethyl, bromopyridinylmethyl, quinolinylmethyl, isoquinolinylmethyl, benzofurylbenzyl, thienylbenzyl, methylthienylbenzyl, acetylthienylbenzyl, benzothienylbenzyl, phenylsulphonylindolylbenzyl, dimethylisoxazolylbenzyl, methylpyrazolylbenzyl, benzylpyrazolylbenzyl, pyridinylbenzyl, fluoropyridinylbenzyl, chloropyridinylbenzyl, methoxypyridinylbenzyl, pyrimidinylbenzyl and phenylpyridinylmethyl.

Typical values of $R^4$ include hydrogen and methyl. In a preferred embodiment, $R^4$ is hydrogen. In another embodiment, $R^4$ is $C_{1-6}$ alkyl, especially methyl.

Alternatively, $R^3$ and $R^4$, when both are attached to the same carbon atom, may together form an optionally substituted spiro linkage. Thus, $R^3$ and $R^4$, when both are attached to the same carbon atom, may represent, when taken together with the carbon atom to which they are both attached, $C_{3-7}$ cycloalkyl or $C_{3-7}$ heterocycloalkyl, either of which groups may be unsubstituted, or substituted by one or more, typically by one or two, substituents. In this context, $R^3$ and $R^4$, when taken together with the carbon atom to which they are both attached, may suitably represent an optionally substituted cyclopentyl, cyclohexyl, pyrrolidine or piperidine ring, especially cyclopentyl or cyclohexyl.

Alternatively, $R^3$ and $R^4$, when attached to adjacent carbon atoms, may together form an optionally benzo-fused and/or substituted cycloalkyl, phenyl or heteroaryl (e.g. pyridinyl) ring fused to the morpholine ring. Thus, $R^3$ and $R^4$, when attached to adjacent carbon atoms, may represent, when taken together with the carbon atoms to which they are attached, $C_{5-7}$ cycloalkyl, phenyl or heteroaryl (e.g. pyridinyl), any of which groups may be benzo-fused and/or unsubstituted, or substituted by one or more, typically by one or two, substituents. In this context, in one embodiment, $R^3$ and $R^4$, when taken together with the adjacent carbon atoms to which they are attached, suitably represent a phenyl ring fused to the morpholine ring. Also in this context, in another embodiment, $R^3$ and $R^4$, when taken together with the adjacent carbon atoms to which they are attached, suitably represent a benzo-fused cyclopentyl ring, i.e. an indanyl moiety fused to the morpholine ring.

Suitably, $R^a$ represents substituted or unsubstituted aryl.

Suitably, $R^c$ represents hydrogen; or aryl, aryl($C_{1-6}$)alkyl, heteroaryl($C_{1-6}$)alkyl or (aryl)(heteroaryl)($C_{1-6}$)alkyl, any of which groups may be optionally substituted by one or more substituents.

Examples of typical substituents on $R^a$ and/or $R^b$ and/or $R^c$ include halogen, cyano, nitro, $C_{1-6}$ alkyl, trifluoromethyl, hydroxy, $C_{1-6}$ alkoxy, difluoromethoxy, trifluoromethoxy, aryloxy, $C_{1-6}$ alkylthio, $C_{1-6}$ alkylsulphonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulphonylamino, formyl, $C_{2-6}$ alkylcarbonyl, carboxy, $C_{2-6}$ alkoxycarbonyl, aminocarbonyl, $C_{1-6}$ alkylamino-carbonyl, di($C_{1-6}$)alkylaminocarbonyl, aminosulphonyl, $C_{1-6}$ alkylaminosulphonyl and di($C_{1-6}$)alkylaminosulphonyl.

Examples of particular substituents on $R^a$ and/or $R^b$ and/or $R^c$ include fluoro, chloro, bromo, cyano, nitro, methyl, trifluoromethyl, hydroxy, methoxy, difluoromethoxy, trifluoromethoxy, phenoxy, methylthio, methylsulphonyl, amino, methylamino, dimethylamino, acetylamino, methoxycarbonylamino, methylsulphonylamino, formyl, acetyl, carboxy, methoxycarbonyl, aminocarbonyl, methylaminocarbonyl, dimethylaminocarbonyl, aminosulphonyl, methylaminosulphonyl and dimethylaminosulphonyl.

A particular value of $R^a$ is phenyl.

In one embodiment, $R^b$ represents hydrogen. In another embodiment, $R^b$ represents $C_{1-6}$ alkyl, especially methyl or ethyl.

Particular values of $R^c$ include hydrogen, phenyl, benzyl, pyridinylmethyl and (phenyl)(pyridinyl)methyl.

In one embodiment, $R^d$ represents hydrogen. In another embodiment, $R^d$ represents $C_{1-6}$ alkyl, especially methyl or ethyl, particularly ethyl.

Suitably, $R^e$ represents methyl.

Generally, $R^5$ represents hydrogen, halogen, cyano, —$SR^a$, —$COR^e$, —$CO_2R^b$ or —$CONR^cR^d$; or $R^5$ represents $C_{1-6}$ alkyl, $C_{2-6}$ alkenylcarbonyl, $C_{2-6}$ alkynyl, $C_{3-7}$ cycloalkyl ($C_{2-6}$)alkynyl, aryl, aryl($C_{1-6}$)alkyl, aryl($C_{2-6}$)alkenyl, aryl ($C_{2-6}$)alkynyl, biaryl, $C_{3-7}$ heterocycloalkyl($C_{1-6}$)alkyl, $C_{3-7}$heterocycloalkyl($C_{2-6}$)alkynyl, $C_{3-7}$ heterocycloalkylcarbonyl($C_{2-6}$)alkynyl, $C_{5-9}$ heterobicycloalkyl($C_{2-6}$)alkynyl, $C_{3-7}$ heterocycloalkyl-aryl, $C_{3-7}$heterocycloalkyl($C_{1-6}$)alkyl-aryl, $C_{3-7}$ heterocycloalkyl-biaryl, heteroaryl, heteroaryl($C_{1-6}$)alkyl, heteroaryl($C_{1-6}$)alkylcarbonyl, heteroaryl($C_{2-6}$)alkenyl, heteroaryl($C_{2-6}$)alkynyl, heteroaroylcarbonyl, $C_{3-7}$ heterocycloalkyl-heteroaryl, $C_{3-7}$ heterocycloalkyl-heteroaryl($C_{2-6}$)alkynyl, heteroaryl-aryl, aryl-heteroaryl, $C_{3-7}$ heterocycloalkyl-aryl-heteroaryl, $C_{3-7}$ heterocycloalkyl($C_{1-6}$)alkyl-aryl-heteroaryl, $C_{5-9}$ heterobicycloalkyl($C_{1-6}$)alkyl-aryl-heteroaryl, heteroaryl-aryl-heteroaryl, bi(heteroaryl), $C_{3-7}$ heterocycloalkylcarbonyl-bi(heteroaryl), aryloxyaryl, aryl($C_{1-6}$)alkoxyaryl, heteroaryl($C_{1-6}$)alkoxyaryl, aryl($C_{1-6}$)alkylaminoaryl, heteroaryl($C_{1-6}$) alkylaminoaryl, $C_{3-7}$ cycloalkylcarbonylaminoaryl, arylcarbonylaminoaryl, aryl($C_{1-6}$)alkylcarbonylaminoaryl, $C_{3-7}$heterocycloalkylcarbonylaminoaryl, heteroarylcarbonylaminoaryl, aryl-($C_{3-7}$)heterocycloalkylcarbonylaminoaryl, arylsulphonylaminoaryl, aryl($C_{1-6}$)alkyl-sulphonylaminoaryl, heteroaryl($C_{1-6}$)alkylsulphonylaminoaryl, $C_{3-7}$ cycloalkylamino-carbonylaminoaryl, arylaminocarbonylaminoaryl, $C_{3-7}$heterocycloalkylaminocarbonyl-aminoaryl, $C_{3-7}$ heterocycloalkylaminocarbonylaminoaryl, heteroaryl($C_{1-6}$)alkyl-aminocarbonylaminoaryl, $C_{3-7}$ heterocycloalkylcarbonylcarbonylaminoaryl, $C_{3-7}$ heterocycloalkyl($C_{1-6}$) alkylaminocarbonylaminoaryl, arylcarbonylaryl, $C_{3-7}$ heterocycloalkylcarbonylaryl, $C_{3-7}$ heterocycloalkylcarbonyl($C_{1-6}$)alkylaryl, aryl($C_{1-6}$)-alkylaminocarbonylaryl, $C_{3-7}$ heterocycloalkyl($C_{1-6}$)alkylaminocarbonylaryl, heteroaryl-aminocarbonylaryl, heteroaryl($C_{1-6}$)alkylaminocarbonylaryl, $C_{3-7}$ heterocycloalkylamino-carbonyl($C_{1-6}$)alkylaryl, $C_{3-7}$ heterocycloalkyl($C_{1-6}$)alkylaminocarbonyl($C_{1-6}$)alkylaryl, heteroarylaminocarbonyl($C_{1-6}$)alkylaryl, heteroaryl($C_{1-6}$)alkylaminocarbonyl($C_{1-6}$)alkyl-aryl, arylaminoheteroaryl, $C_{3-7}$ heterocycloalkylamino-aryl-heteroaryl, $C_{3-7}$ heterocycloalkylcarbonylamino-aryl-heteroaryl, $C_{3-7}$ heterocycloalkylaminocarbonyl-amino-aryl-heteroaryl, $C_{3-7}$ heterocycloalkylcarbonyl-aryl-heteroaryl, $C_{3-7}$ heterocycloalkyl($C_{1-6}$)alkylcarbonyl-aryl-heteroaryl, $C_{5-9}$ heterobicycloalkylcarbonyl-aryl-heteroaryl, $C_{3-7}$ heterocycloalkylcarbonyl($C_{1-6}$)alkyl-aryl-heteroaryl, $C_{3-7}$ heterocycloalkyl-aminocarbonyl-aryl-heteroaryl, $C_{3-7}$ heterocycloalkyl($C_{1-6}$)alkylaminocarbonyl-aryl-heteroaryl or $C_{3-7}$ heterocycloalkylaminocarbonyl($C_{1-6}$)alkyl-aryl-heteroaryl, any of which groups may be optionally substituted by one or more substituents.

Typically, $R^5$ represents hydrogen, halogen, cyano, —$SR^a$, —$CO_2R^b$ or —$CONR^cR^d$; or $R^5$ represents $C_{1-6}$ alkyl, $C_{2-6}$ alkynyl, $C_{3-7}$ cycloalkyl($C_{2-6}$)alkynyl, aryl, aryl($C_{1-6}$)alkyl, aryl($C_{2-6}$)alkynyl, biaryl, $C_{3-7}$ heterocycloalkyl($C_{2-6}$)alkynyl, $C_{5-9}$ heterobicycloalkyl-($C_{2-6}$)alkynyl, $C_{3-7}$ heterocycloalkyl-aryl, $C_{3-7}$ heterocycloalkyl($C_{1-6}$)alkyl-aryl, heteroaryl, heteroaryl($C_{2-6}$)alkynyl, $C_{3-7}$ heterocycloalkyl-heteroaryl($C_{2-6}$)alkynyl, heteroaryl-aryl, aryl-heteroaryl or bi(heteroaryl), any of which groups may be optionally substituted by one or more substituents.

In an illustrative embodiment, $R^5$ represents hydrogen; or $C_{2-6}$ alkynyl, $C_{3-7}$ cycloalkyl($C_{2-6}$)alkynyl, aryl, aryl($C_{2-6}$)alkynyl, biaryl, $C_{3-7}$ heterocycloalkyl($C_{2-6}$)alkynyl, $C_{3-7}$heterocycloalkylcarbonyl($C_{2-6}$)alkynyl, $C_{5-9}$ heterobicycloalkyl($C_{2-6}$)alkynyl, $C_{3-7}$ heterocycloalkyl-aryl, $C_{3-7}$ heterocycloalkyl($C_{1-6}$)alkyl-aryl, $C_{3-7}$heterocycloalkyl-biaryl, heteroaryl, heteroaryl($C_{2-6}$)alkynyl, $C_{3-7}$heterocycloalkyl-heteroaryl, $C_{3-7}$ heterocycloalkyl-heteroaryl($C_{2-6}$)alkynyl, heteroaryl-aryl, aryl-heteroaryl, $C_{3-7}$ heterocycloalkyl-aryl-heteroaryl, $C_{3-7}$ heterocycloalkyl($C_{1-6}$)alkyl-aryl-heteroaryl, $C_{5-9}$ heterobicycloalkyl($C_{1-6}$)alkyl-aryl-heteroaryl, heteroaryl-aryl-heteroaryl, bi(heteroaryl), $C_{3-7}$ heterocycloalkylcarbonyl-bi(heteroaryl), aryloxyaryl, aryl($C_{1-6}$)alkoxyaryl, heteroaryl($C_{1-6}$)alkoxyaryl, aryl($C_{1-6}$)alkylaminoaryl, heteroaryl($C_{1-6}$)alkylaminoaryl, $C_{3-7}$ cycloalkylcarbonylaminoaryl, arylcarbonylaminoaryl, aryl($C_{1-6}$)alkylcarbonylaminoaryl, $C_{3-7}$ heterocycloalkylcarbonylaminoaryl, heteroarylcarbonylaminoaryl, aryl-($C_{3-7}$)heterocycloalkylcarbonylaminoaryl, arylsulphonylaminoaryl, aryl($C_{1-6}$)alkyl-sulphonylaminoaryl, heteroaryl($C_{1-6}$)alkylsulphonylaminoaryl, $C_{3-7}$ cycloalkylamino-carbonylaminoaryl, arylaminocarbonylaminoaryl, $C_{3-7}$ heterocycloalkylaminocarbonyl-aminoaryl, $C_{3-7}$ heterocycloalkylaminocarbonylaminoaryl, heteroaryl($C_{1-6}$)alkylaminocarbonylaminoaryl, $C_{3-7}$ heterocycloalkylcarbonylcarbonylaminoaryl, $C_{3-7}$ heterocycloalkyl($C_{1-6}$)alkylaminocarbonylcarbonylaminoaryl, arylcarbonylaryl, $C_{3-7}$ heterocycloalkylcarbonylaryl, $C_{3-7}$ heterocycloalkylcarbonyl($C_{1-6}$)alkylaryl, aryl($C_{1-6}$)-alkylaminocarbonylaryl, $C_{3-7}$ heterocycloalkyl($C_{1-6}$)alkylaminocarbonylaryl, heteroaryl-aminocarbonylaryl, heteroaryl($C_{1-6}$)alkylaminocarbonylaryl, $C_{3-7}$ heterocycloalkylamino-carbonyl($C_{1-6}$)alkylaryl, $C_{3-7}$ heterocycloalkyl($C_{1-6}$)alkylaminocarbonyl($C_{1-6}$)alkylaryl, heteroarylaminocarbonyl($C_{1-6}$)alkylaryl, heteroaryl($C_{1-6}$)alkylaminocarbonyl($C_{1-6}$)alkyl-aryl, arylaminoheteroaryl, $C_{3-7}$ heterocycloalkylamino-aryl-heteroaryl, $C_{3-7}$ heterocycloalkylcarbonylamino-aryl-heteroaryl, $C_{3-7}$ heterocycloalkylaminocarbonyl-amino-aryl-heteroaryl, $C_{3-7}$ heterocycloalkylcarbonyl-aryl-heteroaryl, $C_{3-7}$ heterocycloalkyl($C_{1-6}$)alkylcarbonyl-aryl-heteroaryl, $C_{5-9}$ heterobicycloalkylcarbonyl-aryl-heteroaryl, $C_{3-7}$ heterocycloalkylcarbonyl($C_{1-6}$)alkyl-aryl-heteroaryl, $C_{3-7}$ heterocycloalkyl-aminocarbonyl-aryl-heteroaryl, $C_{3-7}$ heterocycloalkyl($C_{1-6}$)alkylaminocarbonyl-aryl-heteroaryl or $C_{3-7}$ heterocycloalkylaminocarbonyl($C_{1-6}$)alkyl-aryl-heteroaryl, any of which groups may be optionally substituted by one or more substituents.

In one aspect, $R^5$ represents $C_{2-6}$ alkynyl, $C_{3-7}$ cycloalkyl($C_{2-6}$)alkynyl, aryl-($C_{2-6}$)alkynyl, $C_{3-7}$ heterocycloalkyl($C_{2-6}$)alkynyl, $C_{3-7}$heterocycloalkylcarbonyl-($C_{2-6}$)alkynyl, $C_{5-9}$ heterobicycloalkyl($C_{2-6}$)alkynyl, heteroaryl($C_{2-6}$)alkynyl or $C_{3-7}$ heterocycloalkyl-heteroaryl($C_{2-6}$)alkynyl, any of which groups may be optionally substituted by one or more substituents.

In another aspect, $R^5$ represents aryl, biaryl, $C_{3-7}$ heterocycloalkyl-aryl, $C_{3-7}$ heterocycloalkyl($C_{1-6}$)alkyl-aryl, $C_{3-7}$ heterocycloalkyl-biaryl, heteroaryl, $C_{3-7}$ heterocycloalkyl-heteroaryl, heteroaryl-aryl, aryl-heteroaryl, $C_{3-7}$ heterocycloalkyl-aryl-heteroaryl, $C_{3-7}$ heterocycloalkyl($C_{1-6}$)alkyl-aryl-heteroaryl, $C_{5-9}$ heterobicycloalkyl-($C_{1-6}$)alkyl-aryl-heteroaryl, heteroaryl-aryl-heteroaryl, bi(heteroaryl), $C_{3-7}$ heterocycloalkylcarbonyl-bi(heteroaryl), aryloxyaryl, aryl($C_{1-6}$)alkoxyaryl, heteroaryl-($C_{1-6}$)alkoxyaryl, aryl($C_{1-6}$)alkylaminoaryl, heteroaryl($C_{1-6}$)alkylaminoaryl, $C_{3-7}$ cycloalkylcarbonylaminoaryl, arylcarbonylaminoaryl, aryl($C_{1-6}$)alkylcarbonylaminoaryl, $C_{3-7}$ heterocycloalkylcarbonylaminoaryl, heteroarylcarbonylaminoaryl, aryl-($C_{3-7}$)heterocycloalkylcarbonylaminoaryl, arylsulphonylaminoaryl, aryl($C_{1-6}$)alkyl-sulphonylaminoaryl, heteroaryl($C_{1-6}$)alkylsulphonylaminoaryl, $C_{3-7}$ cycloalkylamino-carbonylaminoaryl, arylaminocarbonylaminoaryl, $C_{3-7}$ heterocycloalkylaminocarbonyl-aminoaryl, $C_{3-7}$ heterocycloalkylaminocarbonylaminoaryl, heteroaryl($C_{1-6}$)alkylaminocarbonylaminoaryl, $C_{3-7}$ heterocycloalkylcarbonylcarbonylaminoaryl, $C_{3-7}$ heterocycloalkyl($C_{1-6}$)alkylaminocarbonylcarbonylaminoaryl, arylcarbonylaryl, $C_{3-7}$ heterocycloalkylcarbonylaryl, $C_{3-7}$ heterocycloalkylcarbonyl($C_{1-6}$)alkylaryl, aryl($C_{1-6}$)-alkylaminocarbonylaryl, $C_{3-7}$ heterocycloalkyl($C_{1-6}$)alkylaminocarbonylaryl, heteroaryl-aminocarbonylaryl, heteroaryl($C_{1-6}$)alkylaminocarbonylaryl, $C_{3-7}$ heterocycloalkylamino-carbonyl($C_{1-6}$)alkylaryl, $C_{3-7}$ heterocycloalkyl($C_{1-6}$)alkylaminocarbonyl($C_{1-6}$)alkylaryl, heteroarylaminocarbonyl($C_{1-6}$)alkylaryl, heteroaryl($C_{1-6}$)alkylaminocarbonyl($C_{1-6}$)alkyl-aryl, arylaminoheteroaryl, $C_{3-7}$ heterocycloalkylamino-aryl-heteroaryl, $C_{3-7}$ heterocycloalkylcarbonylamino-aryl-heteroaryl, $C_{3-7}$ heterocycloalkylaminocarbonyl-amino-aryl-heteroaryl, $C_{3-7}$ heterocycloalkylcarbonyl-aryl-heteroaryl, $C_{3-7}$ heterocycloalkyl($C_{1-6}$)alkylcarbonyl-aryl-heteroaryl, $C_{5-9}$ heterobicycloalkylcarbonyl-aryl-heteroaryl, $C_{3-7}$ heterocycloalkylcarbonyl($C_{1-6}$)alkyl-aryl-heteroaryl, $C_{3-7}$ heterocycloalkyl-aminocarbonyl-aryl-heteroaryl, $C_{3-7}$ heterocycloalkyl($C_{1-6}$)alkylaminocarbonyl-aryl-heteroaryl or $C_{3-7}$ heterocycloalkylaminocarbonyl($C_{1-6}$)alkyl-aryl-heteroaryl, any of which groups may be optionally substituted by one or more substituents.

In a representative embodiment, $R^5$ represents hydrogen; or $C_{2-6}$ alkynyl, $C_{3-7}$ cycloalkyl($C_{2-6}$)alkynyl, aryl, aryl($C_{2-6}$)alkynyl, biaryl, heteroaryl, heteroaryl($C_{2-6}$)alkynyl, heteroaryl-aryl, aryl-heteroaryl or bi(heteroaryl), any of which groups may be optionally substituted by one or more substituents.

Suitably, $R^5$ represents hydrogen, halogen, cyano, —$SR^a$, —$COR^e$, —$CO_2R^b$ or —$CONR^cR^d$; or $R^5$ represents methyl, propyl, ethenylcarbonyl, ethynyl, propynyl, butynyl, 3-methylbutynyl, cyclopropylethynyl, cyclohexylethynyl, phenyl, naphthyl, benzyl, phenylethyl, phenylethenyl, phenylethynyl, phenylpropynyl, biphenyl, piperidinylethyl, pyrrolidinylethynyl, piperidinylethynyl, 1,2,3,4-tetrahydroisoquinolinylpropynyl, piperazinylpropynyl, pyrrolidinylcarbonylethynyl, quinuclidinylethynyl, piperazinyl-phenyl, morpholinylphenyl, piperidinylmethylphenyl, piperazinyl-biphenyl, benzofuryl, dibenzofuryl, benzothienyl, dibenzothienyl, pyridinyl, isoquinolinyl, imidazolylethyl, imidazolylmethylcarbonyl, imidazolylethenyl, indolylethynyl, pyrazolylethynyl, imidazolylethynyl, pyridinylethynyl, pyrimidinylethynyl, imidazo[1,2-a]pyridinylethynyl, imidazolylcarbonylcarbonyl, benzomorpholinyl-pyridinyl, pyrrolidinylpyridinylethynyl, pyrazolylphenyl, pyridinylphenyl, phenylisoxazolyl, phenylthiazolyl, phenylpyridinyl, phenylpyrimidinyl, azetidinylphenylpyridinyl, pyrrolidinylphenylpyridinyl, piperidinylphenylpyridinyl, piperazinylphenylpyridinyl, morpholinylphenylpyridinyl, piperazinylphenylpyrimidinyl, pyrrolidinylmethylphenylpyridinyl, piperidinylmethyl-phenylpyridinyl, piperazinylmethylphenylpyridinyl, homopiperazinylmethylphenyl-pyridinyl, morpholinylmethylphenylpyridinyl, azabicyclo[3.2.1]octylmethylphenyl-pyridinyl, diazabicyclo[3.2.1]octylmethylphenylpyridinyl, tetrazolylphenylpyridinyl, benzofurylpyridinyl, benzothienylpyridinyl, indolylpyridinyl, isoxazolylpyridinyl, bi(pyridinyl), isoquinolinylpyridinyl, morpholinylcarbonylbi(pyridinyl), phenoxyphenyl, benzyloxyphenyl, pyridinylmethoxyphenyl, benzylaminophenyl, furylmethylaminophenyl, pridinylmethylaminophenyl, cyclopentylcarbonylaminophenyl, phenylcarbonylamino-phenyl, benzylcarbonylaminophenyl, pyrrolidinylcarbonylaminophenyl, piperidinyl-carbonylaminophenyl, piperazinylcarbonylaminophenyl, morpholinylcarbonylamino-phenyl, indolylcarbonylaminophenyl, isoxazolylcarbonylaminophenyl, pyridinylcarbonylaminophenyl, phenylpyrrolidinylcarbonylaminophenyl, phenylsulphonylaminophenyl, benzylsulphonylaminophenyl, isoxazolylsulphonylatninophenyl, cyclopentylaminocarbonylaminophenyl, phenylaminocarbonylaminophenyl, azetidinylaminocarbonyl-aminophenyl, morpholinylethylaminocarbonylaminophenyl, imidazolylmethyl-aminocarbonylaminophenyl, morpholinylcarbonylcarbonylaminophenyl, pyrrolidinylethylaminocarbonylcarbonylaminophenyl, phenylcarbonylphenyl, morpholinylcarbonyl-phenyl, pyrrolidinylcarbonylmethylphenyl, piperidinylcarbonylmethylphenyl, benzylaminocarbonylphenyl, morpholinylethylaminocarbonylphenyl, imidazolyl-amino carbonylphenyl, imidazolylmethylaminocarbonylphenyl, pyridinylmethylaminocarbonylphenyl, azetidinylaminocarbonylmethylphenyl, pyrrolidinylmethyl-aminocarbonylmethylphenyl, pyridinylaminocarbonylmethylphenyl, pyridinylmethylaminocarbonylmethylphenyl, phenylaminopyridinyl, azetidinylaminophenylpyridinyl, pyrrolidinylaminophenylpyridinyl, piperazinylcarbonylaminophenylpyridinyl, piperidinylaminocarbonylaminophenylpyridinyl, azetidinylcarbonylphenylpyridinyl, pyrrolidinylcarbonylphenylpyridinyl, piperidinylcarbonylphenylpyridinyl, piperazinylcarbonylphenylpyridinyl, morpholinylcarbonylphenylpyridinyl, pipetidinylcarbonylphenylpyrimidinyl, morpholinylmethylcarbonylphenylpyridinyl, azabicyclo[3.2.1]octylcarbonylphenylpyridinyl, azetidinylcarbonylmethylphenyl-pyridinyl, pyrrolidinylcarbonylmethylphenylpyridinyl, piperidinylcarbonylmethylphenyl-pyridinyl, piperazinylcarbonylmethylphenylpyridinyl, azetidinylaminocarbonylphenyl-pyridinyl, pyrrolidinylaminocarbonylphenylpyridinyl, piperidinylaminocarbonylphenyl-pyridinyl, piperidinylmethylaminocarbonylphenylpyridinyl or azetidinylaminocarbonyl-methylphenylpyridinyl, any of which groups may be optionally substituted by one or more substituents.

Illustratively, $R^5$ represents hydrogen, halogen, cyano, $—SR^a$, $—CO_2R^b$ or $—CONR^cR^d$; or $R^5$ represents methyl, ethynyl, propynyl, butynyl, 3-methylbutynyl, cyclopropylethynyl, cyclohexylethynyl, phenyl, benzyl, phenylethyl, phenylethynyl, biphenyl, 1,2,3,4-tetrahydroisoquinolinylpropynyl, piperazinylpropynyl, quinuclidinylethynyl, piperazinyl-phenyl, morpholinylphenyl, piperidinylmethylphenyl, dibenzofuryl, pyridinyl, pyrazolylethynyl, imidazolylethynyl, pyridinylethynyl, pyrimidinylethynyl, imidazo[1,2-a]pyridinylethynyl, pyrrolidinylpyridinylethynyl, pyrazolylphenyl, phenylisoxazolyl, phenylthiazolyl, phenylpyridinyl, isoxazolylpyridinyl or bi(pyridinyl), any of which groups may be optionally substituted by one or more substituents.

Examples of representative substituents on $R^5$ include halogen, cyano, nitro, oxo, $C_{1-6}$ alkyl, trifluoromethyl, hydroxy, hydroxy($C_{1-6}$)alkyl, $C_{1-6}$ alkoxy, dihydroxy($C_{1-6}$)alkoxy, aryl($C_{1-6}$)alkoxy, methoxyaryl($C_{1-6}$)alkoxy, amino, $C_{1-6}$ alkylamino, di($C_{1-6}$)-alkylamino, amino($C_{1-6}$)alkyl, $C_{1-6}$ alkylamino($C_{1-6}$)alkyl, di($C_{1-6}$)alkylamino($C_{1-6}$)alkyl, di($C_{1-6}$)alkylamino($C_{1-6}$)alkylamino, methoxyaryl($C_{1-6}$)alkylamino, $C_{1-6}$ alkylcarbonyl-amino, $C_{1-6}$ alkoxycarbonyl($C_{1-6}$)alkylcarbonylamino, $C_{1-6}$ alkylcarbonylamino($C_{1-6}$)alkyl, $C_{1-6}$ alkoxycarbonylamino, N—($C_{1-6}$ alkoxycarbonyl)-N—($C_{1-6}$ alkyl)amino, $C_{1-6}$ alkoxy-carbonylamino($C_{1-6}$)alkyl, N—($C_{1-6}$ alkoxycarbonyl)-N—($C_{1-6}$ alkyl)amino($C_{1-6}$)alkyl, $C_{1-6}$ alkylsulphonylamino, $C_{1-6}$ alkylsulphonylamino($C_{1-6}$)alkyl, $C_{1-6}$ alkylaminocarbonylamino, di($C_{1-6}$)alkylamino($C_{1-6}$)alkylaminocarbonylamino, N—($C_{1-6}$ alkyl)-N-[di($C_{1-6}$)alkylamino-($C_{1-6}$)alkyl]aminocarbonylamino, carboxycarbonylamino, $C_1$ alkoxycarbonyl-carbonylamino, $C_{1-6}$ alkylaminocarbonylcarbonylamino, di($C_{1-6}$)alkylamino($C_{1-6}$)alkyl-aminocarbonylcarbonylamino, di($C_{1-6}$)alkylaminosulphonylamino, formyl, $C_{1-6}$ alkylcarbonyl, di($C_{1-6}$)alkylamino($C_{1-6}$)alkylcarbonyl, carboxy, carboxy($C_{1-6}$)alkyl, $C_{1-6}$ alkoxycarbonyl, $C_{1-6}$ alkoxycarbonyl($C_{1-6}$)alkyl, aminocarbonyl, $C_{1-6}$ alkylaminocarbonyl, di($C_{1-6}$)alkylaminocarbonyl, cyano($C_{1-6}$)alkylaminocarbonyl, di($C_{1-6}$)alkylamino($C_{1-6}$)-alkylaminocarbonyl, dihydroxy($C_{1-6}$)alkylaminocarbonyl, N—($C_{1-6}$ alkyl)-N-[amino($C_{1-6}$)-alkyl]aminocarbonyl, N—($C_{1-6}$ alkyl)-N-[di($C_{1-6}$)alkylamino($C_{1-6}$)alkyl]aminocarbonyl, di($C_{1-6}$)alkylaminocarbonyl($C_{1-6}$)alkyl, N—($C_{1-6}$ alkyl)-N-[di($C_{1-6}$)alkylamino($C_{1-6}$)alkyl]-aminocarbonyl($C_{1-6}$)alkyl, aminocarbonyl($C_{1-6}$)alkoxy, $C_{1-6}$ alkoxyaminocarbonyl, N—($C_{1-6}$ alkoxy)-N—($C_{1-6}$ alkyl)aminocarbonyl, $C_{1-6}$ alkylsulphonyl, $C_{1-6}$ alkylsulphonyloxy($C_{1-6}$)-alkyl, trifluoromethylsulphonyloxy and tri($C_{1-6}$)alkylsilyl.

Examples of suitable substituents on $R^5$ include halogen, cyano, nitro, $C_{1-6}$ alkyl, hydroxy, hydroxy($C_{1-6}$)alkyl, $C_{1-6}$ alkoxy, aryl($C_{1-6}$)alkoxy, amino, $C_{1-6}$ alkylamino, di($C_{1-6}$) alkylamino, amino($C_{1-4}$alkyl, $C_{1-6}$ alkylamino($C_{1-6}$)alkyl, di($C_{1-6}$)alkylamino-($C_{1-6}$)alkyl, di($C_{1-6}$)alkylamino($C_{1-6}$) alkylamino, $C_{2-6}$ alkylcarbonylamino, $C_{1-6}$ alkylsulphonylamino, $C_{2-6}$ alkylcarbonyl, carboxy, carboxy($C_{1-6}$)alkyl, $C_{2-6}$ alkoxycarbonyl, aminocarbonyl, $C_{1-6}$ alkylaminocarbonyl, di($C_{1-6}$)alkylaminocarbonyl and tri($C_{1-6}$)alkylsilyl.

Examples of specific substituents on $R^5$ include fluoro, chloro, bromo, cyano, nitro, oxo, methyl, ethyl, isopropyl, trifluoromethyl, hydroxy, hydroxymethyl, methoxy, ethoxy, dihydroxypropoxy, isobutoxy, benzyloxy, methoxybenzyloxy, amino, methylamino, dimethylamino, diethylamino, aminomethyl, methylaminomethyl, dimethylaminomethyl, N-isopropyl-N-methylaminomethyl, dimethylaminoethylamino, methoxybenzylamino, acetylamino, ethoxycarbonylacetylamino, ethylcarbonylamino, methoxycarbonyl-ethylcarbonylamino, acetylaminomethyl, tert-butoxycarbonylamino, N-(tert-butoxy-carbonyl)-N-(methyl) amino, tert-butoxycarbonylaminomethyl, N-(tert-butoxycarbonyl)-N-(methyl)aminomethyl, methylsulphonylamino, ethylsulphonylamino, methylsulphonyl-aminomethyl, ethylaminocarbonylamino, dimethylaminoethylaminocarbonylamino, N-(dimethylaminoethyl)-N-(methyl)aminocarbonylamino, carboxycarbonylamino, ethoxycarbonylcarbonylamino, ethylaminocarbonylcarbonylamino, dimethylaminoethyl-aminocarbonylcarbonylamino, dimethylaminosulphonylamino, formyl, acetyl, dimethyl-aminoacetyl, ethylcarbonyl, carboxy, carboxymethyl, methoxycarbonyl, ethoxycarbonyl, tert-butoxycarbonyl, methoxycarbonylmethyl, tert-butoxycarbonylmethyl, aminocarbonyl, methylaminocarbonyl, cyanomethylaminocarbonyl, ethylaminocarbonyl, dimethylamino-ethylaminocarbonyl, dihydroxypropylaminocarbonyl, isopropylaminocarbonyl, dimethylaminocarbonyl, N-ethyl-N-methylaminocarbonyl, N-(aminoethyl)-N-(methyl)-aminocarbonyl, N-(dimethylaminoethyl)-N-(methypaminocarbonyl, diethylamino-carbonyl, dimethylaminocarbonylmethyl, N-(diethylaminoethyl)-N-(methyl)amino-carbonylmethyl, amino carbonylmethoxy, methoxyaminocarbonyl, N-(methoxy)-N-(methyl)aminocarbonyl, methylsulphonyl, methylsulphonyloxymethyl, trifluoromethyl-sulphonyloxy and tri($C_{1-6}$)alkylsilyl.

Examples of typical substituents on $R^5$ include fluoro, chloro, bromo, nitro, methyl, hydroxy, hydroxymethyl, methoxy, benzyloxy, amino, dimethylamino, diethylamine, aminomethyl, dimethylaminomethyl, dimethylaminoethylamino, acetylamino, methylsulphonylamino, acetyl, carboxy, carboxymethyl, methoxycarbonyl, ethoxycarbonyl, tert-butoxycarbonyl, aminocarbonyl, methylaminocarbonyl and triethylsilyl.

Specific values of $R^5$ include hydrogen, fluoro, chloro, bromo, iodo, cyano, phenylthio, acetyl, carboxy, methoxycarbonyl, ethoxycarbonyl, aminocarbonyl, phenylaminocarbonyl, benzylaminocarbonyl, pyridinylmethylaminocarbonyl, (phenyl)(pyridinyl)methylaminocarbonyl, N-ethyl-N-pyridinylmethylaminocarbonyl, dimethylaminomethyl, dimethylaminosulphonylaminopropyl, dimethylamino-ethenylcarbonyl, ethynyl, triethylsilylethynyl, diethylaminopropynyl, methylsulphonylaminopropynyl, dimethylaminosulphonylaminopropynyl, hydroxybutynyl, 3-hydroxy-3-methylbutynyl, cyclopropylethynyl, hydroxycyclohexylethynyl, amino cyclohexylethynyl, phenyl, bromophenyl, (bromo)(nitro)phenyl, hydroxyphenyl, methoxyphenyl, ethoxyphenyl, isobutoxyphenyl, (benzyloxy)(chloro)-phenyl, aminophenyl, (amino)(bromo)phenyl, aminomethylphenyl, acetylaminophenyl, ethoxycarbonylacetylaminophenyl, ethylcarbonylaminophenyl, methoxycarbonyl-ethylcarbonylaminophenyl, methylsulphonylaminophenyl, ethylsulphonylaminophenyl, ethylaminocarbonylaminophenyl, dimethylaminoethylaminocarbonylaminophenyl, N-(dimethylaminoethyl)-N-(methyl)aminocarbonylaminophenyl, carboxycarbonylamino-phenyl, ethoxycarbonylcarbonylaminophenyl, ethylaminocarbonylcarbonylaminophenyl, dimethylaminoethylaminocarbonylcarbonylaminophenyl, acetylphenyl, carboxyphenyl, carboxymethylphenyl, methoxycarbonylphenyl, (chloro)(methoxycarbonyl)phenyl, ethoxycarbonylphenyl, methoxycarbonylmethylphenyl, aminocarbonylphenyl, methylaminocarbonylphenyl, cyanomethylaminocarbonylphenyl, ethylaminocarbonyl-phenyl, dihydroxypropylaminocarbonylphenyl, isopropylaminocarbonylphenyl, dimethylaminocarbonylphenyl, dimethylaminocarbonylmethylphenyl, N-(diethylaminoethyl)-N-(methyl)aminocarbonylmethylphenyl, naphthyl, benzyl, phenylethyl, phenylethenyl, phenylethynyl, fluorophenylethynyl, nitrophenylethynyl, hydroxyphenylethynyl, methoxyphenylethynyl, dimethylaminophenylethynyl, phenylpropynyl, biphenyl, (bromo)(dinitro)biphenyl, methoxybiphenyl, aminobiphenyl, dimethylaminobiphenyl, dimethylaminomethylbiphenyl, (dimethylaminocarbonyl)-(methyl)biphenyl, acetylpiperidinylethyl, tert-butoxycarbonylpyrrolidinylethynyl, piperidinylethynyl, acetylpiperidinylethynyl, tert-butoxycarbonylpiperidinylethynyl, methylsulphonylpiperidinylethynyl, 1,2,3,4-tetrahydroisoquinolinylpropynyl, methylpiperazinylpropynyl, pyrrolidinylcarbonylethynyl, hydroxyquinuclidinylethynyl, piperazinylphenyl, tert-butoxycarbonylpiperazinylphenyl, morpholinylphenyl, piperidinylmethylphenyl, piperazinylbiphenyl, tert-butoxycarbonylpiperazinylbiphenyl, benzofuryl, dibenzofuryl, benzothienyl, dibenzothienyl, pyridinyl, chloropyridinyl, dichloropyridinyl, bromopyridinyl, carboxypyridinyl, ethoxycarbonylpyridinyl, isoquinolinyl, methylimidazolylethyl, methylimidazolylmethylcarbonyl, methylimidazolylethenyl, indolylethynyl, methylindolylethynyl, pyrazolylethynyl, methyl-pyrazolylethynyl, methylimidazolylethynyl, dimethylimidazolylethynyl, pyridinylethynyl, chloropyridinylethynyl, aminopyridinylethynyl, dimethylaminoethylaminopyridinyl-ethynyl, aminopyrimidinylethynyl, imidazo[1,2-a]pyridinylethynyl, dimethylamino-methylimidazo[1,2-c]pyridinylethynyl, methylimidazolylcarbonylcarbonyl, methyl-benzomorpholinylpyridinyl, hydroxymethylpyrrolidinylpyridinylethynyl, pyrazolylphenyl, methylpyrazolylphenyl, pyridinylphenyl, (amino)(chloropyridinyl)phenyl, phenyl-isoxazolyl, phenylthiazolyl, (methyl)(trifluoromethylphenyl)thiazolyl, phenylpyridinyl, fluorophenylpyridinyl, chlorophenylpyridinyl, cyanophenylpyridinyl, methylphenyl-pyridinyl, (bromo)(methyl)phenylpyridinyl, ethylphenylpyridinyl, hydroxyphenyl-pyridinyl, hydroxymethylphenylpyridinyl, methoxyphenylpyridinyl, aminocarbonyl-methoxyphenylpyridinyl, dihydroxypropoxyphenylpyridinyl, methoxybenzyloxy-phenylpyridinyl, trifluoromethylsulphonyloxyphenylpyridinyl, methylsulphonyl-oxymethylphenylpyridinyl, aminophenylpyridinyl, (amino)(cyano)phenylpyridinyl, dimethylaminophenylpyridinyl, aminomethylphenylpyridinyl, (aminomethyl)(fluoro)-phenylpyridinyl, methylaminomethylphenylpyridinyl, dimethylaminomethylphenyl-pyridinyl, N-isopropyl-N-methylaminomethylphenylpyridinyl, methoxybenzylamino-phenylpyridinyl, acetylaminophenylpyridinyl, acetylaminomethylphenylpyridinyl, tert-butoxycarbonylaminomethylphenylpyridinyl, N-(tert-butoxycarbonyl)-N-(methyl)-aminomethylphenylpyridinyl, methylsulphonylaminomethylphenylpyridinyl, formylphenylpyridinyl, acetylphenylpyridinyl, dimethylaminomethylcarbonyl-phenylpyridinyl, carboxyphenylpyridinyl, (amino)(carboxy)phenylpyridinyl, ethoxycarbonylphenylpyridinyl, tert-butoxycarbonylphenylpyridinyl, methoxycarbonyl-methylphenylpyridinyl, aminocarbonylphenylpyridinyl, methylaminocarbonylphenyl-pyridinyl, dimethylaminoethylaminocarbonylphenylpyridinyl, dihydroxypropylaminocarbonylphenylpyridinyl, dimethylaminocarbonylphenylpyridinyl, (dimethylaminocarbonyl)(fluoro)phenylpyridinyl, (dimethylaminocarbonyl)(nitro)phenylpyridinyl, (amino)(dimethylaminocarbonyl)phenylpyridinyl, N-ethyl-N-methylaminocarbonylphenylpyridinyl, N-(aminoethyl)-N-(methyl)aminocarbonylphenylpyridinyl, N-(dimethylaminoethyl)-N-

(methyl)aminocarbonylphenylpyridinyl, diethylaminocarbonyl-phenylpyridinyl, methoxyaminocarbonylphenylpyridinyl, N-methoxy-N-methylamino-carbonylphenylpyridinyl, dimethylaminocarbonylmethylphenylpyridinyl, N-(diethyl-aminoethyl)-N-(methyl)aminocarbonylmethylphenylpyridinyl, methylsulphonylphenyl-pyridinyl, phenylpyrimidinyl, bromophenylpyrimidinyl, amino azetidinylphenylpyridinyl, methylaminoazetidinylphenylpyridinyl, aminopyrrolidinylphenylpyridinyl, amino-piperidinylphenylpyridinyl, methylaminopiperidinylphenylpyridinyl, piperazinyl-phenylpyridinyl, tert-butoxycarbonylpiperazinylphenylpyridinyl, tert-butoxycarbonyl-methylpiperazinylphenylpyridinyl, morpholinylphenylpyridinyl, piperazinylphenyl-pyrimidinyl, pyrrolidinylmethylphenylpyridinyl, hydroxypyrrolidinylmethylphenyl-pyridinyl, dioxopynolidinylmethylphenylpyridinyl, aminopyrrolidinylmethylphenyl-pyridinyl, carboxypyrrolidinylmethylphenylpyridinyl, tert-butoxycarbonylpyrrolidinyl-methylphenylpyridinyl, aminopiperidinylmethylphenylpyridinyl, methylaminopiperidinyl-methylphenylpyridinyl, piperazinylmethylphenylpyridinyl, methylpiperazinylmethyl-phenylpyridinyl, oxopiperazinylmethylphenylpyridinyl, homopiperazinylmethylphenyl-pyridinyl, morpholinylmethylphenylpyridinyl, dimethylmorpholinylmethylphenyl-pyridinyl, aminoazabicyclo[3.2.1]octylmethylphenylpyridinyl, diazabicyclo[3.2.1]octylmethylphenylpyridinyl, tetrazolylphenylpyridinyl, benzofurylpyridinyl, benzothienylpyridinyl, indolylpyridinyl, dimethylisoxazolylpyridinyl, bi(pyridinyl), chlorobi(pyridinyl), carboxybi(pyridinyl), methoxycarbonylbi(pyridinyl), isoquinolinylpyridinyl, morpholinylcarbonylbi(pyridinyl), phenoxyphenyl, benzyloxyphenyl, methoxybenzyloxyphenyl, pyridinylmethoxyphenyl, N-(benzyl)-N-(ethylcarbonyl)aminophenyl, methylfurylmethylaminophenyl, pyridinylmethylamino-phenyl, cyclopentylcarbonylaminophenyl, phenylcarbonylaminophenyl, benzylcarbonyl-aminophenyl, hydroxypyrrolidinylcarbonylaminophenyl, aminopyrrolidinylcarbonyl-aminophenyl, tert-butoxycarbonylaminopyrrolidinylcarbonylaminophenyl, (isopropyl)-(oxo)pynolidinylcarbonylaminophenyl, tert-butoxycarbonylpiperidinylcarbonylamino-phenyl, piperazinylcarbonylaminophenyl, methylpiperazinylcarbonylaminophenyl, tert-butoxycarbonylpiperazinylcarbonylaminophenyl, morpholinylcarbonylaminophenyl, indolylcarbonylaminophenyl, methylisoxazolylcarbonylaminophenyl, pyridinylcarbonyl-aminophenyl, hydroxypyridinylcarbonylaminophenyl, (oxo)(phenyl)pyrrolidinylcarbonyl-aminophenyl, phenylsulphonylaminophenyl, benzylsulphonylaminophenyl, dimethyl-isoxazolylsulphonylaminophenyl, cyclopentylaminocarbonylaminophenyl, phenylamino-carbonylaminophenyl, methylazetidinylaminocarbonylaminophenyl, morpholinylethyl-aminocarbonylaminophenyl, methylimidazolylmethylaminocarbonylaminophenyl, morpholinylcarbonylcarbonylaminophenyl, pyrrolidinylethylaminocarbonylcarbonyl-aminophenyl, phenylcarbonylphenyl, morpholinylcarbonylphenyl, aminopyrrolidinylcarbonylmethylphenyl, tert-butoxycarbonylaminopyrrolidinylcarbonylmethylphenyl, aminopiperidinylcarbonylmethylphenyl, methylaminopiperidinylmethylphenyl, tert-butoxycarbonylaminopiperidinylcarbonylmethylphenyl, N-(tert-butoxycarbonyl)-N-(methyl)aminopiperidinylcarbonylmethylphenyl, benzylaminocarbonylphenyl, morpholinylethylaminocarbonylphenyl, imidazolylaminocarbonylphenyl, methyl-imidazolylmethylaminocarbonylphenyl, pyridinylmethylaminocarbonylphenyl, azetidinylaminocarbonylmethylphenyl, tert-butoxycarbonylazetidinylaminocarbonyl-methylphenyl, pyrrolidinylmethylaminocarbonylmethylphenyl, tert-butoxycarbonyl-pyrrolidinylmethylaminocarbonylmethylphenyl, pyridinylaminocarbonylmethylphenyl, pyridinylmethylaminocarbonylmethylphenyl, phenylaminopyridinyl, N-methyl-N-phenylaminopyridinyl, azetidinylaminophenylpyridinyl, pyrrolidinylaminophenyl-pyridinyl, tert-butoxycarbonylpyrrolidinylaminophenylpyridinyl, piperazinylcarbonyl-aminophenylpyridinyl, piperidinylaminocarbonylaminophenylpyridinyl, amino azetidinyl-carbonylphenylpyridinyl, methylaminoazetidinylcarbonylphenylpyridinyl, tert-butoxy-carbonylaminoazetidinylcarbonylphenylpyridinyl, N-(tert-butoxycarbonyl)-N-(methyl)-aminoazetidinylcarbonylphenylpyridinyl, pyrrolidinylcarbonylphenylpyridinyl, hydroxypyrrolidinylcarbonylphenylpyridinyl, aminopyrrolidinylcarbonylphenylpyridinyl, aminopyrrolidinylcarbonylphenyl(amino)pyridinyl, methylaminopyrrolidinylcarbonyl-phenylpyridinyl, tert-butoxycarbonylaminopyrrolidinylcarbonylphenylpyridinyl, tert-butoxycarbonylaminopyrrolidinylcarbonylphenyl(methoxybenzylamino)pyridinyl, piperidinylcarbonylphenylpyridinyl, aminopiperidinylcarbonylphenylpyridinyl, methyl-aminopiperidinylcarbonylphenylpyridinyl, tert-butoxycarbonylaminopiperidinylcarbonyl-phenylpyridinyl, dimethylaminopiperidinylcarbonylphenylpyridinyl, N-(tert-butoxy-carbonyl)-N-(methyl)aminopiperidinylcarbonylphenylpyridinyl, piperazinylcarbonyl-phenylpyridinyl, methylpiperazinylcarbonylphenylpyridinyl, tert-butoxycarbonyl-piperazinylcarbonylphenylpyridinyl, morpholinylcarbonylphenylpyridinyl, methylamino-piperidinylcarbonylphenylpyrimidinyl, dimethylaminopiperidinylcarbonylphenyl-pyrimidinyl, morpholinylmethylcarbonylphenylpyridinyl, aminoazabicyclo[3.2.1]octyl-carbonylphenylpyridinyl, aminoazetidinylcarbonylmethylphenylpyridinyl, tert-butoxy-carbonylaminoazetidinylcarbonylmethylphenylpyridinyl, pyrrolidinylcarbonylmethyl-phenylpyridinyl, aminopyrrolidinylcarbonylmethylphenylpyridinyl, tert-butoxycarbonyl-aminopyrrolidinylcarbonylmethylphenylpyridinyl, methylaminopiperidinylcarbonyl-tnethylphenylpyridinyl, N-(tert-butoxycarbonyl)-N-(methyl) aminopiperidinylcarbonyl-methylphenylpyridinyl, methylpiperazinylcarbonylmethylphenylpyridinyl, azetidinyl-amino carbonylphenylpyridinyl, tert-butoxycarbonylazetidinylaminocarbonylphenyl-pyridinyl, N-(tert-butoxycarbonylazetidinyl)-N-(ethyl) aminocarbonylphenylpyridinyl, tert-butoxycarbonylpyrrolidinylaminocarbonylphenylpyridinyl, N-(methylpyrrolidinyl)-N-(methyl)aminocarbonylphenylpyridinyl, N-(methylpiperidinyl)-N-(methyl)aminocarbonyl-phenylpyridinyl, piperidinylmethylaminocarbonylphenylpyridinyl, tert-butoxycarbonyl-piperidinylmethylaminocarbonylphenylpyridinyl, azetidinylaminocarbonylmethylphenyl-pyridinyl and tert-butoxycarbonylazetidinylaminocarbonylmethylphenylpyridinyl.

Typical values of $R^5$ include hydrogen, fluoro, chloro, bromo, iodo, cyano, phenylthio, carboxy, methoxycarbonyl, ethoxycarbonyl, aminocarbonyl, phenylaminocarbonyl, benzylaminocarbonyl, pyridinylmethylaminocarbonyl, (phenyl)(pyridinyl)methylaminocarbonyl, N-ethyl-N-pyridinylmethylaminocarbonyl, dimethylaminomethyl, ethynyl, triethylsilylethynyl, diethylaminopropynyl, methylsulphonylaminopropynyl, hydroxybutynyl, 3-hydroxy-3-methylbutynyl, cyclopropylethynyl, hydroxycyclohexylethynyl, amino cyclohexylethynyl, phenyl, (bromo)(nitro)phenyl, hydroxyphenyl, (benzyloxy)(chloro)phenyl, aminophenyl, aminomethyl-phenyl, acetylaminophenyl, acetylphenyl, carboxymethyl-phenyl, methoxycarbonylphenyl, (chloro)(methoxycarbonyl)phenyl, ethoxycarbonylphenyl, aminocarbonylphenyl, methylaminocarbonyl-phenyl, benzyl, phenylethyl, phenylethynyl, fluorophenylethynyl, nitrophenylethynyl, hydroxyphenylethynyl, methoxyphenylethynyl, dimethylaminophenylethynyl, biphenyl, (bromo)(dinitro)biphenyl, dimethylaminomethyl-biphenyl, 1,2,3,4-tetrahydroisoquinolinylpropynyl, methylpiperazinyl-propynyl, hydroxyquinuclidinyl-ethynyl, piperazinylphenyl, tent-butoxycarbonylpiperazinyl-phenyl, morpholinylphenyl, piperidinylmethylphenyl, dibenzofuryl, pyridinyl, chloropyridinyl, bromopyridinyl, carboxypyridinyl, ethoxycarbonylpyridinyl, pyrazolylethynyl, methylimidazolylethynyl, pyridinylethynyl, chloropyridinylethynyl, dimethylamino-ethylaminopyridinylethynyl, aminopyrimidinylethynyl, imidazo[1,2-a]pyridinylethynyl, dimethylaminomethyl-imidazo[1,2-a]pyridinylethynyl, hydroxymethylpyrrolidinyl-pyridinylethynyl, pyrazolylphenyl, methylpyrazolylphenyl, phenylisoxazolyl, phenylthiazolyl, phenylpyridinyl, hydroxyphenyl-pyridinyl, acetylaminophenyl-pyridinyl, dimethylaminomethyl-phenylpyridinyl, dimethylisoxazolyl-pyridinyl and bi(pyridinyl).

Suitably, when $R^3$ and $R^4$ are both hydrogen, then $R^5$ is other than hydrogen.

Suitably, when $R^5$ is hydrogen, then $R^3$ and/or $R^4$ is other than hydrogen.

In one embodiment, $R^6$ represents hydrogen. In another embodiment, $R^6$ represents $C_{1-6}$ alkyl, especially methyl.

In one embodiment, $R^7$ represents hydrogen. In another embodiment, $R^7$ represents $C_{1-6}$ alkyl, especially methyl.

One sub-class of compounds according to the invention is represented by the compounds of formula (IIA), and pharmaceutically acceptable salts and solvates thereof:

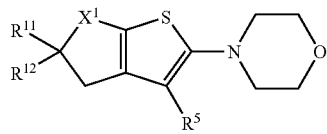

(IIA)

wherein
—$X^1$— represents a group of formula (a), (b) or (c) as defined above;
$R^5$ is as defined above;
$R^{11}$ represents hydrogen or optionally substituted $C_{1-6}$ alkyl; and
$R^{12}$ represents hydrogen; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or
$R^{11}$ and $R^{12}$, when taken together with the carbon atom to which they are both attached, represent $C_{3-7}$ cycloalkyl or $C_{3-7}$ heterocycloalkyl, either of which groups may be optionally substituted by one or more substituents.

In one embodiment, —$X^1$— represents a group of formula (a). In another embodiment, —$X^1$— represents a group of formula (b). In a further embodiment, —$X^1$— represents a group of formula (c).

Suitably, $R^5$ in the compounds of formula (IIA) is other than hydrogen.

Where $R^{11}$ and/or $R^{12}$ in the compounds of formula (IIA) above is stated to be optionally substituted, this group may be unsubstituted, or substituted by one or more substituents. Typically, $R^{11}$ and/or $R^{12}$ will be unsubstituted, or substituted by one or two substitutents. Suitably, $R^{11}$ and/or $R^{12}$ will be unsubstituted or monosubstituted.

Suitably, $R^{11}$ represents hydrogen or unsubstituted $C_{1-6}$ alkyl.

Suitably, $R^{12}$ represents hydrogen; or $C_{1-6}$ alkyl, aryl or heteroaryl, any of which groups may be optionally substituted by one or more substituents. Particular values of $R^{12}$ include hydrogen and unsubstituted $C_{1-6}$ alkyl.

Examples of typical substituents on $R^{11}$ and/or $R^{12}$ include halogen, cyano, nitro, $C_{1-6}$ alkyl, trifluoromethyl, hydroxy, $C_{1-6}$ alkoxy, difluoromethoxy, trifluoromethoxy, aryloxy, $C_{1-6}$ alkylthio, $C_{1-6}$ alkylsulphonyl, amino, $C_{1-6}$ alkylamino, di($C_{1-6}$)alkylamino, alkylcarbonylamino, $C_{2-6}$ alkoxycarbonylamino, $C_{1-6}$ alkylsulphonylamino, formyl, $C_{2-6}$ alkylcarbonyl, carboxy, $C_{2-6}$ alkoxycarbonyl, aminocarbonyl, $C_{1-6}$ alkylamino-carbonyl, di($C_{1-6}$)alkylaminocarbonyl, aminosulphonyl, $C_{1-6}$ alkylaminosulphonyl and di($C_{1-6}$)alkylaminosulphonyl; especially halogen, $C_{1-6}$ alkoxy or $C_{1-6}$ alkylthio.

Examples of particular substituents on $R^{11}$ and/or $R^{12}$ include fluoro, chloro, bromo, cyano, nitro, methyl, trifluoromethyl, hydroxy, methoxy, difluoromethoxy, trifluoromethoxy, phenoxy, methylthio, methylsulphonyl, amino, methylamino, dimethylamino, acetylamino, methoxycarbonylamino, methylsulphonylamino, formyl, acetyl, carboxy, methoxycarbonyl, aminocarbonyl, methylaminocarbonyl, dimethylaminocarbonyl, aminosulphonyl, methylaminosulphonyl and dimethylaminosulphonyl; especially chloro, methoxy or methylthio.

Typical values of $R^{11}$ include hydrogen and methyl. In one embodiment, $R^{11}$ is hydrogen. In another embodiment, $R^{11}$ is methyl.

Typical values of $R^{12}$ include hydrogen, methyl, n-propyl, isopropyl, phenyl, chlorophenyl, methoxyphenyl, methylthiophenyl and furyl, especially hydrogen or methyl. In one embodiment, $R^{12}$ is hydrogen. In another embodiment, $R^{12}$ is methyl.

Alternatively, $R^{11}$ and $R^{12}$ may together form an optionally substituted spiro linkage. Thus, $R^{11}$ and $R^{12}$, when taken together with the carbon atom to which they are both attached, may represent $C_{3-7}$ cycloalkyl or $C_{3-7}$ heterocycloalkyl, either of which groups may be unsubstituted, or substituted by one or more, typically by one or two, substituents. In this context, $R^{11}$ and $R^{12}$, when taken together with the carbon atom to which they are both attached, may suitably represent an optionally substituted cyclopentyl, cyclohexyl, pyrrolidine or piperidine ring, especially cyclopentyl or cyclohexyl.

Another sub-class of compounds according to the invention is represented by the compounds of formula (IIB), and pharmaceutically acceptable salts and solvates thereof:

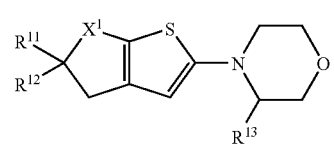

(IIB)

wherein
—$X^1$—, $R^{11}$ and $R^{12}$ are as defined above; and
$R^{13}$ represents hydrogen; or $C_{1-6}$ alkyl, $C_{3-7}$ cycloalkyl, $C_{3-7}$ cycloalkyl($C_{1-6}$)alkyl, aryl, aryl($C_{1-6}$)alkyl, aryl($C_{2-6}$) alkenyl, aryl($C_{2-6}$)alkynyl, biaryl($C_{1-6}$)alkyl, $C_{3-7}$ heterocycloalkyl, $C_{3-7}$ heterocycloalkyl($C_{1-6}$)alkyl, $C_{3-7}$ heterocycloalkylcarbonyl, heteroaryl, heteroaryl($C_{1-6}$)alkyl, heteroaryl-aryl($C_{1-6}$)alkyl or aryl-heteroaryl($C_{1-6}$)alkyl, any of which groups may be optionally substituted by one or more substituents.

Typically, $R^{13}$ represents hydrogen; or $C_{1-6}$ alkyl, aryl($C_{1-6}$)alkyl, aryl($C_{2-6}$)alkynyl, biaryl($C_{1-6}$)alkyl, $C_{3-7}$ heterocycloalkyl($C_{1-6}$)alkyl, $C_{3-7}$ heterocycloalkylcarbonyl, heteroaryl($C_{1-6}$)alkyl, heteroaryl-aryl($C_{1-6}$)alkyl or aryl-heteroaryl($C_{1-6}$)alkyl, any of which groups may be optionally substituted by one or more substituents.

Suitably, $R^{13}$ is other than hydrogen.

In a representative embodiment, $R^{13}$ represents $C_{1-6}$ alkyl, aryl($C_{1-6}$)alkyl, biaryl-($C_{1-6}$)alkyl, heteroaryl($C_{1-6}$)alkyl or heteroaryl-aryl($C_{1-6}$)alkyl, any of which groups may be optionally substituted by one or more substituents. Preferably, $R^{13}$ represents methyl, arylmethyl, biarylmethyl, heteroarylmethyl or heteroaryl-arylmethyl, any of which groups may be optionally substituted by one or more substituents.

In a particular embodiment, $R^{13}$ represents substituted or unsubstituted indolyl-($C_{1-6}$)alkyl. Advantageously, $R^{13}$ represents substituted or unsubstituted indolylmethyl.

Illustratively, $R^{13}$ represents hydrogen; or methyl, benzyl, phenylethyl, naphthylmethyl, phenylpropynyl, biphenylmethyl, naphthylphenylmethyl, indolinylmethyl, 1,2,3,4-tetrahydroquinolinylmethyl, 1,2,3,4-tetrahydroisoquinolinylmethyl, piperidinylcarbonyl, 1,2,3,4-tetrahydroquinolinylcarbonyl, 1,2,3,4-tetrahydroisoquinolinylcarbonyl, 1,2,3,4-tetrahydroquinoxalinylcarbonyl, benzothienylmethyl, indolylmethyl, pyrrolo[2,3-b]pyridinylmethyl, benzimidazolylmethyl, benzotriazolylmethyl, pyridinylmethyl, quinolinylmethyl, isoquinolinylmethyl, benzofurylbenzyl, thienylbenzyl, benzothienylbenzyl, indolylbenzyl, isoxazolylbenzyl, pyrazolylbenzyl, pyridinylbenzyl, pyrimidinylbenzyl or phenylpyridinylmethyl, any of which groups may be optionally substituted by one or more substituents.

Examples of suitable substituents on $R^{13}$ include halogen, cyano, nitro, $C_{1-6}$ alkyl, hydroxy($C_{1-6}$)alkyl, trifluoromethyl, aryl($C_{1-6}$)alkyl, hydroxy, $C_{1-6}$ alkoxy, difluoromethoxy, trifluoromethoxy, aryloxy, aryl($C_{1-6}$)alkoxy, methylenedioxy, $C_{1-6}$ alkylthio, arylthio, $C_{1-6}$ alkylsulphonyl, arylsulphonyl, $C_{1-6}$ alkylsulphonyloxy, amino, $C_{1-6}$ alkylamino, di($C_{1-6}$) alkylamino, phenylamino, [($C_{1-6}$)alkyl](phenyl)amino, pyridinylamino, pyrrolidinyl, morpholinyl, $C_{2-6}$ alkylcarbonylamino, benzofurylcarbonylamino, $C_{2-6}$ alkoxycarbonylamino, $C_{1-6}$ alkylsulphonylamino, arylsulphonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, benzothienylmethylaminocarbonyl, aminosulphonyl, $C_{1-6}$ alkylaminosulphonyl and di($C_{1-6}$)alkylaminosulphonyl.

Examples of representative substituents on $R^{13}$ include fluoro, chloro, bromo, cyano, nitro, methyl, hydroxymethyl, trifluoromethyl, benzyl, hydroxy, methoxy, ethoxy, difluoromethoxy, trifluoromethoxy, phenoxy, benzyloxy, methylenedioxy, methylthio, phenylthio, methylsulphonyl, phenylsulphonyl, methylsulphonyloxy, amino, methylamino, dimethylamino, phenylamino, N-methyl-N-phenylamino, pyridinylamino, pyrrolidinyl, morpholinyl, acetylamino, benzofurylcarbonylamino, methoxycarbonylamino, methylsulphonylamino, phenylsulphonylamino, formyl, acetyl, carboxy, methoxycarbonyl, aminocarbonyl, methylaminocarbonyl, dimethylaminocarbonyl, benzothienylmethylaminocarbonyl, aminosulphonyl, methylaminosulphonyl and dimethylaminosulphonyl.

Specific values of $R^{13}$ include hydrogen, phenoxymethyl, phenylthiomethyl, aminomethyl, phenylaminomethyl, N-methyl-N-phenylaminomethyl, pyridinylamino-methyl, benzofurylcarbonylaminomethyl, phenylsulphonylaminomethyl, benzothienyl-methylaminocarbonylmethyl, benzyl, chlorobenzyl, bromobenzyl, pyrrolidinylbenzyl, morpholinyl-benzyl, phenylethyl, naphthylmethyl, phenylpropynyl, biphenylmethyl, fluorobiphenylmethyl, difluorobiphenylmethyl, chlorobiphenylmethyl, dichlorobiphenylmethyl, bromobiphenylmethyl, cyanobiphenylmethyl, methylbiphenylmethyl, (fluoro)(methyl)biphenylmethyl, dimethylbiphenylmethyl, hydroxymethyl-biphenylmethyl, trifluoromethylbiphenylmethyl, bis(trifluoromethyl)biphenylmethyl, methoxybiphenylmethyl, dimethoxybiphenylmethyl, ethoxybiphenylmethyl, methylenedioxybiphenylmethyl, trifluoromethoxybiphenylmethyl, phenoxybiphenylmethyl, methylthiobiphenylmethyl, aminobiphenylmethyl, acetylamino-biphenylmethyl, methylsulphonylaminobiphenylmethyl, acetylbiphenylmethyl, amino carbonylbiphenylmethyl, naphthylphenylmethyl, indolinylmethyl, 1,2,3,4-tetrahydroquinolinylmethyl, 1,2,3,4-tetrahydroisoquinolinylmethyl, piperidinylcarbonyl, 1,2,3,4-tetrahydroquinolinylcarbonyl, methyl-1,2,3,4-tetrahydroquinolinylcarbonyl, methoxy-1,2,3,4-tetrahydroquinolinylcarbonyl, 1,2,3,4-tetrahydroisoquinolinylcarbonyl, 1,2,3,4-tetrahydroquinoxalinylcarbonyl, benzothienylmethyl, indolylmethyl, methyl-indolylmethyl, hydroxyindolylmethyl, benzyloxyindolylmethyl, acetylindolylmethyl, methylsulphonyloxyindolylmethyl, pyrrolo[2,3-b]pyridinylmethyl, benzimidazolylmethyl, benzotriazolylmethyl, bromopyridinylmethyl, quinolinylmethyl, isoquinolinylmethyl, benzofurylbenzyl, thienylbenzyl, methylthienylbenzyl, acetylthienylbenzyl, benzothienylbenzyl, phenylsulphonylindolylbenzyl, dimethylisoxazolylbenzyl, methylpyrazolylbenzyl, benzylpyrazolylbenzyl, pyridinylbenzyl, fluoropyridinylbenzyl, chloropyridinylbenzyl, methoxypyridinylbenzyl, pyrimidinylbenzyl and phenylpyridinylmethyl.

One particular sub-group of the compounds of formula (IIB) is represented by the compounds of formula (IIC), and pharmaceutically acceptable salts and solvates thereof:

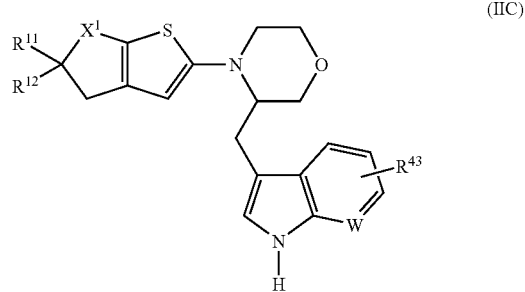

(IIC)

wherein
—$X^1$—, $R^{11}$ and $R^{12}$ are as defined above;
W represents CH or N; and
$R^{43}$ represents hydrogen, halogen, cyano, $C_{1-6}$ alkyl, hydroxy($C_{1-6}$)alkyl, trifluoromethyl, aryl($C_{1-6}$)alkyl, hydroxy, $C_{1-6}$ alkoxy, trifluoromethoxy, aryloxy, aryl($C_{1-6}$) alkoxy, $C_{1-6}$ alkylthio, arylsulphonyl, $C_{1-6}$ alkylsulphonyloxy, amino, $C_{2-6}$ alkylcarbonylamino, $C_{1-6}$ alkylsulphonylamino, $C_{2-6}$ alkylcarbonyl or aminocarbonyl.

In a preferred embodiment, W is CH. In another embodiment, W is N.

Suitable values of $R^{43}$ include hydrogen, $C_{1-6}$ alkyl, hydroxy, aryl($C_{1-6}$)alkoxy and $C_{1-6}$ alkylsulphonyloxy.

Specific values of $R^{43}$ include hydrogen, fluoro, chloro, bromo, cyano, methyl, hydroxymethyl, trifluoromethyl, benzyl, hydroxy, methoxy, ethoxy, trifluoromethoxy, phenoxy, benzyloxy, methylthio, phenylsulphonyl, methylsulphonyloxy, amino, acetylamino, tnethylsulphonylamino, acetyl and aminocarbonyl; especially hydrogen, methyl, hydroxy, benzyloxy or methylsulphonyloxy.

A particular value of $R^{43}$ is hydrogen.

Specific novel compounds in accordance with the present invention include each of the compounds whose preparation is described in the accompanying Examples, and pharmaceutically acceptable salts and solvates thereof.

The present invention also provides a pharmaceutical composition which comprises a novel compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds according to the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds according to the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds according to the present invention may be conveniently formulated as microionized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds according to the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds of formula (I) above may be prepared by a process which comprises reacting a compound of formula (III) with a compound of formula (IV):

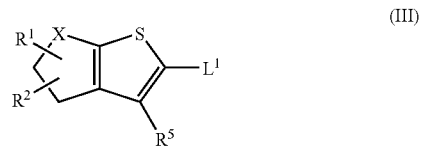

(III)

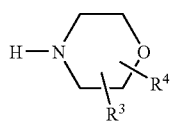
(IV)

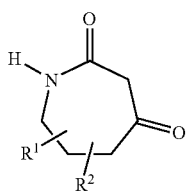
(VIC)

wherein $R^1$, $R^2$, $R^3$, $R^4$, $R^5$ and X are as defined above, and $L^1$ represents a suitable leaving group.

The leaving group $L^1$ is typically a halogen atom, e.g. bromo.

The reaction is conveniently effected at an elevated temperature in a suitable solvent, e.g. acetonitrile, dimethylsulphoxide, a lower alkanol such as isopropanol or a cyclic ether such as tetrahydrofuran, typically under basic conditions, e.g. in the presence of an organic base such as N,N-diisopropylethylamine.

Alternatively, the reaction may be effected at an elevated temperature in a solvent such as 2-ethoxyethanol in the presence of a catalytic quantity of a mineral acid, e.g. concentrated hydrochloric acid.

The intermediates of formula (III) above wherein $L^1$ is bromo may be prepared from a compound of formula (V):

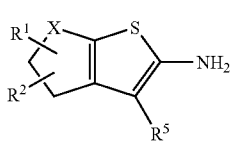
(V)

wherein $R^1$, $R^2$, $R^5$ and X are as defined above; by diazotization/bromination.

The reaction is conveniently effected by stirring compound (V) with tent-butyl nitrite and copper(II) bromide in a suitable solvent, e.g. acetonitrile.

The intermediates of formula (V) above wherein —X— represents a group of formula (a), (b) or (c) in which Y is oxygen, and $R^5$ represents cyano or —$CO_2R^b$, may be prepared by reacting a compound of formula $R^{5a}$—$CH_2$—CN with the appropriate compound of formula (VIA), (VIB) or (VIC):

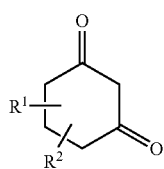
(VIA)

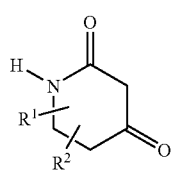
(VIB)

wherein $R^1$ and $R^2$ are as defined above, and $R^{5a}$ represents cyano or —$CO_2R^b$ in which $R^b$ is as defined above; in the presence of sulphur.

The reaction is conveniently effected at an elevated temperature in a suitable solvent, e.g. a lower alkanol such as ethanol, typically under basic conditions, e.g. in the presence of morpholine.

Where they are not commercially available, the starting materials of formula (IV) and (VIA)/(VIB)/(VIC) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of example, a compound of formula (IA), (IB), (IC) or (ID) wherein Y is oxygen may be converted into the corresponding compound wherein Y is sulphur by treatment with Lawesson's Reagent (i.e. 2,4-bis(4-methoxyphenyl)-1,3-dithia-2,4-diphosphetane-2,4-disulphide). A compound of formula (IB) wherein Y is oxygen may be converted into the corresponding compound of formula (ID) by treatment with hydroxylamine-O-sulfonic acid, typically in the presence of formic acid at an elevated temperature. A compound of formula (IB) wherein Y is oxygen may be converted into the corresponding compound of formula (IE) by treatment with a reducing agent such as lithium aluminium hydride. A compound of formula (IB) wherein Y is oxygen may be converted into the corresponding compound of formula (IF) by treatment with a hydroxylamine derivative of formula $H_2N$—$OR^7$. A compound of formula (IB) wherein Y is oxygen may be converted into the corresponding compound of formula (IG) by treatment with hydrazine hydrate. A compound of formula (IF) may be converted into the corresponding compound of formula (IC) by treatment with p-toluenesulphonyl chloride, typically in the presence of pyridine at an elevated temperature. A compound of formula (IB) wherein Y is oxygen and $R^1$ is hydrogen may be converted into the corresponding compound wherein $R^1$ is methyl by treatment with a methyl halide, e.g. iodomethane, in the presence of a strong base, e.g. lithium diisopropylamide.

A compound of formula (I) wherein $R^3$ represents aryl($C_{1-6}$)alkyl, substituted on the aryl moiety by a halogen atom such as bromo, may be converted into the corresponding compound wherein $R^3$ represents biaryl($C_{1-6}$)alkyl or heteroaryl-aryl($C_{1-6}$)alkyl by treatment with, respectively, an aryl or heteroaryl boronic acid, in the presence of a catalyst. Similarly, a compound of formula (I) wherein $R^3$ represents heteroaryl($C_{1-6}$)alkyl, substituted on the heteroaryl moiety by a halogen atom such as bromo, may be converted into the corresponding compound wherein $R^3$ represents aryl-heteroaryl($C_{1-6}$)alkyl by treatment with an aryl boronic acid, in the presence of a catalyst. The catalyst may typically be a transition metal catalyst. A suitable catalyst is tetrakis(triphenylphosphine)palladium(0), in which case the transformation may conveniently be effected at an elevated temperature in the presence of a base such as sodium carbonate or potassium carbonate, in an inert solvent such as 1,2-dimethoxyethane or 1,4-dioxane. Alternatively, the catalyst may be palladium(II) acetate, in which case the transformation may conveniently be effected at an elevated temperature in the presence of 2-dicyclohexylphosphino-2',6'-dimethoxybiphenyl and potassium phosphate.

A compound of formula (I) wherein $R^3$ represents hydroxymethyl may be converted into the corresponding compound wherein $R^3$ represents a substituted aminomethyl moiety, e.g. phenylaminomethyl, N-methyl-N-phenylaminomethyl, pyridin-3-ylaminomethyl, indolin-1-ylmethyl, 1,2,3,4-tetrahydroquinolin-1-ylmethyl or 1,2,3,4-tetrahydroisoquinolin-2-ylmethyl, by a two-stage procedure which comprises (i) Swern oxidation of the hydroxymethyl derivative by treatment with oxalyl chloride and dimethyl sulphoxide in the presence of triethylamine; and (ii) reductive amination of the formyl derivative thereby obtained by treatment with the appropriate amine, e.g. aniline, N-methylaniline, 3-aminopyridine, indoline, 1,2,3,4-tetrahydroquinoline or 1,2,3,4-tetrahydroisoquinoline, in the presence of a reducing agent such as sodium cyanoborohydride.

A compound of formula (I) wherein $R^3$ represents hydroxymethyl may be converted into the corresponding compound wherein $R^3$ represents an optionally substituted $C_{3-7}$ heterocycloalkylcarbonyl moiety, e.g. piperidin-1-ylcarbonyl, 1,2,3,4-tetrahydroquinolin-1-ylcarbonyl, 6-methyl-1,2,3,4-tetrahydroquinolin-1-ylcarbonyl, 6-methoxy-1,2,3,4-tetrahydroquinolin-1-ylcarbonyl, 1,2,3,4-tetrahydroisoquinolin-2-ylcarbonyl or 1,2,3,4-tetrahydroquinoxalin-1-ylcarbonyl, by a two-stage procedure which comprises (i) oxidation of the hydroxymethyl moiety by treatment with potassium permanganate; and (ii) reaction of the carboxy derivative thereby obtained with the appropriate amine, e.g. piperidine, 1,2,3,4-tetrahydroquinoline, 6-methyl-1,2,3,4-tetrahydroquinoline, 6-methoxy-1,2,3,4-tetrahydroquinoline, 1,2,3,4-tetrahydro-isoquinoline or 1,2,3,4-tetrahydroquinoxaline, in the presence of a condensing agent such as 1-(3-dimethylaminopropyl)-3-ethylcarbodiimide (EDC), or O-(benzotriazol-1-yl)-N,N,N'N'-tetramethyluronium hexafluorophosphate (HBTU).

A compound of formula (I) wherein $R^3$ contains a phenyl moiety substituted by chloro may be converted into the corresponding compound wherein the phenyl ring is substituted by morpholin-4-yl by treatment with morpholine in the presence of tris(dibenzylideneacetone)dipalladium(0), 2-(di-tert-butylphosphino)biphenyl and sodium tert-butoxide. A compound of formula (I) wherein $R^3$ contains a phenyl moiety substituted by bromo may be converted into the corresponding compound wherein the phenyl ring is substituted by pyrrolidin-1-yl by treatment with pyrrolidine in the presence of tris(dibenzylideneacetone)dipalladium(0), 2-dicyclohexylphosphino-2',4',6'-triisopropyl-1,1'-biphenyl and a base such as potassium carbonate. A compound of formula (I) wherein $R^3$ contains an indole moiety may be methylated on the indole ring by treatment with a methyl halide, e.g. iodomethane, in the presence of a strong base such as sodium hydride. A compound of formula (I) wherein $R^3$ contains an indole moiety may be acetylated on the indole ring by treatment with acetic anhydride and 4-dimethylamino-pyridine, typically in the presence of an organic base such as triethylamine. A compound of formula (I) wherein $R^3$ contains an indoline moiety may be converted into the corresponding compound wherein $R^3$ contains an indole moiety by treatment with an oxidising agent such as manganese dioxide. A compound of formula (I) wherein $R^3$ contains a hydroxy substituent may be converted into the corresponding compound wherein $R^3$ contains a $C_{1-6}$ alkylsulphonyloxy substituent, e.g. methylsulphonyloxy, by treatment with a $C_{1-6}$ alkylsulphonyl halide, e.g. methanesulphonyl chloride. A compound of formula (I) wherein $R^3$ contains an amino (—NH$_2$) or carboxy (—CO$_2$H) moiety may be converted into the corresponding compound wherein $R^3$ contains an amido moiety (—NHCO— or —CONH— respectively) by treatment with, respectively, a compound containing a carboxy or amino group, in the presence of O-(benzotriazol-1-yl)-N,N,N',N'-tetramethyluronium hexafluorophosphate (HBTU), typically in a dipolar aprotic solvent such as N,N-dimethylformamide. A compound of formula (I) wherein $R^3$ contains an amino substituent may be converted into the corresponding compound wherein $R^3$ contains an arylsulphonylamino substituent, e.g. phenylsulphonylamino, by treatment with an arylsulphonyl halide, e.g. benzenesulphonyl chloride.

A compound of formula (I) wherein $R^5$ represents —CO$_2$R$^b$ in which R$^b$ is other than hydrogen may be saponified and then decarboxylated to give the corresponding compounds in which $R^5$ represents —CO$_2$H and hydrogen respectively by treatment with a base such as lithium hydroxide. In general, any compound of formula (I) wherein $R^5$ contains a lower alkyl ester moiety may be converted into the corresponding compound wherein $R^5$ contains a carboxy (—CO$_2$H) group by treatment with a base such as lithium hydroxide or sodium hydroxide. A compound of formula (I) wherein $R^5$ represents —CO$_2$H may be converted into the corresponding compound wherein $R^5$ represents —CONR$^c$R$^d$ by treatment with an amine of formula H—NR$^c$R$^d$ and a condensing agent such as EDC, typically in the presence of an organic base such as triethylamine. In general, any compound of formula (I) wherein $R^5$ contains a carboxy moiety may be converted into the corresponding compound wherein $R^5$ contains an amide moiety by treatment with the appropriate amine and a condensing agent such as EDC, typically in the presence of 1-hydroxybenzotriazole (HOBT); alternative condensing agents include isobutyl chloroformate/triethylamine and benzotriazol-1-yloxytris (dimethylamino)phosphonium hexafluorophosphate. Likewise, any compound of formula (I) wherein $R^5$ contains an amino moiety may be converted into the corresponding compound wherein $R^5$ contains an amide moiety by treatment with the appropriate carboxylic acid under analogous conditions. A compound of formula (I) wherein $R^5$ represents cyano may be converted into the corresponding compound wherein $R^5$ represents —CONH$_2$ by heating under acidic conditions, e.g. in a mixture of acetic acid and sulphuric acid; prolonged treatment leads to conversion to the corresponding carboxylic acid followed by decarboxylation, i.e. conversion into the corresponding compound wherein $R^5$ represents hydrogen.

A compound of formula (I) wherein $R^5$ contains a carboxy moiety may be converted into the corresponding compound containing an arylcarbonyl moiety (e.g. benzoyl) by a two-stage procedure which comprises (i) treatment with N,O-dimethyl-hydroxylamine hydrochloride and a condensing agent such as EDC, typically in the presence of HBTU; and (ii) reaction of the compound thereby obtained with the appropriate aryl lithium derivative, e.g. phenyllithium.

A compound of formula (I) wherein $R^5$ represents hydrogen may be converted into the corresponding compound wherein $R^5$ represents fluoro by treatment with Selectfluor™ [i.e. 1-(chloromethyl)-4-fluoro-1,4-diazoniabicyclo[2.2.2] octane bis(tetrafluoroborate)]. A compound of formula (I) wherein $R^5$ represents hydrogen may be converted into the corresponding compound wherein $R^5$ represents chloro, bromo or iodo by treatment with N-chlorosuccinimide, N-bromosuccinimide or N-iodosuccinimide respectively. Indeed, the latter procedure is generally applicable for converting any compound of formula (I) wherein $R^5$ contains an aryl or heteroaryl moiety into the corresponding compound wherein the aryl or heteroaryl moiety is substituted by chloro, bromo or iodo respectively. Alternatively, a compound of formula (I) wherein $R^5$ represents hydrogen may be converted into the corresponding compound wherein $R^5$ represents bromo or iodo by treatment with elemental bromine or iodine respectively. A compound of formula (I) wherein $R^5$ represents hydrogen may be converted into the corresponding compound wherein $R^5$ represents —$SR^a$ by reaction with a compound of formula $R^aS$—Cl. A compound of formula (I) wherein $R^5$ represents hydrogen may be converted into the corresponding compound wherein $R^5$ represents dimethylaminomethyl by treatment with Eschenmoser's salt (i.e. N,N-dimethylmethyleneammonium iodide).

A compound of formula (I) wherein $R^5$ represents a halogen atom, e.g. iodo or chloro, may be converted into the corresponding compound wherein $R^5$ represents —$CO_2R^b$ by treatment with carbon monoxide and an alcohol of formula $R^b$—OH, in the presence of a catalyst. Indeed, this procedure is generally applicable for converting any compound of formula (I) wherein $R^5$ contains a halogen atom into the corresponding compound containing a lower alkyl ester functionality. The catalyst may typically be a transition metal catalyst. A suitable catalyst is [1,1'-bis(diphenylphosphino)ferrocene]dichloro-palladium(II)-dichloromethane complex, in which case the transformation may conveniently be effected at an elevated temperature and pressure in the presence of an organic base such as triethylamine.

A compound of formula (I) wherein $R^5$ represents a halogen atom, e.g. bromo or iodo, may be converted into the corresponding compound wherein $R^5$ represents aryl, biaryl, $C_{3-7}$ heterocycloalkyl-aryl, $C_{3-7}$ heterocycloalkyl($C_{1-6}$)alkyl-aryl, heteroaryl or heteroaryl-aryl by treatment with, respectively, an aryl, biaryl, $C_{3-7}$ heterocycloalkyl-aryl, $C_{3-7}$ heterocycloalkyl($C_{1-6}$)alkyl-aryl, heteroaryl or heteroaryl-aryl boronic acid or a cyclic ester thereof formed with an organic diol, e.g. pinacol, in the presence of a catalyst. Similarly, a compound of formula (I) wherein $R^5$ represents aryl, substituted on the aryl moiety by a halogen atom such as bromo, may be converted into the corresponding compound wherein $R^5$ represents biaryl or heteroaryl-aryl by treatment with, respectively, an aryl or heteroaryl boronic acid or a cyclic ester thereof formed with an organic diol, e.g. pinacol, in the presence of a catalyst. Likewise, a compound of formula (I) wherein $R^5$ represents heteroaryl, substituted on the heteroaryl moiety by a halogen atom such as chloro or bromo, may be converted into the corresponding compound wherein $R^5$ represents aryl-heteroaryl or bi(heteroaryl) by treatment with, respectively, an aryl or heteroaryl boronic acid or a cyclic ester thereof formed with an organic diol, e.g. pinacol or N-phenyldiethanolamine, in the presence of a catalyst. The catalyst may typically be a transition metal catalyst. A suitable catalyst is tetrakis(triphenylphosphine)palladium(0), in which case the transformation may conveniently be effected at an elevated temperature in the presence of a base such as sodium carbonate, potassium carbonate, potassium hydroxide or potassium phosphate, in an inert solvent such as 1,2-dimethoxyethane, tetrahydrofuran or 1,4-dioxane. Alternatively, the catalyst may be palladium(II) acetate, in which case the transformation may conveniently be effected at an elevated temperature in the presence of 1,3-bis(diphenylphosphino)propane and potassium phosphate, or in the presence of $PdCl_2$.dppf and potassium phosphate. In general, any compound of formula (I) wherein $R^5$ represents or contains a halogen atom, e.g. bromo or iodo, may be converted by means of the foregoing procedure into the corresponding compound wherein the halogen atom is replaced by a substituted or unsubstituted aryl, heteroaryl or alkenyl group.

A compound of formula (I) wherein $R^5$ represents a halogen atom, e.g. iodo, may be converted into the corresponding compound wherein $R^5$ represents aryl($C_{1-6}$)alkyl, e.g. benzyl, by treatment with a suitable organozinc reagent, in the presence of a catalyst. The organozinc reagent may conveniently be prepared by reacting the appropriate aryl($C_{1-6}$)-alkyl halide, e.g. benzyl bromide, with zinc dust. The catalyst may typically be a transition metal catalyst. A suitable catalyst is dichlorobis(triphenylphosphine)-palladium(II), in which case the transformation may conveniently be effected at an elevated temperature in the presence of an inert solvent such as tetrahydrofuran.

A compound of formula (I) wherein $R^5$ contains a halogen atom, e.g. chloro, may be converted into the corresponding compound wherein the halogen atom is replaced by an arylamino or heteroarylamino moiety, e.g. phenylamino, by treatment with the appropriate amine, e.g. aniline, and a transition metal catalyst, e.g. palladium acetate, typically in the presence of tributylphosphine tetrafluoroborate and a base such as sodium tert-butoxide.

A compound of formula (I) wherein $R^5$ represents a halogen atom, e.g. iodo, may be converted into the corresponding compound wherein $R^5$ represents $C_{2-6}$ alkynyl, $C_{3-7}$ cycloalkyl($C_{2-6}$)alkynyl, aryl($C_{2-6}$)alkynyl, $C_{3-7}$ heterocycloalkyl($C_{2-6}$)alkynyl, $C_{5-9}$ heterobicycloalkyl($C_{2-6}$)alkynyl or heteroaryl($C_{2-6}$)alkynyl by treatment with, respectively, a suitable $C_{2-6}$ alkyne, $C_{3-7}$ cycloalkyl($C_{2-6}$)alkyne, aryl($C_{2-6}$) alkyne, $C_{3-4}$ heterocycloalkyl-($C_{2-6}$)alkyne, $C_{5-9}$ heterobicycloalkyl($C_{2-6}$)alkyne or heteroaryl($C_{2-6}$)alkyne, in the presence of a catalyst. Similarly, a compound of formula (I) wherein $R^5$ represents $C_{2-6}$ alkynyl, e.g. ethynyl, may be converted into the corresponding compound wherein $R^5$ represents aryl($C_{2-6}$)alkynyl, heteroaryl($C_{2-6}$)alkynyl or $C_{3-7}$ cycloalkyl-heteroaryl($C_{2-6}$)alkynyl by treatment with, respectively, a suitable aryl, heteroaryl or $C_{3-7}$ cycloalkyl-heteroaryl iodide, in the presence of a catalyst. The catalyst may typically be a transition metal catalyst. A suitable catalyst is dichlorobis(triphenylphosphine)palladium(II), in which case the transformation may conveniently be effected at an elevated temperature in the presence of copper(I) iodide and an organic base such as diisopropylamine.

A compound of formula (I) wherein $R^5$ represents arylethynyl, e.g. phenylethynyl, may be converted into the corresponding compound wherein $R^5$ represents arylethyl, e.g. 2-phenylethyl, by catalytic hydrogenation. Indeed, this procedure is generally applicable for converting any compound of formula (I) wherein $R^5$ contains a —C≡C— moiety into the corresponding compound containing a —$CH_2CH_2$— moiety. A suitable hydrogenation catalyst is palladium on carbon, in which case the conversion can conveniently be accomplished at an elevated temperature in a suitable solvent, e.g. a lower alkanol such as ethanol, in the presence of a hydrogen donor such as ammonium formate. Under appropriate, generally less forcing, hydrogenation conditions, it is also possible to convert a compound of formula (I) wherein $R^5$ contains a —C≡C— moiety into the corresponding compound containing a —CH═CH— moiety.

A compound of formula (I) wherein $R^5$ contains a —C≡C— moiety may be converted into the corresponding compound containing a —$COCH_2$— moiety by treatment with a pH 2 buffer solution. Moreover, a compound of formula (I) wherein $R^5$ contains a —C≡C— moiety may be converted into the corresponding compound containing a —COCO— moiety by treatment with a mineral acid such as hydrochloric acid.

A compound of formula (I) wherein $R^5$ represents nitro may be converted into the corresponding compound wherein $R^5$ represents amino by catalytic hydrogenation, which typically comprises reacting the nitro compound with hydrogen in the presence of a catalyst such as palladium on charcoal.

A compound of formula (I) wherein $R^5$ contains a hydroxy moiety may be converted into the corresponding compound containing a —OCH$_2$— moiety by treatment with the appropriate alkyl halide, typically in the presence of a base such as potassium carbonate. A compound of formula (I) wherein $R^5$ contains a hydroxy moiety may be converted into the corresponding compound containing a —OSO$_2$— moiety by treatment with the appropriate sulphonyl halide, typically in the presence of a base such as triethylamine. A compound of formula (I) wherein $R^5$ contains a hydroxy moiety may be converted into the corresponding compound containing a trifluoromethylsulphonyloxy moiety by treatment with N-phenyltrifluoromethanesulphonimide, typically in the presence of a base such as triethylamine.

A compound of formula (I) wherein $R^5$ contains a methylsulphonyloxymethyl moiety may be converted into the corresponding compound containing an aminomethyl moiety by treatment with the appropriate amine derivative, typically in the presence of a base such as triethylamine. Similarly, a compound of formula (I) wherein $R^5$ contains a halomethyl (e.g. chloromethyl) moiety may be converted into the corresponding compound containing an aminomethyl moiety by treatment with the appropriate amine derivative (including cyclic amines), typically in the presence of a base such as potassium carbonate. Furthermore, a compound of formula (I) wherein $R^5$ contains a hydroxymethyl moiety may be converted into the corresponding compound containing an aminomethyl moiety by treatment with the appropriate amine derivative (including cyclic amines), generally in the presence of triphenylphosphine and diethyl azodicarboxylate.

A compound of formula (I) wherein $R^5$ contains a trifluoromethylsulphonyloxy moiety may be converted into the corresponding compound wherein the trifluoromethyl-sulphonyloxy moiety is replaced by an amino functionality by treatment with the appropriate amine derivative (including cyclic amines) and a transition metal catalyst, e.g. acetato(2'-di-tert-butylphosphino-1,1'-biphenyl-2-yl)palladium(II), typically at an elevated temperature in the presence of a base such as potassium tert-butoxide.

A compound of formula (I) wherein $R^5$ contains an amino moiety may be alkylated by treatment with the appropriate alkyl halide (e.g. methyl iodide, ethyl bromide, benzyl bromide or tert-butyl bromoacetate), typically in the presence of a base such as sodium hydride or triethylamine. A compound of formula (I) wherein $R^5$ contains an amino moiety may be converted into the corresponding compound containing a —NCH$_2$— motif by a reductive amination procedure which comprises treatment with the appropriate aldehyde derivative in the presence of a base such as sodium triacetoxyborohydride. A compound of formula (I) wherein $R^5$ contains an amino moiety may be converted into the corresponding compound containing a carbonylamino moiety by treatment with the appropriate carbonyl halide, typically in the presence of a base such as triethylamine. A compound of formula (I) wherein $R^5$ contains an amino moiety may be converted into the corresponding compound containing a urea functionality by treatment with the appropriate isocyanate derivative. Alternatively, a compound of formula (I) wherein $R^5$ contains an amino moiety may be converted into the corresponding compound containing a urea functionality by a two-stage procedure which comprises (i) treatment with triphosgene, typically in the presence of a base such as triethylamine; and (ii) reaction of the compound thereby obtained with the appropriate amine derivative (including cyclic amines). A compound of formula (I) wherein $R^5$ contains an amino moiety may be converted into the corresponding compound containing a sulphonylamino moiety by treatment with the appropriate sulphonyl halide, typically in the presence of a base such as triethylamine.

A compound of formula (I) wherein $R^5$ represents a halogen atom, e.g. iodo, may be converted into the corresponding compound wherein $R^5$ represents acetyl by a two-stage procedure which comprises (i) reaction with butyl vinyl ether and a transition metal catalyst such as tris(dibenzylideneacetone)dipalladium(0), typically in the presence of 1,3-bis(diphenylphosphino)propane and a base such as potassium carbonate; and (ii) hydrolysis of the resulting compound by treatment with a mineral acid, e.g. hydrochloric acid. A compound of formula (I) wherein $R^5$ represents acetyl may be converted into the corresponding compound wherein $R^5$ represents 3-(dimethylamino)-1-oxoprop-2-en-1-yl by treatment with N,N-dimethylformamide dimethyl acetal, typically at an elevated temperature. A compound of formula (I) wherein $R^5$ represents 3-(dimethylamino)-1-oxoprop-2-en-1-yl may be converted into the corresponding compound wherein $R^5$ represents a substituted or unsubstituted pyrimidinyl moiety by treatment with the appropriate amidine derivative, typically at an elevated temperature in the presence of a base such as sodium ethoxide.

A compound of formula (I) wherein $R^6$ represents hydrogen may be converted into the corresponding compound wherein $R^6$ represents $C_{1-6}$ alkyl, e.g. methyl, by treatment with the appropriate alkyl halide, e.g. methyl iodide, typically in the presence of a base such as sodium hydride.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T.W. Greene & P.G.M. Wuts, *Protective Groups in Organic Synthesis*, John Wiley & Sons, 3$^{rd}$ edition, 1999. The protecting groups may be removed at any convenient subsequent stage utilising methods known from the art.

The following Examples illustrate the preparation of compounds according to the invention.

The compounds in accordance with this invention potently inhibit the activity of human PI3Kα and/or PI3Kβ and/or PI3Kγ and/or PI3Kδ.

Enzyme Inhibition Assays

Measurement of the ability of compounds to inhibit the lipid kinase activity of the four class 1 PI3 kinase isoforms (α, β, γ and δ) was performed using a commercially available homogeneous time-resolved fluorescence assay as described by Gray et al., *Anal. Biochem.*, 2003, 313, 234-245, according to the manufacturer's instructions (Upstate). All assays were performed at 2 µM ATP and a concentration of purified class 1 PI3 kinase known to generate product within the linear range of the assay. Dilutions of inhibitor in DMSO were added to the assay and compared with assays run in the presence of 2% (v/v) DMSO alone (100% activity). The concentration of inhibitor required to inhibit the enzyme activity by 50% is quoted as the IC$_{50}$.

When tested in the above assay, the compounds of the accompanying Examples were all found to possess IC$_{50}$ values for inhibition of activity of human PI3Kα and/or PI3Kβ and/or PI3Kγ and/or PI3Kδ of 50 µM or better.

EXAMPLES

Abbreviations

| | |
|---|---|
| DCM: dichloromethane | DMF: N,N-dimethylformamide |
| DME: ethylene glycol dimethyl ether | DMSO: dimethylsulphoxide |
| $^i$Pr: isopropyl | Et$_2$O: diethyl ether |
| THF: tetrahydrofuran | r.t.: room temperature |
| sat.: saturated | DMAP: 4-(dimethylamino)pyridine |
| EtOAc: ethyl acetate | MeOH: methanol |
| AcOH: acetic acid | EtOH: ethanol |
| IPA: isopropyl alcohol | RT: retention time |
| Me: methyl | h: hour |
| MeCN: acetonitrile | SiO$_2$: silica |
| br.: broad | wt: weight |
| brine: saturated aqueous sodium chloride solution | |
| HPLC: High Performance Liquid Chromatography | |
| LCMS: Liquid Chromatography Mass Spectrometry | |
| DIPEA: N,N-diisopropylethylamine | TFA: trifluoroacetic acid |
| ES+: Electrospray Positive Ionisation | ES−: Electrospray Negative Ionisation |
| M: mass | |
| EDC: 1-(3-dimethylaminopropyl)-3-ethylcarbodiimide hydrochloride | |
| Eschenmoser's salt: N,N-dimethylmethyleneammonium iodide | |
| NIS: N-iodosuccinimide | NCS: N-chlorosuccinimide |
| NBS: N-bromosuccinimide | dppf 1,1'-bis(diphenylphosphino)ferrocene |

Hydrogenation Procedure

Hydrogenations were performed using either a balloon filled with hydrogen and with 10% wt palladium on carbon, or a Thales H-cube™ hydrogenation kit, software 24/33 using a continuous flow and 10% Pd/C CatCart™.

Analytical Conditions

All NMRs were obtained either at 300 MHz or 400 MHz.

Compounds were named with the aid of ACD Labs Name (v. 7.0 or 9.0) supplied by Advanced Chemical Development, Toronto, Canada.

All reactions involving air- or moisture-sensitive reagents were performed under a nitrogen atmosphere using dried solvents and glassware.

Procedure Used for Preparative HPLC:

Column: Luna C18 250 mm×21.2 mm, 5 µm particle size ex. Phenomenex

Mobile Phase for pH 2.5:
Mobile Phase A: 0.08% formic acid in water
Mobile Phase B: 0.08% formic acid in MeCN
Mobile Phase for pH 5.8:
Mobile Phase A: 10 mM ammonium acetate in water
Mobile Phase B: 10 mM ammonium acetate in MeCN
Injection: 1 mL in DMSO Intermediate 1

(Method A)

Ethyl 2-bromo-7-oxo-4,5,6,7-tetrahydro-1-benzothiophene-3-carboxylate

To a stirred solution of CuBr$_2$ (5.0 g, 22.5 mmol) in MeCN (60 mL) at 0° C. was slowly added tert-butyl nitrite (2.4 mL, 18.5 mmol). The reaction mixture was then stirred for 15 minutes before 2-amino-7-oxo-4,5,6,7-tetrahydrobenzo[b]thiophene-3-carboxylic acid ethyl ester (3.9 g, 16.1 mmol) was added portionwise. The reaction mixture was then allowed to warm, with stirring, to r.t. and, after stirring for 4 h, it was partitioned between 2M HCl (200 mL) and EtOAc (3×200 mL). The combined organics were dried over MgSO$_4$, filtered and concentrated in vacuo. Purification by column chromatography (SiO$_2$, 1:6 EtOAc/hexanes) gave the title compound as a pale brown solid (3.5 g, 71%). δ$_H$(DMSO-d$_6$) 4.33 (2H, q, J=7.1 Hz), 3.00 (2H, t, J=6.0 Hz), 2.58-2.51 (2H, m), 2.12-2.04 (2H, m), 1.33 (3H, t, J 7.1 Hz).

Intermediate 2

3-Iodo-2-morpholino-5,6-dihydro-1-benzothiophen-7(4H)-one

To a stirred solution of Example 2 (0.62 g, 2.61 mmol) in THF (20 mL) at 0° C. was added I$_2$ (0.67 g, 2.61 mmol) and the reaction mixture was stirred for 10 minutes before being poured into brine (200 mL). The mixture was then extracted with EtOAc (3×150 mL) and the combined organics were washed with brine (200 mL), dried (MgSO$_4$), filtered and concentrated in vacuo. Purification by column chromatography (SiO$_2$, 0-30% EtOAc in hexanes) gave the title compound as an off-white solid (0.54 g, 56%). δ$_H$ (CDCl$_3$) 3.84-3.81 (4H, m), 3.22-3.19 (4H, m), 2.73 (2H, t, J 6.0 Hz), 2.57-2.53 (2H, m), 2.17-2.09 (2H, m). LCMS (ES+) 364.0 (M+H)$^+$.

Intermediate 3

2-Bromo-7-oxo-4,5,6,7-tetrahydro-1-benzothiophene-3-carboxylic Acid

To a stirred solution of Intermediate 1 (1.0 g, 3.3 mmol) in THF (10 mL) was added LiOH (0.2 g, 5.0 mmol) in water (5 mL) and the reaction mixture was heated to 70° C. for 18 h. The volatiles were then removed in vacuo and the crude residue was dissolved in hot water (10 mL). The solution was allowed to cool and was then acidified to pH 1 by the addition of aqueous 2M HCl dropwise. The resultant precipitate was collected via filtration and dried in a vacuum oven to give the title compound as an off-white solid (0.8 g, 92%). $\delta_H$ (DMSO-$d_6$) 13.52 (1H, br. s), 3.00 (2H, t, J 6.0 Hz), 2.57-2.49 (2H, m), 2.09-2.04 (2H, m). LCMS (ES+) 275.0 and 277.0 (M+H)$^+$.

Intermediate 4

2-Bromo-7-oxo-N-phenyl-4,5,6,7-tetrahydro-1-benzothiophene-3-carboxamide

To a stirred solution of Intermediate 3 (0.20 g, 0.73 mmol) in DCM (5 mL) was added EDC (0.20 g, 1.00 mmol) and, after stirring for 15 minutes, aniline (0.10 g, 1.00 mmol) was added. The reaction mixture was then stirred at r.t. for 18 h before being diluted with DCM (100 mL) and washed with brine (2×100 mL). The organic phase was dried over MgSO$_4$, filtered and the solvent removed in vacuo. Purification by column chromatography (SiO$_2$, 1:6 EtOAc/hexanes) gave the title compound as an off-white solid (0.72 g, 28%). $\delta_H$ (DMSO-$d_6$) 7.64-7.60 (3H, m), 7.42-7.37 (2H, m), 7.23-7.19 (1H, m), 3.04 (2H, t, J 6.0 Hz), 2.64-2.60 (2H, m), 2.23-2.16 (2H, m). LCMS (ES+) 350.0 and 352.0 (M+H)$^+$.

Intermediate 5

Ethyl 2-[3(S)-3-(1H-indol-3-ylmethyl)morpholin-4-yl]-7-oxo-4,5,6,7-tetrahydro-1-benzothiophene-3-carboxylate To a stirred solution of Intermediate 1 (0.47 g, 1.60 mmol) in MeCN (5 mL) was added DIPEA (0.34 mL, 1.90 mmol) and Intermediate 9 (0.42 g, 1.90 mmol). The reaction mixture was then heated to 180° C. in a sealed tube, under microwave irradiation, for 1 h. After cooling, the solution was partitioned between DCM (100 mL) and brine (200 mL) and the aqueous phase was further extracted with DCM (2×100 mL). The combined organic phases were then dried over MgSO$_4$, filtered and concentrated in vacuo. Purification by column chromatography (SiO$_2$, 10-50% EtOAc in hexanes) gave the title compound as an off-white solid (0.23 g, 33%). $\delta_H$ (CDCl$_3$) 7.99 (1H, br. s), 7.51 (1H, d, J 9.8 Hz), 7.33 (1H, d, J 8.0 Hz), 7.21-7.03 (3H, m), 4.29 (2H, q, J 7.2 Hz), 4.15-4.02 (2H, m), 3.82-3.72 (4H, m), 3.36 (1H, m), 3.19-3.16 (1H, m), 3.06-2.87 (3H, m), 2.57-2.51 (2H, m), 2.15-2.06 (2H, m), 1.36 (3H, t, J 7.2 Hz). LCMS (ES+) 439.0 (M+H)$^+$.

Intermediate 6

(2S)-2-Amino-3-(1H-indol-3-yl)propan-1-ol

To a stirred solution of (S)-tryptophan (4.0 g, 20.0 mmol) in THF (100 mL) at 0° C. was slowly added BH$_3$.Me$_2$S complex (5.9 mL, 10M solution in THF, 59.0 mmol). The reaction mixture was heated to 70° C. for 16 h and, after cooling, the excess borane was quenched by the addition of MeOH (10 mL) at 0° C. The reaction mixture was then concentrated in vacuo and the resultant white solid was dissolved in EtOAc (100 mL) and washed with aqueous 20% NaOH solution (2×70 mL). The organic layer was then extracted into aqueous 2M HCl (2×100 mL). The combined acidic aqueous layers were then basified to pH 14 (addition of solid NaOH) and were re-extracted with EtOAc (2×150 mL). The combined organic fractions were washed with brine (70 mL), dried over MgSO$_4$, filtered and concentrated in vacuo to give the title compound (3.5 g, 92%) as a white solid that required no further purification. $\delta_H$ (CD$_3$OD) 7.46 (1H, d, J 7.9 Hz), 7.21 (1H, d, J 8.0 Hz), 6.96 (3H, m), 3.79 (1H, dd, J 11.3 and 3.6 Hz), 3.54 (1H, dd, J 11.2 and 6.2 Hz), 3.05 (1H, m), 2.80 (1H, m), 2.61 (1H, m). Exchangeable protons were not observed.

Intermediate 7

2-Chloro-N-[(1S)-2-hydroxy-1-(1H-indol-3-ylmethyl)ethyl]acetamide

To a stirred solution of Intermediate 6 (2.0 g, 10.0 mmol) and NEt$_3$ (1.3 g, 1.8 mL, 13.0 mmol) in THF (120 mL) at 0° C. was added chloroacetyl chloride (1.3 g, 1.0 mL, 12.0 mmol) dropwise. The reaction mixture was stirred at r.t. for 1.5 h and was then quenched by the addition of water (5 mL). The reaction mixture was diluted with EtOAc (120 mL) and partitioned with water (100 mL). The organic fraction was washed with brine (100 mL), dried over MgSO$_4$, filtered and concentrated in vacuo to give the title compound (2.4 g, 90%) as a beige solid that was used without further purification. $\delta_H$ (CDCl$_3$) 8.15 (1H, br. s), 7.59 (1H, d, J 7.9 Hz), 7.28 (1H, d, J 8.0 Hz), 7.11 (3H, m), 6.97 (1H, d, J 2.3 Hz), 4.19 (1H, m), 3.92 (2H, d, J 2.9 Hz), 3.59 (2H, m), 2.98 (2H, d, J 6.0 Hz), 2.52 (1H, br. s).

Intermediate 8

(5S)-5-(1H-Indol-3-ylmethyl)morpholin-3-one

To a stirred solution of Intermediate 7 (2.4 g, 9.5 mmol) in THF (100 mL) at 0° C. was added NaH (0.8 g, 60% dispersion in oil, 19.0 mmol) portionwise. The reaction mixture was stirred at r.t. for 1.5 h and then quenched at 0° C. by the addition of ice. The solution was then partitioned between EtOAc (100 mL) and water (100 mL) and the organic fraction was dried over MgSO$_4$, filtered and concentrated in vacuo to give the title compound (1.8 g, 82%) as a yellow solid that was used without further purification. $\delta_H$ (CD$_3$OD) 7.46 (1H, d, J 7.8 Hz), 7.25 (1H, d, J 7.8 Hz), 6.95 (3H, m), 3.99 (2H, s), 3.65 (2H, m), 3.52 (1H, m), 2.91 (2H, d, J=6.3 Hz). Exchangeable protons were not observed. LCMS (ES+) 231.0 (M+H)$^+$.

Intermediate 9

3-[(3S)-Morpholin-3-ylmethyl]-1H-indole

To a stirred solution of Intermediate 8 (1.8 g, 7.8 mmol) in THF (100 mL) was slowly added, at 0° C., LiAlH$_4$ (1.0 g, 27.0 mmol). After stirring for 16 h at r.t. the reaction mixture was quenched by the dropwise addition of aqueous sat. NaHCO$_3$ solution (20 mL). The resulting mixture was filtered through Celite® and the filtrate was concentrated in vacuo. The resulting solid was dissolved in toluene and the solvent removed by evaporation in vacuo. Purification by column chromatography (SiO$_2$, EtOAc) yielded the title compound (1.5 g, 89%) as a cream solid. $\delta_H$ (CDCl$_3$) 8.11 (1H, br. s), 7.55 (1H, d, J 7.8 Hz), 7.28 (1H, d, J 8.0 Hz), 7.11 (3H, m), 3.83 (1H, dd, J 10.9 and 2.8 Hz), 3.71 (1H, dt, J 11.3 and 2.2 Hz), 3.47 (1H, m), 3.24 (1H, t, J 9.8 Hz), 3.06 (1H, m), 2.78 (3H, m), 2.56 (1H, m), 1.92 (1H, br. s). LCMS (ES+) 217.0 (M+H)$^+$.

Intermediate 10

(3,3-Dimethyl-5-oxocyclohexylidene)malonitrile

To a stirred solution of dimedone (98.0 g, 700.0 mmol) and malonitrile (46.2 g, 700.0 mmol) in EtOH (400 mL) at r.t. was added piperidine (8.5 g, 9.9 mL, 100.0 mmol) dropwise over 15 minutes. The reaction mixture was then heated to reflux for 3 days before cooling. The solvent was removed in vacuo and the residue was re-dissolved in EtOAc (500 mL) and dried (MgSO$_4$). Filtration and concentration in vacuo gave a black oil that was purified by column chromatography (SiO$_2$, 1:6 MeOH/DCM) to give the title compound as a yellow solid (108.0 g, 82%). $\delta_H$ (DMSO-d$_6$) 8.31 (2H, br. s), 2.51 (2H, t, J 1.8 Hz), 2.30 (2H, s), 1.04 (6H, s). LCMS (ES−) 187.3 (M−H)$^-$.

Intermediate 11

2-Amino-5,5-dimethyl-7-oxo-4,5,6,7-tetrahydro-1-benzothiophene-3-carbonitrile To a stirred solution of Intermediate 10 (50.8 g, 270.0 mmol) and sulphur (10.3 g, 320.0 mmol), in EtOH (600 mL), was slowly added morpholine (46.0 g, 46.0 mL, 530.0 mmol) at r.t. The reaction mixture was stirred at 80° C. for 24 h and then cooled. The solids formed were isolated by filtration and washed with cold Et$_2$O to give the title compound as a buff solid (41.2 g, 53%). $\delta_H$ (DMSO-d$_6$) 8.31 (2H, br. s), 2.51 (2H, t, J 1.8 Hz), 2.30 (2H, s), 1.04 (6H, s). LCMS (ES−) 219.2 (M−H)$^-$.

Intermediate 12

2-Bromo-5,5-dimethyl-7-oxo-4,5,6,7-tetrahydro-1-benzothiophene-3-carbonitrile The title compound was prepared from Intermediate 11 according to Method A and was isolated as a pale tan solid (40%) after purification by column chromatography (SiO$_2$, 1:3 DCM/hexanes). $\delta_H$ (DMSO-d$_6$) 2.84 (2H, s), 2.51 (2H, s), 1.07 (6H, s). LCMS (ES+) 285.9 (M+H)$^+$.

Intermediate 13

3-[(Dimethylamino)methyl]-6-iodoimidazo[1,2-a]pyridine

A stirred solution of 6-iodoimidazo[1,2-a]pyridine (2.0 g, 8.2 mmol) and Eschenmoser's salt (5.0 g, 2.7 mmol) in THF (50 mL) was heated to reflux for 24 h. The reaction mixture was then diluted with EtOAc (50 mL), washed with water (3×20 mL), dried (MgSO$_4$), filtered and concentrated in vacuo. The residual solid was triturated from Et$_2$O, collected by filtration and dried to give the title compound (1.1 g, 45%) as a brown powder. $\delta_H$ (DMSO-d$_6$) 8.67 (1H, m), 7.45 (1H, s), 7.43-7.41 (2H, m), 3.72 (2H, s), 2.14 (6H, s). LCMS (ES+) 302.2 (M+H)$^+$.

Intermediate 14

N,N-Dimethyl-N'-(5-iodopyridin-2-yl)ethane-1,2-diamine

A stirred solution of 2-chloro-5-iodopyridine (0.50 g, 2.18 mmol) and N,N-dimethylethylenediamine (0.81 g, 1.00 mL, 9.20 mmol) in 2-ethoxyethanol (5 mL) was heated in a sealed tube under microwave irradiation at 125° C. for 1 h. The reaction mixture was then diluted with EtOAc (50 mL), washed with water (3×20 mL), dried (MgSO$_4$), filtered and concentrated in vacuo. The residual oil was purified by column chromatography (SiO$_2$, 3:1 EtOAc/MeOH) to give the title compound (0.22 g, 36%) as a viscous oil which solidified on standing. $\delta_H$ (CDCl$_3$) 8.19 (1H, br. s), 7.53 (1H, m), 6.23 (1H, m), 3.29 (2H, m), 2.52 (2H, m), 2.24 (6H, s). Exchangeable proton not observed. LCMS (ES+) 292.0 (M+H)$^+$.

Intermediate 15

[2(S)-1-(5-Iodopyridin-2-yl)pyrrolidin-2-yl]methanol

A stirred solution of 2-chloro-5-iodopyridine (0.50 g, 2.18 mmol) and 2(S)-2-hydroxymethylpyrrolidine (1.00 g, 10.00 mmol) in 2-ethoxyethanol (5 mL) was heated in a sealed tube under microwave irradiation at 125° C. for 30 minutes. The reaction mixture was then diluted with EtOAc (50 mL), washed with water (3×20 mL), dried (MgSO$_4$), filtered and concentrated in vacuo. The residual oil was purified by column chromatography (SiO$_2$, 3:1 EtOAc/MeOH) to give the title compound (0.42 g, 63%) as a viscous oil which solidified on standing. $\delta_H$ (DMSO-d$_6$) 8.19 (1H, d, J 2.3 Hz), 7.70 (1H, dd, J 8.9 and 2.3 Hz), 6.41 (1H, d, J 8.9 Hz), 4.77 (1H, t, J 5.8 Hz), 3.95 (1H, m), 3.55-3.21 (4H, m), 2.05-1.81 (4H, m). LCMS (ES+) 305.1 (M+H)$^+$.

Intermediate 16

Ethyl 2-amino-5,5-dimethyl-7-oxo-4,5,6,7-tetrahydrothieno[2,3-c]pyridine-3-carboxylate To a stirred solution of sulphur (1.0 g, 31.0 mmol), 6,6-dimethylpiperidine-2,4-dione (4.0 g, 28.0 mmol) and ethyl cyanoacetate (3.7 g, 3.5 mL, 29.0 mmol) in EtOH (20 mL) at 45° C. was added morpholine (2.9 g, 2.9 mL, 33.0 mmol) dropwise over 15 minutes. The reaction mixture was stirred at this temperature for 15 minutes and then at 65° C. for 48 h before it was cooled and concentrated in vacuo. To the residue was added water and the resulting solid was filtered and washed with water to give the title compound as a pale brown solid (4.1 g, 54%). $\delta_H$ (DMSO-d$_6$) 7.86 (2H, s), 7.28 (1H, s), 4.21 (2H, q, J 7.0 Hz), 2.88 (2H, s), 1.27 (3H, t, J 7.1 Hz), 1.23 (6H, s). LCMS (ES+) 269.1 (M+H)$^+$.

Intermediate 17

(Method E)

Ethyl 2-bromo-5,5-dimethyl-7-oxo-4,5,6,7-tetrahydrothieno[2,3-c]pyridine-3-carboxylate To a stirred suspension of Intermediate 16 (0.20 g, 0.75 mmol) in MeCN (5 mL) at 0-5° C. was added CuBr$_2$ (0.20 g, 0.90 mmol) followed by tent-butyl nitrite (0.10 g, 0.10 mL, 0.80 mmol) dropwise. The reaction mixture was stirred at this temperature for 10 minutes before it was partitioned between EtOAc (50 mL) and water (50 mL). The organics were separated, washed with water (3×20 mL) and brine (20 mL), dried (Na$_2$SO$_4$), filtered and concentrated in vacuo. The crude residue was washed with Et$_2$O to give the title compound as a pale brown solid (0.15 g, 61%). $\delta_H$ (DMSO-d$_6$) 8.53 (1H, s), 4.32 (2H, q, J 7.0 Hz), 3.10 (2H, s), 1.33 (3H, t, J 17.1 Hz), 1.26 (6H, s). LCMS (ES+) 332.0 and 334.0 (M+H)$^+$.

Intermediate 18

(Method F)

Ethyl 5,5-dimethyl-2-(morpholin-4-yl)-7-oxo-4,5,6,7-tetrahydrothieno[2,3-c]pyridine-3-carboxylate To a stirred solution of Intermediate 17 (1.4 g, 4.1 mmol) in IPA (25 mL) at r.t. was added morpholine (1.0 g, 1.0 mL, 11.5 mmol) and the reaction mixture was heated at 60° C. for 48 h. After cooling, the mixture was partitioned between EtOAc (100 mL) and water (50 mL). The organics were separated, washed with water (2×20 mL), dried ($Na_2SO_4$), filtered and concentrated in vacuo. The residue was then purified by column chromatography ($SiO_2$, EtOAc) to give the title compound as an off-white solid (1.0 g, 76%). $\delta_H$ (DMSO-$d_6$) 7.56 (1H, s), 4.23 (2H, q, J 7.0 Hz), 3.74 (4H, br. m), 3.17 (4H, br. m), 2.90 (2H, s), 1.28 (3H, t, J 7.1 Hz), 1.23 (6H, s). LCMS (ES+) 339.0 (M+H)$^+$.

Intermediate 19

(Method H)

5,5-Dimethyl-3-iodo-2-(morpholin-4-yl)-5,6-dihydrothieno[2,3-c]pyridin-7(4H)-one To a stirred solution of Example 49 (0.45 g, 1.67 mmol) in THF (20 mL) at r.t. was added NIS (0.39 g, 1.76 mmol). After stirring for 2 h, $Na_2CO_3$ (2.00 g, 18.87 mmol) was added and the reaction mixture was stirred for a further minute, prior to the addition of sat. aqueous $Na_2CO_3$ (10 mL). The resulting solid was filtered and washed with water and $Et_2O$ to give the title compound as a white solid (0.35 g, 53%). $\delta_H$ (DMSO-$d_6$) 7.63 (1H, s), 3.76 (4H, br. m), 3.07 (4H, m), 2.64 (2H, s), 1.25 (6H, s). LCMS (ES+) 393.0 (M+H)$^+$.

Intermediate 20

Ethyl 2-amino-5,5-dimethyl-8-oxo-5,6,7,8-tetrahydro-4H-thieno[2,3-c]azepine-3-carboxylate To a stirred solution of 6,6-dimethylazepane-2,4-dione (0.50 g, 3.20 mmol), sulphur (0.12 g, 3.75 mmol) and ethyl cyanoacetate (0.39 g, 0.37 mL, 3.48 mmol) in EtOH (2.5 mL) at 45° C. was added morpholine (0.30 g, 0.30 mL, 3.48 mmol) over a period of 20 minutes. The reaction mixture was then heated to 50° C. for 3 h before it was stirred for 12 h at 40° C. The solution was cooled to r.t. and the resulting solid was filtered, washed (3:1 water/EtOH) and dried to give the title compound as an off-white powder (0.45 g, 50%). $\delta_H$ (DMSO-$d_6$) 7.73 (2H, t, J 5.1 Hz), 7.69 (1H, s), 4.22 (2H, q, J 7.1 Hz), 2.82 (2H, s), 2.79 (2H, d, J 5.2 Hz), 1.28 (3H, t, J 7.1 Hz), 0.95 (6H, s). LCMS (ES+) 283.0 (M+H)$^+$.

Intermediate 21

Ethyl 2-bromo-5,5-dimethyl-8-oxo-5,6,7,8-tetrahydro-4H-thieno[2,3-c]azepine-3-carboxylate The title compound was prepared from Intermediate 20 according to Method E and was isolated as a brown solid (74%). $\delta_H$ (CDCl$_3$) 6.20 (1H, br. s), 4.41 (2H, q, J 7.0 Hz), 2.99 (2H, d, J 5.5 Hz), 2.90 (2H, s), 1.44 (3H, t, J 7.1 Hz), 1.08 (6H, s). LCMS (ES+) 346.0 and 348.0 (M+H)$^+$.

Intermediate 22

Ethyl 5,5-dimethyl-2-(morpholin-4-yl)-8-oxo-5,6,7,8-tetrahydro-4H-thieno[2,3-c]azepine-3-carboxylate To a stirred solution of Intermediate 21 (0.31 g, 0.90 mmol) in DMSO (4 mL) at r.t. was added morpholine (0.10 g, 0.10 mL, 1.10 mmol) and the reaction mixture was heated to 90° C. for 12 h. The reaction mixture was then partitioned between EtOAc (50 mL) and water (20 mL) and the organics were separated, washed with water (3×15 mL) and brine (15 mL), dried ($Na_2SO_4$), filtered and concentrated in vacuo to give the title compound as a white powder (0.28 g, 90%). $\delta_H$ (DMSO-$d_6$) 7.94 (1H, t, J 5.0 Hz) 4.24 (2H, q, J 7.1 Hz), 3.73 (4H, m), 3.08 (4H, m), 2.80 (2H, d, J 4.2 Hz), 2.64 (2H, s), 1.28 (3H, t, J 7.1 Hz), 0.94 (6H, s). LCMS (ES+) 353.0 (M+H)$^+$.

Intermediate 23

(Method N)

2-Ethynyl-1-methyl-1H-imidazole

To a stirred solution of 1-methyl-2-imidazolecarboxaldehyde (0.25 g, 2.27 mmol) and $K_2CO_3$ (0.63 g, 4.54 mmol) in MeOH (5 mL) was added dimethyl-1-diazo-2-oxypropylphosphate (0.44 g, 2.27 mmol) in MeOH (5 mL) dropwise at r.t. The reaction mixture was stirred for 3 h and concentrated in vacuo to give a green oil. The residue was dissolved in $Et_2O$ (15 mL) and aqueous sat. $NaHCO_3$ (10 mL) was added. The layers were separated and the aqueous layer was extracted with $Et_2O$ (2×10 mL). The combined organic layers were dried ($Na_2SO_4$), filtered and concentrated in vacuo. Purification by column chromatography ($SiO_2$, EtOAc) gave the title compound (0.14 g, 58%) as a pale brown oil. $\delta_H$ (CDCl$_3$) 7.06 (1H, s), 6.92 (1H, s), 3.76 (3H, s), 3.34 (1H, s). MS (ES+) 107.1 (M+H)$^+$.

Intermediate 24

Tert-Butyl 4-ethynylpiperidine-1-carboxylate

The title compound was prepared from 4-formylpiperidine-1-carboxylic acid tert-butyl ester according to Method N and was isolated as an off-white solid (48%) after purification by column chromatography ($SiO_2$, EtOAc). $\delta_H$ (CDCl$_3$) 3.82-3.63 (2H, m), 3.21 (2H, ddd, J 13.4, 8.3 and 3.3 Hz), 2.67-2.52 (1H, m), 2.12 (1H, d, J 2.3 Hz), 1.90-1.73 (2H, m), 1.69-1.54 (2H, m), 1.48 (9H, s). MS (ES+) 154.0 (M-$^t$Bu+H)$^+$.

Intermediate 25

(Method P)

4-Ethynylpiperidine trifluoroacetate

To a stirred solution of Intermediate 24 (0.12 g, 0.57 mmol) in DCM (5 mL) was added TFA (0.5 mL). The reaction mixture was stirred at r.t. for 16 h and concentrated in vacuo to give the title compound (0.19 g, quantitative) as a brown oil that was used without further purification. $\delta_H$ (CDCl$_3$) 8.85 (2H, br. s), 3.54-3.30 (2H, m), 3.29-3.13 (2H, m), 2.97-2.80

(1H, m), 2.25 (1H, d, J 2.5 Hz), 2.18-2.06 (2H, m), 2.03-1.87 (2H, m). MS (ES+) 110.0 (M+H)$^+$.

Intermediate 26

(Method O)

(2S)-1-(tert-Butoxycarbonyl)pyrrolidine-2-carbaldehyde

To a stirred solution of tert-butyloxycarbonyl-L-prolinol (3.50 g, 17.41 mmol) in DCM (25 mL) at 0° C. was added triethylamine (9.7 mL, 60.93 mmol), followed by sulfur trioxide-pyridine complex (8.30 g, 6.96 mmol) in DMSO (10 mL). The reaction mixture was stirred at 0° C. for 1 h. Hexanes (20 mL), Et$_2$O (10 mL) and aqueous sat. NaHCO$_3$ (30 mL) were added and the layers separated. The aqueous layer was extracted with a mixture of hexanes (20 mL) and Et$_2$O (10 mL) twice. The combined organic layers were washed with 1M aqueous NaH$_2$PO$_4$ (30 mL), then brine (30 mL), dried (Na$_2$SO$_4$), filtered and concentrated in vacuo. Purification by column chromatography (SiO$_2$, 20% EtOAc/hexanes) gave the title compound (2.70 g, 77%) as a colourless oil. $\delta_H$ (DMSO-d$_6$), mixture of rotamers: 9.49-9.36 (1H, m), 4.14-4.02 (1H, m), 3.45-3.26 (2H, m), 2.14-2.00 (1H, m), 1.96-1.69 (3H, m), 1.42 and 1.34 (9H, s, rotameric).

Intermediate 27

(2S)-1-(tert-Butoxycarbonyl)-2-ethynylpyrrolidine

The title compound was prepared from Intermediate 26 according to Method N and was isolated as an off-white solid (80%) that was used without further purification. $\delta_H$ (DMSO-d$_6$) 4.37 (1H, br. s), 3.34-3.26 (1H, m), 3.27-3.09 (2H, m), 2.16-1.98 (1H, m), 1.88 (3H, s), 1.40 (9H, s). MS (ES+) 140.1 (M-$^t$Bu+H)$^+$.

Intermediate 28

(Method Z)

Tert-Butyl 2-(hydroxymethyl)piperidine-1-carboxylate

To a stirred solution of 2-piperidinemethanol (3.0 g, 25.60 mmol) in DCM (100 mL) was added triethylamine (14.5 mL, 91.08 mmol) and then di-tent-butyl dicarbonate (7.2 g, 31.0 mmol) portionwise. The reaction mixture was stirred at r.t. for 16 h. Water (70 mL) was added and the layers were separated. The organic layer was washed with water (2×50 mL), dried (Na$_2$SO$_4$), filtered and concentrated in vacuo to give the title compound (6.0 g, quantitative) as a pale brown oil that was used without further purification. $\delta_H$ (CDCl$_3$) 4.42-4.22 (1H, m), 4.05-3.91 (1H, m), 3.89-3.77 (1H, m), 3.71-3.53 (1H, m), 2.97-2.81 (1H, m), 2.32-2.08 (1H, m), 1.90 (1H, s), 1.77-1.57 (3H, m), 1.54 (1H, s), 1.52-1.38 (10H, m).

Intermediate 29

Tert-Butyl 2-formylpiperidine-1-carboxylate

The title compound was prepared from Intermediate 28 according to Method O and was isolated as a pale yellow oil (75%) after purification by column chromatography (SiO$_2$, 20% EtOAc/hexanes). $\delta_H$ (DMSO-d$_6$) 9.52 (1H, s), 4.50 (1H, s), 3.91-3.61 (1H, m), 3.03-2.60 (1H, m), 2.24-2.04 (1H, m), 1.74-1.48 (3H, m), 1.49-1.24 (10H, m), 1.24-1.02 (1H, m).

Intermediate 30

Tert-Butyl 2-ethynylpiperidine-1-carboxylate

The title compound was prepared from Intermediate 29 according to Method N (90%) and was used without further purification. $\delta_H$ (DMSO-d$_6$) 4.95 (1H, s), 3.80 (1H, dd, J 13.1 and 3.0 Hz), 3.28 (1H, d, J 2.3 Hz), 2.88 (1H, s), 1.77-1.50 (5H, m), 1.40 (9H, s), 1.37-1.17 (1H, m).

Intermediate 31

Tert-Butyl 3-(hydroxymethyl)piperidine-1-carboxylate

The title compound was prepared from 3-piperidinemethanol according to Method Z and was isolated as a yellow oil (quantitative) that was used without further purification. $\delta_H$ (CDCl$_3$) 3.94-3.63 (1H, m), 3.62-3.40 (2H, m), 3.25-2.73 (2H, m), 2.09 (1H, s), 1.89-1.58 (3H, m), 1.54 (1H, s), 1.47 (10H, s), 1.37-1.18 (1H, m).

Intermediate 32

Tert-Butyl 3-formylpiperidine-1-carboxylate

The title compound was prepared from Intermediate 31 according to Method O and was isolated as a colourless oil (63%) after purification by column chromatography (SiO$_2$, 20% EtOAc/hexanes). $\delta_H$ (DMSO-d$_6$) 9.60 (1H, s), 3.83-3.58 (1H, m), 3.54-3.22 (1H, m), 3.16-2.98 (1H, m), 2.54-2.36 (1H, m), 1.99-1.78 (1H, m), 1.73-1.47 (2H, m), 1.39 (11H, s).

Intermediate 33

Tert-Butyl 3-ethynylpiperidine-1-carboxylate

The title compound was prepared from Intermediate 32 according to Method N (96%) and was used without further purification. $\delta_H$ (DMSO-d$_6$) 3.75-3.30 (2H, m), 3.18-2.93 (2H, m), 2.89 (1H, d, J 2.3 Hz), 2.42-2.29 (1H, m), 1.87-1.71 (1H, m), 1.63-1.51 (1H, m), 1.51-1.39 (1H, m), 1.34 (9H, s), 1.31-1.21 (1H, m).

Intermediate 34

2-Ethynylpiperidine trifluoroacetate

The title compound was prepared from Intermediate 30 according to Method P (quantitative) and was used without further purification.

Intermediate 35

(Method V)

3-Ethynylpiperidine hydrochloride

To Intermediate 33 (1.50 g, 7.18 mmol) was added HCl (4N in dioxane, 50 mL). The reaction mixture was stirred at r.t. for 16 h and concentrated in vacuo. Trituration with Et$_2$O gave the title compound (0.91 g, 86%). $\delta_H$ (DMSO-d$_6$) 9.02 (2H, br. s), 3.38-3.24 (1H, m), 3.21-3.08 (2H, m), 2.94-2.76 (3H, m), 2.00-1.87 (1H, m), 1.83-1.73 (1H, m), 1.73-1.60 (1H, m), 1.60-1.48 (1H, m).

Intermediate 36

(Method Y)

5-[(Triethylsilyl)ethynyl]-1H-indole

To a stirred solution of 5-iodoindole (0.50 g, 2.0 mmol) and (triethylsilyl)-acetylene (0.58 g, 4.0 mmol) in diisopropylamine (15 mL) was added $Pd(PPh_3)_2Cl_2$ (0.07 g, 0.10 mmol) and CuI (0.04 g, 0.20 mmol) and the reaction mixture was stirred at r.t. for 16 h. The solvent was then removed in vacuo. EtOAc (15 mL) and water (15 mL) were added and the layers separated. The aqueous layer was extracted with EtOAc (2×10 mL). The combined organic layers were washed with water (2×20 mL), dried ($Na_2SO_4$), filtered and concentrated in vacuo. Purification by column chromatography ($SiO_2$, 10% EtOAc/hexanes) gave the title compound (0.52 g, quantitative). $\delta_H$ (DMSO-$d_6$) 11.30 (1H, br. s), 7.69 (1H, s), 7.45-7.41 (1H, m), 7.37 (1H, d, J 8.4 Hz), 7.15 (1H, dd, J 8.4 and 1.5 Hz), 6.48-6.40 (1H, m), 1.02 (9H, t, J 7.8 Hz), 0.65 (6H, q, J 7.9 Hz). MS (ES−) 254.0 (M−H)⁻.

Intermediate 37

5-Ethynyl-1H-indole

To a stirred solution of Intermediate 36 (0.52 g, 0.02 mmol) in MeOH (15 mL) was added $K_2CO_3$ (0.28 g, 0.02 mmol). The reaction mixture was stirred at 45° C. for 2 h and concentrated in vacuo. EtOAc (15 mL) and water (15 mL) were added and the layers separated. The aqueous layer was extracted with EtOAc (2×10 mL). The combined organic layers were washed with water (2×20 mL), dried ($Na_2SO_4$), filtered and concentrated in vacuo. Purification by column chromatography ($SiO_2$, 15% EtOAc/hexanes) gave the title compound (0.11 g, 39%) as a pale yellow oil that solidified on standing. $\delta_H$ (DMSO-$d_6$) 11.29 (1H, br. s), 7.70 (1H, s), 7.46-7.39 (2H, m), 7.16 (1H, dd, J 8.4 and 1.1 Hz), 6.45 (1H, s), 3.89 (1H, s). MS (ES−) 140.0 (M−H)⁻.

Intermediate 38

1,2-Dimethyl-4-iodo-1H-imidazole

To a stirred solution of 2-methyl-4(5)-iodo-1H-imidazole (5.0 g, 24.0 mmol) in THF (50 mL) at 0° C. was added sodium hydride (60% dispersion in mineral oil, 1.15 g, 28.80 mmol). The reaction mixture was stirred at this temperature for 30 minutes, then methyl iodide (1.65 mL, 26.40 mmol) was added dropwise. The reaction mixture was stirred for 2 h. EtOAc (50 mL) and water (50 mL) were added and the layers separated. The organic layer was dried ($Na_2SO_4$), filtered and concentrated in vacuo. Purification by column chromatography ($SiO_2$, 1% EtOAc/hexanes) gave the title compound (1.01 g, 19%) as a yellow oil that solidified on standing. $\delta_H$ (DMSO-$d_6$) 7.19 (1H, s), 3.52 (3H, s), 2.24 (3H, s). MS (ES+) 223.0 (M+H)⁺.

Intermediate 39

(Method R)

1,2-Dimethyl-4-[(triethylsilyl)ethynyl]-1H-imidazole

To a stirred solution of Intermediate 38 (1.01 g, 4.50 mmol) in diisopropylamine (5 mL) and THF (5 mL) were added (triethylsilyl)acetylene (1.28 g, 9.0 mmol), CuI (0.086 g, 0.50 mmol) and $Pd(PPh_3)_2Cl_2$ (0.159 g, 0.20 mmol). The reaction mixture was stirred at 50° C. for 16 h, then cooled to r.t. The salts formed were filtered and the solvent removed in vacuo. The residue was purified by column chromatography ($SiO_2$, 0-20% EtOAc/hexanes) to give the title compound (0.94 g, 90%) as a yellow solid. $\delta_H$ (DMSO-$d_6$) 7.37 (1H, s), 3.51 (3H, s), 2.23 (3H, s), 0.98 (9H, t, J 7.9 Hz), 0.60 (6H, q, J 7.9 Hz). MS (ES+) 235.0 (M+H)⁺.

Intermediate 40

1,2-Dimethyl-4-ethynyl-1H-imidazole

To a stirred solution of Intermediate 39 (0.84 g, 3.50 mmol) in MeOH (25 mL) was added 2M aqueous NaOH (1 mL). The reaction mixture was stirred at 45° C. for 6 h then cooled to r.t. The pH was adjusted to 7 by slow addition of 2M aqueous HCl. The solvent was removed in vacuo and the residue purified by column chromatography ($SiO_2$, 0-100% EtOAc/hexanes) to give the title compound (0.29 g, 69%) as a white solid. $\delta_H$ (DMSO-$d_6$) 7.34 (1H, s), 3.87 (1H, s), 3.52 (3H, s), 2.24 (3H, s). MS (ES+) 121.0 (M+H)⁴.

Intermediate 41

1-Methyl-4-[(triethylsilyl)ethynyl]-1H-indole

The title compound was prepared from 4-bromo-1-methyl-1H-indole according to Method R and was isolated as a brown solid (92%) after aqueous work-up (EtOAc/water) and purification by column chromatography ($SiO_2$, 0-15% EtOAc/hexanes). $\delta_H$ (DMSO-$d_6$) 7.30 (1H, d, J 7.9 Hz), 7.22 (1H, d, J 3.0 Hz), 7.03-6.87 (2H, m), 6.22 (1H, dd, J 3.0 and 0.6 Hz), 3.60 (3H, s), 0.84 (9H, t, J 7.9 Hz), 0.49 (6H, q, J 7.9 Hz).

Intermediate 42

4-Ethynyl-1-methyl-1H-indole

To a stirred solution of Intermediate 41 (2.0 g, 7.40 mmol) in MeOH (15 mL) was added $K_2CO_3$ (1.03 g, 7.40 mmol). The reaction mixture was stirred at 45° C. for 2 h. 2M aqueous NaOH (2 mL) was added and the reaction mixture stirred at 45° C. for a further 2 h then cooled to r.t. The pH was adjusted to 7 by slow addition of 2M aqueous HCl. The organic solvent was removed in vacuo. EtOAc (15 mL) and water (10 mL) were added and the layers separated. The aqueous layer was extracted with EtOAc (2×10 mL). The combined organic layers were washed with water (2×20 mL), dried ($Na_2SO_4$), filtered and concentrated in vacuo. Purification by column chromatography ($SiO_2$, hexanes) gave the title compound (0.35 g, 31%) as a yellow oil. $\delta_H$ (DMSO-$d_6$) 7.27 (1H, d, J 8.0 Hz), 7.18 (1H, d, J 3.0 Hz), 7.02-6.78 (2H, m), 6.22 (1H, d, J 3.0 Hz), 4.04 (1H, s), 3.57 (3H, s). MS (ES+) 156.0 (M+H)⁺.

Intermediate 43

N-(Prop-2-yn-1-yl)methanesulfonamide

To a stirred solution of propargylamine (1.25 mL, 18.20 mmol) in pyridine (20 mL) at 0° C. was added methanesulfonyl chloride (1.5 mL, 20.0 mmol) dropwise. The reaction mixture was allowed to warm to r.t., then evaporated in vacuo. EtOAc (50 mL) and aqueous sat. $NaHCO_3$ (50 mL) were added and the layers separated. The organic layer was dried ($Na_2SO_4$), filtered and concentrated in vacuo. Purification by column chromatography (SiO$_2$, 50% EtOAc/hexanes) gave the title compound (2.40 g, quantitative) as a white solid. $\delta_H$ (DMSO-d$_6$) 7.59 (1H, s), 3.87 (2H, d, J 2.5 Hz), 3.41-3.36 (4H, m). MS (ES+) 134.1 (M+H)$^+$.

Intermediate 44

N,N-Dimethyl-N-(prop-2-yn-1-yl)sulfamide

To a stirred solution of propargylamine (1.25 mL, 18.0 mmol) and triethylamine (5.00 mL, 36.0 mmol) in DCM (15 mL) at 0° C. was added N,N-dimethylsulfamoyl chloride (2.14 mL, 20.0 mmol) dropwise. The reaction mixture was allowed to warm to r.t. and stirred for 16 h. EtOAc (100 mL) and water (50 mL) were added and the layers separated. The organic layer was washed with water (3×30 mL), then brine (30 mL), dried (Na$_2$SO$_4$), filtered and concentrated in vacuo. Purification by column chromatography (SiO$_2$, 50% EtOAc/hexanes) gave the title compound (2.10 g, 72%) as a white solid. $\delta_H$ (DMSO-d$_6$) 4.61 (1H, s), 3.87 (2H, dd, J 6.1 and 2.5 Hz), 2.87 (6H, s), 2.35 (1H, t, J 2.5 Hz). MS (ES+) 163.1 (M+H)$^+$.

Intermediate 45

1-Benzoyl-4-iodo-1H-pyrazole

To a stirred solution of 4-iodopyrazole (10.30 g, 53.1 mmol) in toluene (50 mL) at r.t. was added triethylamine (8.10 mL, 58.1 mmol), followed by benzoyl chloride (8.20 g, 58.3 mmol). The reaction mixture was then heated to 100° C. and stirred for 4 h. The solid was filtered and washed with toluene (50 mL). The organic filtrate was diluted with EtOAc (100 mL), washed with water (3×50 ml), then brine (50 mL), dried (Na$_2$SO$_4$), filtered and concentrated in vacuo. Recrystallisation from hexanes gave the title compound (13.80 g, 87%) as a white solid. $\delta_H$ (DMSO-d$_6$) 8.77 (1H, s), 8.05 (1H, s), 8.02-7.95 (2H, m), 7.74-7.67 (1H, m), 7.61-7.53 (2H, m).

Intermediate 46

1-Benzoyl-4-[(triethylsilyl)ethynyl]-1H-pyrazole

The title compound was prepared from Intermediate 45 according to Method Y and was isolated as a brown oil (quantitative) after purification by column chromatography (SiO$_2$, 50% EtOAc/hexanes). MS (ES+) 311.0 (M+H)$^+$.

Intermediate 47

4-Ethynyl-1H-pyrazole

To a stirred solution of Intermediate 46 (7.50 g, 24.0 mmol) in MeOH (80 mL) was added 2M aqueous NaOH (30 mL) and the reaction mixture was stirred at r.t. for 48 h. The pH was adjusted to 5-6 by slow addition of concentrated HCl and the reaction mixture was concentrated in vacuo. EtOAc (50 mL) and water (50 mL) were added and the layers separated. The aqueous layer was extracted with Et$_2$O (2×50 mL). The combined organic layers were dried (Na$_2$SO$_4$), filtered and concentrated in vacuo. Purification by column chromatography (SiO$_2$, 50-100% Et$_2$O/hexanes) gave the title compound (2.10 g, 95%) as a white solid. $\delta_H$ (DMSO-d$_6$) 13.09 (1H, br. s), 8.04 (1H, br. s), 7.66 (1H, br. s), 3.95 (1H, s).

Intermediate 48

4-Ethynyl-1-methyl-1H-pyrazole

To a stirred solution of Intermediate 47 (0.50 g, 5.40 mmol) in DMF (5 mL) at 0° C. was added sodium hydride (60% dispersion in mineral oil, 0.26 g, 6.50 mmol). The reaction mixture was stirred at this temperature for 1 h, then methyl iodide (0.35 mL, 5.40 mmol) was added. The reaction mixture was stirred at 0° C. for another hour then allowed to warm to r.t. Et$_2$O (50 mL) and water (25 mL) were added and the layers separated. The organic layer was washed with water (4×20 mL), then brine (20 mL), dried (Na$_2$SO$_4$), filtered and concentrated in vacuo. Purification by column chromatography (SiO$_2$, 20% Et$_2$O/hexanes) gave the title compound (0.52 g, 91%) as a clear oil. $\delta_H$ (CDCl$_3$) 7.61 (1H, s), 7.54 (1H, s), 3.91 (3H, s), 3.01 (1H, s). MS (ES+) 107.1 (M+H)$^+$.

Intermediate 49

4-Ethynylpiperidine Hydrochloride

The title compound was prepared from Intermediate 24 according to Method V and was isolated as a pale brown solid (97%). $\delta_H$ (DMSO-d$_6$) 8.80 (21-1, br.s), 3.20-3.10 (2H, m), 3.09 (1H, d, J 2.5 Hz), 3.02-2.85 (2H, m), 2.79-2.65 (1H, m), 2.07-1.87 (2H, m), 1.78-1.59 (2H, m).

Intermediate 50

(Method W)

1-Acetyl-3-ethynylpiperidine

To a stirred solution of Intermediate 35 (0.20 g, 1.36 mmol), triethylamine (0.42 mL, 2.99 mmol), and 4-(dimethylamino)pyridine (catalytic) in DCM (10 mL) was added acetic anhydride (0.15 mL, 1.63 mmol) dropwise. The reaction mixture was stirred at r.t. for 4 h then poured onto aqueous sat. NH$_4$Cl (10 mL). DCM (10 mL) was added and the layers were separated. The organic layer was washed with 1M aqueous HCl (2×10 mL), then aqueous sat. NaHCO$_3$ (2×10 mL), dried (Na$_2$SO$_4$), filtered and concentrated in vacuo to give the title compound (0.18 g, 88%) as a pale yellow oil. $\delta_H$ (CDCl$_3$), mixture of rotamers: 4.40-1.19 (9H, m), 2.06 and 2.02 (3H, s, rotameric), 2.05 and 2.00 (1H, d, J 2.3 Hz, rotameric).

Intermediate 51

1-Acetyl-4-ethynylpiperidine

The title compound was prepared from Intermediate 49 according to Method W and was isolated as a brown oil (71%) that was used without further purification. $\delta_H$ (CDCl$_3$) 3.88-3.71 (1H, m), 3.66-3.50 (1H, m), 3.45-3.30 (1H, m), 3.31-3.14 (1H, m), 2.72-2.52 (1H, m), 2.16 (1H, s), 2.06 (1H, d, J 2.5 Hz), 2.02 (3H, s), 1.83-1.68 (2H, m), 1.64-1.55 (1H, m).

Intermediate 52

(Method X)

3-Ethynyl-1-(methylsulfonyppiperidine

To a stirred solution of Intermediate 35 (0.20 g, 1.36 mmol) and triethylamine (0.42 mL, 2.99 mmol) in DCM (10 mL) at 0° C. was added methanesulphonyl chloride (0.13 mL, 1.63 mmol) dropwise. The reaction mixture was stirred at this temperature for 4 h then poured into EtOAc (50 mL). Water (25 mL) was added and the layers were separated. The organic layer was washed with water (2×25 mL), then brine (25 mL), dried (Na$_2$SO$_4$), filtered and concentrated in vacuo. Purification by column chromatography (SiO$_2$, 30% EtOAc/hexanes) gave the title compound (0.21 g, 86%) as a white solid. MS (ES+) 188.1 (M+H)$^+$.

Intermediate 53

4-Ethynyl-1-(methylsulfonyl)piperidine

The title compound was prepared from Intermediate 49 according to Method X and was isolated as a white solid (58%) after purification by column chromatography (SiO$_2$, 30% EtOAc/hexanes).

Intermediate 54

1-Propioloylpyrrolidine

To a stirred solution of pyrrolidine (4.2 mL, 50.0 mmol) in water (25 mL) and MeOH (35 mL) at −50° C. was added methylpropiolate (4.5 mL, 50.0 mmol) dropwise. The reaction mixture was stirred at this temperature for 5 h then diluted with DCM (200 mL). 2M aqueous HCl (200 mL) was added and the layers were separated. The aqueous layer was extracted with DCM (2×100 mL). The combined organic layers were washed with aqueous sat. NaHCO$_3$ (200 mL), water (200 mL), then brine (200 mL), dried (Na$_2$SO$_4$), filtered and concentrated in vacuo to give the title compound (6.0 g, 98%) as a white solid that was used without further purification. $\delta_H$ (CDCl$_3$) 3.68 (2H, t, J 6.8 Hz), 3.50 (2H, t, J 6.3 Hz), 3.04 (1H, s), 2.01-1.90 (4H, m).

Intermediate 55

3-[(2E)-3-(Dimethylamino)prop-2-enoyl]-5,5-dimethyl-2-(morpholin-4-yl)-5,6-dihydrothieno[2,3-c]pyridin-7(4H)-one The title compound was prepared from Example 289 according to Method AX and was isolated as a yellow solid (70%). $\delta_H$ (CDCl$_3$) 7.79-7.55 (1H, br m), 5.81-5.61 (1H, br m), 5.20 (1H, s), 3.87-3.76 (4H, m), 3.26-3.19 (4H, m), 3.17-3.08 (2H, br s), 3.05-2.84 (6H, br s), 1.33 (6H, s). LCMS (ES+) 364.1 (M+H)$^+$.

Intermediate 56

3-{2-[3-(Chloroacetyl)phenyl]pyridin-4-yl}-5,5-dimethyl-2-(morpholin-4-yl)-5,6-dihydrothieno[2,3-c]pyridin-7(4H)-one Benzyltrimethylammonium dichloroiodate (128 mg, 0.37 mmol) was added to a solution of Example 334 (85 mg, 0.18 mmol) in DCE (4.5 mL) and MeOH (2.0 mL) and the reaction mixture was heated at reflux for 4 h. The solvent was removed in vacuo and the residue was partitioned between DCM (30 mL) and 3% aqueous sodium metabisulfite solution (30 mL). The aqueous phase was extracted with further DCM (30 mL) and the combined organic phases were dried (magnesium sulfate) and the solvent was removed in vacuo. The residue was triturated with Et$_2$O to give the title compound (71 mg, 78%) as a yellow solid. $\delta_H$ (DMSO-d$_6$) 8.81-8.75 (1H, m), 8.69 (1H, s), 8.48-8.42 (1H, m), 8.23-8.18 (1H, m), 8.09-8.02 (1H, m), 7.71 (1H, t, J 7.9 Hz), 7.58 (1H, s), 7.55-7.48 (1H, m), 3.67-3.56 (4H, m), 3.31 (2H, s), 2.96-2.86 (4H, m), 2.73 (2H, s), 1.20 (6H, s).

Intermediate 57

(Method BN)

3-(1-Butoxyvinyl)-5,5-dimethyl-2-(morpholin-4-yl)-5,6-dihydro-1-benzothiophen-7(4R)-one A mixture of Example 17 (500 mg, 1.28 mmol), butyl vinyl ether (641 mg, 6.40 mmol), potassium carbonate (212 mg, 1.54 mmol), tris(dibenzylideneacetone)-dipalladium(0) (101 mg, 0.11 mmol) and 1,3-bis(diphenylphosphino)propane (103 mg, 0.25 mmol) in DMF (3.0 mL) was heated in a sealed tube at 120° C., under microwave irradiation, for 2 h. The solvent was removed in vacuo and the residue was purified by column chromatography (SiO$_2$, 0-100% EtOAc/heptane) to give the title compound (365 mg, 63%) as a beige solid. $\delta_H$ (CDCl$_3$) 4.41 (1H, d, J 2.0 Hz), 4.20 (1H, d, J 2.0 Hz), 3.82-3.72 (6H, m), 3.33-3.27 (4H, m), 2.54 (2H, s), 2.38 (2H, s), 1.77-1.67 (2H, m), 1.52-1.39 (2H, m), 1.09 (6H, s), 0.96 (3H, t, J 7.3 Hz). LCMS (ES+) 364.2 (M+H)$^+$.

Intermediate 58

3-(1-Butoxyvinyl)-5,5-dimethyl-2-(morpholin-4-yl)-5,6-dihydrothieno[2,3-c]pyridin-7(4R)-one The title compound was prepared from Intermediate 19 according to Method BN and was isolated as a pale orange solid (41%) after purification by column chromatography (SiO$_2$, 0-100% EtOAc/heptane) and trituration with Et$_2$O. $\delta_H$ (DMSO-d$_6$) 7.37 (1H, s), 4.46 (1H, d, J 1.8 Hz), 4.20 (1H, d, J 1.8 Hz), 3.78-3.65 (6H, m), 3.14-3.06 (4H, m), 2.59 (2H, s), 1.69-1.58 (2H, m), 1.46-1.33 (2H, m), 1.20 (6H, s), 0.91 (3H, t, J 7.2 Hz). LCMS (ES+) 365.2 (M+H)$^+$.

Intermediate 59

(Method BO)

3-({(3S)-3-[(tert-Butoxycarbonybamino]pyrrolidin-1-yl}carbonyl)phenylboronic Acid A mixture of (3S)-(−)-3-(tert-butoxycarbonylamino)pyrrolidine (106 mg, 0.57 mmol), (3-chlorocarbonylphenyl)boronic anhydride (100 mg, 0.29 mmol) and triethylamine (119 μL, 0.86 mmol) in DCM (5.0 mL) was stirred at room temperature for 18 h. The solvent was removed in vacuo and the residue was purified by column chromatography (SiO$_2$, 0-100% EtOAc/heptane) to give the title compound (58 mg, 30%) as a white solid. LCMS (ES+) 335 (M+H)$^+$.

Intermediate 60

3-({(3R)-3-[(tert-Butoxycarbonyl)amino]pyrrolidin-1-yl}carbonyl)phenylboronic Acid The title compound was prepared from (3R)-(+)-3-(tert-butoxycarbonylamino)-pyrrolidine according to Method BO and was obtained as an off-white solid (30%). LCMS (ES+) 335 (M+H)$^+$.

Intermediate 61

3-Benzyl 8-tert-butyl 3,8-diazabicyclo[3.2.1]octane-3,8-dicarboxylate

A mixture of 8-tert-butoxycarbonyl-3,8-diazabicyclo [3.2.1]octane (238 mg, 1.12 mmol), benzyl chloroformate (160 μL, 1.12 mmol) and triethylamine (280 μL, 2.0 mmol) in DCM (20 mL) was stirred at room temperature for 22 h. The reaction mixture was diluted with DCM (20 mL) and washed with water (25 mL). The organic phase was dried (magnesium sulfate) and the solvent was removed in vacuo to give the title compound (336 mg, 87%) as a clear oil. $\delta_H$ (DMSO-$d_6$) 7.45-7.28 (5H, m), 5.17-5.03 (2H, m), 4.18-4.06 (2H, m), 3.79-3.69 (2H, m), 3.10-2.90 (2H, m), 1.85-1.72 (2H, m), 1.60-1.49 (2H, m), 1.41 (9H, s).

Intermediate 62

Benzyl 3,8-diazabicyclo[3.2.1]octane-3-carboxylate

A solution of Intermediate 61 (336 mg, 0.97 mmol) in trifluoroacetic acid (2.0 mL) and DCM (20 mL) was stirred at room temperature for 17.5 h. The solvent was removed in vacuo and the residue was partitioned between DCM (30 mL) and aqueous sodium hydroxide solution (2N, 20 mL). The organic phase was dried (magnesium sulfate) and the solvent was removed in vacuo to give the title compound (328 mg; containing some impurity) as a clear gum. $\delta_H$ (DMSO-$d_6$) 7.47-7.26 (5H, m), 5.11 (2H, s), 4.11-3.94 (2H, m), 3.92-3.79 (2H, m), 3.47-3.08 (2H, m), 2.00-1.80 (2H, m), 1.77-1.66 (2H, m). LCMS (ES+) 247.1 (M+H)$^+$.

Intermediate 63

2-[(3-endo)-8-Azabicyclo[3.2.1]oct-3-yl]-1H-isoindole-1,3(2H)-dione, Hydrochloride Salt To a suspension of 2-[(3-endo)-8-methyl-8-azabicyclo [3.2.1]oct-3-yl]-1H-isoindole-1,3(2H)-dione (52.4 g, 194 mmol) in toluene (500 mL) was added α-chloroethyl chloroformate (30.6 g, 214 mmol) in a dropwise manner and the mixture was heated at reflux for 3 h. The reaction mixture was cooled to room temperature and the solvent was removed in vacuo. The residue was taken up in MeOH (500 mL) and refluxed gently at 70° C. for 1.5 h until gas evolution ceased, then allowed to stir at room temperature for 18 h. The reaction mixture was filtered and the solid washed with MeOH and then dried in vacuo. The filtrate was evaporated in vacuo and slurried with hot MeOH, refiltered and the solid washed with further MeOH. This procedure was repeated once more and the combined solids were dried in vacuo to give the title compound (45.5 g, 80%) as a white solid. $\delta_H$ (CD$_3$OD) 7.93-7.78 (4H, m), 4.76-4.60 (1H, m), 4.24-4.12 (2H, m), 2.83-2.70 (2H, m), 2.30-2.11 (4H, m), 2.06-1.86 (2H, m). LCMS (ES+) 257.2 (M+H)$^+$.

Example 1

Ethyl 2-(morpholin-4-yl)-7-oxo-4,5,6,7-tetrahydro-1-benzothiophene-3-carboxylate The title compound was prepared from Intermediate 1 according to Method F and was isolated as a beige solid (94%). $\delta_H$ (CDCl$_3$) 4.25 (2H, q, J 7.1 Hz), 3.78 (4H, m), 3.22 (4H, m), 2.92 (2H, t, J 6.1 Hz), 2.47 (2H, t, J 6.1 Hz), 2.06 (2H, m), 1.31 (3H, t, J 7.1 Hz). $\delta$ $^{13}$C(CDCl$_3$) 191.3, 171.8, 163.9, 155.2, 124.4, 113.9, 66.5 (2×CH$_2$), 61.0, 53.7 (2×CH$_2$), 37.8, 27.4, 24.3, 14.8. LCMS (ES+) 310.0 (M+H)$^+$.

Example 2

2-(Morpholin-4-yl)-5,6-dihydro-1-benzothiophen-7(4H)-one

To a stirred suspension of Example 1 (0.92 g, 2.98 mmol) in THF (10 mL) and water (10 mL) was added LiOH (0.25 g, 6.00 mmol) and the reaction mixture was stirred at r.t. for 24 h. The volatiles were then removed in vacuo and the residue was re-dissolved in water (10 mL). To this was added aqueous 2M HCl (10 mL) and the reaction mixture was stirred for 3 h. The mixture was then extracted with EtOAc (3×100 mL), the combined organics dried over MgSO$_4$, filtered and concentrated in vacuo. Purification by column chromatography (SiO$_2$, 0-40% EtOAc in hexanes) gave the title compound as an off-white solid (0.70 g, 99%). $\delta_H$ (CDCl$_3$) 5.85 (1H, m), 3.77-3.74 (4H, m), 3.22-3.19 (4H, m), 2.65 (2H, t, J 6.1 Hz), 2.47 (2H, t, J 6.1 Hz), 2.08-2.00 (2H, m). $\delta$ $^{13}$C (CDCl$_3$) 190.4, 167.2, 156.5, 121.6, 104.7, 66.3 (2×CH$_2$), 49.9 (2×CH$_2$), 37.5, 26.7, 24.5. LCMS (ES+) 238.0 (M+H)$^+$.

Example 3

3-Bromo-2-(morpholin-4-yl)-5,6-dihydro-1-benzothiophen-7(4H)-one

To a stirred solution of Example 2 (0.83 g, 3.50 mmol) in THF (50 mL) at 0° C. was added, dropwise, Br$_2$ (0.56 g, 3.50 mmol) and the reaction mixture was stirred for 20 minutes. The reaction mixture was then poured into brine (200 mL) and extracted with EtOAc (3×100 mL). The combined organics were dried over MgSO$_4$, filtered and concentrated in vacuo. Purification by column chromatography (SiO$_2$, 1:5 EtOAc/hexanes) gave the title compound as a pale brown solid (0.79 g, 72%). $\delta_H$ (DMSO-$d_6$) 3.77-3.74 (4H, m), 3.22-3.18 (4H, m), 2.70-2.67 (2H, m), 2.52-2.47 (2H, m), 2.10-2.04 (2H, m). $\delta$ $^{13}$C (DMSO-$d_6$) 189.7, 160.2, 152.7, 124.6, 97.4, 65.9 (2×CH$_2$), 51.9 (2×CH$_2$), 37.3, 25.9, 23.4. LCMS (ES+) 315.0 and 317.0 (M+H)$^+$.

Example 4

2-(Morpholin-4-yl)-3-phenyl-5,6-dihydro-1-benzothiophen-7(4H)-one

To a stirred solution of Example 3 (0.16 g, 0.50 mmol) and Pd(PPh$_3$)$_4$ (0.06 g, 0.05 mmol) in DME (5 mL) was added phenylboronic acid (0.07 g, 0.60 mmol) and aqueous 2M Na$_2$CO$_3$ solution (0.50 mL). The reaction mixture was then heated to 85° C. for 18 h before it was poured into brine (50 mL) and extracted with EtOAc (3×100 mL). The combined organics were dried over MgSO$_4$, filtered and concentrated in vacuo. Purification by column chromatography (SiO$_2$, 1:9 Et$_2$O/DCM) gave the title compound as a white solid (0.03 g, 19%). $\delta_H$ (DMSO-$d_6$) 7.49-7.32 (5H, m), 3.57-3.54 (4H, m) 2.92-2.89 (4H, m), 2.56-2.44 (4H, m), 2.02-1.94 (2H, m). $\delta$ $^{13}$C (DMSO-$d_6$) 189.9, 162.8, 153.9, 135.2, 129.6 (2×CH), 129.1 (2×CH), 127.8, 124.0, 123.3, 65.7 (2×CH$_2$), 51.6 (2×CH$_2$), 37.8, 25.8, 24.3. LCMS (ES+) 314.0 (M+H)$^+$.

Example 5

3-Benzyl-2-(morpholin-4-yl)-5,6-dihydro-1-benzothiophen-7(4H)-one

To a stirred suspension of activated zinc dust (0.07 g, 0.92 mmol) in THF (5 mL) was added benzyl bromide (0.16 g, 0.92 mmol) and the reaction mixture was heated to reflux for 15 minutes until the zinc disappeared. After cooling to r.t., a solution of Intermediate 2 (0.22 g, 0.61 mmol) and Pd(PPh$_3$)$_2$Cl$_2$ (0.04 g, 0.06 mmol) in THF (2 mL) was added and the reaction mixture was heated to reflux for 18 h. The reaction mixture was then partitioned between brine (100 mL) and EtOAc (100 mL). The aqueous layer was further extracted with EtOAc (2×100 mL) and the combined organics were washed with brine (200 mL), dried over MgSO$_4$, filtered and concentrated in vacuo. Purification by column chromatography (SiO$_2$, 0-40% EtOAc in hexanes) gave the title compound as a white solid (0.05 g, 25%). $\delta_H$ (CDCl$_3$) 7.33-7.28 (3H, m), 7.25-7.09 (2H, m), 3.93 (2H, s), 3.78-3.72 (4H, m), 3.00-2.97 (4H, m), 2.57-2.47 (4H, m), 2.12-2.04 (2H, m). LCMS (ES+) 328.0 (M+H)$^+$.

Example 6

2-Morpholin-4-yl)-3-(phenylethyl)-5,6-dihydro-1-benzothiophen-7(4H)-one

To a stirred solution of Intermediate 2 (0.25 g, 0.69 mmol), Pd(PPh$_3$)$_2$Cl$_2$ (0.03 g, 0.04 mmol) and phenylacetylene (0.08 g, 0.76 mmol) in diisopropylamine (5 mL) was added CuI (0.01 g, 0.07 mmol). The reaction mixture was then heated to 60° C. for 3 h after which time it was partitioned between EtOAc (100 mL) and brine (200 mL). The aqueous phase was extracted with further EtOAc (2×100 mL) and the combined organic phases were dried (MgSO$_4$), filtered and concentrated in vacuo. Purification by column chromatography (SiO$_2$, 10-40% EtOAc in hexanes) gave the title compound as an off-white solid (0.15 g, 66%). $\delta_H$ (DMSO-d$_6$) 7.56-7.42 (5H, m), 3.87-3.83 (4H, m), 3.72-3.69 (4H, m), 2.85 (2H, t, J 6.0 Hz), 2.57-2.50 (2H, m), 2.18-2.04 (2H, m). LCMS (ES+) 338.0 (M+H)$^+$.

Example 7

2-(Morpholin-4-yl)-3-(2-phenylethyl)-5,6-dihydro-1-benzothiophen-7(4H)-one

To a stirred solution of Example 6 (0.10 g, 0.31 mmol) in EtOH (10 mL) was added Pd (10 wt % on carbon, 0.03 g) and ammonium formate (0.39 g, 6.20 mmol). The reaction mixture was then heated at reflux for 18 h, cooled, filtered and concentrated in vacuo. The crude residue was partitioned between EtOAc (100 mL) and brine (200 mL) and the aqueous phase was extracted with further EtOAc (2×100 mL). The combined organic phases were then dried over MgSO$_4$, filtered and concentrated in vacuo. Purification by column chromatography (SiO$_2$, 1:6 EtOAc/hexanes) gave the title compound as an off-white solid (0.07 g, 60%). $\delta_H$ (DMSO-d$_6$) 7.36-7.31 (2H, m), 7.26-7.21 (3H, m), 3.78-3.75 (4H, m), 2.92-2.89 (4H, m), 2.87-2.81 (4H, m), 2.73-2.70 (2H, m), 2.55-2.48 (2H, m), 2.09-2.03 (2H, m). LCMS (ES+) 342.0 (M+H)$^+$.

Example 8

2-(Morpholin-4-yl)-7-oxo-N-phenyl-4,5,6,7-tetrahydro-1-benzothiophene-3-carboxamide To a stirred solution of Intermediate 4 (0.07 g, 0.20 mmol) in DMSO (5 mL) was added morpholine (0.10 g, 0.10 mL, 1.15 mmol) and the reaction mixture was heated at 70° C. for 18 h. After cooling, water (20 mL) was added and the resultant precipitate was collected via filtration, washed with water and dried in vacuo to give the title compound as an off-white solid (0.07 g, 93%). $\delta_H$ (DMSO-d$_6$) 10.34 (1H, s), 7.71-7.68 (2H, m), 7.37-7.31 (2H, m), 7.09 (1H, t, J 7.3 Hz), 3.70-3.67 (4H, m), 3.29-3.22 (4H, m), 2.76-2.73 (2H, m), 2.47-2.43 (2H, m), 2.05-2.02 (2H, m). $\delta$ $^{13}$C (DMSO-d$_6$) 189.7, 164.5, 163.1, 153.8, 139.2, 129.2 (2×CH), 124.1, 121.6, 119.8 (2×CH), 118.6, 65.7 (2×CH$_2$), 51.9 (2×CH$_2$), 37.5, 25.3, 24.0. LCMS (ES+) 357.0 (M+H)$^+$.

Example 9

2-[(3S)-3-(1H-Indol-3-ylmethyl)morpholin-4-yl]-5,6-dihydro-1-benzothiophen-7(4H)-one To a stirred solution of Intermediate 5 (0.23 g, 0.58 mmol) in THF (2 mL) was added LiOH (0.09 g, 2.00 mmol) in water (1 mL) and the reaction mixture was heated at 70° C. for 4 days. The volatiles were then removed in vacuo and the residue was re-dissolved in hot water (2 mL). To the solution was added aqueous 2M HCl (3 mL) and the reaction mixture was stirred at r.t. for 48 h. The resultant precipitate was collected via filtration and triturated with DCM and MeCN to give the title compound as a pale yellow solid (0.06 g, 31%). $\delta_H$ (DMSO-d$_6$) 10.94 (1H, br. s), 7.59 (1H, d, J 7.7 Hz), 7.35 (1H, d, J 7.7 Hz), 7.16-7.03 (2H, m), 6.12 (1H, s), 4.00-3.96 (2H, m), 3.76-3.60 (2H, m), 3.57-3.25 (5H, m), 2.85 (1H, dd, J 14.2 and 3.9 Hz), 2.70-2.66 (2H, m), 2.49-2.35 (2H, m), 2.02-1.98 (2H, m). $\delta$ $^{13}$C (DMSO-d$_6$) 188.3, 165.1, 156.3, 136.6, 127.7, 124.2, 121.4, 119.4, 118.9, 118.3, 111.9, 110.5, 104.0, 66.7, 65.9, 58.4, 44.8, 37.3, 26.1, 24.2, 21.9. LCMS (ES+) 367.0 (M+H)$^+$.

Example 10

5,5-Dimethyl-2-[(3S)-3-(1H-indol-3-ylmethyl)morpholin-4-yl]-7-oxo-4,5,6,7-tetrahydro-1-benzothiophene-3-carbonitrile To a stirred solution of Intermediate 12 (0.24 g, 0.84 mmol) in DMSO (1 mL) was added DIPEA (0.22 g, 0.30 mL, 1.76 mmol) and Intermediate 9 (0.20 g, 0.93 mmol) and the reaction mixture was heated to 190° C. for 2 h in a sealed tube under microwave irridation. After cooling, the reaction mixture was partitioned between brine (100 mL) and EtOAc (100 mL). The aqueous phase was further extracted with EtOAc (2×100 mL) and the combined organics were washed with brine (200 mL), dried (MgSO$_4$), filtered and the solvents removed in vacuo. Purification by column chromatography (SiO$_2$, 1:1 EtOAc/hexanes) gave the title compound as a white solid (0.08 g, 23%). $\delta_H$ (DMSO-d$_6$) 8.16 (1H, br. s), 7.75-7.72 (1H, m), 7.37-7.31 (1H, m), 7.24-7.15 (3H, m), 4.38-4.32 (1H, m), 4.18-4.09 (1H, m), 3.92-3.88 (1H, m), 3.79-3.68 (3H, m), 3.64 (1H, dd, J 3.0 and 1.0 Hz), 3.60 (1H, dd, J 3.0 and 1.0 Hz), 3.15 (1H, dd, J 14.0 and 9.0 Hz), 2.71-2.69 (2H, m), 2.40 (2H, s), 1.05 (6H, s). LCMS (ES+) 420.0 (M+H)$^+$.

Example 11

5,5-Dimethyl-2-(morpholin-4-D-7-oxo-4,5,6,7-tetrahydro-1-benzothiophene-3-carbonitrile To a stirred solution of Intermediate 12 (18.3 g, 64.4 mmol) in DMSO (150 mL) was slowly added morpholine (14.6 g, 14.6 mL, 168.0 mmol) and the reaction mixture was heated to 100° C. for 30 minutes. After cooling, the reaction mixture was diluted with water (450 mL) with rigorous stirring and the resultant precipitate was filtered, washed with water and dried to give the title compound as a pale green solid (14.4 g, 77%). $\delta_H$ (DMSO-d$_6$) 3.77 (4H, m), 3.64 (4H, m), 2.64 (2H, s), 2.35 (2H, s), 1.05 (6H, s). LCMS (ES+) 291.0 (M+H)$^+$.

Example 12

5,5-Dimethyl-2-(morpholin-4-yl)-7-oxo-4,5,6,7-tetrahydro-1-benzothiophene-3-carboxamide To a stirred solution of Example 11 (10.0 g, 34.5 mmol) in glacial AcOH (100 mL) at 120° C. was added concentrated H$_2$SO$_4$ (40 mL). After stirring for 4 h, a small aliquot (5 mL) was removed and partitioned between EtOAc (50 mL) and aqueous 2M NaOH (20 mL). The organic phase was washed with brine (20 mL), dried (MgSO$_4$), filtered and concentrated in vacuo. The resulting residue was triturated with 1:1 EtOAc/Et$_2$O and the solid collected by filtration to give the title compound (0.2 g) as a white solid. $\delta_H$ (DMSO-d$_6$) 7.67 (1H, br. s), 7.49 (1H, br. s), 3.72 (4H, m), 3.21 (4H, m), 2.64 (2H, s), 2.31 (2H, s), 1.01 (6H, s). LCMS (ES+) 308.9 (M+H)$^+$; LCMS (ES−) 307.0 (M−H)$^-$.

Example 13

5,5-Dimethyl-2-(morpholin-4-yl)-5,6-dihydro-1-benzothiophen-7-one

To a stirred solution of Example 11 (10.0 g, 34.5 mmol) in glacial AcOH (100 mL) at 120° C. was added concentrated H$_2$SO$_4$ (40 mL). After stirring for 24 h the reaction mixture was cooled to r.t. prior to pouring into a well-stirred mixture of EtOAc (950 mL) and water (950 mL) at 0° C. The resulting emulsion was filtered through Celite® and the organic phase was separated, washed with brine (3×100 mL), dried (MgSO$_4$), filtered and concentrated in vacuo. Purification by column chromatography (SiO$_2$, 1:1 EtOAc/hexanes) gave the title compound (5.3 g, 58%) as a white powder. $\delta_H$ (DMSO-d$_6$) 6.15 (1H, s), 3.72 (4H, m), 3.25 (4H, m), 2.58 (2H, s), 2.26 (2H, s), 1.01 (6H, s). LCMS (ES+) 266.0 (M+H)$^+$.

Example 14

5,5-Dimethyl-3-fluoro-2-(morpholin-4-yl)-5,6-dihydro-1-benzothiophen-7(4H)-one

To a stirred solution of Example 13 (0.20 g, 0.75 mmol) in THF (10 mL) at 20° C. was added Selectfluor® (0.53 g, 1.50 mmol) portionwise. The reaction mixture was then heated to reflux for 24 h before it was cooled and filtered. The filtrate was concentrated in vacuo and the resulting solid was purified by column chromatography (SiO$_2$, 1:1 EtOAc/hexanes) to give the title compound (0.11 g, 50%) as a white powder. $\delta_H$ (CDCl$_3$) 3.86 (4H, m), 3.32 (4H, m), 2.59 (2H, s), 2.43 (2H, s), 1.13 (6H, s). LCMS (ES+) 285.0 (M+H)$^+$.

Example 15

(Method B)

3-Chloro-5,5-dimethyl-2-(morpholin-4-yl)-5,6-dihydro-1-benzothiophen-7(4H)-one

To a stirred solution of Example 13 (0.20 g, 0.75 mmol) in THF (10 mL) was added NCS (0.11 g, 0.82 mmol) portionwise. After stirring for 30 minutes the reaction mixture was diluted with EtOAc (100 mL), washed with aqueous sat. Na$_2$CO$_3$ (3×25 mL), dried (MgSO$_4$), filtered and concentrated in vacuo. Purification by column chromatography (SiO$_2$, 1:1 EtOAc/hexanes) gave the title compound (0.18 g, 80%) as a white powder. $\delta_H$ (DMSO-d$_6$) 3.76 (4H, m), 3.24 (4H, m), 2.61 (2H, s), 2.40 (2H, s), 1.05 (6H, s). LCMS (ES+) 300.0 (M+H)$^+$.

Example 16

3-Bromo-5,5-dimethyl-2-(morpholin-4-yl)-5,6-dihydro-1-benzothiophen-7(4H)-one

The title compound was prepared from Example 13 according to Method B, using NBS in place of NCS, and was isolated as a white powder (74%). $\delta_H$ (DMSO-d$_6$) 3.83 (4H, m), 3.61 (4H, m), 2.63 (2H, s), 2.47 (2H, s), 1.04 (6H, s). LCMS (ES+) 345.3 (M+H)$^+$.

Example 17

5,5-Dimethyl-3-iodo-2-(morpholin-4-yl)-5,6-dihydro-1-benzothiophen-7(4H)-one

The title compound was prepared from Example 13 according to Method B, using NIS in place of NCS, and was isolated as a white powder (90%). $\delta_H$ (DMSO-d$_6$) 3.76 (4H, m), 3.16 (4H, m), 2.60 (2H, s), 2.41 (2H, s), 1.05 (6H, s). LCMS (ES+) 391.7 (M+H)$^+$.

Example 18

5,5-Dimethyl-2-(morpholin-4-yl)-3-(phenylthio)-5,6-dihydro-1-benzothiophen-7(4H)-one To a stirred solution of Example 13 (0.20 g, 0.75 mmol) in THF (10 mL) was added, dropwise, a solution of benzenesulfenyl chloride (0.13 g, 0.90 mmol) in THF (2 mL). After stirring for 30 minutes, finely powdered NaHCO$_3$ (10.00 g) was added and the reaction mixture was filtered and concentrated in vacuo. Purification by column chromatography (SiO$_2$, 1:1 EtOAc/hexanes) gave the title compound (0.21 g, 75%) as a white powder. $\delta_H$ (DMSO-d$_6$) 7.31 (2H, m), 7.17 (1H, m), 7.04 (2H, m), 3.62 (4H, m), 3.45 (4H, m), 2.51 (2H, s), 2.37 (2H, s), 0.95 (6H, s). LCMS (ES+) 374.0 (M+H)$^+$.

Example 19

3-[(Dimethylamino)methyl]-5,5-dimethyl-2-(morpholin-4-yl)-5,6-dihydro-1-benzothiophen-7(4H)-one A stirred solution of Example 13 (0.20 g, 0.75 mmol) and Eschenmoser's salt (0.50 g, 2.70 mmol) in THF (20 mL) was heated to reflux for 2 h. The reaction mixture was then cooled to r.t., filtered through Celite® and the filtrate was concentrated in vacuo. Purification by column chromatography (SiO$_2$, 20:1 EtOAc/MeOH) gave the title compound (0.08 g, 31%) as a white powder. $\delta_H$ (DMSO-d$_6$) 3.73 (4H, m), 3.32 (2H, s), 3.18 (4H, m), 2.67 (2H, s), 2.35 (2H, s), 2.13 (6H, s), 1.02 (6H, s). LCMS (ES+) 323.0 (M+H)$^+$.

Example 20

(Method C)

5,5-Dimethyl-3-[(1-methyl-1H-imidazol-5-yl)ethynyl]-2-(morpholin-4-yl)-5,6-dihydro-1-benzothiophen-7(4H)-one To a stirred solution of Example 17 (1.63 g, 4.17 mmol) and 5-ethynyl-1-methyl-1H-imidazole (0.66 g, 6.26 mmol) in diisopropylamine (150 mL) at 60° C. was added Pd(PPh$_3$)$_2$Cl$_2$ (0.20 g, 0.28 mmol) and CuI (0.05 g, 0.26 mmol), and the reaction mixture was stirred for 45 minutes. The solvent was then removed in vacuo and the resulting residue was diluted with EtOAc (250 mL) and washed with sat. aqueous NaHCO$_3$ (3×100 mL). The organic phase was dried over MgSO$_4$, filtered and concentrated in vacuo. Purification by column chromatography (SiO$_2$, 10:1 EtOAc/MeOH) gave the title compound (1.43 g, 93%) as a pale yellow powder. δ$_H$ (DMSO-d$_6$) 7.80 (1H, br. s), 7.31 (1H, br. s), 3.76 (4H, m), 3.66 (3H, s), 3.63 (4H, m), 2.65 (2H, s), 2.36 (2H, s), 1.05 (6H, s). LCMS (ES+) 370.1 (M+H)$^+$.

Example 21

5,5-Dimethyl-3-[(3-methoxyphenyl)ethynyl]-2-(morpholin-4-yl)-5,6-dihydro-1-benzothiophen-7(4H)-one The title compound was prepared from Example 17 and 1-ethynyl-3-methoxybenzene according to Method C and was isolated as a tan powder (88%). δ$_H$ (DMSO-d$_6$) 7.33 (1H, m), 7.07 (1H, m), 6.98 (2H, m), 3.79 (7H, br. s), 3.64 (4H, m), 2.69 (2H, s), 2.36 (2H, s), 1.07 (6H, s). LCMS (ES+) 396.1 (M+H)$^+$.

Example 22

3-{[4-(Dimethylamino)phenyl]ethynyl}-5,5-dimethyl-2-(morpholin-4-yl)-5,6-dihydro-1-benzothiophen-7(4H)-one The title compound was prepared from Example 17 and 4-ethynyl-N,N-dimethylaniline according to Method C and was isolated as a tan powder (84%). δ$_H$ (DMSO-d$_6$) 7.29 (2H, d, J 8.8 Hz), 6.71 (2H, d, J 8.8 Hz), 3.79 (4H, m), 3.60 (4H, m), 2.94 (6H, s), 2.66 (2H, s), 2.35 (2H, s), 1.06 (6H, s). LCMS (ES+) 409.1 (M+H)$^+$.

Example 23

5,5-Dimethyl-3-[(3-fluorophenyl)ethynyl]-2-(morpholin-4-yl)-5,6-dihydro-1-benzothiophen-7(4H)-one The title compound was prepared from Example 17 and 1-ethynyl-3-fluorobenzene according to Method C and was isolated as a tan powder (84%). δ$_H$ (DMSO-d$_6$) 7.49-7.23 (4H, m), 3.79 (4H, m), 3.65 (4H, m), 2.70 (2H, s), 2.36 (2H, s), 1.07 (6H, s). LCMS (ES+) 384.1 (M+H)$^+$.

Example 24

5,5-Dimethyl-2-(morpholin-4-yl)-3-(pyridin-3-yl-ethynyl)-5,6-dihydro-1-benzothiophen-7(4H)-one The title compound was prepared from Example 17 and 3-ethynylpyridine according to Method C and was isolated as a pale yellow powder (82%). δ$_H$ (DMSO-d$_6$) 8.71 (1H, d, J 1.5 Hz), 8.56 (1H, dd, J 4.8 and 1.5 Hz), 7.92 (1H, dt, J 7.9 and 1.8 Hz), 7.44 (1H, dd, J 7.9 and 4.8 Hz), 3.78 (4H, m), 3.66 (4H, m), 2.71 (2H, s), 2.36 (2H, s), 1.07 (6H, s). LCMS (ES+) 367.1 (M+H)$^+$.

Example 25

5,5-Dimethyl-2-(morpholin-4-yl)-3-[(4-nitrophenyl)ethynyl]-5,6-dihydro-1-benzothiophen-7(4H)-one The title compound was prepared from Example 17 and 1-ethynyl-4-nitrobenzene according to Method C and was isolated as a yellow powder (82%). δ$_H$ (DMSO-d$_6$) 8.26 (2H, d, J 8.7 Hz), 7.74 (2H, d, J 8.7 Hz), 3.80 (4H, m), 3.70 (4H, m), 2.72 (2H, s), 2.37 (2H, s), 1.08 (6H, s). LCMS (ES+) 411.0 (M+H)$^+$.

Example 26

5,5-Dimethyl-2-(morpholin-4-yl)-3-[(triethylsilyl)ethynyl]-5,6-dihydro-1-benzothiophen-7(4H)-one The title compound was prepared from Example 17 and triethyl(ethynyl)silane according to Method C and was isolated as a pale grey powder (86%). δ$_H$ (CDCl$_3$) 3.85 (4H, m), 3.67 (4H, m), 2.72 (2H, s), 2.41 (2H, s), 1.12 (6H, s), 1.04 (9H, t, J 7.8 Hz), 0.68 (6H, q, J 7.8 Hz). LCMS (ES+) 404.0 (M+H)$^+$.

Example 27

3-(Cyclopropylethynyl)-5,5-dimethyl-2-(morpholin-4-yl)-5,6-dihydro-1-benzothiophen-7(4H)-one The title compound was prepared from Example 17 and ethynylcyclopropane according to Method C and was isolated as an off-white powder (77%). δ$_H$ (DMSO-d$_6$) 3.74 (4H, m), 3.51 (4H, m), 2.56 (2H, s), 2.31 (2H, s), 1.56 (1H, m), 1.03 (6H, s), 0.89 (2H, m), 0.68 (2H, m). LCMS (ES+) 330.1 (M+H)$^+$.

Example 28

5,5-Dimethyl-3-(4-hydroxybut-1-yn-1-yl)-2-(morpholin-4-yl)-5,6-dihydro-1-benzothiophen-7(4H)-one The title compound was prepared from Example 17 and but-3-yn-1-ol according to Method C and was isolated as an off-white powder (89%). δ$_H$ (DMSO-d$_6$) 4.85 (1H, t, J 5.3 Hz), 3.73 (4H, m), 3.59-3.54 (6H, m), 2.58 (4H, m), 2.57 (2H, s), 1.02 (6H, s). LCMS (ES+) 334.1 (M+H)$^+$.

Example 29

5,5-Dimethyl-3-[(1-hydroxycyclohexyl)ethynyl]-2-(morpholin-4-yl)-5,6-dihydro-1-benzothiophen-7(4H)-one The title compound was prepared from Example 17 and 1-ethynylcyclohexanol according to Method C and was isolated as an off-white powder (87%). δ$_H$ (DMSO-d$_6$) 5.41 (1H, s), 3.74 (4H, m), 3.56 (4H, m), 2.59 (2H, s), 2.33 (2H, s), 1.82-1.79 (2H, m), 1.67-1.63 (2H, m), 1.47-1.41 (5H, m), 1.24-1.18 (1H, m), 1.03 (6H, s). LCMS (ES+) 388.0 (M+H)$^+$.

Example 30

3-[(1-Aminocyclohexyl)ethynyl]-5,5-dimethyl-2-(morpholin-4-yl)-5,6-dihydro-1-benzothiophen-7(4H)-one The title compound was prepared from Example 17 and 1-ethynyl-cyclohexanamine according to Method C and was isolated as a pale yellow powder (61%). $\delta_H$ (DMSO-d$_6$) 3.67 (4H, m), 3.47 (4H, m), 2.51 (2H, s), 2.24 (2H, s), 2.01 (2H, br. s), 1.70-1.67 (2H, m), 1.59-1.50 (2H, m), 1.49-1.46 (2H, m), 1.42-1.32 (3H, m), 1.29-1.26 (1H, m), 0.95 (6H, s). LCMS (ES+) 370.1 (M-NH$_2$)$^+$.

Example 31

3-[3-(Diethylamino)prop-1-yn-1-yl]-5,5-dimethyl-2-(morpholin-4-yl)-5,6-dihydro-1-benzothiophen-7(4H)-one The title compound was prepared from Example 17 and N,N-diethylprop-2-yn-1-amine according to Method C and was isolated as a pale yellow powder (76%). $\delta_H$ (DMSO-d$_6$) 3.74 (4H, m), 3.63 (2H, s), 3.55 (4H, s), 2.58 (2H, s), 2.48 (4H, q, J 7.1 Hz), 2.33 (2H, s), 1.03 (6H, s), 1.02 (6H, t, J 7.1 Hz). LCMS (ES+) 302.1 (M-NEt$_2$)$^+$.

Example 32

5,5-Dimethyl-3-(3-hydroxy-3-methylbut-1-yn-1-yl)-2-(morpholin-4-yl)-5,6-dihydro-1-benzothiophen-7(4H)-one The title compound was prepared from Example 17 and 2-methylbut-3-yn-2-ol according to Method C and was isolated as a pale yellow powder (77%). $\delta_H$ (DMSO-d$_6$) 5.42 (1H, s), 3.74 (4H, m), 3.55 (4H, m), 2.57 (2H, s), 2.33 (2H, s), 1.44 (6H, s), 1.03 (6H, s). LCMS (ES+) 348.1 (M+H)$^+$.

Example 33

5,5-Dimethyl-3-[(3-hydroxy-1-azabicyclo[2.2.2]oct-3-yl)ethyl]-2-(morpholin-4-yl)-5,6-dihydro-1-benzothiophen-7(4H)-one The title compound was prepared from Example 17 and 3-ethynylquinuclidin-3-ol according to Method C and was isolated as a pale yellow powder (86%). $\delta_H$ (CD$_3$OD) 3.84 (4H, m), 3.66 (4H, m), 3.19 (1H, d, J 14.0 Hz), 3.01 (1H, d, J 14.0 Hz), 2.88-2.79 (4H, m), 2.70 (2H, s), 2.40 (2H, s), 2.10-1.95 (3H, m), 1.81 (1H, m), 1.57-1.51 (1H, m), 1.11 (6H, s). Exchangeable proton not observed. LCMS (ES+) 415.1 (M+H)$^+$.

Example 34

5,5-Dimethyl-3-[3-(4-methylpiperazin-1-yl)prop-1-yn-1-yl]-2-(morpholin-4-yl)-5,6-dihydro-1-benzothiophen-7(4H)-one The title compound was prepared from Example 17 and 1-methyl-4-(prop-2-yn-1-yl)piperazine according to Method C and was isolated as a yellow powder (96%). $\delta_H$ (DMSO-d$_6$) 3.74 (4H, m), 3.56 (4H, m), 3.53 (2H, s), 2.59 (2H, s), 2.33 (2H, s), 1.03 (6H, s). LCMS (ES+) 402.2 (M+H)$^+$.

Example 35

N-{3-[5,5-Dimethyl-2-(morpholin-4-yl)-7-oxo-4,5,6,1-tetrahydro-1-benzothien-3-yl]prop-2-yn-1-yl}methanesulfonamide The title compound was prepared from Example 17 and N-(prop-2-yn-1-yl)methanesulfonamide according to Method C and was isolated as a tan powder (65%). $\delta_H$ (DMSO-d$_6$) 7.61 (1H, br, s), 4.09 (2H, s), 3.73 (4H, m), 3.56 (4H, m), 2.99 (3H, s), 2.60 (2H, s), 2.32 (2H, s), 1.03 (6H, s). LCMS (ES+) 397.0 (M+H)$^+$.

Example 36

3-[3-(3,4-Dihydroisoquinolin-2(1H)-yl]-5,5-dimethyl-2-morpholin-4-yl)-5,6-dihydro-1-benzothiophen-7(4H)-one The title compound was prepared from Example 17 and 2-(prop-2-yn-1-yl)-1,2,3,4-tetrahydroisoquinoline according to Method C and was isolated as a tan powder (95%). $\delta_H$ (DMSO-d$_6$) 7.14-7.07 (4H, m), 3.74 (2H, s), 3.72 (4H, m), 3.70 (2H, s), 3.55 (4H, m), 2.85 (2H, m), 2.77 (2H, m), 2.61 (2H, s), 2.32 (2H, s), 1.02 (6H, s). LCMS (ES+) 435.2 (M+H)$^+$.

Example 37

5,5-Dimethyl-3-[(3-hydroxyphenyl)ethyl]-2-(morpholin-4-yl)-5,6-dihydro-1-benzothiophen-7(4H)-one The title compound was prepared from Example 17 and 3-ethynylphenol according to Method C and was isolated as a white powder (86%). $\delta_H$ (DMSO-d$_6$) 9.66 (1H, br. s), 7.21 (1H, t, J 7.8 Hz), 6.90 (1H, d, J 7.5 Hz), 6.85 (1H, s), 6.79 (1H, d, J 8.0 Hz), 3.78 (4H, m), 3.69 (4H, m), 2.68 (2H, m), 2.36 (2H, s), 1.06 (6H, s). LCMS (ES+) 382.1 (M+H)$^+$.

Example 38

5,5-Dimethyl-3-ethynyl-2-(morpholin-4-yl)-5,6-dihydro-1-benzothiophen-7(4H)-one

A stirred solution of Example 26 (0.39 g, 0.96 mmol) in MeOH (12 mL) at 45° C. was treated with finely powdered K$_2$CO$_3$ (0.70 g, 5.07 mmol). After stirring for 50 minutes, the reaction mixture was cooled to r.t., diluted with Et$_2$O (50 mL) and filtered. The filtrate was washed with water (3×20 mL), dried (MgSO$_4$), filtered and concentrated in vacuo at r.t. The residual solid was purified by column chromatography (SiO$_2$, 1:1 EtOAc/hexanes) to give the title compound (0.27 g, 98%) as a pale grey powder. $\delta_H$ (DMSO-d$_6$) 4.52 (1H, s), 3.74 (4H, m), 3.57 (4H, m), 2.60 (2H, s), 2.33 (2H, s), 1.03 (6H, s). LCMS (ES+) 290.1 (M+H)$^+$.

Example 39

(Method D)

5,5-Dimethyl-3-[(4-hydroxyphenyl)ethynyl]-2-(morpholin-4-yl)-5,6-dihydro-1-benzothiophen-7(4H)-one To a stirred solution of Example 38 (0.10 g, 0.35 mmol) and 4-iodophenol (0.11 g, 0.52 mmol) in diisopropylamine (7 mL) at 60° C. was added Pd(PPh$_3$)$_2$Cl$_2$ (0.02 g, 0.03 mmol) followed by CuI (0.01 g, 0.05 mmol). After stirring for 50 minutes, the reaction mixture was concentrated in vacuo and the resulting residue was diluted with EtOAc (25 mL). The organics were then washed with sat. aqueous NaHCO$_3$ (10 mL), dried (MgSO$_4$), filtered and concentrated in vacuo. Purification by column chromatography (SiO$_2$, 3:1 EtOAc/hexanes) gave the title compound (0.11 g, 85%) as an off-white powder. $\delta_H$ (DMSO-d$_6$) 9.89 (1H, br. s), 7.31 (2H, d, J 8.2

Hz), 6.79 (2H, d, J 8.2 Hz), 3.78 (4H, m), 3.68 (4H, m), 2.67 (2H, s), 2.35 (2H, s), 1.06 (6H, s). LCMS (ES−) 380.4 (M−H)−.

Example 40

3-[(2-Aminopyrimidin-5-yl)ethynyl]-5,5-dimethyl-2-(morpholin-4-yl)-5,6-dihydro-1-benzothiophen-7(4H)-one The title compound was prepared from Example 38 and 2-amino-5-iodopyrimidine according to Method D and was isolated as a pale yellow powder (77%). $\delta_H$ (DMSO-$d_6$) 8.39 (2H, s), 7.12 (2H, br. s), 3.77 (4H, m), 3.60 (4H, m), 2.66 (2H, s), 2.34 (2H, s), 1.05 (6H, s). LCMS (ES+) 383.1 (M+H)+.

Example 41

5,5-Dimethyl-3-[(1-methyl-1H-imidazol-4-yl)ethynyl]-2-(morpholin-4-yl)-5,6-dihydro-1-benzothiophen-7(4H)-one The title compound was prepared from Example 38 and 4-iodo-1-methyl-1H-imidazole according to Method D and was isolated as a pale yellow powder (84%). $\delta_H$ (DMSO-$d_6$) 7.65 (1H, s), 7.50 (1H, s), 3.75 (4H, m), 3.65 (3H, s), 3.58 (4H, m), 2.62 (2H, s), 2.35 (2H, s), 1.05 (6H, s). LCMS (ES+) 370.1 (M+H)+.

Example 42

5,5-Dimethyl-2-(morpholin-4-yl)-3-(pyridin-4-yl-ethynyl)-5,6-dihydro-1-benzothiophen-7(4H)-one The title compound was prepared from Example 38 and 4-iodopyridine according to Method D and was isolated as a pale yellow powder (64%). $\delta_H$ (DMSO-$d_6$) 8.71 (2H, br. s), 7.52 (2H, br. s), 3.80 (4H, m), 3.68 (4H, m), 2.70 (2H, s), 2.36 (2H, s), 1.07 (6H, s). LCMS (ES+) 367.1 (M+H)+.

Example 43

5,5-Dimethyl-3-(imidazo[1,2-a]pyridin-6-ylethynyl)-2-(morpholin-4-yl)-5,6-dihydro-1-benzothiophen-7(4H)-one The title compound was prepared from Example 38 and 6-iodoimidazo[1,2-a]pyridine according to Method D and was isolated as a pale yellow powder (64%). $\delta_H$ (DMSO-$d_6$) 8.88 (1H, s), 7.96 (1H, s), 7.64 (1H, s), 7.60 (1H, d, J 9.3 Hz), 7.27 (1H, d, J 9.3 Hz), 3.80 (4H, m), 3.65 (4H, m), 2.71 (2H, s), 2.36 (2H, s), 1.08 (6H, s). LCMS (ES+) 406.0 (M+14)+.

Example 44

3-({3-[(Dimethylamino)methyl]imidazo[1,2-a]pyridin-6-yl}ethynyl)-5,5-dimethyl-2-(morpholin-4-yl)-5,6-dihydro-1-benzothiophen-7(4H)-one The title compound was prepared from Example 38 and Intermediate 13 according to Method D and was isolated as a yellow powder (72%). $\delta_H$ (DMSO-$d_6$) 8.59 (1H, s), 7.60 (1H, d, J 9.2 Hz), 7.55 (1H, s), 7.30 (1H, dd, J 9.2 and 1.6 Hz), 3.81 (4H, m), 3.77 (4H, m), 3.65 (4H, m), 2.72 (2H, s), 2.37 (2H, s), 2.17 (6H, s), 1.08 (6H, s). LCMS (ES+) 463.1 (M+H)+.

Example 45

3-[(6-{[2-(Dimethylamino)ethyl]amino}pyridin-3-yl)ethynyl]-5,5-dimethyl-2-(morpholin-4-yl)-5,6-dihydro-1-benzothiophen-7(4H)-one The title compound was prepared from Example 38 and intermediate 14 according to Method D and was isolated as a yellow powder (64%). $\delta_H$ (DMSO-$d_6$) 8.13 (1H, s), 7.43 (1H, dd, J 8.6 and 1.9 Hz), 6.85 (1H, s), 6.52 (1H, d, J 8.6 Hz), 3.77 (4H, m), 3.61 (4H, m), 3.36 (2H, m), 2.65 (2H, s), 2.40 (2H, t, J 6.5 Hz), 2.34 (2H, s), 2.18 (6H, s), 1.05 (6H, s). LCMS (ES+) 453.2 (M+H)+.

Example 46

3-[(6-Chloropyridin-3-yl)ethynyl]-5,5-dimethyl-2-(morpholin-4-yl)-5,6-dihydro-1-benzothiophen-7(4H)-one The title compound was prepared from Example 38 and 2-chloro-5-iodopyridine according to Method D and was isolated as a yellow powder (44%). $\delta_H$ (DMSO-$d_6$) 8.57 (1H, d, J 2.2 Hz), 7.99 (1H, dd, J 8.3 and 2.2 Hz), 7.58 (1H, d, J 8.3 Hz), 3.77 (4H, m), 3.65 (4H, m), 2.70 (2H, s), 2.36 (2H, s), 1.07 (6H, s). LCMS (ES+) 401.0 (M+H)+.

Example 47

5,5-Dimethyl-2-(morpholin-4-yl)-3-(1H-pyrazol-4-ylethynyl)-5,6-dihydro-1-benzothiophen-7(4H)-one The title compound was prepared from Example 38 and 4-iodo-1H-pyrazole according to Method D and was isolated as a yellow powder (33%). $\delta_H$ (DMSO-$d_6$) 13.18 (1H, br. s), 8.10 (1H, s), 7.70 (1H, s), 3.76 (4H, m), 3.58 (4H, m), 2.64 (2H, s), 2.34 (2H, s), 1.05 (6H, s). LCMS (ES+) 354.4 (M−H)+.

Example 48

5,5-Dimethyl-3-({6-[(2S)-2-(hydroxymethyl)pyrrolidin-1-yl]pyridin-3-yl}ethynyl)-2-(morpholin-4-yl)-5,6-dihydro-1-benzothiophen-7(4H)-one The title compound was prepared from Example 38 and Intermediate 15 according to Method D and was isolated as a pale yellow powder (32%). $\delta_H$ (DMSO-$d_6$) 8.16 (1H, d, J 2.2 Hz), 7.52 (1H, dd, J 8.3 and 2.2 Hz), 6.47 (1H, d, J 8.3 Hz), 4.77 (1H, t, J 5.6 Hz), 4.00 (1H, br. m), 3.72 (4H, m), 3.55 (4H, m), 3.52 (1H, m), 3.49 (1H, m), 3.24 (2H, m), 2.61 (2H, s), 2.30 (2H, s), 1.98-1.82 (4H, m), 1.01 (6H, s). LCMS (ES+) 466.0 (M+H)+.

Example 49

(Method G)

5,5-Dimethyl-2-(morpholin-4-yl)-5,6-dihydrothieno[2,3-c]pyridin-7(4H)-one

To a stirred solution of Intermediate 18 (0.86 g, 2.50 mmol) in THF (9 mL) and water (8 mL) at r.t. was added LiOH (0.16 g, 3.80 mmol). The reaction mixture was then heated at 60° C. for 48 h before it was cooled and concentrated in vacuo. To the residue was added aqueous 2M HCl (8 mL) and the reaction mixture was stirred at r.t. for 6 h before it was cooled and basified to pH 10 by the addition of aqueous sat. Na₂CO₃. The resulting solid was filtered and dried to give the title compound as a white powder (0.52 g, 80%). δ$_H$ (DMSO-d₆) 7.56 (1H, s), 6.08 (1H, s), 3.72 (4H, br. m) 3.15 (4H, m), 2.64 (2H, s), 1.22 (6H, s). LCMS (ES+) 267.0 (M+H)⁺.

Example 50

5,5-Dimethyl-2-(morpholin-4-yl)-3-(phenylethynyl)-5,6-dihydrothieno[2,3-c]pyridin-7(4H)-one To a stirred solution of Intermediate 19 (0.070 g, 0.180 mmol) in DMF (3 mL) and diisopropylamine (1 mL) was added phenylacetylene (0.093 g, 0.100 mL, 0.911 mmol), Pd(PPh₃)₂Cl₂ (0.009 g, 0.011 mmol) and CuI (0.004 g, 0.022 mmol). The reaction mixture was then heated to 90° C. for 2 h before it was cooled and partitioned between EtOAc (20 mL) and water (20 mL). The organics were separated, washed with water (3×20 mL) and brine (20 mL), dried (Na₂SO₄), filtered and concentrated in vacuo. The resultant crude solid was washed sequentially with Et₂O, EtOAc and Et₂O to give the title compound as a pale grey solid (0.030 g, 44%). δ$_H$ (DMSO-d₆) 7.49-7.40 (6H, m), 3.80 (4H, m), 3.50 (4H, m), 2.74 (2H, s), 1.28 (6H, s). LCMS (ES+) 367.0 (M+H)⁺.

Example 51

5,5-Dimethyl-2-(morpholin-4-yl)-4,5,6,7-tetrahydro-8H-thieno[2,3-c]azepin-8-one

The title compound was prepared from Intermediate 22 according to Method G and was isolated as a white solid (95%). δ$_H$ (DMSO-d₆) 7.53 (1H, t, J 5.0 Hz) 5.98 (1H, s), 3.70 (4H, m), 3.10 (4H, m), 2.87 (2H, d, J 5.0 Hz), 2.57 (2H, s), 0.95 (6H, s). LCMS (ES+) 281.0 (M+H)⁺.

Example 52

5,5-Dimethyl-3-iodo-2-(morpholin-4-yl)-4,5,6,7-tetrahydro-8H-thieno[2,3-c]azepin-8-one The title compound was prepared from Example 51 according to Method H and was isolated as a white solid (48%). δ$_H$ (DMSO-d₆) 8.02 (1H, t, J 5.0 Hz), 3.73 (4H, m), 3.03 (4H, m), 2.85 (2H, d, J 5.2 Hz), 2.58 (2H, s), 0.98 (6H, s). LCMS (ES+) 407.0 (M+H)⁺.

Example 53

5,5-Dimethyl-2-(morpholin-4-yl)-3-(phenylethynyl)-4,5,6,7-tetrahydro-8H-thieno[2,3-e]azepin-8-one To a stirred suspension of Example 52 (0.60 g, 1.50 mmol) in diisopropylamine (12 mL) at r.t. was added phenylacetylene (0.41 g, 0.45 mL, 4.10 mmol), Pd(PPh₃)₂Cl₂ (0.05 g, 0.08 mmol) and CuI (0.04 g, 0.20 mmol), and the reaction mixture was heated to 60° C. for 12 h. The reaction mixture was then cooled, filtered and washed with EtOAc and Et₂O to give a mixture of Example 52 and the title compound. The crude mixture was re-suspended in diisopropylamine (15 mL) and treated with phenylacetylene (1.37 g, 1.50 mL, 13.67 mmol), Pd(PPh₃)₂Cl₂ (0.07 g, 0.11 mmol) and CuI (0.06 g, 0.28 mmol) prior to heating to 65° C. for a further 60 h. The reaction mixture was then cooled, filtered and washed sequentially with water, EtOAc, water, Et₂O and DCM to give the title compound as an off-white powder (0.15 g, 27%). δ$_H$ (DMSO-d₆) 7.83 (1H, t, J 4.7 Hz) 7.47-7.38 (5H, m), 3.79 (4H, m), 3.47 (4H, m), 2.89 (2H, d, J 5.0 Hz), 2.69 (2H, s), 0.98 (6H, s). LCMS (ES+) 381.0 (M+H)⁺.

Example 54

3-(Biphenyl-3-yl)-5,5-dimethyl-2-(morpholin-4-yl)-5,6-dihydro-1-benzothiophen-7(4H)-one To a stirred solution of Example 16 (0.065 g, 0.190 mmol) in DME (2 mL) and water (0.5 mL) was added Pd(OAc)₂ (0.003 g, 0.011 mmol), 1,3-bis(diphenylphosphino)-propane (0.010 g, 0.024 mmol), K₃PO₄ (0.134 g, 0.630 mmol) and 3-biphenylboronic acid (0.081 g, 0.410 mmol). The reaction mixture was then heated to 80° C. for 19 h before it was quenched with sat. aqueous NaHCO₃ solution (20 mL) and extracted with EtOAc (2×20 mL). The combined organic phases were dried (MgSO₄), filtered and concentrated in vacuo. Purification by column chromatography (SiO₂, 0-30% EtOAc/heptane) gave the title compound (0.056 g, 71%) as a beige powder. δ$_H$(CDCl₃) 7.65-7.30 (9H, m), 3.68-3.61 (4H, m), 3.05-2.98 (4H, m), 2.51 (2H, s), 2.44 (2H, s), 1.05 (6H, s). LCMS (ES+) 418.3 (M+H)⁺.

Example 55

5,5-Dimethyl-2-(morpholin-4-yl)-3-(3-phenylisoxazol-5-yl)-5,6-dihydro-1-benzothiophen-7(4H)-one To a degassed, stirred solution of Example 16 (0.098 g, 0.285 mmol), 3-phenylisoxazol-5-ylboronic acid (0.108 g, 0.571 mmol) and aqueous KOH (0.048 g, 0.855 mmol in 1 mL) in THF (4 mL) was added Pd(PPh₃)₄ (0.033 g, 0.029 mmol) and the reaction mixture was heated at 65° C. for 12 h. Further 3-phenylisoxazol-5-ylboronic acid (0.055 g, 0.290 mmol) was added and the reaction mixture was heated for a further 12 h at 85° C. The reaction was then quenched with sat. aqueous NaHCO₃ solution (20 mL) and extracted with ethyl acetate (2×20 mL). The combined organic phases were dried (MgSO₄), filtered and concentrated in vacuo. Purification by column chromatography (SiO₂, 0-30% EtOAc/heptane) gave the title compound (0.030 g, 26%) as a white powder. δ$_H$ (DMSO-d₆) 7.99-7.94 (2H, m), 7.58-7.52 (3H, m), 7.28 (1H, s), 3.76-3.70 (4H, m), 3.13-3.06 (4H, m), 2.69 (2H, s), 2.40 (2H, s), 1.04 (6H, s). LCMS (ES+) 409.3 (M+H)⁺.

Example 56

5,5-Dimethyl-2-(morpholin-4-yl)-7-oxo-4,5,6,7-tetrahydro-1-benzothiophene-3-carboxylic Acid To a stirred solution of Example 104 (0.82 g, 2.54 mmol) in a mixture of MeOH (5 mL), water (1 mL) and THF (5 mL) was added LiOH (0.16 g, 3.81 mmol). After stirring at r.t. for 5 days, the reaction mixture was concentrated in vacuo to give a beige solid which was dissolved in aqueous 1M HCl and extracted with EtOAc (3×25 mL). The combined organics were dried over MgSO₄, filtered and concentrated in vacuo to give the title compound (0.68 g, 87%) as a yellow solid. δ$_H$ (DMSO-d₆) 12.85 (1H, br. s), 3.75-3.70 (4H, m), 3.30-3.25 (4H, m), 2.80 (2H, s), 2.35 (2H, s), 1.00 (6H, s). LCMS (ES+) 310.0 (M+H)⁺.

Example 57

(Method I)

5,5-Dimethyl-2-(morpholin-4-yl)-7-oxo-N-[phenyl(pyridin-2-yl)methyl]-4,5,6,7-tetrahydro-1-benzothiophene-3-carboxamide To a stirred solution of Example 56 (0.084 g, 0.272 mmol) in DCM (10 mL), was added EDC (0.063 g, 0.330 mmol), NEt$_3$ (0.080 g, 0.110 mL, 0.790 mmol), and phenyl(2-pyridyl)methylamine.HCl (0.072 g, 0.330 mmol). The reaction mixture was then stirred at r.t. for 12 h before it was concentrated in vacuo. Purification by column chromatography (SiO$_2$, 0-100% EtOAc/heptane) gave the title compound (0.017 g, 13%) as a yellow solid. $\delta_H$ (CD$_3$OD) 8.65-8.60 (1H, m), 7.85-7.80 (1H, m), 7.50-7.30 (7H, m), 6.40 (1H, s), 3.60-3.55 (4H, m), 3.20-3.15 (4H, m), 2.70 (2H, s), 2.40 (2H, s), 1.10 (6H, s). Exchangeable proton not observed. LCMS (ES+) 476.0 (M+H)$^+$.

Example 58

N-Benzyl-5,5-dimethyl-2-morpholin-4-yl-tetrahydro-1-benzothiophene-3-carboxamide The title compound was prepared from Example 56 and benzylamine according to Method I and was isolated as an off-white solid (26%) after purification by column chromatography (SiO$_2$, 0-100% EtOAc/heptane). $\delta_H$ (CDCl$_3$) 7.75 (1H, br. s), 7.40-7.30 (5H, m), 4.60 (2H, d, J 5.7 Hz), 3.45-3.40 (4H, m), 3.05 (2H, s), 3.00-2.95 (4H, m), 2.45 (2H, s), 1.10 (6H, s). LCMS (ES+) 399.0 (M+H)$^+$.

Example 59

5,5-Dimethyl-2-(morpholin-4-yl)-7-oxo-N-(pyridin-2-ylmethyl)-4,5,6,7-tetrahydro-1-benzothiophene-3-carboxamide The title compound was prepared from Example 56 and 2-(aminomethyl)pyridine according to Method I and was isolated as a beige solid (34%) after purification by column chromatography (SiO$_2$, 0-100% EtOAc/heptane). $\delta_H$ (CDCl$_3$) 8.70 (1H, br. s), 8.60 (1H, d, J 4.8 Hz), 7.75-7.65 (1H, m), 7.35-7.30 (1H, d, J 7.8 Hz), 7.25-7.20 (1H, m), 4.70 (2H, d, J 4.8 Hz), 3.85-3.78 (4H, m), 3.15-3.10 (4H, m), 3.00 (2H, s), 2.45 (2H, s), 1.10 (6H, s). LCMS (ES+) 400.0 (M+H)$^+$.

Example 60

5,5-Dimethyl-2-(morpholin-4-yl)-7-oxo-N-(pyridin-4-ylmethyl)-4,5,6,7-tetrahydro-1-benzothiophene-3-carboxamide The title compound was prepared from Example 56 and 4-(aminomethyl)pyridine according to Method I and was isolated as a yellow solid (30%) after purification by preparative HPLC (pH 2.5). $\delta_H$ (DMSO-d$_6$) 8.95-8.90 (1H, m), 8.54 (2H, d, J 5.8 Hz), 7.32 (2H, d, J 6.0 Hz), 4.42 (2H, d, J 6.0 Hz), 3.65-3.60 (4H, m), 3.15-3.10 (4H, m), 2.60 (2H, s), 2.35 (2H, s), 1.00 (6H, s). LCMS (ES+) 400.0 (M+H)$^+$.

Example 61

5,5-Dimethyl-N-ethyl-2-(morpholin-4-yl)-7-oxo-N-(pyridin-4-ylmethyl)-4,5,6,7-tetrahydro-1-benzothiophene-3-carboxamide The title compound was prepared from Example 56 and N-(4-pyridylmethyl)-ethylamine according to Method I and was isolated as a yellow solid (30%) after purification by preparative HPLC (pH 5.8). $\delta_H$ (DMSO-d$_6$) 8.57 (1H, d, J 6.0 Hz), 8.49 (1H, d, J 5.8 Hz), 7.38 (1H, d, J 5.8 Hz), 7.11 (1H, d, J 6.0 Hz), 4.50-4.45 (2H, m), 3.80-3.70 (2H, m), 3.60-3.50 (2H, m), 3.45-3.40 (2H, m), 3.20-3.05 (4H, m), 2.40-2.10 (4H, m), 1.15-0.95 (9H, m). LCMS (ES+) 428.0 (M+H)$^+$.

Example 62

5,5-Dimethyl-2-(morpholin-4-yl)-7-oxo-4,5,6,7-tetrahydrothieno[2,3-c]pyridine-3-carboxylic Acid To a stirred solution of Intermediate 18 (1.00 g, 2.96 mmol) in THF (120 mL) was added LiOH (0.19 g, 4.40 mmol) in water (30 mL) and the reaction mixture was stirred at r.t. for 3 days. A further portion of LiOH (0.19 g, 4.40 mmol) in water (30 mL) was added and stirring continued for a further 3 days. Removal of the solvent in vacuo and addition of aqueous 2M HCl led to a thick yellow precipitate which was filtered, washed with water and dried to give the title compound (0.80 g, 87%) as a pale yellow powder. $\delta_H$ (DMSO-d$_6$) 12.67 (1H, br. s), 7.54 (1H, s), 3.78-3.69 (4H, m), 3.23-3.14 (4H, m), 2.91 (2H, s), 1.25 (6H, s). LCMS (ES+) 311.1 (M+H)$^+$.

Example 63

5,5-Dimethyl-2-(morpholin-4-yl)-7-oxo-N-[phenyl(pyridin-2-yl)methyl]-4,5,6,7-tetrahydrothieno[2,3-c]pyridine-3-carboxamide The title compound was prepared from Example 62 and phenyl(2-pyridyl)methylamine hydrochloride according to Method I and was isolated as a pink solid (100%). $\delta_H$ (DMSO-d$_6$) 9.78 (1H, d, J 7.3 Hz), 8.66 (1H, d, J 4.7 Hz), 7.90-7.83 (1H, m), 7.68 (1H, s), 7.58 (1H, d, J 7.7 Hz), 7.48-7.25 (6H, m), 6.33 (1H, d, J 7.3 Hz), 3.78-3.64 (4H, m), 3.10-3.03 (4H, m), 2.94 (2H, s), 1.25 (6H, s). LCMS (ES+) 477.0 (M+H)$^+$.

Example 64

(Method J)

Methyl 4-[5,5-dimethyl-2-(morpholin-4-yl)-7-oxo-4,5,6,7-tetrahydro-1-benzothien-3-yl]benzoate To a stirred solution of Example 17 (0.050 g, 0.128 mmol), 4-(methoxycarbonyl-phenyl)boronic acid (0.023 g, 0.128 mmol) and K$_3$PO$_4$ (0.035 g, 0.165 mmol) in a mixture of DME (1.5 mL) and water (0.5 mL) was added Pd(PPh$_3$)$_4$ (0.020 g, 0.017 mmol) and the reaction mixture was heated to 120° C. in a sealed tube, under microwave irradiation, for 40 minutes. The crude reaction mixture was then concentrated in vacuo and purification by column chromatography (SiO$_2$, 0-100% EtOAc/heptane) gave the title compound (0.028 g, 53%) as a pale brown solid. $\delta_H$ (DMSO-d$_6$) 8.04 (2H, m), 7.57

(2H, m), 3.88 (3H, s), 3.57 (4H, m), 2.91 (4H, m), 2.51 (2H, s), 2.37 (2H, s), 0.98 (6H, s). LCMS (ES+) 400.2 (M+H)$^+$.

Example 65

N-{4-[5,5-Dimethyl-2-(morpholin-4-yl)-7-oxo-4,5,6, 7-tetrahydro-1-benzothien-3-yl]phenyl}acetamide The title compound was prepared from Example 17 and 4-(4,4,5,5-tetramethyl-1,3,2-dioxaborolan-2-yl)acetanilide according to Method J and was isolated as a white solid (58%) after purification by column chromatography (SiO$_2$, 0-100% EtOAc/heptane). $\delta_H$ (CD$_3$OD) 7.66 (2H, m), 7.33 (2H, m), 3.65 (4H, m), 3.03 (4H, m), 2.51 (2H, s), 2.43 (2H, s), 2.16 (3H, s), 1.03 (6H, s). Exchangeable proton not observed. LCMS (ES+) 399.3 (M+H)$^+$.

Example 66

Ethyl 3-[5,5-dimethyl-2-(morpholin-4-yl)-7-oxo-4,5, 6,7-tetrahydro-1-benzothien-3-yl]benzoate The title compound was prepared from Example 17 and ethyl 3-(4,4,5,5-tetramethyl-1,3,2-dioxaborolan-2-yl)benzoate according to Method J and was isolated as a pale brown solid (11%) after purification by column chromatography (SiO$_2$, 0-100% EtOAc/heptane). $\delta_H$ (CD$_3$OD) 8.09 (1H, s), 8.08 (1H, m), 7.64 (2H, m), 4.42 (2H, q, J 7.1 Hz), 3.64 (4H, m), 3.02 (4H, m), 2.53 (2H, s), 2.46 (2H, s), 1.42 (3H, t, J 7.1 Hz) 1.04 (6H, s). LCMS (ES+) 414.2 (M+H)$^+$.

Example 67

Tert-Butyl 4-{3-[5,5-dimethyl-2-(morpholin-4-yl)-7-oxo-4,5,6,7-tetrahydro-1-benzothien-3-yl] phenyl}piperazine-1-carboxylate The title compound was prepared from Example 17 and 3-[4-(tert-butoxycarbonyl)piperazin-1-yl]phenylboronic acid pinacol ester according to Method J and was isolated as a white solid (89%) after purification by column chromatography (SiO$_2$, 0-100% EtOAc/heptane). $\delta_H$ (DMSO-d$_6$) 7.34 (1H, m), 6.98 (2H, m), 6.83 (1H, d, J 7.5 Hz), 3.60 (8H, m), 3.16 (4H, m), 3.01 (4H, m), 2.49 (2H, s), 2.41 (2H, s), 1.47 (9H, s), 1.01 (6H, s). LCMS (ES+) 526.2 (M+H)$^+$.

Example 68

5,5-Dimethyl-2-(morpholin-4-yl)-3-[3-(morpholin-4-yl)phenyl]-5,6-dihydro-1-benzothiophen-7(4H)-one The title compound was prepared from Example 17 and 3-morpholinophenyl-boronic acid pinacol ester according to Method J and was isolated as an off-white solid (38%) after purification by preparative HPLC (pH 2.5). $\delta_H$ (CD$_3$OD) 7.36 (1H, t, J 8.0 Hz), 7.04-6.94 (2H, m), 6.86 (1H, d, J 8.0 Hz), 3.90-3.84 (4H, m), 3.68-3.62 (4H, m), 3.22-3.16 (4H, m), 3.08-3.02 (4H, m), 2.52 (2H, s), 2.44 (2H, s), 1.04 (6H, s). LCMS (ES+) 427.3 (M+H)$^+$.

Example 69

3-[3-(Aminomethyl)phenyl]-5,5-dimethyl-2-(morpholin-4-yl)-5,6-dihydro-1-benzothiophen-7(4H)-one, Formic Acid Salt The title compound was prepared from Example 17 and 3-(aminomethyl)-phenylboronic acid according to Method J and was isolated as a yellow gum (31%) after purification by preparative HPLC (pH 2.5). $\delta_H$ (CD$_3$OD) 8.44 (1H, s), 7.66-7.44 (4H, m), 4.22 (2H, s), 3.70-3.60 (4H, m), 3.10-2.98 (4H, m), 2.52 (2H, s), 2.48 (2H, s), 1.04 (6H, s). LCMS (ES+) 371.2 (M+H)$^+$.

Example 70

5,5-Dimethyl-2-(morpholin-4-yl)-3-[3-(piperidin-1-ylmethyl)phenyl]-5,6-dihydro-1-benzothiophen-7 (4H)-one, Formic Acid Salt The title compound was prepared from Example 17 and 3-(piperidinomethyl)-phenylboronic acid pinacol ester according to Method J and was isolated as a yellow gum (14%) after purification by preparative HPLC (pH 2.5). $\delta_H$ (CD$_3$OD) 8.44 (1H, s), 7.66-7.48 (4H, m), 4.32 (2H, s), 3.68-3.62 (4H, m), 3.30-3.12 (4H, m), 3.08-2.98 (4H, m), 2.56 (2H, s), 2.48 (2H, s), 1.94-1.80 (4H, m), 1.76-1.62 (2H, m), 1.04 (6H, s). LCMS (ES+) 439.2 (M+H)$^+$.

Example 71

{3-[5,5-Dimethyl-2-(morpholin-4-yl)-7-oxo-4,5,6,7-tetrahydro-1-benzothien-3-yl]phenyl}acetic Acid The title compound was prepared from Example 17 and 3-(pinacolboronyl)-phenylacetic acid according to Method J and was isolated as a yellow solid (35%) after purification by preparative HPLC (pH 2.5). $\delta_H$ (CD$_3$OD) 7.44 (1H, t, J 7.5 Hz), 7.36 (1H, s), 7.32-7.24 (2H, m) 3.68 (2H, s), 3.70-3.60 (4H, m), 3.08-2.98 (4H, m), 2.56 (2H, s), 2.46 (2H, s), 1.04 (6H, s). Exchangeable proton not observed. LCMS (ES+) 400.3 (M+H)$^+$.

Example 72

Ethyl 5-[5,5-dimethyl-2-(morpholin-4-yl)-7-oxo-4,5, 6,7-tetrahydro-1-benzothien-3-yl]nicotinate The title compound was prepared from Example 17 and 3-ethoxycarbonylpyridin-5-ylboronic acid pinacol ester according to Method J and was isolated as an off-white solid (47%) after purification by column chromatography (SiO$_2$, 0-100% EtOAc/heptane) followed by preparative HPLC (pH 2.5). $\delta_H$(DMSO-d$_6$) 9.05 (1H, s), 8.84 (1H, s), 8.38-8.34 (1H, m), 4.38 (2H, q, J 8.0 Hz), 3.59-3.53 (4H, m), 2.95-2.88 (4H, m), 2.53 (2H, s), 2.41 (2H, s), 1.34 (3H, t, J 8.0 Hz), 0.96 (6H, s). LCMS (ES+) 415.0 (M+H)$^+$.

Example 73

3-(2-Chloropyridin-4-yl)-5,5-dimethyl-2-(morpholin-4-yl)-5,6-dihydro-1-benzothiophen-7(4H)-one The title compound was prepared from Example 17 and 2-chloropyridin-4-ylboronic acid according to Method J and was isolated as an off-white solid (47%) after purification by preparative HPLC (pH 2.5). $\delta_H$ (DMSO-d$_6$) 8.50 (1H, s), 7.59 (1H, s), 7.49 (1H, d, J 6.0 Hz), 3.64-3.58 (4H, m), 2.96-2.92 (4H, m), 2.54 (2H, s), 2.38 (2H, s), 0.97 (6H, s). LCMS (ES+) 377.3 (M+H)$^+$.

Example 74

3-(5-Bromopyridin-3-yl)-5,5-dimethyl-2-(morpholin-4-yl)-5,6-dihydro-1-benzothiophen-7(4H)-one The title compound was prepared from Example 17 and 3-bromopyridin-5-ylboronic acid according to Method J and was isolated as an off-white solid (24%) after purification by preparative HPLC (pH 2.5). $\delta_H$ (DMSO-d$_6$) 8.59 (1H, d, J 3.0 Hz), 8.51 (1H, d, J 3.0 Hz), 8.16 (1H, t, J 3.0 Hz), 3.62-3.56 (4H, m), 2.94-2.91 (4H, m), 2.50 (2H, s), 2.37 (2H, s), 0.98 (6H, s). LCMS (ES+) 421.2 and 423.2 (M+H)$^+$.

Example 75

5,5-Dimethyl-2-(morpholin-4-yl)-3-(pyridin-3-yl)-5,6-dihydro-1-benzothiophen-7(4H)-one The title compound was prepared from Example 17 and 3-(4,4,5,5-tetramethyl-1,3,2-dioxaborolan-2-yl)pyridine according to Method J and was isolated as a beige solid (15%) after purification by preparative HPLC (pH 2.5). $\delta_H$ (DMSO-d$_6$) 9.05 (1H, s), 8.61 (1H, d, J 1.7 Hz), 7.88-7.82 (1H, m), 7.50 (1H, dd, J 7.7 and 4.8 Hz), 3.60-3.54 (4H, m), 2.94-2.87 (4H, m), 2.46 (2H, s), 2.37 (2H, s), 0.96 (6H, s). LCMS (ES+) 343.2 (M+H)$^+$.

Example 76

N-{3-[5,5-Dimethyl-2-(morpholin-4-yl)-7-oxo-4,5,6,7-tetrahydro-1-benzothien-3-yl]phenyl}acetamide The title compound was prepared from Example 17 and 3-acetamido-phenylboronic acid according to Method J and was isolated as a pale brown oil (27%) after purification by column chromatography (SiO$_2$, 0-100% EtOAc/heptane). $\delta_H$ (CD$_3$OD) 7.69 (1H, t, J 2.3 Hz), 7.53-7.48 (1H, m), 7.41 (1H, t, J 7.8 Hz), 7.13-7.09 (1H, m), 3.70-3.64 (4H, m), 3.05-3.00 (4H, m), 2.53 (2H, s), 2.43 (2H, s), 2.16 (3H, s), 1.04 (6H, s). Exchangeable proton not observed. LCMS (ES+) 399.0 (M+H)$^+$.

Example 77

3-(3-Aminophenyl)-5,5-dimethyl-2-(morpholin-4-yl)-5,6-dihydro-1-benzothiophen-7(4H)-one The title compound was prepared from Example 17 and 3-aminophenylboronic acid monohydrate according to Method J and was isolated as a brown solid (30%) after purification by preparative HPLC (pH 5.8). $\delta_H$ (CD$_3$OD) 7.19 (1H, t, J 8.1 Hz), 6.74-6.70 (2H, m), 6.65 (1H, d, J 7.5 Hz), 3.68-3.65 (4H, m), 3.09-3.05 (4H, m), 2.51 (2H, s), 2.42 (2H, s), 1.03 (6H, s). LCMS (ES+) 357.2 (M+H)$^+$.

Example 78

3-(4-Aminophenyl)-5,5-dimethyl-2-(morpholin-4-yl)-5,6-dihydro-1-benzothiophen-7(4H)-one The title compound was prepared from Example 17 and 4-aminophenylboronic acid monohydrate according to Method J and was isolated as a pale brown solid (16%) after purification by preparative HPLC (pH 2.5). $\delta_H$ (CD$_3$OD) 7.09 (2H, d, J 8.5 Hz), 6.81 (2H, d, J 8.5 Hz), 3.68-3.63 (4H, m), 3.07-3.03 (4H, m), 2.50 (2H, s), 2.42 (2H, s), 1.03 (6H, s). Exchangeable protons not observed. LCMS (ES+) 357.2 (M+H)$^+$.

Example 79

3-(3-Acetylphenyl)-5,5-dimethyl-2-(morpholin-4-yl)-5,6-dihydro-1-benzothiophen-7(4H)-one The title compound was prepared from Example 17 and 3-acetylphenylboronic acid according to Method J and was isolated as an off-white solid (73%) after purification by column chromatography (SiO$_2$, 0-100% EtOAc/heptane). $\delta_H$ (CD$_3$OD) 8.04-8.00 (2H, m), 7.69-7.62 (2H, m), 3.66-3.62 (4H, m), 3.04-2.99 (4H, m), 2.66 (3H, s), 2.53 (2H, s), 2.46 (2H, s), 1.04 (6H, s). LCMS (ES+) 384.2 (M+H)$^+$.

Example 80

3-[5,5-Dimethyl-2-(morpholin-4-yl)-7-oxo-4,5,6,7-tetrahydro-1-benzothien-3-yl]-N-methylbenzamide The title compound was prepared from Example 17 and 3-(N-methylamino-carbonyl)phenylboronic acid according to Method J and was isolated as an off-white solid (73%) after purification by column chromatography (SiO$_2$, 0-100% EtOAc/heptane). $\delta_H$ (CD$_3$OD) 7.88-7.87 (1H, m), 7.85-7.80 (1H, m), 7.59-7.55 (2H, m), 3.65-3.60 (4H, m), 3.01-2.98 (4H, m), 2.95 (3H, s), 2.52 (2H, s), 2.43 (2H, s), 1.03 (6H, s). LCMS (ES+) 399.3 (M+H)$^+$.

Example 81

3-(Dibenzo[b,d]furan-4-yl)-5,5-dimethyl-2-(morpholin-4-yl)-5,6-dihydro-1-benzothiophen-7(4H)-one The title compound was prepared from Example 17 and dibenzofuran-4-boronic acid according to Method J and was isolated as a pale orange powder (41%) after purification by column chromatography (SiO$_2$, 0-30% EtOAc/heptane). $\delta_H$ (DMSO-d$_6$) 8.24-8.15 (2H, m), 7.73 (1H, m), 7.59-7.40 (4H, m), 3.50-3.36 (4H, m), 2.97-2.87 (4H, m), 2.44-2.29 (4H, m), 0.95 (3H, s), 0.92 (3H, s). LCMS (ES+) 432.2 (M+H)$^+$.

Example 82

5,5-Dimethyl-3-(4-methyl-2-phenyl-1,3-thiazol-5-yl)-2-(morpholin-4-yl)-5,6-dihydro-1-benzothiophen-7(4H)-one The title compound was prepared from Example 17 and 4-methyl-2-phenyl-5-(4,4,5,5-tetramethyl-1,3,2-dioxaborolan-2-yl)-1,3-thiazole according to Method J and was isolated as a white powder (33%) after purification by column chromatography (SiO$_2$, 0-30% EtOAc/heptane). $\delta_H$ (DMSO-d$_6$) 8.00-7.90 (2H, m), 7.56-7.45 (3H, m), 3.69-3.55 (4H, m), 3.15-3.01 (4H, m), 2.45-2.32 (4H, m), 2.27 (3H, s), 1.00 (6H, s). LCMS (ES+) 439.2 (M+H)$^+$.

Example 83

3-[4-(Benzyloxy)-3-chlorophenyl]-5,5-dimethyl-2-(morpholin-4-yl)-5,6-dihydro-1-benzothiophen-7(4B)-one The title compound was prepared from Example 17 and (4-benzyloxy-3-chloro-phenyl)boronic acid according to Method J and was isolated as an off-white solid (2%) after purification by preparative HPLC (pH 5.8). $\delta_H$ (DMSO-d$_6$) 7.54-7.31 (8H, m), 5.25 (2H, s), 3.61-3.53 (4H, m), 2.96-2.87 (4H, m), 2.48 (2H, s), 2.35 (2H, s), 0.97 (6H, s). LCMS (ES+) 482.2 and 484.1 (M+H)$^+$.

Example 84

Methyl 2-chloro-4-[5,5-dimethyl-2-(morpholin-4-yl)-7-oxo-4,5,6,7-tetrahydro-1-benzothien-3-yl]benzoate The title compound was prepared from Example 17 and (4-methoxycarbonyl-3-chlorophenyl)boronic acid according to Method J and was isolated as an off-white solid (71%) after purification by column chromatography (SiO$_2$, 0-100% EtOAc/heptane). $\delta_H$ (DMSO-d$_6$) 7.95 (1H, d, J 8.1 Hz), 7.62 (1H, d, J 1.5 Hz), 7.47 (1H, dd, J 8.1 and 1.6 Hz), 3.95 (3H, s), 3.72-3.65 (4H, m), 3.07-3.00 (4H, m), 2.56 (2H, s), 2.46 (2H, s), 1.04 (6H, s). LCMS (ES+) 434.2 and 436.2 (M+H)$^+$.

Example 85

3-[5,5-Dimethyl-2-(morpholin-4-yl)-7-oxo-4,5,6,7-tetrahydro-1-benzothien-3-yl]benzamide The title compound was prepared from Example 17 and (3-aminocarbonyl-phenyl)boronic acid according to Method J and was isolated as a brown solid (18%) after purification by preparative HPLC (pH 2.5). $\delta_H$ (CD$_3$OD) 7.97-7.85 (2H, m), 7.65-7.55 (2H, m), 3.70-3.59 (4H, m), 3.07-2.96 (4H, m), 2.53 (2H, s), 2.45 (2H, s), 1.04 (6H, s). Exchangeable protons not observed. LCMS (ES+) 385.2 (M+H)$^+$.

Example 86

5,5-Dimethyl-3-(4-hydroxyphenyl)-2-(morpholin-4-yl)-5,6-dihydro-1-benzothiophen-7(4H)-one The title compound was prepared from Example 17 and 4-hydroxyphenylboronic acid according to Method J and was isolated as a pale yellow solid (34%) after purification by preparative HPLC (pH 5.8). $\delta_H$ (DMSO-d$_6$) 9.60 (1H, s), 7.21-7.15 (2H, m), 6.87-6.80 (2H, m), 3.61-3.52 (4H, m), 2.95-2.86 (4H, m), 2.45 (2H, s), 2.34 (2H, s), 0.95 (6H, s). LCMS (ES+) 358.2 (M+H)$^+$.

Example 87

5-[5,5-Dimethyl-2-(morpholin-4-yl)-7-oxo-4,5,6,7-tetrahydro-1-benzothien-3-yl]nicotinic Acid To a stirred solution of Example 72 (0.056 g, 0.135 mmol) in EtOH (8 mL) and water (1 mL) was added LiOH (0.011 g, 0.270 mmol) and the reaction mixture was stirred at r.t. for 1.5 h. The solvent was then removed in vacuo and the residue was purified by preparative HPLC (pH 2.5) to give the title compound (0.028 g, 54%) as a beige solid. $\delta_H$ (DMSO-d$_6$) 9.12 (1H, m), 8.83 (1H, d, J 2.1 Hz), 8.29 (1H, t, J 2.0 Hz), 3.60-3.54 (4H, m), 2.94-2.89 (4H, m), 2.50 (2H, s), 2.39 (2H, s), 0.97 (6H, s). Exchangeable proton not observed. LCMS (ES+) 387.2 (M+H)$^+$.

Example 88

5,5-Dimethyl-2-(morpholin-4-yl)-3-[3-(piperazin-1-yl)phenyl]-5,6-dihydro-1-benzothiophen-7(4H)-one To a stirred solution of Example 67 (0.060 g, 0.114 mmol) in MeOH (20 mL) was added 2M HCl in Et$_2$O solution (1.000 mL, 2.000 mmol). After stirring for 12 h at r.t. the reaction mixture was concentrated in vacuo and purified by column chromatography (SiO$_2$, 0-10% MeOH/DCM) to give the title compound (0.034 g, 80%) as a yellow solid. $\delta_H$ (CD$_3$OD) 7.35 (1H, m), 7.00 (2H, m), 6.87 (1H, d, J 7.5 Hz), 3.59 (4H, m), 3.40 (4H, m), 3.33 (4H, m), 2.97 (4H, m), 2.45 (2H, s), 2.37 (2H, s), 0.97 (6H, s). Exchangeable proton not observed. LCMS (ES+) 426.3 (M+H)$^+$.

Example 89

(Method K)

5,5-Dimethyl-2-(morpholin-4-yl)-3-(2-phenylpyridin-4-yl)-5,6-dihydro-1-benzothiophen-7(4H)-one To a stirred solution of Example 17 (0.150 g, 0.384 mmol), Pd(PPh$_3$)$_4$ (0.050 g, 0.040 mmol) and K$_3$PO$_4$ (0.100 g, 0.470 mmol) in a mixture of water (1 mL) and DME (3 mL) was added 2-chloropyridin-4-ylboronic acid (0.060 g, 0.384 mmol) and the reaction mixture was heated to 120° C. in a sealed tube, under microwave irradiation, for 20 minutes. Phenylboronic acid (0.060 g, 0.492 mmol) was then added and the reaction mixture was heated again to 120° C. in a sealed tube, under microwave irradiation, for 30 minutes. The reaction mixture was concentrated in vacuo and purified by preparative HPLC (pH 2.5) to give the title compound (0.033 g, 21%) as an off-white solid. $\delta_H$ (DMSO-d$_6$) 8.75 (2H, d, J 4.9 Hz), 8.15 (1H, d, J 6.8 Hz), 8.06 (1H, s), 7.60-7.40 (4H, m), 3.63 (4H, m), 3.01 (4H, m), 2.62 (2H, s), 2.42 (2H, s), 1.01 (6H, s). LCMS (ES+) 419.0 (M+H)$^+$.

Example 90

5,5-Dimethyl-2-(morpholin-4-yl)-3-(5-phenylpyridin-3-yl)-5,6-dihydro-1-benzothiophen-7(4H)-one The title compound was prepared from Example 17, 3-bromopyridin-5-ylboronic acid and phenylboronic acid according to Method K and was isolated as a white solid (14%). $\delta_H$ (DMSO-d$_6$) 8.94 (1H, d, J 2.1 Hz), 8.64 (1H, d, J 1.9 Hz), 8.16 (1H, t, J 2.2 Hz), 7.84 (2H, d, J 7.2 Hz), 7.65-7.45 (3H, m), 3.61 (4H, m), 3.00 (4H, m), 2.59 (2H, s), 2.42 (2H, s), 1.02 (6H, s). LCMS (ES+) 419.0 (M+H)$^+$.

Example 91

3-(2,3'-Bipyridin-4-yl)-5,5-dimethyl-2-(morpholin-4-yl)-5,6-dihydro-1-benzothiophen-7(4H)-one The title compound was prepared from Example 17, 2-chloropyridin-4-ylboronic acid and 3-(4,4,5,5-tetramethyl-1,3,2-dioxaborolan-2-yl)pyridine according to Method K and was isolated as a beige solid (16%). $\delta_H$ (DMSO-d$_6$) 9.37 (1H, d, 1.9 Hz), 8.82 (1H, d, J 4.9 Hz), 8.70 (1H, dd, J 4.9 and 1.6 Hz), 8.54 (1H, m), 8.16 (1H, s), 7.59 (1H, m), 7.52 (1H, m), 3.63 (4H, m), 3.01 (4H, m), 2.64 (2H, s), 2.42 (2H, s), 1.01 (6H, s). LCMS (ES+) 420.0 (M+H)$^+$.

Example 92

3-(2-{3-[(Dimethylamino)methyl]phenyl}pyridin-4-yl)-5,5-dimethyl-2-(morpholin-4-yl)-5,6-dihydro-1-benzothiophen-7(4H)-one The title compound was prepared from Example 17, 2-chloropyridin-4-ylboronic acid and 3-[(N,N-dimethylamino)methyl]phenylboronic acid according to Method K and was isolated as a brown solid (11%). $\delta_H$ (DMSO-d$_6$) 8.78 (1H, d, J 5.1 Hz), 8.14 (1H, s), 8.09 (1H, s), 8.06 (1H, d, J 7.9 Hz), 7.50 (1H, t, J 7.5 Hz), 7.42 (2H, m), 3.63 (4H, m), 3.50

(2H, s), 3.01 (4H, m), 2.63 (2H, s), 2.43 (2H, s), 2.23 (6H, s), 1.01 (6H, s). LCMS (ES+) 476.0 (M+H)$^+$.

Example 93

3-(3,3'-Bipyridin-5-yl)-5,5-dimethyl-2-(morpholin-4-yl)-5,6-dihydro-1-benzothiophen-7(4H)-one

The title compound was prepared from Example 17, 3-bromopyridin-5-ylboronic acid and 3-(4,4,5,5-tetramethyl-1,3,2-dioxaborolan-2-yl)pyridine according to Method K and was isolated as a beige solid (8%). $\delta_H$ (DMSO-d$_6$) 9.20-9.00 (3H, m), 8.75-8.65 (2H, m), 8.26 (1H, m), 7.60 (1H, m), 3.61 (4H, m), 3.00 (4H, m), 2.60 (2H, s), 2.42 (2H, s), 1.02 (6H, s). LCMS (ES+) 420.0 (M+H)$^+$.

Example 94

5,5-Dimethyl-2-(morpholin-4-yl)-3-(2-phenylpyridin-4-yl)-5,6-dihydrothieno[2,3-c]pyridin-7(4H)-one

The title compound was prepared from Intermediate 19, 2-chloropyridin-4-ylboronic acid and phenylboronic acid according to Method K and was isolated as a pink solid (11%) after purification by preparative HPLC (pH 2.5). $\delta_H$ (DMSO-d$_6$) 8.73 (1H, d, J 5.1 Hz), 8.14 (2H, d, J 6.8 Hz), 8.04 (1H, s), 7.58-7.42 (5H, m), 3.64-3.57 (4H, m), 2.94-2.87 (4H, m), 2.71 (2H, s), 1.19 (6H, s). LCMS (ES+) 420.2 (M+H)$^+$.

Example 95

3-[2-(3,5-Dimethylisoxazol-4-yl)pyridin-4-yl]-5,5-dimethyl-2-(morpholin-4-yl)-5,6-dihydro-1-benzothiophen-7(4H)-one

The title compound was prepared from Example 17, 2-chloropyridin-4-ylboronic acid and 3,5-dimethylisoxazol-4-ylboronic acid according to Method K and was isolated as a white solid (2%) after purification by preparative HPLC (pH 2.5). $\delta_H$ (DMSO-d$_6$) 8.74 (1H, d, J 6.8 Hz), 7.52 (1H, s), 7.46 (1H, d, J 5.1 Hz), 3.64-3.57 (4H, m), 3.00-2.93 (4H, m), 2.63 (3H, s), 2.59 (3H, s), 2.44 (2H, s), 2.38 (2H, s), 0.98 (6H, s). LCMS (ES+) 438.2 (M+H)$^+$.

Example 96

3-(2,2'-Bipyridin-4-yl)-5,5-dimethyl-2-morpholin-4-yl-5,6-dihydro-1-benzothiophen-7(4H)-one

The title compound was prepared from Example 17, 2-chloropyridin-4-ylboronic acid and 2-pyridineboronic acid N-phenyldiethanolamine ester according to Method K and was isolated as an off-white solid (4%) after purification by preparative HPLC (pH 5.8). $\delta_H$ (DMSO-d$_6$) 8.77 (1H, d, J 5.1 Hz), 8.72 (1H, d, J 4.7 Hz), 8.51-8.46 (1H, m), 8.44 (1H, d, J 8.1 Hz), 7.98 (1H, td, J 7.5 and 1.8 Hz), 7.53-7.46 (1H, m), 7.37-7.30 (1H, m), 3.64-3.56 (4H, m), 3.03-2.94 (4H, m), 2.58 (2H, s), 2.41 (2H, s), 0.97 (6H, s). LCMS (ES+) 420.3 (M+H)$^+$.

Example 97

5,5-Dimethyl-2-(morpholin-4-yl)-3-[3-(1H-pyrazol-4-yl)phenyl]-5,6-dihydro-1-benzothiophen-7(4H)-one

The title compound was prepared from Example 17, 3-bromophenylboronic acid and 4-(4,4,5,5-tetramethyl-1,3,2-dioxaborolan-2-yl)-1H-pyrazole according to Method K and was isolated as an off-white solid (18%) after purification by preparative HPLC (pH 2.5). $\delta_H$ (CD$_3$OD) 8.03 (2H, s), 7.65-7.59 (2H, m), 7.48 (1H, t, J 7.7 Hz), 7.26-7.19 (1H, m), 3.67-3.60 (4H, m), 3.10-3.02 (4H, m), 2.56 (2H, s), 2.44 (2H, s), 1.05 (6H, s). Exchangeable proton not observed. LCMS (ES+) 408.2 (M+H)$^+$.

Example 98

3-(3-Bromo-5-nitrophenyl)-5,5-dimethyl-2-(morpholin-4-yl)-5,6-dihydro-1-benzothiophen-7(4H)-one

To a stirred solution of Example 17 (0.30 g, 0.77 mmol), Pd(Ph$_3$P)$_4$ (0.05 g, 0.04 mmol) and K$_3$PO$_4$ (0.20 g, 0.94 mmol) in a mixture of water (1 mL) and DME (3 mL) was added (3-bromo-5-nitrophenyl)boronic acid (0.19 g, 0.77 mmol). The reaction mixture was then heated to 140° C. in a sealed tube under microwave irradiation for 1 h. The reaction mixture was then cooled, concentrated in vacuo and purified by preparative HPLC (pH 2.5) to give the title compound as a yellow solid (0.04 g, 10%). Example 99 was also isolated. $\delta_H$ (DMSO-d$_6$) 8.40 (1H, s), 8.27 (1H, s), 8.16 (1H, m), 3.62 (4H, m), 2.98 (4H, m), 2.59 (2H, s), 2.42 (2H, s), 1.01 (6H, s). LCMS (ES+) 465.0 and 467.0 (M+H)$^+$.

Example 99

3-(3'-Bromo-5,5'-dinitrobiphenyl-3-yl)-5,5-dimethyl-2-yl)-5,6-dihydro-1-benzothiophen-7(4H)-one

The title compound was isolated by preparative HPLC (pH 2.5) (from the crude material produced in the synthesis of Example 98) as a brown solid (0.02 g, 4%). $\delta_H$ (DMSO-d$_6$) 8.67 (2H, s), 8.62 (1H, s), 8.52 (1H, s), 8.40 (1H, s), 8.37 (1H, s), 3.61 (4H, m), 3.01 (4H, m), 2.62 (2H, s), 2.43 (2H, s), 1.01 (6H, s). LCMS (ES+) 586.0 and 588.0 (M+H)$^+$.

Example 100

5,5-Dimethyl-3-[3-(1-methyl-1H-pyrazol-4-yl)phenyl]-2-(morpholin-4-yl)-5,6-dihydro-1-benzothiophen-7(4H)-one, Formic Acid Salt

The title compound was prepared from Example 17, 3-bromophenylboronic acid and 1-methyl-4-(4,4,5,5-tetramethyl-1,3,2-dioxaborolan-2-yl)-1H-pyrazole according to Method K and was isolated as an off-white solid (18%) after purification by preparative HPLC (pH 2.5). $\delta_H$ (CD$_3$OD) 8.04 (1H, s), 7.88 (1H, s), 7.62-7.54 (2H, m), 7.48 (1H, t, J 7.5 Hz), 7.22 (1H, d, J 7.5 Hz), 3.96 (3H, s), 3.68-3.60 (4H, m), 3.10-3.02 (4H, m), 2.58 (2H, s), 2.46 (2H, s), 1.04 (6H, s). LCMS (ES+) 422.3 (M+H)$^+$.

Example 101

3-{3'-[(Dimethylamino)methyl]biphenyl-3-yl}-5,5-dimethyl-2-(morpholin-4-yl)-5,6-dihydro-1-benzothiophen-7(4H)-one, Formic Acid Salt

The title compound was prepared from Example 17, 3-bromophenylboronic acid and 3-(dimethylaminomethyl)phenylboronic acid according to Method K and was isolated as a yellow gum (10%) after purification by preparative HPLC (pH 2.5). $\delta_H$ (CD$_3$OD) 8.52 (1H, s), 7.84-7.68 (4H, m), 7.66-7.54 (2H, m), 7.48 (1H, d, J 7.5 Hz), 7.42 (1H, d, J 7.5 Hz), 4.12 (2H, s), 3.68-3.60 (4H, m), 3.10-3.02 (4H, m), 2.70 (6H, s), 2.56 (2H, s), 2.48 (2H, s), 1.06 (6H, s). LCMS (ES+) 475.2 (M+H)+.

Example 102

(Method L)

N-(3-{4-[5,5-Dimethyl-2-(morpholin-4-yl)-7-oxo-4,5,6,7-tetrahydro-1-benzothien-3-yl]pyridin-2-yl}phenyl)acetamide To a stirred solution of 3-acetamidophenylboronic acid (0.028 g, 0.160 mmol), Example 73 (0.060 g, 0.160 mmol) and $K_3PO_4$ (0.050 g, 0.240 mmol) in DME (1.5 mL) and water (0.5 mL) was added $Pd(PPh_3)_4$ (0.010 g, 0.009 mmol) and the reaction mixture was heated to 140° C. in a sealed tube, under microwave irradiation, for 2 h. The solvent was then removed in vacuo and the residue was purified by preparative HPLC (pH 2.5) to give the title compound (0.058 g, 76%) as an off-white solid. $\delta_H$ (DMSO-$d_6$) 10.09 (1H, s), 8.75 (1H, d, J 5.1 Hz), 8.47 (1H, s), 7.95 (1H, s), 7.81-7.75 (1H, m), 7.68-7.61 (1H, m), 7.47-7.38 (2H, m), 3.66-3.55 (4H, m), 3.02-2.93 (4H, m), 2.59 (2H, s), 2.40 (2H, s), 2.08 (3H, s), 0.97 (6H, s). LCMS (ES+) 476.2 (M+H)+.

Example 103

5,5-Dimethyl-3-[2-(3-hydroxyphenyl)pyridin-4-yl]-2-(morpholin-4-yl)-5,6-dihydro-1-benzothiophen-7(4H)-one The title compound was prepared from Example 73 and 3-hydroxyphenylboronic acid according to Method L and was isolated as a white solid (56%) after purification by preparative HPLC (pH 5.8). $\delta_H$ (DMSO-$d_6$) 9.61 (1H, s), 8.72 (1H, d, J 5.1 Hz), 7.92 (1H, s), 7.59-7.51 (2H, m), 7.42-7.37 (1H, m), 7.34-7.28 (1H, m), 6.89-6.82 (1H, m), 3.65-3.55 (4H, m), 3.02-2.93 (4H, m), 2.59 (2H, s), 2.39 (2H, s), 0.97 (6H, s). LCMS (ES+) 435.2 (M+H)+.

Example 104

Methyl 5,5-dimethyl-2-(morpholin-4-yl)-7-oxo-4,5,6,7-tetrahydro-1-benzothiophene-3-carboxylate A mixture of Example 17 (1.00 g, 2.56 mmol), [1,1'-bis(diphenylphosphino)-ferrocene]dichloropalladium(II)-DCM complex (0.10 g, 0.13 mmol) and $NEt_3$ (4.20 g, 3.00 mL, 41.58 mmol) in MeOH (100 mL) was heated in a Parr bomb at 100 psi under an atmosphere of CO for 48 h. The reaction mixture was then filtered through Celite® and washed with MeOH. After removal of the solvent in vacuo, the residue was purified by column chromatography (SiO$_2$, 30-50% EtOAc/heptane) to give the title compound (0.82 g, 99%) as a pale pink solid. $\delta_H$ (DMSO-$d_6$) 3.78 (3H, s), 3.76-3.70 (4H, m), 3.27-3.21 (4H, m), 2.77 (2H, s), 2.34 (2H, s), 1.02 (6H, s). LCMS (ES+) 324.3 (M+H)+.

Example 105

(Method M)

5,5-Dimethyl-3-[(1-methyl-1H-imidazol-2-yl)ethynyl]-2-(morpholin-4-yl)-5,6-dihydro-1-benzothiophen-7(4H)-one To a stirred solution of Example 17 (0.20 g, 0.51 mmol) in diisopropylamine (1 mL) and DMF (5 mL) were added Intermediate 23 (0.13 g, 1.03 mmol) and $Pd(PPh_3)_2Cl_2$ (0.02 g, 0.03 mmol), followed by CuI (0.01 g, 0.05 mmol). The reaction mixture was stirred at 60° C. for 1 h, then cooled to r.t. The precipitate formed was filtered, purified by column chromatography (SiO$_2$, EtOAc), then triturated with DCM, Et$_2$O and hexanes to give the title compound (0.02 g, 8%) as a beige solid. $\delta_H$ (CDCl$_3$) 7.21-7.11 (1H, m), 7.06-6.96 (1H, m), 3.93-3.85 (4H, m), 3.80 (3H, s), 3.75-3.68 (4H, m), 2.72 (2H, s), 2.43 (2H, s), 1.14 (6H, s). MS (ES+) 370.0 (M+H)+.

Example 106

5,5-Dimethyl-2-(morpholin-4-yl)-3-(piperidin-4-ylethynyl)-5,6-dihydro-1-benzothiophen-7(4H)-one The title compound was prepared from Example 17 and Intermediate 25 according to Method M and was isolated as an off-white solid (8%) after purification by column chromatography (SiO$_2$, hexanes, to EtOAc, to MeOH). $\delta_H$ (CDCl$_3$) 3.92-3.81 (4H, m), 3.64-3.56 (4H, m), 3.18-3.05 (2H, m), 2.86-2.69 (3H, m), 2.62 (2H, s), 2.41 (2H, s), 2.02-1.87 (2H, m), 2.01-1.86 (2H, m), 1.12 (6H, s). Exchangeable proton not observed. MS (ES+) 373.2 (M+H)+.

Example 107

Tert-Butyl(2S)-2-{[5,5-dimethyl-2-(morpholin-4-yl)-7-oxo-4,5,6,7-tetrahydro-1-benzothien-3-yl]ethynyl}pyrrolidine-1-carboxylate The title compound was prepared from Example 17 and Intermediate 27 according to Method M and was isolated as an off-white solid (61%) after purification by column chromatography (SiO$_2$, 10-20% EtOAc/hexanes). $\delta_H$ (CDCl$_3$) 4.87-4.61 (1H, m), 4.00-3.77 (4H, m), 3.77-3.55 (4H, m), 3.54-3.44 (1H, m), 3.44-3.27 (1H, m), 2.62 (2H, s), 2.40 (2H, s), 2.30-1.88 (4H, m), 1.50 (9H, s), 1.12 (3H, s), 1.11 (3H, s). MS (ES+) 459.0 (M+H)+.

Example 108

Tert-Butyl 2-{[5,5-dimethyl-2-(morpholin-4-yl)-7-oxo-4,5,6,7-tetrahydro-1-benzothien-3-yl]ethynyl}piperidine-1-carboxylate The title compound was prepared from Example 17 and Intermediate 30 according to Method M and was isolated as an off-white solid (55%) after purification by column chromatography (SiO$_2$, 10-20% EtOAc/hexanes). $\delta_H$ (CDCl$_3$) 5.46-5.22 (1H, m), 4.10-3.92 (1H, m), 3.95-3.75 (4H, m), 3.69-3.51 (4H, m), 3.16-2.85 (1H, m), 2.63 (2H, s), 2.41 (2H, s), 1.95-1.64 (5H, m), 1.58 (10H, s), 1.12 (6H, s). MS (ES+) 473.1 (M+H)+.

Example 109

Tert-Butyl 3-{[5,5-dimethyl-2-(morpholin-4-yl)-7-oxo-4,5,6,7-tetrahydro-1-benzothien-3-yl]ethynyl}piperidine-1-carboxylate The title compound was prepared from Example 17 and Intermediate 33 according to Method M and was isolated as an off-white solid (56%) after purification by column chromatography (SiO$_2$, 10-20% EtOAc/hexanes). $\delta_H$ (CDCl$_3$) 4.20-3.92 (1H, m), 3.98-3.80 (4H, m), 3.83-3.70 (1H, m), 3.67-3.51 (4H, m), 3.16-2.94 (2H, m), 2.82-2.68 (1H, m), 2.61 (2H, s), 2.40 (2H, s), 2.13-1.99 (1H, m), 1.84-1.70 (1H, m), 1.68-1.59 (1H, m), 1.68-1.38 (10H, m), 1.13 (6H, s). MS (ES+) 473.0 (M+H)+.

Example 110

5,5-Dimethyl-2-(morpholin-4-yl)-3-(piperidin-2-ylethynyl)-5,6-dihydro-1-benzothiophen-7(4H)-one The title compound was prepared from Example 17 and Intermediate 34 according to Method M and was isolated as a pale brown solid (10%) after purification by column chromatography (SiO$_2$, 0-50% MeOH/EtOAc). $\delta_H$ (DMSO-d$_6$) 3.89-3.78 (1H, m), 3.82-3.69 (4H, m), 3.64-3.45 (4H, m), 2.99-2.80 (1H, m), 2.61-2.59 (3H, m), 2.33 (2H, s), 1.82-1.60 (2H, m), 1.62-1.31 (4H, m), 1.03 (6H, s). Exchangeable proton not observed. MS (ES+) 373.1 (M+H)+.

Example 111

5,5-Dimethyl-2-(morpholin-4-yl)-3-(piperidin-3-ylethynyl)-5,6-dihydro-1-benzothiophen-7(4H)-one The title compound was prepared from Example 17 and Intermediate 35 according to Method M and was isolated as a pale brown solid (14%) after purification by column chromatography (SiO$_2$, 0-50% MeOH/EtOAc). $\delta_H$ (DMSO-d$_6$) 3.84-3.67 (4H, m), 3.63-3.48 (4H, m), 3.09-2.95 (1H, m), 2.84-2.71 (1H, m), 2.66-2.54 (4H, m), 2.55-2.44 (2H, m), 2.32 (2H, s), 2.02-1.85 (1H, m), 1.66-1.43 (2H, m), 1.43-1.30 (1H, m), 1.03 (6H, s). MS (ES+) 373.1 (M+H)+.

Example 112

(Method Q)

5,5-Dimethyl-3-(1H-indol-5-ylethynyl)-2-(morpholin-4-yl)-5,6-dihydro-1-benzothiophen-7(4H)-one To a stirred solution of Example 17 (0.20 g, 0.52 mmol) and Intermediate 37 (0.11 g, 0.78 mmol) in diisopropylamine (5 mL) and THF (5 mL) were added CuI (0.01 g, 0.05 mmol) and Pd(PPh$_3$)$_2$Cl$_2$ (0.02 g, 0.03 mmol). The reaction mixture was stirred at 70° C. for 16 h, then cooled to r.t. EtOAc (10 mL) and water (10 mL) were added. The layers were separated and the aqueous layer was extracted with EtOAc (2×15 mL). The combined organic layers were dried (Na$_2$SO$_4$), filtered and concentrated in vacuo. Purification by column chromatography (SiO$_2$, 30% EtOAc/hexanes) gave the title compound (0.09 g, 43%) as a yellow solid. $\delta_H$ (DMSO-d$_6$) 11.30 (1H, br. s), 7.72 (1H, s), 7.51-7.37 (2H, m), 7.19 (1H, d, J 8.8 Hz), 6.47 (1H, s), 3.86-3.75 (4H, m), 3.69-3.59 (4H, m), 2.72 (2H, s), 2.36 (2H, s), 1.08 (6H, s). MS (ES−) 403.0 (M−H)−.

Example 113

3-[(1,2-Dimethyl-1H-imidazol-4-yl)ethynyl]-5,5-dimethyl-2-(morpholin-4-yl)-5,6-dihydro-1-benzothiophen-7(4H)-one The title compound was prepared from Example 17 and Intermediate 40 according to Method Q and was isolated as a yellow solid (2%) after purification by column chromatography (SiO$_2$, 5% MeOH/DCM), followed by trituration with EtOAc and EtOH. $\delta_H$ (DMSO-d$_6$) 7.42 (1H, s), 3.79-3.72 (4H, m), 3.64-3.57 (4H, m), 3.55 (3H, s), 2.62 (2H, s), 2.34 (2H, s), 2.27 (3H, s), 1.04 (6H, s). MS (ES+) 384.0 (M+H)+.

Example 114

5,5-Dimethyl-3-[(1-methyl-1H-indol-4-yl)ethynyl]-2-(morpholin-4-yl)-5,6-dihydro-1-benzothiophen-7(4H)-one The title compound was prepared from Example 17 and Intermediate 42 according to Method Q and was isolated as a beige solid (9%) after purification by column chromatography (SiO$_2$, 10% EtOAc/hexane). $\delta_H$ (DMSO-d$_6$) 7.51 (1H, d, J 8.2 Hz), 7.47 (1H, s), 7.25-7.14 (2H, m), 6.45 (1H, s), 3.83 (3H, s), 3.87-3.78 (4H, m), 3.74-3.66 (4H, m), 2.77 (2H, s), 2.38 (2H, s), 1.09 (6H, s). MS (ES+) 419.0 (M+H)+.

Example 115

Omitted

Example 116

3-Bromo-5,5-dimethyl-2-(morpholin-4-yl)-4,5,6,7-tetrahydro-8H-thieno[2,3-c]azepin-8-one To a stirred solution of Example 51 (4.0 g, 14.30 mmol) in THF (150 mL) at r.t. was added NBS (3.0 g, 17.20 mmol) portionwise over 5 minutes. The reaction mixture was stirred at r.t. for 3 h. EtOAc (250 mL) and water (150 mL) were added. The organic layer was washed with water (3×100 mL), then brine (100 mL), dried (Na$_2$SO$_4$), filtered and concentrated in vacuo. Purification by column chromatography (SiO$_2$, 50% EtOAc/hexanes) gave the title compound (4.50 g, 88%) as a pale yellow solid. $\delta_H$ (DMSO-d$_6$) 8.01 (1H, s), 3.75-3.73 (4H, m), 3.09-3.06 (4H, m), 2.89 (2H, d, J 5.1 Hz), 2.58 (2H, s), 1.54 (6H, s). MS (ES+) 358.8 and 360.8 (M+H)+.

Example 117

5,5-Dimethyl-2-(morpholin-4-yl)-3-phenyl-4,5,6,7-tetrahydro-8H-thieno[2,3-c]azepin-8-one To a mixture of Example 116 (0.15 g, 0.41 mmol), phenyl-boronic acid (0.08 g, 0.63 mmol), palladium acetate (0.005 g, 0.02 mmol), 1,3-bis(diphenylphosphino)propane (0.02 g, 0.04 mmol) and K$_3$PO$_4$ (0.18 g, 0.82 mmol) was added DMF (2 mL). The reaction mixture was heated at 80° C. for 5 h and left standing for 16 h at r.t. Phenyl-boronic acid (0.08 g, 0.63 mmol), palladium acetate (0.005 g, 0.02 mmol), 1,3-bis(diphenylphosphino)propane (0.02 g, 0.04 mmol), K$_3$PO$_4$ (0.07 g, 0.33 mmol) and DMF (2 mL) were again added. The reaction mixture was heated at 90° C. for 16 h, then cooled to r.t. and diluted with EtOAc (5 mL). The solid was filtered and washed with EtOAc (25 mL). The organic filtrate was washed with water (5×10 mL), then brine (10 mL), dried (Na$_2$SO$_4$), filtered and concentrated in vacuo. Purification by column chromatography (SiO$_2$, 30% EtOAc/hexanes) gave the title compound (0.05 g, 37%) as a white solid. $\delta_H$ (DMSO-d$_6$) 7.83 (1H, t, J 5.1 Hz), 7.46 (2H, t, J 7.4 Hz), 7.37-7.29 (3H, m), 3.49-3.47 (4H, m), 2.85 (2H, d, J 5.2 Hz), 2.79-2.77 (4H, m), 2.29 (2H, s), 0.86 (6H, s). MS (ES+) 357.0 (M+H)+.

Example 118

5,5-Dimethyl-2-(morpholin-4-yl)-3-(pyridin-4-yl)-5,6-dihydro-1-benzothiophen-7(4H)-one To a suspension of Example 17 (0.43 g, 1.10 mmol) in DME (10 mL) at r.t. were added pyridine-4-boronic acid (0.20 g, 1.65 mmol), $K_3PO_4$ (0.70 g, 3.30 mmol) and water (1 mL), followed by $PdCl_2$.dppf (0.02 g, 0.05 mmol). The reaction mixture was heated at 90° C. for 6 h. EtOAc (50 mL) and water (20 mL) were added. The organic layer was washed with water (2×20 mL), then brine (20 mL), dried ($Na_2SO_4$), filtered and concentrated in vacuo. Purification by column chromatography ($SiO_2$, EtOAc) gave the title compound (0.03 g, 7%) as an off-white solid. $\delta_H$ (DMSO-$d_6$) 8.71 (2H, d, J 4.0 Hz), 7.35 (2H, d, J 4.0 Hz), 3.75-3.64 (4H, m), 3.08-2.95 (4H, m), 2.51 (2H, s), 2.47 (2H, s), 1.07 (6H, s). MS (ES+) 343.0 (M+H)$^+$.

Example 119

(Method S)

5,5-Dimethyl-3-[(1-methyl-1H-imidazol-5-yl)ethynyl]-2-(morpholin-4-yl)-5,6-dihydrothieno[2,3-c]pyridin-7(4H)-one To a stirred solution of Intermediate 19 (0.20 g, 0.51 mmol) and 5-ethynyl-1-methyl-1H-imidazole (0.08 mL, 0.77 mmol) in diisopropylamine (2 mL) and DMF (5 mL) were added CuI (0.01 g, 0.05 mmol) and Pd(PPh$_3$)$_2$Cl$_2$ (0.018 g, 0.03 mmol). The reaction mixture was stirred at 70° C. for 16 h, then cooled to r.t. EtOAc (50 mL) and water (50 mL) were added. The layers were separated and the aqueous layer was extracted with EtOAc (2×20 mL). The combined organic layers were washed with brine (5×5 mL), dried ($Na_2SO_4$), filtered and concentrated in vacuo. The crude solid was washed with hot DCM and hexanes to give the title compound (0.12 g, 63%) as a white solid. $\delta_H$ (DMSO-$d_6$) 7.77 (1H, br. s), 7.49 (1H, s), 7.27 (1H, br. s), 3.78-3.75 (4H, m), 3.65 (3H, s), 3.49-3.46 (4H, m), 2.70 (2H, s), 1.26 (6H, s). MS (ES+) 371.1 (M+H)$^+$.

Example 120

5,5-Dimethyl-3-[(1-methyl-1H-imidazol-5-yl)ethynyl]-2-(morpholin-4-yl)-4,5,6,7-tetrahydro-8H-thieno[2,3-c]azepin-8-one The title compound was prepared from Example 52 and 5-ethynyl-1-methyl-1H-imidazole according to Method S and was isolated as a pale yellow solid (43%) after recrystallisation from MeOH. $\delta_H$ (DMSO-$d_6$) 7.84 (1H, t, J 4.8 Hz), 7.75 (1H, s), 7.25 (1H, s), 3.77-3.74 (4H, m), 3.66 (3H, s), 3.45-3.43 (4H, m), 2.89 (211, d, J 5.0 Hz), 2.65 (2H, s), 0.95 (6H, s). MS (ES+) 385.1 (M+H)$^+$.

Example 121

N-{3-[5,5-Dimethyl-2-(morpholin-4-yl)-8-oxo-5,6,7,8-tetrahydro-4H-thieno[2,3-c]azepin-3-yl]prop-2-yn-1-yl}methanesulfonamide The title compound was prepared from Example 52 and Intermediate 43 according to Method S and was isolated as a white solid (15%) after trituration from hot DCM. $\delta_H$ (DMSO-$d_6$) 7.79 (1H, br. s), 7.60 (1H, br. s), 4.08 (2H, s), 3.75-3.70 (4H, m), 3.40-3.35 (4H, m), 2.99 (3H, s), 2.87 (2H, d, J 4.7 Hz), 2.60 (2H, s), 0.97 (6H, s). MS (ES+) 412.1 (M+H)$^+$.

Example 122

N-{3-[5,5-Dimethyl-2-(morpholin-4-yl)-7-oxo-4,5,6,7-tetrahydrothieno[2,3-c]pyridin-3-yl]prop-2-yn-1-yl}methanesulfonamide The title compound was prepared from Intermediate 19 and Intermediate 43 according to Method S and was isolated as an off-white solid (10%) after purification by column chromatography ($SiO_2$, EtOAc). $\delta_H$ (DMSO-$d_6$) 7.60 (1H, t, J 5.8 Hz), 7.42 (1H, s), 4.07 (2H, d, J 5.9 Hz), 3.75-3.73 (4H, m), 3.43-3.40 (4H, m), 2.99 (3H, s), 2.65 (2H, s), 1.23 (6H, s). MS (ES+) 398.0 (M+H)$^+$.

Example 123

N'-{3-[5,5-Dimethyl-2-(morpholin-4-yl)-7-oxo-4,5,6,7-tetrahydrothieno[2,3-c]pyridin-3-yl]prop-2-yn-1-yl}-N,N-dimethylsulfamide The title compound was prepared from Intermediate 19 and Intermediate 44 according to Method S and was isolated as an off-white solid (5%) after purification by column chromatography ($SiO_2$, 5% MeOH/EtOAc). $\delta_H$ (DMSO-$d_6$) 7.70 (1H, t, J 5.8 Hz), 7.41 (1H, s), 4.00 (2H, d, J 5.8 Hz), 3.75-3.73 (4H, m), 3.44-3.41 (4H, m), 2.70 (6H, s), 2.65 (2H, s), 1.24 (6H, s). MS (ES+) 427.0 (M+H)$^+$.

Example 124

N'-{3-[5,5-Dimethyl-2-(morpholin-4-yl)-7-oxo-4,5,6,7-tetrahydro-1-benzothien-3-yl]prop-2-yn-1-yl}-N,N-dimethylsulfamide The title compound was prepared from Example 17 and Intermediate 44 according to Method S (further addition of Intermediate 44, CuI and Pd(PPh$_3$)$_2$Cl$_2$ was required after 16 h and the reaction mixture was stirred for a further 24 h) and was isolated as a pale grey solid (40%) after purification by column chromatography ($SiO_2$, 50-100% EtOAc/hexanes). $\delta_H$ (DMSO-$d_6$) 7.72 (1H, d, J 5.8 Hz), 4.01 (2H, d, J 5.8 Hz), 3.75-3.72 (4H, m), 3.58-3.55 (4H, m), 2.70 (6H, s), 2.60 (2H, s), 2.33 (2H, s), 1.03 (6H, s). MS (ES+) 426.0 (M+H)$^+$.

Example 125

N'-{3-[5,5-Dimethyl-2-(morpholin-4-yl)-8-oxo-5,6,7,8-tetrahydro-4H-thieno[2,3-c]azepin-3-yl]prop-2-yn-1-yl}-N,N-dimethylsulfamide The title compound was prepared from Example 52 and Intermediate 44 according to Method S (further addition of Intermediate 44, CuI and Pd(PPh$_3$)$_2$Cl$_2$ was required after 5 h and the reaction mixture was stirred for a further 16 h) and was isolated as an off-white solid (16%) after purification by column chromatography ($SiO_2$, 50-100% EtOAc/hexanes). $\delta_H$ (DMSO-$d_6$) 7.78 (1H, br. s), 7.70 (1H, t, J 5.9 Hz), 4.00 (2H, d, J 5.7 Hz), 3.73-3.71 (4H, m), 3.40-3.37 (4H, m), 2.87 (2H, d, J 5.0 Hz), 2.70 (6H, s), 2.60 (2H, s), 0.97 (6H, s). MS (ES+) 441.1 (M+H)$^+$.

Example 126

5,5-Dimethyl-3-[(1-methyl-1H-pyrazol-4-yl)ethynyl]-2-(morpholin-4-yl)-5,6-dihydrothieno[2,3-c]pyridin-7(4H)-one To a suspension of Intermediate 19 (0.3 g, 0.76 mmol) in DMF (10 mL) were added diisopropylamine (2 mL) and a solution of Intermediate 48 (0.11 g, 1.05 mmol) in DMF (0.5 mL), followed by CuI (0.01 g, 0.05 mmol) and Pd(PPh$_3$)$_2$Cl$_2$ (0.02 g, 0.03 mmol). The reaction mixture was stirred at 75° C. for 16 h, then cooled to r.t. EtOAc (50 mL) and water (50 mL) were added. The layers were separated and the aqueous layer was extracted with EtOAc (2×20 mL). The combined organic layers were washed with brine (5×5 mL), dried (Na$_2$SO$_4$), filtered and concentrated in vacuo. Purification by column chromatography (SiO$_2$, EtOAc), followed by washing of the purified solid with Et$_2$O, gave the title compound (0.05 g, 18%) as an off-white solid. $\delta_H$ (CDCl$_3$) 7.60 (1H, s), 7.53 (1H, s), 5.17 (1H, s), 3.93 (3H, s), 3.89-3.87 (4H, m), 3.54-3.52 (4H, m), 2.80 (2H, s), 1.38 (6H, s). MS (ES+) 371.0 (M+H)$^+$.

Example 127

5,5-Dimethyl-3-[(1-methyl-1H-pyrazol-4-yl)ethynyl]-2-(morpholin-4-yl)-5,6-dihydro-1-benzothiophen-7(4H)-one The title compound was prepared from Example 17 and Intermediate 48 according to Method S and was isolated as an off-white solid (27%) after purification by column chromatography (SiO$_2$, EtOAc). $\delta_H$ (DMSO) 8.04 (1H, s), 7.65 (1H, s), 3.85 (3H, s), 3.77-3.75 (4H, m), 3.60-3.57 (4H, m), 2.68 (2H, s), 2.34 (2H, s), 1.04 (6H, s). MS (ES+) 370.0 (M+H)$^+$.

Example 128

3-[(1-Acetylpiperidin-3-yl)ethynyl]-5,5-dimethyl-2-(morpholin-4-yl)-5,6-dihydro-1-benzothiophen-7(4H)-one The title compound was prepared from Example 17 and Intermediate 50 according to Method S and was isolated as an off-white solid (29%) after purification by column chromatography (SiO$_2$, 0-5% MeOH/EtOAc). $\delta_H$ (CDCl$_3$), mixture of rotamers: 4.48-1.42 (9H, m), 3.89-3.83 (4H, m), 3.61-3.55 (4H, m), 2.60 (2H, s), 2.41 and 2.40 (2H, s, rotameric), 2.16 and 2.13 (3H, s, rotameric), 1.58 (6H, s). MS (ES+) 415.0 (M+H)$^+$.

Example 129

3-[(1-Acetylpiperidin-4-yl)ethynyl]-5,5-dimethyl-2-(morpholin-4-yl)-5,6-dihydro-1-benzothiophen-7(4H)-one The title compound was prepared from Example 17 and Intermediate 51 according to Method S and was isolated as an off-white solid (31%) after purification by column chromatography (SiO$_2$, 0-2.5% MeOH/EtOAc). $\delta_H$ (CDCl$_3$) 4.02-3.88 (1H, m), 3.84-3.70 (4H, m), 3.63-3.61 (1H, m), 3.56-3.41 (4H, m), 3.34-3.17 (2H, m), 2.99-2.73 (1H, m), 2.51 (2H, s), 2.32 (2H, s), 2.04 (3H, s), 1.92-1.76 (2H, m), 1.68-1.53 (2H, m), 1.03 (6H, s). MS (ES+) 415.0 (M+H)$^+$.

Example 130

5,5-Dimethyl-3-{[1-(methylsulfonyl)piperidin-3-yl]ethynyl}-2-(morpholin-4-yl)-5,6-dihydro-1-benzothiophen-7(4H)-one The title compound was prepared from Example 17 and Intermediate 52 according to Method S and was isolated as a white solid (19%) after purification by column chromatography (SiO$_2$, 60-80% EtOAc/hexanes). $\delta_H$ (CDCl$_3$) 3.99-3.77 (4H, m), 3.71-3.55 (5H, m), 3.48-3.39 (1H, m), 3.18-3.03 (2H, m), 3.03-2.90 (1H, m), 2.87-2.77 (3H, m), 2.65-2.56 (2H, m), 2.41 (2H, s), 2.06-1.88 (2H, m), 1.82-1.61 (2H, m), 1.13 (6H, s). MS (ES+) 451.0 (M+H)$^+$.

Example 131

5,5-Dimethyl-3-{[1-(methylsulfonyl)piperidin-4-yl]ethynyl}-2-(morpholin-4-yl)-5,6-dihydro-1-benzothiophen-7(4R)-one The title compound was prepared from Example 17 and Intermediate 53 according to Method S and was isolated as a white solid (10%) after purification by column chromatography (SiO$_2$, first column 66% EtOAc/hexanes, second column 2% MeOH/DCM). $\delta_H$ (DMSO-d$_6$) 3.85-3.69 (4H, m), 3.64-3.48 (4H, m), 3.43-3.33 (2H, m), 3.12-2.94 (2H, m), 2.93-2.82 (1H, m), 2.88 (3H, s), 2.58 (2H, s), 2.32 (2H, s), 2.04-1.86 (2H, m), 1.75-1.56 (2H, m), 1.03 (6H, s). MS (ES+) 451.0 (M+H)$^+$.

Example 132

5,5-Dimethyl-2-(morpholin-4-yl)-3-[3-oxo-3-(pyrrolidin-1-yl)prop-1-yn-1-yl]-5,6-dihydro-1-benzothiophen-7(4H)-one The title compound was prepared from Example 17 and Intermediate 54 according to Method S and was isolated as a white solid (10%) after purification by column chromatography (SiO$_2$, EtOAc). $\delta_H$ (CDCl$_3$) 4.00-0.80 (4H, m), 3.77-3.67 (4H, m), 3.69-3.61 (2H, m), 3.60-3.47 (2H, m), 2.67 (2H, s), 2.42 (2H, s), 2.04-1.91 (2H, m), 1.13 (6H, s), 0.97-0.78 (2H, m). MS (ES+) 387.0 (M+H)$^+$.

Example 133

5,5-Dimethyl-2-(morpholin-4-yl)-3-(3-phenylprop-1-yn-1-yl)-5,6-dihydro-1-benzothiophen-7(4H)-one The title compound was prepared from Example 17 and 3-phenyl-1-propyne according to Method S and was isolated as a white solid (24%) after purification by column chromatography (SiO$_2$, 20-50% EtOAc/hexanes), followed by trituration with Et$_2$O, $\delta_H$ (CDCl$_3$) 7.40-7.34 (4H, m), 7.32-7.23 (1H, m), 3.91 (2H, s), 3.69-3.61 (4H, m), 3.54-3.45 (4H, m), 2.61 (2H, s), 2.33 (2H, s), 1.03 (6H, s). MS (ES+) 380.0 (M+H)$^+$.

Example 134

(Method T)

5,5-Dimethyl-3-[2-(1-methyl-1H-imidazol-5-yl)ethyl]-2-(morpholin-4-yl)-5,6-dihydro-1-benzothiophen-7(4H)-one A solution of Example 20 (0.08 g, 0.21 mmol) in MeOH (10 mL) was hydrogenated using an H-cube™ apparatus under 30 psi of H$_2$ for 3 cycles, then 40 psi at 40° C. for 2 cycles. The solvent was removed in vacuo. EtOAc (5 mL) was added. The solid formed was washed with Et$_2$O and filtered to give the title compound (0.05 g, 62%) as an off-white solid that required no further purification. $\delta_H$ (DMSO-d$_6$) 8.84 (1H, s), 7.33 (1H, s), 3.75 (3H, s), 3.73-3.67 (4H, m), 2.94-2.86

(4H, m), 2.87-2.77 (4H, m), 2.62 (2H, s), 2.38 (2H, s), 1.03 (6H, s). MS (ES+) 374.0 (M+H)$^+$.

Example 135

5,5-Dimethyl-3-[2-(1-methyl-1H-imidazol-4-yl) ethyl]-2-(morpholin-4-yl)-5,6-dihydro-1-benzothiophen-7(4H)-one The title compound was prepared from Example 41 according to Method T (40 psi at 40° C. for 5 cycles) and was isolated as a white solid (57%) that required no further purification. $\delta_H$ (DMSO-d$_6$) 7.60 (1H, s), 6.87 (1H, s), 3.79-3.69 (4H, m), 3.59 (3H, s), 3.02-2.90 (4H, m), 2.81-2.70 (2H, m), 2.69-2.61 (2H, m), 2.57 (2H, s), 2.35 (2H, s), 1.01 (6H, s). MS (ES+) 374.0 (M+H)$^+$.

Example 136

3-[2-(1-Acetylpiperidin-4-yl)ethyl]-5,5-dimethyl-2-(morpholin-4-yl)-5,6-dihydro-1-benzothiophen-7(4H)-one The title compound was prepared from Example 129 according to Method T (50 psi at 50° C.) and was isolated as a pale yellow solid (75%) that required no further purification. $\delta_H$ (CDCl$_3$) 4.74-4.56 (1H, m), 3.86-3.84 (5H, m), 3.02-2.99 (5H, m), 2.56-2.50 (5H, m), 2.45 (2H, s), 2.11 (3H, s), 1.86-1.82 (2H, m), 1.51-1.44 (2H, m), 1.23-1.05 (3H, m), 1.12 (6H, s). MS (ES+) 419.0 (M+H)$^+$.

Example 137

N'-{3-[5,5-Dimethyl-2-(morpholin-4-yl)-7-oxo-4,5,6,7-tetrahydro-1-benzothien-3-yl]propyl}-N,N-dimethylsulfamide The title compound was prepared from Example 124 according to Method T (50 psi at 50° C.) and was isolated as a pale yellow solid (73%) that required no further purification. $\delta_H$ (CDCl$_3$) 5.75 (1H, br. s), 3.93-3.90 (4H, m), 3.04-3.02 (4H, m), 3.01-2.96 (2H, m), 2.81 (6H, s), 2.64 (2H, t, J 7.0 Hz), 2.58 (2H, s), 2.46 (2H, s), 1.82-1.79 (2H, m), 1.13 (6H, s). MS (ES+) 430.0 (M+H)$^+$.

Example 138

5,5-Dimethyl-3-[(1-methyl-1H-imidazol-4-yl) acetyl]-2-(morpholin-4-yl)-5,6-dihydro-1-benzothiophen-7(4H)-one To a pH 2 buffer solution (100 mL) was added a solution of Example 41 (0.16 g, 0.43 mmol) in DMSO (2 mL). The reaction mixture was stirred at r.t. for 16 h then freeze dried. The resulting semi-solid was dissolved in water (50 mL), and EtOAc (50 mL) was added. The layers were separated. The aqueous layer was extracted with DCM (4×20 mL). The combined organic layers were dried (Na$_2$SO$_4$), filtered and concentrated in vacuo. Purification by column chromatography (SiO$_2$, 8% MeOH/EtOAc) gave the title compound (0.04 g, 21%) as an off-white solid. $\delta_H$ (DMSO-d$_6$), mixture of ketone (major form) and enol (minor form); Ketone form: 7.42 (1H, s), 7.05 (1H, s), 4.08-4.00 (2H, m), 3.82-3.75 (4H, m), 3.58 (3H, s), 3.21-3.12 (4H, m), 2.56 (2H, s), 2.34 (2H, s), 0.95 (6H, s); Enol form: 7.77 (1H, s), 6.91 (1H, s), 5.47 (1H, s), 3.72-3.64 (4H, m), 3.58 (3H, s), 3.29-3.23 (4H, m), 2.61 (2H, s), 2.32 (2H, s), 1.00 (6H, s). Exchangeable proton not visible. MS (ES+) 388.0 (M+H)$^+$.

Example 139

(Method U)

1-[5,5-Dimethyl-2-(morpholin-4-yl)-7-oxo-4,5,6,7-tetrahydro-1-benzothien-3-yl]-2-(1-methyl-1H-imidazol-4-yl)ethane-1,2-dione To a stirred solution of Example 41 (0.10 g, 0.27 mmol) in DMSO (5 mL) was added aqueous 2M HCl (2 mL). The reaction mixture was stirred at r.t. for 16 h. EtOAc (40 mL) and water (20 mL) were added and the layers separated. The aqueous layer was taken to pH 9 by slow addition of aqueous sat. NaHCO$_3$ then extracted into EtOAc (2×20 mL). The combined organic layers were washed with brine (20 ml), dried (Na$_2$SO$_4$), filtered and concentrated in vacuo. Purification by column chromatography (SiO$_2$, 8% MeOH/EtOAc) gave the title compound (0.03 g, 30%) as a pale yellow solid. $\delta_H$ (DMSO-d$_6$) 8.12 (1H, s), 7.79 (1H, s), 3.75 (3H, s), 3.49-3.46 (4H, m), 3.07-3.05 (4H, m), 2.75 (2H, s), 2.42 (2H, s), 1.00 (6H, s). MS (ES+) 402.0 (M+H)$^+$.

Example 140

1-[5,5-Dimethyl-2-(morpholin-4-yl)-7-oxo-4,5,6,7-tetrahydro-1-benzothien-3-yl]-2-(1-methyl-1H-imidazol-5-yl)ethane-1,2-dione The title compound was prepared from Example 20 according to Method U and was isolated as a pale yellow solid (16%) after purification by column chromatography (SiO$_2$, 8% MeOH/EtOAc). $\delta_H$ (DMSO-d$_6$) 8.15 (1H, s), 7.69 (1H, s), 3.97 (3H, s), 3.51-3.46 (4H, m), 3.10-3.08 (4H, m), 2.73 (2H, s), 2.43 (2H, s), 1.01 (6H, s). MS (ES+) 401.9 (M+H)$^+$.

Example 141

5,5-Dimethyl-3-[(Z)-2-(1-methyl-1H-imidazol-5-yl) vinyl]-2-(morpholin-4-yl)-5,6-dihydro-1-benzothiophen-7(4H)-one A solution of Example 20 (0.05 g, 0.14 mmol) in EtOH (5 mL) was hydrogenated using palladium on carbon (0.01 g) and a balloon at r.t. for 48 h. The reaction mixture was then filtered through Celite®, and the solvent removed in vacuo to give the title compound (0.02 g, 32%) that required no further purification. $\delta_H$ (DMSO-d$_6$) 7.59 (1H, s), 6.61 (1H, dd, J 11.7 and 0.6 Hz), 6.41 (1H, s), 6.30 (1H, d, J 11.7 Hz), 3.63 (3H, s), 3.64-5.52 (4H, m), 3.25-3.15 (4H, m), 2.27 (2H, s), 2.26 (2H, s), 0.89 (6H, s). MS (ES+) 372.1 (M+H)$^+$.

Example 142

5,5-Dimethyl-2-(morpholin-4-yl)-3-(phenylethynyl)-5,6-dihydro-1-benzothiophen-7(4H)-one The title compound was prepared from Example 17 and phenylacetylene according to Method C and was isolated as a fluffy white solid (78%) after trituration of the precipitate, formed upon completion of the reaction, with water. $\delta_H$ (DMSO-d$_6$) 7.53-7.48 (2H, m), 7.46-7.38 (3H, m), 3.83-3.75 (4H, m), 3.68-3.60 (4H, m), 2.70 (2H, s), 2.36 (2H, s), 1.07 (6H, s). MS (ES+) 366.0 (M+H)$^+$.

Example 143

3-[(4-Aminopyridin-3-yl)ethynyl]-5,5-dimethyl-2-(morpholin-4-yl)-5,6-dihydro-1-benzothiophen-7(4H)-one The title compound was prepared from Example 38 and 4-amino-3-iodopyridine according to Method C and was isolated as an off-white solid (87%) after purification by column chromatography (SiO$_2$, 10% MeOH/EtOAc), followed by trituration with EtOAc. $\delta_H$(DMSO-d$_6$) 8.20 (1H, s), 7.98 (1H, d, J 5.7 Hz), 6.62 (1H, d, J 5.7 Hz), 6.22 (2I4, br. s), 3.78-3.75 (4H, m), 3.65-3.62 (4H, m), 2.74 (2H, s), 2.34 (2H, s), 1.06 (6H, s). MS (ES+) 382.0 (M+H)$^+$.

Example 144

5,5-Dimethyl-2-(morpholin-4-yl)-3-[(E)-2-phenylvinyl]-5,6-dihydro-1-benzothiophen-7(4H)-one A mixture of Example 16 (0.32 g, 0.93 mmol), styreneboronic acid (0.41 g, 2.79 mmol), palladium acetate (0.02 g, 0.08 mmol), 1,3-bis(diphenylphosphino)propane (0.038 g, 0.08 mmol) and K$_3$PO$_4$ (0.59 g, 3.30 mmol) in 1,4-dioxane (30 mL) was heated at 90° C.' for 36 h. The reaction mixture was then concentrated in vacuo. Purification by column chromatography (SiO$_2$, 0-25% EtOAc/hexanes) gave the title compound (0.02 g, 7%) as an off-white solid. $\delta_H$ (DMSO-d$_6$) 7.61-7.40 (2H, m), 7.40-7.37 (2H, m), 7.30-7.26 (1H, m), 6.99 (2H, s), 3.83-3.73 (4H, m), 3.18-3.08 (4H, m), 2.80 (2H, s), 2.40 (2H, s), 0.96 (6H, s). MS (ES+) 368.0 (M+H)$^+$.

Example 145

5,5-Dimethyl-3-(4-methoxyphenyl)-2-(morpholin-4-yl)-5,6-dihydro-1-benzothiophen-7(4H)-one The title compound was prepared from Example 17 and 4-methoxyphenylboronic acid according to Method J and was isolated as a beige solid (40%) after purification by preparative HPLC (pH 2.5). $\delta_H$ (DMSO-d$_6$) 7.34-7.28 (2H, m), 7.05-7.00 (2H, m), 3.79 (3H, s), 3.60-3.54 (4H, m), 2.94-2.88 (4H, m), 2.45 (2H, s), 2.35 (2H, s), 0.95 (6H, s). LCMS (ES+) 372.2 (M+H)$^+$.

Example 146

5,5-Dimethyl-3-(3-hydroxyphenyl)-2-(morpholin-4-yl)-5,6-dihydro-1-benzothiophen-7(4H)-one The title compound was prepared from Example 17 and 3-hydroxyphenylboronic acid according to Method J and was isolated as an off-white solid (71%) after purification by preparative HPLC (pH 2.5). $\delta_H$(DMSO-d$_6$) 9.57 (1H, s), 7.25 (1H, t, J 8.1 Hz), 6.80-6.71 (3H, m), 3.61-3.54 (4H, m), 2.96-2.90 (4H, m), 2.45 (2H, s), 2.35 (2H, s), 0.96 (6H, s). LCMS (ES+) 358.2 (M+H)$^+$.

Example 147

N-{3-[4-(5,5-Dimethyl-2-(morpholin-4-yl)-7-oxo-4,5,6,7-tetrahydro-1-benzothien-3-yl)pyridin-2-yl]phenyl}acetamide The title compound was prepared from Example 73 and 3-acetamidobenzene-boronic acid according to Method L and was isolated as an off-white solid (77%) after purification by preparative HPLC (pH 2.5). $\delta_H$ (DMSO-d$_6$) 10.09 (1H, s), 8.75 (1H, d, J 5.1 Hz), 8.47 (1H, s), 7.95 (1H, s), 7.78 (1H, d, J 7.9 Hz), 7.64 (1H, dd, J 7.9, 0.9 Hz), 7.47-7.38 (2H, m), 3.64-3.58 (4H, m), 3.01-2.95 (4H, m), 2.58 (2H, s), 2.39 (2H, s), 2.08 (3H, s), 0.97 (6H, s). LCMS (ES+) 476.3 (M+H)$^+$.

Example 148

3-(2-{4-[(Dimethylamino)methyl]phenyl}pyridin-4-yl)-5,5-dimethyl-2-(morpholin-4-yl)-5,6-dihydro-1-benzothiophen-7(4H)-one, Acetic Acid Salt The title compound was prepared from Example 73 and N,N-(dimethylamino-methyl)phenyl-4-boronic acid pinacol ester according to Method L and was isolated as a brown solid (82%) after purification by preparative HPLC (pH 5.8). $\delta_H$ (DMSO-d$_6$) 8.73 (1H, d, J 5.1 Hz), 8.11 (2H, d, J 8.3 Hz), 8.01 (1H, s), 7.45-7.37 (3H, m), 3.64-3.55 (4H, m), 3.45 (2H, s), 3.03-2.95 (4H, m), 2.58 (2H, s), 2.39 (2H, s), 2.17 (6H, s), 1.89 (6H, s), 0.97 (6H, s). LCMS (ES+) 476.2 (M+H)$^+$.

Example 149

3-[3-(Benzyloxy)phenyl]-5,5-dimethyl-2-(morpholin-4-yl)-5,6-dihydro-1-benzothiophen 7(4H)-one The title compound was prepared from Example 17 and 3-benzyloxyphenyl-boronic acid according to Method L and was isolated as an off-white solid (3%) after purification by preparative HPLC (pH 5.8). $\delta_H$ (DMSO-d$_6$) 7.49-7.30 (6H, m), 7.04-6.92 (3H, m), 5.16 (2H, s), 3.56-3.49 (4H, m), 2.93-2.86 (4H, m), 2.39 (2H, s), 2.34 (2H, s), 0.94 (6H, s). LCMS (ES+) 448.2 (M+H)$^+$.

Example 150

5,5-Dimethyl-3-[2-(4-hydroxyphenyl)pyridin-4-yl]-2-(morpholin-4-yl)-5,6-dihydro-1-benzothiophen-7(4H)-one The title compound was prepared from Example 73 and 4-hydroxyphenylboronic acid according to Method L and was isolated as a brown solid (40%) after purification by preparative HPLC (pH 2.5). $\delta_H$ (DMSO-d$_6$) 9.82 (1H, br s), 8.66 (1H, d, J 5.1 Hz), 7.99 (2H, d, J 8.9 Hz), 7.87 (1H, s), 7.29 (1H, dd, J 4.9, 1.3 Hz), 6.88 (2H, d, J 8.9 Hz), 3.64-3.54 (4H, m), 3.02-2.93 (4H, m), 2.57 (2H, s), 2.38 (2H, s), 0.97 (6H, s). LCMS (ES+) 435.3 (M+H)$^+$.

Example 151

5,5-Dimethyl-3-[2-(4-methoxyphenyl)pyridin-4-yl]-2-(morpholin-4-yl)-5,6-dihydro-1-benzothiophen-7(4H)-one, Formic Acid Salt The title compound was prepared from Example 73 and 4-methoxyphenylboronic acid according to Method L and was isolated as an off-white solid (30%) after purification by preparative HPLC (pH 2.5). $\delta_H$(DMSO-d$_6$) 8.69 (1H, d, J 4.9 Hz), 8.17 (1H, s), 8.11 (2H, d, J 8.9 Hz), 7.95 (1H, s), 7.33 (1H, dd, J 5.1, 1.3 Hz), 7.07 (2H, d, J 8.9 Hz), 3.83 (3H, s), 3.63-3.55 (4H, m), 3.02-2.94 (4H, m), 2.58 (2H, s), 2.39 (2H, s), 0.97 (6H, s). LCMS (ES+) 435.3 (M+H)$^+$.

Example 152

3-{2-[3-(Dimethylamino)phenyl]pyridin-4-yl}-5,5-dimethyl-2-(morpholin-4-yl)-5,6-dihydro-1-benzothiophen-7(4H)-one The title compound was prepared from Example 73 and 3-(N,N-dimethylamino)-phenylboronic acid according to Method L and was isolated as an off-white solid (50%) after purification by preparative HPLC (pH 2.5). $\delta_H$ (DMSO-$d_6$) 8.73 (1H, d, J 4.9 Hz), 8.01 (1H, s), 7.49-7.28 (4H, m), 6.83 (1H, dd, J 7.9, 2.1 Hz), 3.66-3.56 (4H, m), 3.05-2.94 (10H, m), 2.60 (2H, s), 2.39 (2H, s), 0.97 (6H, s). LCMS (ES+) 462.3 (M+H)$^+$.

Example 153

N-{4-[4-(5,5-Dimethyl-2-(morpholin-4-yl)-7-oxo-4,5,6,7-tetrahydro-1-benzothien-3-yl)pyridin-2-yl]phenyl}acetamide The title compound was prepared from Example 73 and 4-acetamidophenyl-boronic acid according to Method L and was isolated as an off-white solid (44%) after purification by preparative HPLC (pH 2.5). $\delta_H$ (DMSO-$d_6$) 10.12 (1H, s), 8.70 (1H, d, J 4.9 Hz), 8.10 (2H, d, J 8.7 Hz), 7.96 (1H, s), 7.72 (2H, d, J 8.7 Hz), 7.35 (1H, dd, J 5.1, 1.3 Hz), 3.64-3.56 (4H, m), 3.03-2.94 (4H, m), 2.58 (2H, s), 2.39 (2H, s), 2.08 (3H, s), 0.97 (6H, s). LCMS (ES+) 476.3 (M+H)$^+$.

Example 154

3-{2-[4-(Dimethylamino)phenyl]-4-yl}-5,5-dimethyl-2-(morpholin-4-yl)-5,6-dihydro-1-benzothiophen-7(4H)-one The title compound was prepared from Example 73 and 4-(N,N-dimethylamino)-phenylboronic acid according to Method L and was isolated as a green-blue solid (10%) after purification by preparative HPLC (pH 2.5). $\delta_H$ (DMSO-$d_6$) 8.63 (1H, d, J 4.9 Hz), 8.01 (2H, d, J 9.0 Hz), 7.86 (1H, s), 7.22 (1H, dd, J 5.1, 1.3 Hz), 6.81 (2H, d, J 9.0 Hz), 3.56-3.64 (4H, m), 3.04-2.95 (10H, m), 2.58 (2H, s), 2.38 (2H, s), 0.97 (6H, s). LCMS (ES+) 462.3 (M+H)$^+$.

Example 155

5,5-Dimethyl-3-{2-[3-(hydroxymethyl)phenyl]pyridin-4-yl}-2-(morpholin-4-yl)-5,6-dihydro-1-benzothiophen-7(4H)-one The title compound was prepared from Example 73 and 3-(hydroxymethyl)-phenylboronic acid according to Method L and was isolated as a white solid (50%) after purification by preparative HPLC (pH 2.5). $\delta_H$ (DMSO-$d_6$) 8.75 (1H, d, J 4.9 Hz), 8.12 (1H, s), 8.04-7.97 (2H, m), 7.51-7.38 (3H, m), 5.29 (1H, t, J 5.8 Hz), 4.60 (2H, d, J 5.8 Hz), 3.65-3.55 (4H, m), 3.04-2.94 (4H, m), 2.58 (2H, s), 2.39 (2H, s), 0.97 (6H, s). LCMS (ES+) 449.2 (M+H)$^+$.

Example 156

5,5-Dimethyl-3-(3-methoxyphenyl)-2-(morpholin-4-yl)-5,6-dihydro-1-benzothiophen-7(4H)-one The title compound was prepared from Example 17 and 3-methoxyphenylboronic acid according to Method J and was isolated as a pale yellow solid (56%) after purification by column chromatography (SiO$_2$, 0-100% EtOAc/heptane). $\delta_H$ (CD$_3$OD) 7.43-7.35 (1H, m), 6.97-6.91 (3H, m), 3.84 (3H, s), 3.71-3.61 (4H, m), 3.09-3.00 (4H, m), 2.51 (2H, s), 2.43 (2H, s), 1.03 (6H, s). LCMS (ES+) 372.3 (M+H)$^+$.

Example 157

5,5-Dimethyl-3-(3-ethoxyphenyl)-2-(morpholin-4-yl)-5,6-dihydro-1-benzothiophen-7(4H)-one The title compound was prepared from Example 17 and 3-ethoxyphenylboronic acid according to Method J and was isolated as a white solid (44%) after purification by column chromatography (SiO$_2$, 0-100% EtOAc/heptane). $\delta_H$ (CDCl$_3$) 7.36-7.29 (1H, m), 6.92-6.84 (3H, m), 4.06 (2H, q, J 7.0 Hz), 3.70-3.62 (4H, m), 3.04-2.96 (4H, m), 2.46 (2H, s), 2.42 (2H, s), 1.45 (3H, t, J 7.0 Hz), 1.03 (6H, s). LCMS (ES+) 386.3 (M+H)$^+$.

Example 158

3-[4-(5,5-Dimethyl-2-(morpholin-4-yl)-7-oxo-4,5,6,7-tetrahydro-1-benzothien-3-yl)pyridin-2-yl]benzaldehyde The title compound was prepared from Example 73 and 3-formylphenylboronic acid according to Method L and was isolated as an off-white solid (10%) after purification by preparative HPLC (pH 2.5). $\delta_H$ (DMSO-$d_6$) 10.14 (1H, s), 8.80 (1H, d, J 4.9 Hz), 8.73-8.71 (1H, m), 8.52-8.47 (1H, m), 8.16 (1H, d, J 0.4 Hz), 8.00 (1H, d, J 7.5 Hz), 7.76 (1H, t, J 7.7 Hz), 7.48 (1H, dd, J 5.3, 1.5 Hz), 3.65-3.56 (4H, m), 3.04-2.96 (4H, m), 2.59 (2H, s), 2.39 (2H, s), 0.98 (6H, s). LCMS (ES+) 447.2 (M+H)$^+$.

Example 159

3-{2-[3-(Aminomethyl)phenyl]pyridin-4-yl}-5,5-dimethyl-2-(morpholin-4-yl)-5,6-dihydro-1-benzothiophen-7(4B)-one A solution of Example 224 (115 mg, 0.21 mmol) in methanol (8.0 mL) was treated with a 2N solution of HCl in Et$_2$O (4.0 mL, 2.0 mmol). After stirring for 19 h at room temperature, the solvent was removed in vacuo. The orange residue was purified by preparative HPLC (pH 2.5), then partitioned between 1M NaOH solution (3 mL) and EtOAc (10 mL). The organic phase was purified by column chromatography (SiO$_2$, 2% NH$_4$OH, 20% MeOH in EtOAc) to give the title compound (35 mg, 49%) as an off-white solid. $\delta_H$ (CD$_3$OD) 8.76-8.71 (1H, m), 8.07-8.03 (1H, m), 8.00-7.93 (2H, m), 7.60-7.45 (3H, m), 4.02 (2H, s), 3.73-3.63 (4H, m), 3.13-3.04 (4H, m), 2.63 (2H, s), 2.48 (2H, s), 1.06 (6H, s). LCMS (ES+) 448.3 (M+H)$^+$.

Example 160

3-{2-[3-(Aminomethyl)phenyl]pyridin-4-yl}-5,5-dimethyl-2-(morpholin-4-yl)-5,6-dihydro-1-benzothiophen-7(4H)-one, Formic Acid Salt The title compound was prepared from Example 73 and 3-(aminomethyl)phenyl-boronic acid hydrochloride according to Method L and was isolated as a clear glass (15%) after purification by preparative HPLC (pH 2.5). $\delta_H$ (DMSO-$d_6$) 8.75 (1H, d, J 5.1 Hz), 8.29 (1H, s), 8.19 (1H, s), 8.10-8.02

(2H, m), 7.55-7.40 (3H, m), 3.97 (2H, s), 3.65-3.56 (4H, m), 3.03-2.95 (4H, m), 2.57 (2H, s), 2.39 (2H, s), 0.97 (6H, s). LCMS (ES+) 448.4 (M+H)$^+$.

Example 161

3-[2-(1-Benzothien-3-yl)pyridin-4-yl]-5,5-dimethyl-2-(morpholin-4-yl)-5,6-dihydro-1-benzothiophen-7(4H)-one The title compound was prepared from Example 73 and 1-benzothiophen-3-ylboronic acid according to Method L and was isolated as a clear glass (8%) after purification by preparative HPLC (pH 2.5). $\delta_H$ (DMSO-d$_6$) 8.78-8.84 (2H, m), 8.43 (1H, s), 8.07-8.12 (1H, m), 7.98 (1H, s), 7.43-7.54 (3H, m), 3.59-3.66 (4H, m), 2.97-3.05 (4H, m), 2.62 (2H, s), 2.40 (2H, s), 0.99 (6H, s). LCMS (ES+) 475.2 (M+H)$^+$.

Example 162

3-[2-(1-Benzofuran-2-yl)pyridin-4-yl]-5,5-dimethyl-2-(morpholin-4-yl)-5,6-dihydro-1-benzothiophen-7(4H)-one, Formic Acid Salt The title compound was prepared from Example 73 and benzo[b]furan-2-boronic acid according to Method L and was isolated as a clear glass (3%) after purification by preparative HPLC (pH 2.5). $\delta_H$ (DMSO-d$_6$) 8.76 (1H, d, J 5.1 Hz), 8.30 (1H, s), 8.04 (1H, s), 7.79-7.65 (3H, m), 7.48-7.29 (3H, m), 3.65-3.58 (4H, m), 3.05-2.98 (4H, m), 2.60 (2H, s), 2.41 (2H, s), 0.98 (6H, s). LCMS (ES+) 459.3 (M+H)$^+$.

Example 163

3-[2-(Benzyloxy)phenyl]-5,5-dimethyl-2-(morpholin-4-yl)-5,6-dihydro-1-benzothiophen-7(4H)-one The title compound was prepared from Example 17 and 2-benzyloxyphenyl-boronic acid according to Method J and was isolated as a white solid (44%) after purification by preparative HPLC (pH 2.5). $\delta_H$ (CD$_3$OD) 7.43-7.18 (8H, m), 7.10-7.03 (1H, m), 5.13 s), 3.61-3.48 (4H, m), 3.09-2.98 (4H, m), 2.44-2.26 (4H, m), 0.98 (3H, s), 0.93 (3H, s). LCMS (ES+) 448.2 (M+H)$^+$.

Example 164

5,5-Dimethyl-2-(morpholin-4-yl)-3-(1-naphthyl)-5,6-dihydro-1-benzothiophen-7(4H)-one The title compound was prepared from Example 17 and 1-naphthaleneboronic acid according to Method J and was isolated as an off-white solid (31%) after purification by preparative HPLC (pH 2.5). $\delta_H$ (CDCl$_3$) 7.95-7.87 (2H, m), 7.67-7.61 (1H, m), 7.58-7.45 (3H, m), 7.41-7.37 (1H, m), 3.51-3.33 (4H, m), 2.98-2.85 (4H, m), 2.42 (2H, s), 0.96 (3H, s), 2.16 (2H, q, J 16.8 Hz), 0.97 (3H, s). LCMS (ES+) 392.3 (M+H)$^+$.

Example 165

3-(Dibenzo[b,d]thien-4-yl)-5,5-dimethyl-2-(morpholin-4-yl)-5,6-dihydro-1-benzothiophen-7(4H)-one The title compound was prepared from Example 17 and dibenzothiophene-4-boronic acid according to Method J and was isolated as an off-white solid (48%) after purification by preparative HPLC (pH 2.5). $\delta_H$ (CDCl$_3$) 8.23-8.16 (2H, m), 7.89-7.83 (1H, m), 7.59-7.46 (3H, m), 7.37-7.32 (1H, m), 3.60-3.44 (4H, m), 3.05-2.97 (4H, m), 2.42 (2H, s), 2.30 (2H, m), 0.99 (6H, s). LCMS (ES+) 448.3 (M+H)$^+$.

Example 166

5,5-Dimethyl-3-{2-[4-(hydroxymethyl)phenyl]pyridin-4-yl}-2-(morpholin-4-yl)-5,6-dihydro-1-benzothiophen-7(4H)-one The title compound was prepared from Example 73 and 4-(hydroxymethyl)-phenylboronic acid according to Method L and was isolated as an off-white solid (61%) after purification by preparative HPLC (pH 2.5). $\delta_H$ (DMSO-d$_6$) 8.72 (1H, d, J 5.1 Hz), 8.11 (2H, d, J 8.3 Hz), 8.01 (1H, s), 7.45 (2H, d, J 8.3 Hz), 7.36-7.41 (1H, m), 5.27 (1H, t, J 5.7 Hz), 4.57 (2H, d, J 5.5 Hz), 3.65-3.55 (4H, m), 3.04-2.94 (4H, m), 2.58 (2H, s), 2.38 (2H, s), 0.97 (6H, s). LCMS (ES+) 449.3 (M+H)$^+$.

Example 167

3-[2-(1-Benzothien-2-yl)pyridin-4-yl]-5,5-dimethyl-2-(morpholin-4-yl)-5,6-dihydro-1-benzothiophen-7(4H)-one The title compound was prepared from Example 73 and benzo[b]thiophene-2-boronic acid according to Method L and was isolated as an off-white solid (7%) after purification by preparative HPLC (pH 2.5). $\delta_H$ (DMSO-d$_6$) 8.68 (1H, d, J 5.1 Hz), 8.28 (1H, s), 8.19 (1H, s), 8.04-7.99 (1H, m), 7.92-7.87 (1H, m), 7.45-7.39 (3H, m), 3.67-3.59 (4H, m), 3.06-2.98 (4H, m), 2.61 (2H, s), 2.40 (2H, s), 0.98 (6H, s). LCMS (ES+) 475.2 (M+H)$^+$.

Example 168

5,5-Dimethyl-3-[2-(1H-indol-6-yl)pyridin-4-yl]-2-(morpholin-4-D-5,6-dihydro-1-benzothiophen-7(4H)-one The title compound was prepared from Example 73 and indole-6-boronic acid according to Method L and was isolated as an off-white solid (42%) after purification by preparative HPLC (pH 2.5). $\delta_H$ (DMSO-d$_6$) 11.30 (1H, s), 8.71 (1H, d, J 4.9 Hz), 8.21 (1H, s), 7.99 (1H, s), 7.83-7.76 (1H, m), 7.68-7.61 (1H, m), 7.49-7.44 (1H, m), 7.35-7.29 (1H, m), 6.48 (1H, s), 3.67-3.57 (4H, m), 3.06-2.96 (4H, m), 2.61 (2H, s), 2.40 (2H, s), 0.98 (6H, s). LCMS (ES+) 458.2 (M+H)$^+$.

Example 169

N-{3-[4-(5,5-Dimethyl-2-(morpholin-4-yl)-7-oxo-4,5,6,7-tetrahydro-1-benzothien-3-yl)pyridin-2-yl]benzyl}methanesulfonamide The title compound was prepared from Example 73 and 3-(methanesulfonyl-aminomethyl)phenylboronic acid according to Method L and was isolated as an off-white solid (39%) after purification by preparative HPLC (pH 5.8). $\delta_H$ (DMSO-d$_6$) 8.76 (1H, d, J 4.9 Hz), 8.16 (1H, s), 8.08-8.02 (2H, m), 7.69-7.62 (1H, m), 7.55-7.40 (3H, m), 4.26 (2H, d, J 6.2 Hz), 3.64-3.56 (4H, m), 3.02-2.95 (4H, m), 2.90 (3H, s), 2.58 (2H, s), 2.39 (2H, s), 0.97 (6H, s). LCMS (ES+) 526.2 (M+H)$^+$.

Example 170

3-[4-(5,5-Dimethyl-2-(morpholin-4-yl)-7-oxo-4,5,6,7-tetrahydro-1-benzothien-3-yl)pyridin-2-yl]-N,N-dimethylbenzamide The title compound was prepared from Example 73 and 3-(N,N-dimethyl-aminocarbonyl)phenylboronic acid according to Method L and was isolated as an off-white solid (33%) after purification by preparative HPLC (pH 5.8). $\delta_H$ (DMSO-$d_6$) 8.76 (1H, d, J 5.1 Hz), 8.26-8.21 (1H, m), 8.18 (1H, s), 8.10 (1H, s), 7.59 (1H, t, J 7.7 Hz), 7.52-7.47 (1H, m), 7.44 (1H, dd, J 4.9, 1.1 Hz), 3.64-3.55 (4H, m), 3.08-2.93 (10H, m), 2.59 (2H, s), 2.39 (2H, s), 0.97 (6H, s). LCMS (ES+) 490.2 (M+H)$^+$.

Example 171

(Method AA)

N-[4-(5,5-Dimethyl-2-(morpholin-4-yl)-7-oxo-4,5,6,7-tetrahydro-1-benzothien-3-yl)phenyl]-1-phenyl-methanesulfonamide A solution of Example 78 (50 mg, 0.14 mmol) in anhydrous DMF (2.0 mL) was treated with α-toluenesulfonyl chloride (40 mg, 0.21 mmol) and triethylamine (0.06 mL, 0.42 mmol). The reaction mixture was stirred at room temperature for 18 h, then quenched by the addition of a few drops of water and the solvent removed in vacuo. The title compound was obtained as a pale orange solid (26 mg, 36%) after purification by preparative HPLC (pH 2.5). $\delta_H$ (CDCl$_3$) 7.41-7.28 (7H, m), 7.20-7.14 (2H, m), 6.28 (1H, s), 4.42 (2H, s), 3.72-3.63 (4H, m), 3.03-2.94 (4H, m), 2.46 (4H, d, J 7.5 Hz), 1.06 (6H, s). LCMS (ES+) 511.1 (M+H)$^+$.

Example 172

N-[4-(5,5-Dimethyl-2-(morpholin-4-yl)-7-oxo-4,5,6,7-tetrahydro-1-benzothien-3-yl)phenyl]-3,5-dimethylisoxazole-4-sulfonamide The title compound was prepared from Example 78 and 3,5-dimethylisoxazole-4-sulfonyl chloride according to Method AA and was isolated as a pale yellow solid (9%) after purification by preparative HPLC (pH 2.5). $\delta_H$ (CDCl$_3$) 7.36-7.30 (2H, m), 7.19-7.14 (2H, m), 6.78 (1H, s), 3.68-3.60 (4H, m), 2.99-2.91 (4H, m), 2.53 (3H, s), 2.43 (2H, s), 2.40 (2H, s), 2.32 (3H, s), 1.03 (6H, s). LCMS (ES+) 516.1 (M+H)$^+$.

Example 173

5,5-Dimethyl-3-(2-methoxyphenyl)-2-(morpholin-4-yl)-5,6-dihydro-1-benzothiophen-7(4H)-one The title compound was prepared from Example 17 and 2-methoxyphenylboronic acid according to Method J and was isolated as a clear oil (14%) after purification by preparative HPLC (pH 2.5). $\delta_H$ (CDCl$_3$) 7.40-7.33 (1H, m), 7.25-7.20 (1H, m), 7.05-6.96 (2H, m), 3.81 (3H, s), 3.66-3.58 (4H, m), 3.05-2.96 (4H, m), 2.51-2.33 (3H, m), 2.25-2.15 (1H, m), 1.05 (3H, s), 0.98 (3H, s). LCMS (ES+) 372.2 (M+H)$^+$.

Example 174

3-[3'-(Dimethylamino)biphenyl-3-yl]-5,5-dimethyl-2-(morpholin-4-yl)-5,6-dihydro-1-benzothiophen-7(4H)-one The title compound was prepared from Example 17, 3-bromophenylboronic acid and 3-(N,N-dimethylamino)phenylboronic acid according to Method K and was isolated as a white solid (31%) after purification by preparative HPLC (pH 5.8). $\delta_H$ (CD$_3$OD) 7.66-7.60 (2H, m), 7.59-7.51 (1H, m), 7.39-7.28 (2H, m), 7.02-6.95 (2H, m), 6.86-6.80 (1H, m), 3.71-3.62 (4H, m), 3.12-3.04 (4H, m), 3.02 (6H, s), 2.59 (2H, s), 2.46 (2H, s), 1.05 (6H, s). LCMS (ES+) 461.3 (M+H)$^+$.

Example 175

5,5-Dimethyl-3-(isoquinolin-5-yl)-2-(morpholin-4-yl)-5,6-dihydro-1-benzothiophen-7(4H)-one, Acetic Acid Salt The title compound was prepared from Example 17 and isoquinoline-5-boronic acid according to Method J and was isolated as a white solid (31%) after purification by preparative HPLC (pH 5.8). $\delta_H$ (CD$_3$OD) 9.36 (1H, s), 8.49 (1H, d, J 6.0 Hz), 8.22 (1H, dd, J 7.9, 0.9 Hz), 7.88-7.77 (2H, m), 7.58 (1H, d, J 6.0 Hz), 3.52-3.35 (4H, m), 3.05-2.89 (4H, m), 2.45 (2H, d, J 5.5 Hz), 2.41-2.10 (2H, m), 1.01 (3H, s), 0.96 (3H, s). LCMS (ES+) 393.2 (M+H)$^+$.

Example 176

3-[4-(5,5-Dimethyl-2-(morpholin-4-yl)-7-oxo-4,5,6,7-tetrahydro-1-benzothien-3-yl)pyridin-2-yl]benzonitrile The title compound was prepared from Example 73 and 3-cyanophenylboronic acid according to Method L and was isolated as an off-white solid (52%) after purification by preparative HPLC (pH 5.8). $\delta_H$ (DMSO-$d_6$) 8.79 (1H, d, 15.1 Hz), 8.59 (1H, s), 8.51 (1H, m), 8.18 (1H, s), 7.94 (1H, m), 7.74 (1H, t, J 7.9 Hz), 7.49 (1H, dd, J 4.9, 1.3 Hz), 3.64-3.54 (4H, m), 3.04-2.94 (4H, m), 2.58 (2H, s), 2.39 (2H, s), 0.97 (6H, s). LCMS (ES+) 444.3 (M+H)$^+$.

Example 177

4-[4-(5,5-Dimethyl-2-(morpholin-4-yl)-7-oxo-4,5,6,7-tetrahydro-1-benzothien-3-yl)pyridin-2-yl]benzonitrile The title compound was prepared from Example 73 and 4-cyanophenylboronic acid according to Method L and was isolated as an off-white solid (33%) after purification by preparative HPLC (pH 2.5). $\delta_H$ (DMSO-$d_6$) 8.81 (1H, d, J 5.1 Hz), 8.36 (2H, d, J 8.5 Hz), 8.18 (1H, s), 7.99 (2H, d, J 8.5 Hz), 7.51 (1H, dd, J 4.9, 1.3 Hz), 3.64-3.54 (4H, m), 3.02-2.94 (4H, m), 2.59 (2H, s), 2.39 (2H, s), 0.97 (6H, s). LCMS (ES+) 444.2 (M+H)$^+$.

Example 178

5,5-Dimethyl-2-(morpholin-4-yl)-3-[3-(pyridin-3-yl)phenyl]-5,6-dihydro-1-benzothiophen-7(4H)-one The title compound was prepared from Example 17, 3-bromophenylboronic acid and pyridine-3-boronic acid 1,3-propanediol cyclic ester according to Method K and was isolated as a white solid (25%) after purification by preparative HPLC (pH 5.8). $\delta_H$ (CDCl$_3$) 8.89 (1H, d, J 1.9 Hz), 8.64 (1H, dd, J 4.7, 1.5 Hz), 7.95-7.89 (1H, m), 7.63-7.60 (1H, m), 7.59-7.55 (2H, m), 7.45-7.38 (2H, m), 3.70-3.62 (4H, m), 3.05-2.98 (4H, m), 2.51 (2H, s), 2.45 (2H, s), 1.05 (6H, s). LCMS (ES+) 419.2 (M+H)$^+$.

Example 179

5,5'-Dimethyl-2'-(morpholin-4-yl)-5',6'-dihydro-2,3'-bi-1-benzothiophen-7'(4'H)-one The title compound was prepared from Example 17 and thianaphthene-2-boronic acid according to Method J and was isolated as an off-white solid (10%) after purification by preparative HPLC (pH 2.5). $\delta_H$ (DMSO-d$_6$) 8.02-7.96 (1H, m), 7.93-7.86 (1H, m), 7.47 (1H, s), 7.44-7.35 (2H, m), 3.71-3.62 (4H, m), 3.11-3.03 (4H, m), 2.63 (2H, s), 2.40 (2H, s), 0.99 (6H, s). LCMS (ES+) 398.2 (M+H)$^+$.

Example 180

3-(1-Benzofuran-2-yl)-5,5-dimethyl-2-(morpholin-4-yl)-5,6-dihydro-1-benzothiophen-7(4H)-one The title compound was prepared from Example 17 and 2-benzofuranboronic acid according to Method J and was isolated as an off-white solid (5%) after purification by preparative HPLC (pH 2.5). $\delta_H$ (DMSO-d$_6$) 7.71-7.66 (1H, m), 7.62 (1H, d, J 7.5 Hz), 7.37-7.25 (2H, m), 7.04 (1H, s), 3.74-3.65 (4H, m), 3.12-3.03 (4H, m), 2.68 (2H, s), 2.39 (2H, s), 1.01 (6H, s). LCMS (ES+) 382.2 (M+H)$^+$.

Example 181

N-{4-[4-(5,5-Dimethyl-2-(morpholin-4-yl)-7-oxo-4,5,6,7-tetrahydro-1-benzothien-3-yl)pyridin-2-yl]benzyl}methanesulfonamide, Formic Acid Salt The title compound was prepared from Example 73 and 4-(methanesulfonyl-aminomethyl)phenylboronic acid according to Method L and was isolated as a brown solid (52%) after purification by preparative HPLC (pH 2.5). $\delta_H$ (DMSO-d$_6$) 8.74 (1H, d, J 4.9 Hz), 8.15 (2H, d, J 8.1 Hz), 8.04 (1H, s), 7.68-7.60 (2H, m), 7.49 (2H, d, J 8.3 Hz), 7.43-7.37 (1H, m), 4.27-4.22 (2H, m), 3.65-3.56 (4H, m), 3.03-2.96 (4H, m), 2.90 (3H, s), 2.59 (2H, s), 2.39 (2H, s), 0.97 (6H, s). LCMS (ES+) 526.2 (M+H)$^+$.

Example 182

3-[4-(5,5-Dimethyl-2-(morpholin-4-yl)-7-oxo-4,5,6,7-tetrahydro-1-benzothien-3-yl)pyridin-2-yl]-N-methylbenzamide The title compound was prepared from Example 73 and 3-(N-methylamino-carbonyl)phenylboronic acid according to Method L and was isolated as a pale yellow solid (24%) after purification by preparative HPLC (pH 2.5). $\delta_H$ (DMSO-d$_6$) 8.78 (1H, d, J 4.9 Hz), 8.64-8.57 (2H, m), 8.30 (1H, d, J 7.7 Hz), 8.13 (1H, s), 7.92 (1H, d, J 7.9 Hz), 7.61 (1H, t, J 7.7 Hz), 7.44 (1H, dd, J 4.9, 1.1 Hz), 3.64-3.56 (4H, m), 3.04-2.95 (4H, m), 2.83 (3H, d, J 4.5 Hz), 2.59 (2H, s), 2.39 (2H, s), 0.97 (6H, s). LCMS (ES+) 476.4 (M+H)$^+$.

Example 183

N-{4-[4-(5,5-Dimethyl-2-(morpholin-4-yl)-7-oxo-4,5,6,7-tetrahydro-1-benzothien-3-yl)pyridin-2-yl]benzyl}acetamide The title compound was prepared from Example 73 and 4-(acetamidomethyl)-phenylboronic acid according to Method L and was isolated as a yellow solid (59%) after purification by preparative HPLC (pH 2.5). $\delta_H$ (DMSO-d$_6$) 8.73 (1H, d, J 5.1 Hz), 8.42 (1H, t, J 5.8 Hz), 8.11 (2H, d, J 8.3 Hz), 8.02 (1H, s), 7.44-7.34 (3H, m), 4.32 (2H, d, J 5.8 Hz), 3.65-3.55 (4H, m), 3.05-2.93 (4H, m), 2.59 (2H, s), 2.39 (2H, s), 1.90 (3H, s), 0.97 (6H, s). LCMS (ES+) 490.4 (M+H)$^+$.

Example 184

4-[4-(5,5-Dimethyl-2-(morpholin-4-yl)-7-oxo-4,5,6,7-tetrahydro-1-benzothien-3-yl)pyridin-2-yl]-N-methylbenzamide The title compound was prepared from Example 73 and 4-(N-methylamino-carbonyl)phenylboronic acid according to Method L and was isolated as a pale yellow solid (46%) after purification by preparative HPLC (pH 2.5). $\delta_H$ (DMSO-d$_6$) 8.77 (1H, d, J 5.1 Hz), 8.60-8.51 (1H, m), 8.25 (2H, d, J 8.5 Hz), 8.12 (1H, s), 7.97 (2H, d, J 8.5 Hz), 7.45 (1H, dd, J 5.1, 1.3 Hz), 3.64-3.55 (4H, m), 3.03-2.94 (4H, m), 2.81 (3H, d, J 4.5 Hz), 2.59 (2H, s), 2.39 (2H, s), 0.97 (6H, s). LCMS (ES+) 476.4 (M+H)$^+$.

Example 185

5,5-Dimethyl-3-(3-isobutoxyphenyl)-2-(morpholin-4-yl)-5,6-dihydro-1-benzothiophen-7(4H)-one The title compound was prepared from Example 17 and 3-isobutoxyphenylboronic acid according to Method J and was isolated as an off-white solid (58%) after purification by preparative HPLC (pH 2.5). $\delta_H$ (DMSO-d$_6$) 7.41-7.33 (1H, m), 6.97-6.88 (3H, m), 3.77 (2H, d, J 6.6 Hz), 3.63-3.52 (4H, m), 2.98-2.88 (4H, m), 2.47 (2H, s), 2.35 (2H, s), 2.10-1.97 (1H, m), 0.99 (6H, d, J 6.8 Hz), 0.96 (6H, s). LCMS (ES+) 414.3 (M+H)$^+$.

Example 186

3-[4-(5,5-Dimethyl-2-(morpholin-4-yl)-7-oxo-4,5,6,7-tetrahydro-1-benzothien-3-yl)pyridin-2-yl]benzamide The title compound was prepared from Example 73 and 3-(aminocarbonyl)-phenylboronic acid according to Method L and was isolated as an off-white solid (51%) after purification by preparative HPLC (pH 2.5). $\delta_H$ (DMSO-d$_6$) 8.78 (1H, d, J 5.1 Hz), 8.62 (1H, s), 8.31 (1H, d, J 7.9 Hz), 8.15 (2H, s), 7.96 (1H, d, J 7.5 Hz), 7.61 (1H, t, J 7.7 Hz), 7.51-7.41 (2H, m), 3.65-3.55 (4H, m), 3.05-2.94 (4H, m), 2.59 (2H, s), 2.39 (2H, s), 0.97 (6H, s). LCMS (ES+) 462.4 (M+H)$^+$.

Example 187

4-[(4-(5,5-Dimethyl-2-(morpholin-4-yl)-7-oxo-4,5,6,7-tetrahydro-1-benzothien-3-yl)pyridin-2-yl]benzamide The title compound was prepared from Example 73 and 4-(aminocarbonyl)-phenylboronic acid according to Method L and was isolated as a pale yellow solid (31%) after purification by preparative HPLC (pH 2.5). $\delta_H$ (DMSO-d$_6$) 8.78 (1H, d, J 5.1 Hz), 8.24 (2H, d, J 8.5 Hz), 8.12 (1H, s), 8.07 (1H, s), 8.01 (2H, d, J 8.3 Hz), 7.45 (2H, d, J 3.6 Hz), 3.65-3.56 (4H, m), 3.05-2.94 (4H, m), 2.60 (2H, s), 2.39 (2H, s), 0.97 (6H, s). LCMS (ES+) 462.2 (M+H)$^+$.

Example 188

3-{2-[2-(Aminomethyl)-4-fluorophenyl]pyridin-4-yl}-5,5-dimethyl-2-(morpholin-4-yl)-5,6-dihydro-1-benzothiophen-7(4H)-one, Formic Acid Salt The title compound was prepared from Example 73 and 2-(aminomethyl)-4-fluorophenylboronic acid hydrochloride according to Method L and was isolated as an off-white solid (25%) after purification by preparative HPLC (pH 2.5). $\delta_H$ (DMSO-d$_6$) 8.74 (1H, d, J 5.1 Hz), 8.28 (1H, s), 7.64 (1H, s), 7.58 (1H, dd, J 8.5, 6.0 Hz), 7.53-7.46 (2H, m), 7.27 (1H, td, J 8.5, 2.6 Hz), 3.87 (2H, s), 3.67-3.56 (4H, m), 3.03-2.93 (4H, m), 2.58 (2H, s), 2.39 (2H, s), 0.98 (6H, s). LCMS (ES+) 466.2 (M+H)$^+$.

Example 189

3-{2-[2-(Aminomethyl)-5-fluorophenyl]pyridin-4-yl}-5,5-dimethyl-2-(morpholin-4-yl)-5,6-dihydro-1-benzothiophen-7(4H)-one, Formic Acid Salt The title compound was prepared from Example 73 and 2-(aminomethyl)-5-fluorophenylboronic acid hydrochloride according to Method L and was isolated as a brown solid (49%) after purification by preparative HPLC (pH 2.5). $\delta_H$ (DMSO-d$_6$) 8.76 (1H, d, J 5.1 Hz), 8.33 (1H, s), 7.76 (1H, s), 7.66 (1H, dd, J 8.5, 6.0 Hz), 7.55 (1H, dd, J 5.3, 1.5 Hz), 7.43 (1H, dd, J 10.0, 2.6 Hz), 7.35 (1H, td, J 8.5, 2.6 Hz), 3.88 (2H, s), 3.65-3.55 (4H, m), 3.03-2.92 (4H, m), 2.59 (2H, s), 2.39 (2H, s), 0.98 (6H, s). LCMS (ES+) 466.1 (M+H)$^+$.

Example 190

3-Amino-4-[4-(5,5-dimethyl-2-(morpholin-4-yl)-7-oxo-4,5,6,7-tetrahydro-1-benzothien-3-yl)pyridin-2-yl]benzonitrile The title compound was prepared from Example 73 and 2-amino-4-cyanophenyl-boronic acid hydrochloride according to Method L and was isolated as an off-white solid (45%) after purification by preparative HPLC (pH 2.5). $\delta_H$ (DMSO-d$_6$) 8.73 (1H, d, J 5.1 Hz), 7.91 (1H, s), 7.79 (1H, d, J 8.3 Hz), 7.45 (1H, dd, J 5.1, 1.1 Hz), 7.17 (1H, d, J 1.7 Hz), 7.08 (2H, s), 7.01 (1H, dd, J 8.1, 1.7 Hz), 3.65-3.56 (4H, m), 3.03-2.93 (4H, m), 2.57 (2H, s), 2.38 (2H, s), 0.97 (6H, s). LCMS (ES+) 459.2 (M+H)$^+$.

Example 191

3-[2-(2-Aminophenyl)pyridin-4-yl]-5,5-dimethyl-2-(morpholin-4-yl)-5,6-dihydro-1-benzothiophen-7(4H)-one The title compound was prepared from Example 73 and 2-aminophenylboronic acid according to Method L and was isolated as a pale yellow solid (47%) after purification by preparative HPLC (pH 5.8). $\delta_H$ (DMSO-d$_6$) 8.67 (1H, d, J 5.1 Hz), 7.80 (1H, s), 7.62-7.57 (1H, m), 7.35 (1H, dd, J 4.9, 0.8 Hz), 7.15-7.08 (1H, m), 6.79 (1H, d, J 7.9 Hz), 6.73-6.61 (3H, m), 3.66-3.56 (4H, m), 3.03-2.94 (4H, m), 2.58 (2H, s), 2.39 (2H, s), 0.97 (6H, s). LCMS (ES+) 434.4 (M+H)$^+$.

Example 192

5,5-Dimethyl-3-{4-methyl-2-[4-(trifluoromethyl)phenyl]-1,3-thiazol-5-yl}-2-(morpholin-4-yl)-5,6-dihydro-1-benzothiophen-7(4H)-one The title compound was prepared from Example 17 and 4-methyl-5-(4,4,5,5-tetramethyl-1,3,2-dioxaborolan-2-yl)-2-[4-(trifluoromethyl)phenyl]-1,3-thiazole according to Method J, heating for 40 minutes at 130° C., and was isolated as a yellow solid (30%) after purification by column chromatography (SiO$_2$, 0-50% EtOAc/heptane). $\delta_H$ (DMSO-d$_6$) 8.17 (2H, d, J 8.5 Hz), 7.88 (2H, d, J 8.5 Hz), 3.67-3.59 (4H, m), 3.13-3.04 (4H, m), 2.41 (2H, s), 2.38 (2H, s), 2.30 (3H, s), 0.99 (6H, s). LCMS (ES+) 507.2 (M+H)$^+$.

Example 193

5,5-Dimethyl-3-(4-methoxybiphenyl-3-yl)-2-(morpholin-4-yl)-5,6-dihydro-1-benzothiophen-7(4H)-one A mixture of Example 17 (50 mg, 0.13 mmol), 5-bromo-2-methoxyphenylboronic acid (30 mg, 0.13 mmol), 2M aqueous sodium carbonate solution (0.14 mL, 0.28 mmol) and Pd(PPh$_3$)$_4$ (4.4 mg, 0.004 mmol) in DME (0.3 mL) and water (0.1 mL) was heated to 150° C. in a sealed tube, under microwave irradiation, for 10 minutes. Phenylboronic acid (16 mg, 0.13 mmol) was then added and the reaction mixture was heated again to 150° C. in a sealed tube, under microwave irradiation, for 5 minutes. The reaction mixture was concentrated in vacuo and purified by preparative HPLC (pH 2.5) to give the title compound (3.2 mg, 6%) as a cream solid. $\delta_H$ (CDCl$_3$) 7.64-7.56 (3H, m), 7.53-7.31 (4H, m), 7.05 (1H, d, J 8.5 Hz), 3.85 (3H, s), 3.65-3.59 (4H, m), 3.07-3.00 (4H, m), 2.51-2.21 (4H, m), 1.07 (3H, s), 0.99 (3H, s). LCMS (ES+) 448.2 (M+H)$^+$.

Example 194

3-{2-[4-(Aminomethyl)phenyl]pyridin-4-yl}-5,5-dimethyl-2-(morpholin-4-yl)-5,6-dihydro-1-benzothiophen-7(4H)-one, Formic Acid Salt The title compound was prepared from Example 73 and 4-(aminomethyl)phenyl-boronic acid hydrochloride according to Method L and was isolated as a pale yellow solid (36%) after purification by preparative HPLC (pH 2.5). $\delta_H$ (DMSO-d$_6$) 8.74 (1H, d, J 5.1 Hz), 8.32 (1H, s), 8.21-8.01 (4H, m), 7.54 (2H, d, J 8.3 Hz), 7.41 (2H, dd, J 4.9, 1.1 Hz), 3.95 (2H, s), 3.64-3.55 (4H, m), 3.04-2.94 (4H, m), 2.59 (2H, s), 2.39 (2H, s), 0.97 (6H, s). LCMS (ES+) 448.4 (M+H)$^+$.

Example 195

N-{3-[4-(5,5-Dimethyl-2-(morpholin-4-yl)-7-oxo-4,5,6,7-tetrahydro-1-benzothien-3-yl)pyridin-2-yl]benzyl}acetamide The title compound was prepared from Example 73 and 3-(acetamidomethyl)-phenylboronic acid according to Method L and was isolated as a yellow solid (61%) after purification by preparative HPLC (pH 2.5). $\delta_H$ (DMSO-d$_6$) 8.75 (1H, d, J 5.1 Hz), 8.43 (1H, t, J 5.7 Hz), 8.08-7.97 (3H, m), 7.47 (1H, t, J 7.7 Hz), 7.41 (1H, dd, J 5.1, 1.3 Hz), 7.37-7.32 (1H, m), 4.35 (2H, d, J 6.0 Hz), 3.64-3.56 (4H, m), 3.02-2.94 (4H, m), 2.58 (2H, s), 2.39 (2H, s), 1.89 (3H, s), 0.97 (6H, s). LCMS (ES+) 490.4 (M+H)$^+$.

Example 196

4-[4-(5,5-Dimethyl-2-(morpholin-4-yl)-7-oxo-4,5,6,7-tetrahydro-1-benzothien-3-yl)pyridin-2-yl]-N,N-dimethylbenzamide The title compound was prepared from Example 73 and 4-(N,N-dimethyl-aminocarbonyl)phenylboronic acid according to Method L and was isolated as a yellow solid (9%) after purification by preparative HPLC (pH 2.5). $\delta_H$ (DMSO-d$_6$) 8.77 (1H, d, J 5.1 Hz), 8.21 (2H, d, J 8.3 Hz), 8.07 (1H, s), 7.54 (2H, d, J 8.1 Hz), 7.44 (1H, dd, J 4.9, 1.1 Hz), 3.63-3.56 (4H, m), 3.06-2.94 (10H, m), 2.59 (2H, s), 2.39 (2H, s), 0.97 (6H, s). LCMS (ES+) 490.4 (M+H)$^+$.

Example 197

5,5-Dimethyl-3-[2-(isoquinolin-5-yl)pyridin-4-yl]-2-(morpholin-4-yl)-5,6-dihydro-1-benzothiophen-7(4H)-one The title compound was prepared from Example 73 and 5-isoquinolineboronic acid according to Method L and was isolated as a brown solid (64%) after purification by preparative HPLC (pH 2.5). $\delta_H$ (DMSO-d$_6$) 9.43 (1H, s), 8.87 (1H, d, J 5.1 Hz), 8.54 (1H, d, J 6.0 Hz), 8.26 (1H, d, J 8.1 Hz), 8.10 (1H, d, J 6.0 Hz), 7.99 (1H, dd, J 7.0, 0.9 Hz), 7.89-7.80 (1H, m), 7.74 (1H, s), 7.59 (1H, dd, J 5.1, 1.5 Hz), 3.68-3.57 (4H, m), 3.06-2.96 (4H, m), 2.64 (2H, s), 2.39 (2H, s), 1.00 (6H, s). LCMS (ES+) 470.4 (M+H)$^+$.

Example 198

3-(2-{2-[(Dimethylamino)methyl]phenyl}pyridin-4-yl)-5,5-dimethyl-2-(morpholin-4-yl)-5,6-dihydro-1-benzothiophen-7(4H)-one The title compound was prepared from Example 73 and 2-(N,N-dimethyl-aminomethyl)phenylboronic acid according to Method L and was isolated as a yellow glass (30%) after purification by preparative HPLC (pH 5.8). $\delta_H$ (DMSO-d$_6$) 8.72 (1H, d, J 5.1 Hz), 8.18 (1H, s), 7.59 (1H, s), 7.56-7.38 (4H, m), 3.64-3.53 (6H, m), 3.03-2.95 (4H, m), 2.55 (2H, s), 2.38 (2H, s), 2.06 (6H, s), 0.97 (6H, s). LCMS (ES+) 476.4 (M+H)$^+$.

Example 199

3-Amino-4-[4-(5,5-dimethyl-2-(morpholin-4-yl)-7-oxo-4,5,6,7-tetrahydro-1-benzothien-3-yl)pyridin-2-yl]benzoic Acid, Acetic Acid Salt The title compound was prepared from Example 73 and 2-amino-4-carboxy-phenylboronic acid according to Method L and was isolated as a brown solid (6%) after purification by preparative HPLC (pH 5.8). $\delta_H$ (DMSO-d$_6$) 8.69 (1H, d, J 5.1 Hz), 7.84 (1H, s), 7.62 (1H, d, J 8.3 Hz), 7.41-7.34 (2H, m), 7.15 (1H, dd, J 8.1, 1.5 Hz), 6.75 (1H, br s), 3.66-3.57 (4H, m), 3.03-2.95 (4H, m), 2.58 (2H, s), 2.39 (2H, s), 1.89 (6H, s), 0.97 (6H, s). LCMS (ES+) 478.4 (M+H)$^+$.

Example 200

4-(5,5-Dimethyl-2-(morpholin-4-yl)-7-oxo-4,5,6,7-tetrahydro-1-benzothien-3-yl)benzoic Acid The title compound was prepared from Example 17 and 4-carboxyphenylboronic acid according to Method J and was isolated as a pale yellow solid (23%) after purification by preparative HPLC (pH 2.5). $\delta_H$ (CDCl$_3$) 8.19 (2H, d, J 8.2 Hz), 7.51 (2H, d, J 8.2 Hz), 3.72-3.64 (4H, m), 3.03-2.94 (4H, m), 2.48 (2H, s), 2.45 (2H, s), 1.04 (6H, s). LCMS (ES+) 386.2 (M+H)$^+$.

Example 201

3-(5,5-Dimethyl-2-(morpholin-4-yl)-7-oxo-4,5,6,7-tetrahydro-1-benzothien-3-yl)benzoic Acid The title compound was prepared from Example 17 and 3-carboxyphenylboronic acid according to Method J and was isolated as a pale yellow solid (19%) after purification by preparative HPLC (pH 2.5). $\delta_H$ (CDCl$_3$) 8.16 (1H, s), 8.09 (1H, d, J 7.3 Hz), 7.67-7.54 (2H, m), 3.71-3.63 (4H, m), 3.03-2.94 (4H, m), 2.48 (2H, s), 2.46 (2H, s), 1.05 (6H, s). LCMS (ES+) 386.2 (M+H)$^+$.

Example 202

(Method AB)

5,5-Dimethyl-3-{3-[(3-methoxybenzyl)oxy]phenyl}-2-(morpholin-4-yl)-5,6-dihydro-1-benzothiophen-7(4H)-one A solution of Example 146 (50 mg, 0.14 mmol) in DMF (5.0 mL) was treated with potassium carbonate (23 mg, 0.16 mmol) and 3-methoxybenzyl bromide (22 µL, 0.15 mmol) and the reaction mixture was stirred for 18 h at room temperature. The solvent was removed in vacuo and the residue purified by preparative HPLC (pH 2.5) to give the title compound (41.5 mg, 62%) as an off-white solid. $\delta_H$ (CDCl$_3$) 7.39-7.28 (2H, m), 7.06-6.84 (6H, m), 5.09 (2H, s), 3.82 (3H, s), 3.65-3.57 (4H, m), 3.02-2.92 (4H, m), 2.41 (2H, s), 2.39 (2H, s), 1.01 (6H, s). LCMS (ES+) 478.2 (M+H)$^+$.

Example 203

5,5-Dimethyl-2-(morpholin-4-yl)-3-[3-(pyridin-4-ylmethoxy)phenyl]-5,6-dihydro-1-benzothiophen-7(4H)-one The title compound was prepared from Example 146 and 4-picolyl chloride hydrochloride according to Method AB, followed by heating to 100° C. in a sealed tube under microwave irradiation for 30 minutes. The title compound was isolated as an off-white solid (37%) after purification by preparative HPLC (pH 2.5). $\delta_H$ (CD$_3$OD) 8.60-8.55 (2H, m), 7.56 (2H, d, J 6.0 Hz), 7.42 (1H, t, J 7.9 Hz), 7.10-7.04 (1H, m), 7.02-6.96 (2H, m), 5.27 (2H, s), 3.66-3.58 (4H, m), 3.06-2.98 (4H, m), 2.41 (4H, s), 1.00 (6H, s). LCMS (ES+) 449.2 (M+H)$^+$.

Example 204

(Method AC)

5,5-Dimethyl-3-(3-{[(5-methyl-2-furyl)methyl]amino}phenyl)-2-(morpholin-4-yl)-5,6-dihydro-1-benzothiophen-7(4H)-one, Acetic Acid Salt To a stirred solution of Example 77 (42 mg, 0.12 mmol) and 5-methylfurfural (13 mg, 0.12 mmol) in DCM (5.0 mL)

was added sodium triacetoxyborohydride (38 mg, 0.18 mmol) and the reaction mixture was stirred at room temperature for 18 h. The solvent was removed in vacuo and the residue purified by preparative HPLC (pH 2.5) to give the title compound (19.5 mg, 32%) as an orange gum. $\delta_H$ (CDCl$_3$) 7.22 (1H, t, J 7.7 Hz), 6.71-6.59 (3H, m), 6.12 (1H, d, J 3.0 Hz), 4.27 (2H, s), 5.93-5.89 (1H, m), 3.67-3.60 (4H, m), 3.03-2.96 (4H, m), 2.43 (2H, s), 2.41 (2H, s), 2.28 (3H, s), 1.02 (6H, s). LCMS (ES+) 451.2 (M+H)$^+$.

Example 205

5,5-Dimethyl-2-(morpholin-4-yl)-3-{3-[(pyridin-4-ylmethyl)amino]phenyl}-5,6-dihydro-1-benzothiophen-7(4H)-one The title compound was prepared from Example 77 and 4-pyridinecarboxaldehyde according to Method AC and was isolated as an off-white solid (7 mg, 13%) after purification by preparative HPLC (pH 2.5). $\delta_H$ (CD$_3$OD) 8.51-8.46 (2H, m), 7.51-7.46 (2H, m), 7.19 (1H, t, J 7.7 Hz), 6.68-6.63 (1H, m), 6.60 (1H, dd, J 7.3, 1.1 Hz), 6.45-6.42 (1H, m), 4.46 (2H, s), 3.60-3.53 (4H, m), 3.02-2.96 (4H, m), 2.37 (2H, s), 2.31 (2H, s), 0.96 (6H, s). LCMS (ES+) 448.2 (M+H)$^+$.

Example 206

3-[4-(5,5-Dimethyl-2-(morpholin-4-yl)-7-oxo-4,5,6,7-tetrahydro-1-benzothien-3-yl)pyridin-2-yl]-N-methoxy-N-methylbenzamide The title compound was prepared from Example 73 and 3-(N,O-dimethyl-hydroxylaminocarbonyl)phenylboronic acid according to Method L and was isolated as an off-white solid (7%) after purification by preparative HPLC (pH 5.8). $\delta_H$ (DMSO-d$_6$) 8.77 (1H, d, J 5.1 Hz), 8.37 (1H, s), 8.27 (1H, d, J 7.7 Hz), 8.10 (1H, s), 7.69-7.57 (2H, m), 7.44 (1H, dd, J 5.1, 1.3 Hz), 3.64-3.55 (7H, m), 3.33 (3H, s), 3.02-2.94 (4H, m), 2.60 (2H, s), 2.39 (2H, s), 0.97 (6H, s). LCMS (ES+) 506.2 (M+H)$^+$.

Example 207

5,5-Dimethyl-2-morpholin-4-yl)-3-{2-[3-(morpholin-4-ylcarbonyl)phenyl]pyridin-4-yl}-5,6-dihydro-1-benzothiophen-7(4H)-one The title compound was prepared from Example 73 and 3-(morpholin-4-yl-carbonyl)phenylboronic acid according to Method L and was isolated as a white solid (48%) after purification by preparative HPLC (pH 5.8). $\delta_H$ (DMSO-d$_6$) 8.76 (1H, d, J 5.1 Hz), 8.25 (1H, d, J 7.9 Hz), 8.18 (1H, s), 8.10 (1H, s), 7.60 (1H, t, J 7.5 Hz), 7.52-7.43 (2H, m), 3.73-3.37 (12H, m), 3.03-2.94 (4H, m), 2.59 (2H, s), 2.39 (2H, s), 0.97 (6H, s). LCMS (ES+) 532.3 (M+H)$^+$.

Example 208

3-[2-(3-Acetylphenyl)pyridin-4-yl]-5,5-dimethyl-2-(morpholin-4-yl)-5,6-dihydro-1-benzothiophen-7(4H)-one The title compound was prepared from Example 73 and 3-acetylphenylboronic acid according to Method L and was isolated as an off-white solid (39%) after purification by preparative HPLC (pH 5.8). $\delta_H$ (DMSO-d$_6$) 8.79 (1H, d, J 5.1 Hz), 8.69 (1H, s), 8.44-8.38 (1H, m), 8.17 (1H, s), 8.08-8.03 (1H, m), 7.69 (1H, t, J 7.7 Hz), 7.47 (1H, dd, J 5.1, 1.3 Hz), 3.65-3.55 (4H, m), 3.04-2.95 (4H, m), 2.68 (3H, s), 2.61 (2H, s), 2.40 (2H, s), 0.98 (6H, s). LCMS (ES+) 461.4 (M+H)$^+$.

Example 209

3-[4-(5,5-Dimethyl-2-(morpholin-4-yl)-7-oxo-4,5,6,7-tetrahydro-1-benzothien-3-yl)pyridin-2-yl]-N-methoxybenzamide The title compound was prepared from Example 73 and 3-(O-methyl-hydroxylaminocarbonyl)phenylboronic acid according to Method L and was isolated as an off-white solid (36%) after purification by preparative HPLC (pH 2.5). $\delta_H$ (DMSO-d$_6$) 11.89 (1H, s), 8.78 (1H, d, J 5.1 Hz), 8.50 (1H, s), 8.32 (1H, d, J 8.1 Hz), 8.12 (1H, s), 7.84 (1H, d, J 7.7 Hz), 7.63 (1H, t, J 7.7 Hz), 7.45 (1H, dd, J 5.1, 1.3 Hz), 3.74 (3H, s), 3.64-3.56 (4H, m), 3.03-2.95 (4H, m), 2.59 (2H, s), 2.40 (2H, s), 0.98 (6H, s). LCMS (ES+) 492.4 (M+H)$^+$.

Example 210

5,5-Dimethyl-2-(morpholin-4-yl)-3-{2-[3-(pyrrolidin-1-ylcarbonyl)phenyl]pyridin-4-yl}-5,6-dihydro-1-benzothiophen-7(4H)-one The title compound was prepared from Example 73 and 3-(pyrrolidin-1-yl-carbonyl)phenylboronic acid according to Method L and was isolated as a white solid (44%) after purification by preparative HPLC (pH 5.8). $\delta_H$ (DMSO-d$_6$) 8.76 (1H, d, J 5.1 Hz), 8.29 (1H, s), 8.27-8.21 (1H, m), 8.10 (1H, s), 7.62-7.57 (2H, m), 7.44 (1H, dd, J 4.9, 1.1 Hz), 3.63-3.56 (4H, m), 3.55-3.41 (4H, m), 3.03-2.94 (4H, m), 2.59 (2H, s), 2.39 (2H, s), 1.96-1.77 (4H, m), 0.97 (6H, s). LCMS (ES+) 516.5 (M+H)$^+$.

Example 211

3-[4-(5,5-Dimethyl-2-(morpholin-4-yl)-7-oxo-4,5,6,7-tetrahydro-1-benzothien-3-yl)pyridin-2-yl]-N,N-dimethyl-5-fluorobenzamide The title compound was prepared from Example 73 and 3-(N,N-dimethylamino-carbonyl)-5-fluorophenylboronic acid according to Method L and was isolated as an off-white solid (49%) after purification by preparative HPLC (pH 2.5). $\delta_H$ (DMSO-d$_6$) 8.77 (1H, d, J 5.1 Hz), 8.17 (1H, s), 8.10-8.03 (2H, m), 7.48 (1H, dd, J 5.1, 1.3 Hz), 7.36 (1H, ddd, J 8.7, 2.4, 1.3 Hz), 3.62-3.54 (4H, m), 3.06-2.92 (10H, m), 2.58 (2H, s), 2.39 (2H, s), 0.97 (6H, s). LCMS (ES+) 508.5 (M+H)$^+$.

Example 212

(Method AD)

3-(2-Anilinopyridin-4-yl)-5,5-dimethyl-2-(morpholin-4-yl)-5,6-dihydro-1-benzothiophen-7(4H)-one A mixture of Example 73 (50 mg, 0.133 mmol), sodium tert-butoxide (32 mg, 0.332 mmol), tributylphosphine tetrafluoroborate (7.6 mg, 0.027 mmol), palladium(II) acetate (8.9 mg, 0.013 mmol) and aniline (60 µL, 0.66 mmol) in THF (3.0 mL) was heated to 140° C. in a sealed tube under microwave irradiation for 1 h. The solvent was removed in vacuo and the residue purified by preparative HPLC (pH 2.5) to give the title compound (23 mg, 40%) as a brown solid. $\delta_H$ (DMSO-d$_6$) 9.13 (1H, s), 8.22 (2H, dd, J 3.2, 1.3 Hz), 7.71

(2H, d, J 8.5 Hz), 7.32-7.23 (2H, m), 6.94-6.86 (1H, m), 6.84-6.78 (2H, m), 3.68-3.58 (4H, m), 3.04-2.96 (4H, m), 2.54 (2H, s), 2.39 (2H, s), 0.99 (6H, s). LCMS (ES+) 434.3 (M+H)$^+$.

Example 213

5,5-Dimethyl-3-[2-(N-methyl-N-phenylamino)pyridin-4-yl]-2-(morpholin-4-yl)-5,6-dihydro-1-benzothiophen-7(4H)-one The title compound was prepared from Example 73 and N-methylaniline according to Method AD, heating for 2 h, and was isolated as an off-white solid (32%) after purification by preparative HPLC (pH 5.8). $\delta_H$ (DMSO-d$_6$) 8.24 (1H, d, J 5.3 Hz), 7.51-7.43 (2H, m), 7.40-7.34 (2H, m), 7.32-7.25 (1H, m), 6.75 (1H, dd, J 5.3, 1.3 Hz), 6.39 (1H, s), 3.60-3.52 (4H, m), 3.43 (3H, s), 2.94-2.87 (4H, m), 2.39 (2H, s), 2.33 (2H, s), 0.95 (6H, s). LCMS (ES+) 448.3 (M+H)$^+$.

Example 214

N-[2-(Dimethylamino)ethyl]-3-[4-(5,5-dimethyl-2-(morpholin-4-yl)-7-oxo-4,5,6,7-tetrahydro-1-benzothien-3-yl)pyridin-2-yl]benzamide, Formic Acid Salt The title compound was prepared from Example 73 and 3-[2-(N,N-dimethyl-amino)ethylaminocarbonyl]phenylboronic acid according to Method L and was isolated as an off-white solid (52%) after purification by preparative HPLC (pH 2.5). $\delta_H$ (DMSO-d$_6$) 8.78 (1H, d, J 4.9 Hz), 8.65-8.55 (2H, m), 8.30 (1H, d, J 7.5 Hz), 8.17 (1H, s), 8.13 (1H, s), 7.93 (1H, d, J 7.9 Hz), 7.62 (1H, t, J 7.7 Hz), 7.47-7.42 (1H, m), 3.64-3.56 (4H, m), 3.46-3.38 (4H, m), 3.03-2.95 (4H, m), 2.59 (2H, s), 2.40 (2H, s), 2.25 (6H, s), 0.98 (6H, s). LCMS (ES+) 533.3 (M+H)$^+$.

Example 215

Methyl 4-(5,5-dimethyl-2-(morpholin-4-yl)-7-oxo-4,5,6,7-tetrahydro-1-benzothien-3-yl)-2,4'-bipyridine-2'-carboxylate A mixture of Example 217 (160 mg, 0.35 mmol), [1,1'-bis(diphenylphosphino)-ferrocene]dichloropalladium(II) (catalytic amount), methanol (20 mL) and triethylamine (0.5 mL) was heated at 100° C. in a Parr vessel under 100 psi pressure of carbon monoxide for 18 h. The solvent was removed in vacuo and the residue was purified by column chromatography (SiO$_2$, 0-100% EtOAc/heptane) to give the title compound (80 mg, 48%) as an off-white solid. $\delta_H$ (CDCl$_3$) 8.90 (1H, d, J 5.1 Hz), 8.85 (1H, d, J 4.9 Hz), 8.75 (1H, d, J 1.1 Hz), 8.21 (1H, dd, J 4.9, 1.7 Hz), 8.02 (1H, s), 7.41 (1H, dd, J 4.9, 1.3 Hz), 4.07 (3H, s), 3.73-3.66 (4H, m), 3.07-3.00 (4H, m), 2.55 (2H, s), 2.47 (2H, s), 1.06 (6H, s). LCMS (ES+) 478.2 (M+H)$^+$.

Example 216

5,5-Dimethyl-2-(morpholin-4-yl)-3-(2-phenoxyphenyl)-5,6-dihydro-1-benzothiophen-7(4H)-one The title compound was prepared from Example 17 and 2-phenoxyphenylboronic acid according to Method J, heating for 140 minutes, and was isolated as a white solid (32%) after purification by preparative HPLC (pH 2.5). $\delta_H$ (CDCl$_3$) 7.36-7.23 (4H, m), 7.21-7.14 (1H, m), 7.08-7.00 (2H, m), 6.89-6.84 (2H, m), 3.70-3.59 (4H, m), 3.05-2.99 (4H, m), 2.37 (2H, s), 2.48-2.30 (2H, m), 1.01 (3H, s), 0.94 (3H, s). LCMS (ES+) 434.3 (M+H)$^+$.

Example 217

3-(2'-Chloro-2,4'-bipyridin-4-yl)-5,5-dimethyl-2-(morpholin-4-yl)-5,6-dihydro-1-benzothiophen-7(4H)-one The title compound was prepared from Example 73 and 2-chloropyridine-4-boronic acid according to Method J and was isolated as a white solid (88%) after purification by column chromatography (SiO$_2$, 0-100% EtOAc/heptane). $\delta_H$ (CDCl$_3$) 8.82 (1H, d, J 4.9 Hz), 8.54 (1H, d, J 5.3 Hz), 8.01 (1H, s), 7.89-7.83 (2H, m), 7.41-7.37 (1H, m), 3.71-3.64 (4H, m), 3.04-2.97 (4H, m), 2.52 (2H, s), 2.47 (2H, s), 1.06 (6H, s). LCMS (ES+) 454.2 (M+H)$^+$.

Example 218

(Method AE)

N-[3-(5,5-Dimethyl-2-(morpholin-4-yl)-7-oxo-4,5,6,7-tetrahydro-1-benzothien-3-yl)phenyl]ethanesulfonamide To a solution of Example 77 (50 mg, 0.14 mmol) in DCM (5.0 mL) was added pyridine (35 µL, 0.42 mmol) and ethanesulfonyl chloride (20 µL, 0.21 mmol) and the reaction mixture was stirred at room temperature for 4 h. The solvent was removed in vacuo and the residue was purified by preparative HPLC (pH 5.8) to give the title compound (30 mg, 48%) as a cream solid. $\delta_H$ (CDCl$_3$) 7.40 (1H, t, J 7.9 Hz), 7.26 (1H, s), 7.18-7.10 (2H, m), 6.55 (1H, m), 3.70-3.62 (4H, m), 3.19 (2H, q, J 7.3 Hz), 3.01-2.93 (4H, m), 2.46 (2H, s), 2.43 (2H, s), 1.42 (3H, t, J 7.3 Hz), 1.04 (6H, s). LCMS (ES+) 449.4 (M+H)$^+$.

Example 219

N-[3-(5,5-Dimethyl-2-(morpholin-4-yl)-7-oxo-4,5,6,7-tetrahydro-1-benzothien-3-yl)phenyl]benzenesulfonamide The title compound was prepared from Example 77 and benzenesulfonyl chloride according to Method AE and was isolated as a beige solid (45%) after purification by preparative HPLC (pH 2.5). $\delta_H$ (CDCl$_3$) 7.84-7.78 (2H, m), 7.61-7.54 (1H, m), 7.51-7.43 (2H, m), 7.35-7.28 (1H, m), 7.13-7.02 (3H, m), 6.69 (1H, s), 3.60-3.53 (4H, m), 2.93-2.86 (4H, m), 2.41 (2H, s), 2.32 (2H, s), 1.01 (6H, s). LCMS (ES+) 497.4 (M+H)$^+$.

Example 220

N-[3-(5,5-Dimethyl-2-(morpholin-4-yl)-7-oxo-4,5,6,7-tetrahydro-1-benzothien-3-yl)phenyl]-1-phenylmethanesulfonamide The title compound was prepared from Example 77 and α-toluenesulfonyl chloride according to Method AE and was isolated as a cream solid (43%) after purification by preparative HPLC (pH 2.5). $\delta_H$ (CDCl$_3$) 7.44-7.28 (6H, m), 7.18-7.10 (2H, m), 7.06-7.01 (1H, m), 6.28 (1H, s), 4.40 (2H, s), 3.71-

3.64 (4H, m), 3.02-2.95 (4H, m), 2.47 (2H, s), 2.45 (2H, s), 1.06 (6H, s). LCMS (ES+) 511.5 (M+H)+.

Example 221

N-[3-(5,5-Dimethyl-2-(morpholin-4-yl)-7-oxo-4,5,6,7-tetrahydro-1-benzothien-3-yl)phenyl]-3,5-dimethylisoxazole-4-sulfonamide The title compound was prepared from Example 77 and 3,5-dimethylisoxazole-4-sulfonyl chloride according to Method AE and was isolated as a cream solid (58%) after purification by preparative HPLC (pH 2.5). $\delta_H$ (CDCl$_3$) 7.42-7.35 (1H, m), 7.25-7.20 (1H, m), 7.09-7.03 (2H, m), 6.71 (1H, s), 3.68-3.60 (4H, m), 2.97-2.89 (4H, m), 2.50 (3H, s), 2.43 (2H, s), 2.34 (2H, s), 2.31 (3H, s), 1.03 (6H, s). LCMS (ES+) 516.5 (M+H)+.

Example 222

3-(Dibenzo[b,d]thien-2-yl)-5,5-dimethyl-2-(morpholin-4-yl)-5,6-dihydro-1-benzothiophen-7(4H)-one A mixture of Example 17 (50 mg, 0.13 mmol), dibenzo[b,d]thiophene-2-ylboronic acid (44 mg, 0.19 mmol), sodium carbonate (27 mg, 0.26 mmol) and palladium(II) acetate (1.0 mg, 0.004 mmol) in acetone (1.35 mL) and water (1.50 mL) was stirred at 35° C. for 80 minutes. Water (5 mL) was added and the mixture was extracted with EtOAc (2×35 mL). The combined organic phases were dried (magnesium sulfate); the solvent was removed in vacuo and the residue was purified by column chromatography (SiO$_2$, 0-40% EtOAc/heptane) to give the title compound (35 mg, 61%) as an off-white solid. $\delta_H$(DMSO-d$_6$) 8.49-8.44 (1H, m), 8.42 (1H, d, J 1.5 Hz), 8.12 (1H, d, J 8.3 Hz), 8.09-8.04 (1H, m), 7.59-7.50 (3H, m), 3.59-3.51 (4H, m), 3.01-2.93 (4H, m), 2.55 (2H, s), 2.39 (2H, s), 0.96 (6H, s). LCMS (ES+) 448.3 (M+H)+.

Example 223

4-(5,5-Dimethyl-2-(morpholin-4-yl)-7-oxo-4,5,6,7-tetrahydro-1-benzothien-3-yl)-2,4'-bipyridine-2'-carboxylic Acid Sodium hydroxide (11 mg, 0.27 mmol) was added to a mixture of Example 215 (65 mg, 0.14 mmol) in EtOH (5 mL) and water (1 mL) and the reaction mixture was stirred at room temperature for 2 h. Water (5 mL) was added; the reaction mixture was adjusted to pH 6 with 1N aqueous hydrochloric acid and then extracted with EtOAc (2×15 mL). The combined organic layers were dried (magnesium sulfate) and the solvent was removed in vacuo to give the title compound (60 mg, 92%) as a yellow solid. $\delta_H$ (CDCl$_3$) 8.91-8.78 (3H, m), 8.37 (1H, d, J 4.3 Hz), 8.04 (1H, s), 7.43 (1H, d, J 4.9 Hz), 3.74-3.62 (4H, m), 3.09-2.97 (4H, m), 2.54 (2H, s), 2.48 (2H, s), 1.06 (6H, s). LCMS (ES+) 464.0 (M+H)+.

Example 224

Tert-Butyl{3-[4-(5,5-dimethyl-2-(morpholin-4-yl)-7-oxo-4,5,6,7-tetrahydro-1-benzothien-3-yl)pyridin-2-yl]benzyl}carbamate The title compound was prepared from Example 73 and 3-(N-tert-butoxycarbonyl-aminomethyl)phenylboronic acid according to Method L and was isolated as an off-white solid (79%) after purification by column chromatography (SiO$_2$, 30-100% EtOAc/heptane). $\delta_H$ (DMSO-d$_6$) 8.75 (1H, d, J 4.9 Hz), 8.04 (1H, s), 8.02-7.96 (2H, m), 7.51-7.43 (2H, m), 7.40 (1H, d, J 4.9 Hz), 7.35-7.30 (1H, m), 4.25-4.19 (2H, m), 3.63-3.55 (4H, m), 3.02-2.93 (4H, m), 2.57 (2H s), 2.39 (2H, s), 1.40 (9H, s), 0.97 (6H, s). LCMS (ES+) 548.1 (M+H)+.

Example 225

5,5-Dimethyl-3-[2-(4-methyl-3,4-dihydro-2H-1,4-benzoxazin-7-yl)pyridin-4-yl]-2-(morpholin-4-yl)-5,6-dihydro-1-benzothiophen-7(4H)-one, Formic Acid Salt The title compound was prepared from Example 73 and 4-methyl-7-(4,4,5,5-tetramethyl-1,3,2-dioxaborolan-2-yl)-3,4-dihydro-2H-1,4-benzoxazine according to Method L and was isolated as a brown solid (47%) after purification by preparative HPLC (pH 2.5). $\delta_H$ (DMSO-d$_6$) 8.62 (1H, d, J 4.9 Hz), 8.21 (1H, s), 7.83 (1H, s), 7.61 (1H, dd, J 8.5, 2.1 Hz), 7.48 (1H, d, J 2.1 Hz), 7.23 (1H, dd, J 5.1, 1.3 Hz), 6.78 (1H, d, J 8.5 Hz), 4.31-4.23 (2H, m), 3.64-3.54 (4H, m), 3.36-3.29 (2H, m), 3.02-2.94 (4H, m), 2.57 (2H, s), 2.38 (2H, s), 0.97 (6H, s). LCMS (ES+) 490.4 (M+H)+.

Example 226

5,5-Dimethyl-2-(morpholin-4-yl)-3-{2-[3-(morpholin-4-yl)phenyl]pyridin-4-yl}-5,6-dihydro-1-benzothiophen-7(4H)-one The title compound was prepared from Example 73 and 3-(morpholin-4-yl)phenyl-boronic acid according to Method L and was isolated as a pale yellow solid (54%) after purification by preparative HPLC (pH 2.5). $\delta_H$ (DMSO-d$_6$) 8.72 (1H, d, J 4.9 Hz), 8.04 (1H, s), 7.72-7.66 (1H, m), 7.58 (1H, d, J 7.5 Hz), 7.42-7.34 (2H, m), 7.06 (1H, dd, J 8.1, 2.1 Hz), 3.83-3.73 (4H, m), 3.64-3.55 (4H, m), 3.26-3.16 (4H, m), 3.03-2.93 (4H, m), 2.59 (2H, s), 2.39 (2H, s), 0.97 (6H, s). LCMS (ES+) 504.4 (M+H)+.

Example 227

Tert-Butyl 4-{3-[4-(5,5-dimethyl-2-(morpholin-4-yl)-7-oxo-4,5,6,7-tetrahydro-1-benzothien-3-yl)pyridin-2-yl]phenyl}piperazine-1-carboxylate The title compound was prepared from Example 73 and 3-[4-(tert-butoxy-carbonyl)piperazin-1-yl]phenylboronic acid pinacol ester according to Method L and was isolated as a pale yellow solid (45%) after purification by preparative HPLC (pH 2.5). $\delta_H$ (DMSO-d$_6$) 8.73 (1H, d, J 4.9 Hz), 8.04 (1H, s), 7.70 (1H, s), 7.62-7.56 (1H, m), 7.42-7.33 (2H, m), 7.10-7.03 (1H, m), 3.63-3.55 (4H, m), 3.54-3.45 (4H, m), 3.25-3.16 (4H, m), 3.03-2.94 (4H, m), 2.59 (2H, s), 2.39 (2H, s), 1.43 (9H, s), 0.97 (6H, s). LCMS (ES+) 603.2 (M+H)+.

Example 228

5,5-Dimethyl-2-(morpholin-4-yl)-3-{2-[3-(2H-tetrazol-5-yl)phenyl]pyridin-4-yl}-5,6-dihydro-1-benzothiophen-7(4H)-one The title compound was prepared from Example 73 and 3-(2H-tetrazol-5-yl)-phenylboronic acid according to Method L and was isolated as a yellow solid (10%) after purification by preparative HPLC (pH 5.8). $\delta_H$ (DMSO-d$_6$) 8.84-8.77 (2H, m), 8.18-8.05 (3H, m), 7.62 (1H, t, J 7.7 Hz), 7.44 (1H, dd, J 4.9, 1.3 Hz), 7.08 (1H, br s), 3.67-3.56 (4H m), 3.05-2.95 (4H, m), 2.60 (2H, s), 2.40 (2H, s), 0.98 (6H, s). LCMS (ES+) 487.2 (M+H)$^+$.

Example 229

5,5-Dimethyl-2-(morpholin-4-yl)-3-{2-[3-(morpholin-4-ylmethyl)phenyl]pyridin-4-yl}-5,6-dihydro-1-benzothiophen-7(4H)-one, Formic Acid Salt The title compound was prepared from Example 73 and 4-[3-(4,4,5,5-tetramethyl-1,3,2-dioxaborolan-2-yl)benzyl] morpholine according to Method L and was isolated as an off-white solid (32%) after purification by preparative HPLC (pH 2.5). $\delta_H$ (DMSO-d$_6$) 8.75 (1H, d, J 5.1 Hz), 8.21 (1H, s), 8.11 (1H, s), 8.07-8.01 (2H, m), 7.47 (1H, t, J 7.5 Hz), 7.43-7.37 (2H, m), 3.65-3.52 (10H, m), 3.02-2.94 (4H, m), 2.60 (2H, s), 2.43-2.34 (6H, m), 0.98 (6H, s). LCMS (ES+) 518.3 (M+H)$^+$.

Example 230

(Method AF)

3-[4-(5,5-Dimethyl-2-(morpholin-4-yl)-7-oxo-4,5,6,7-tetrahydrothieno[2,3-c]pyridin-3-yl)pyridin-2-yl]-N,N-dimethylbenzamide A mixture of Intermediate 19 (700 mg, 1.79 mmol), 2-chloropyridine-4-boronic acid (284 mg, 1.81 mmol), K$_3$PO$_4$ (456 mg, 2.15 mmol) and Pd(PPh$_3$)$_4$ (240 mg, 0.208 mmol) in DME (22 mL) and water (6.8 mL) was heated in a sealed tube at 120° C., under microwave irradiation, for 40 minutes. The reaction was quenched with saturated aqueous NaHCO$_3$ solution and extracted into EtOAc (4×85 mL). The combined organic phases were dried (magnesium sulfate) and the solvent was removed in vacuo. The residue was purified by column chromatography (SiO$_2$, 0-100% EtOAc/heptane) to give a pale orange solid (235 mg). A portion of this intermediate (75 mg) was combined with 3-(N,N-dimethylaminocarbonyl)phenylboronic acid (43 mg, 0.22 mmol), K$_3$PO$_4$ (63 mg, 0.30 mmol) and Pd(PPh$_3$)$_4$ (13 mg, 0.011 mmol) in DME (4.0 mL) and water (1.3 mL) and was heated in a sealed tube at 140° C., under microwave irradiation, for 2 h. The reaction mixture was diluted with dilute aqueous NaHCO$_3$ solution (30 mL) and extracted into EtOAc (2×40 mL). The combined organic phases were dried (magnesium sulfate) and the solvent was removed in vacuo. The residue was purified by column chromatography (SiO$_2$, 0-100% EtOAc/heptane) to give the title compound (28 mg, 10%) as a pale yellow solid. $\delta_H$(DMSO-d$_6$) 8.74 (1H, d, J 5.0 Hz), 8.24-8.16 (2H, m), 8.11 (1H, s), 7.61-7.55 (2H, m), 7.50-7.44 (2H, m), 3.63-3.56 (4H, m), 3.06-2.94 (6H, m), 2.93-2.87 (4H, m), 2.72 (2H, s), 1.19 (6H, s). LCMS (ES+) 491.3 (M+H)$^+$.

Example 231

3-(2-{3-[(Dimethylamino)methyl]phenyl}pyridin-4-yl)-5,5-dimethyl-2-(morpholin-4-yl)-5,6-dihydrothieno[2,3-c]pyridin-7(4H)-one The title compound was prepared from Intermediate 19, 2-chloropyridine-4-boronic acid and 3-(N,N-dimethylaminomethyl)phenylboronic acid pinacol ester hydrochloride according to Method AF and was isolated as an off-white solid (6%). $\delta_H$(DMSO-d$_6$, 70° C.) 8.73 (1H, d, J 5.0 Hz), 8.10 (1H, s), 8.04-7.99 (2H, m), 7.48 (1H, t, J 7.5 Hz), 7.42-7.36 (2H, m), 7.22 (1H, s), 3.67-3.56 (6H, m), 2.98-2.91 (4H, m), 2.69 (2H, s), 2.29 (6H, s), 1.24 (6H, s). LCMS (ES+) 477.2 (M+H)$^+$.

Example 232

(Method AG)

1-[3-(5,5-Dimethyl-2-(morpholin-4-yl)-7-oxo-4,5,6,7-tetrahydro-1-benzothien-3-yl)phenyl]-3-ethylurea Ethyl isocyanate (11 µL, 0.14 mmol) was added to a solution of Example 77 (50 mg 0.14 mmol) in DCM (7.0 mL) and the reaction mixture was stirred at room temperature for 42 h. Further ethyl isocyanate (11 µL, 0.14 mmol) was added and the reaction mixture was stirred for a further 96 h at room temperature The solvent was removed in vacuo and the residue was purified by preparative HPLC (pH 2.5) to give the title compound (39 mg, 65%) as a yellow solid. $\delta_H$ (CDCl$_3$) 7.39-7.33 (2H, m), 7.30-7.26 (1H, m), 7.04-6.99 (1H, m), 6.52 (1H, s), 4.82-4.75 (1H, m), 3.69-3.61 (4H, m), 3.33 (2H, dq, J 7.2, 5.4 Hz), 3.02-2.95 (4H, m), 2.44 (2H, s), 2.42 (2H, s), 1.20 (3H, t, J 7.2 Hz), 1.02 (6H, s). LCMS (ES+) 428.3 (M+H)$^+$.

Example 233

1-Cyclopentyl-3-[3-(5,5-dimethyl-2-(morpholin-4-0)-7-oxo-4,5,6,7-tetrahydro-1-benzothien-3-yl)phenyl]urea The title compound was prepared from Example 77 and cyclopentyl isocyanate according to Method AG and was isolated as a yellow solid (33 mg, 50%) after purification by preparative HPLC (pH 2.5). $\delta_H$ (CDCl$_3$) 7.38-7.33 (2H, m), 7.31-7.27 (1H, m), 7.02-6.97 (1H, m), 6.49 (1H, s), 4.75 (1H, d, J 7.0 Hz), 4.19-4.07 (1H, m), 3.69-3.60 (4H, m), 3.02-2.94 (4H, m), 2.44 (2H, s), 2.41 (2H, s), 2.10-1.96 (2H, m), 1.75-1.54 (4H, m), 1.49-1.36 (2H, m), 1.02 (6H, s). LCMS (ES+) 468.3 (M+H)$^+$.

Example 234

1-[3-(5,5-Dimethyl-2-(morpholin-4-yl)-7-oxo-4,5,6,7-tetrahydro-1-benzothien-3-yl)phenyl]-3-phenylurea Phenyl isocyanate (15 µL, 0.14 mmol) was added to a solution of Example 77 (50 mg, 0.14 mmol) in DCM (7.0 mL) and the reaction mixture was stirred at room temperature for 18 h. The precipitate was filtered off, washed with Et$_2$O and dried in vacuo to give the title compound (32 mg, 48%) as a yellow solid. $\delta_H$(CDCl$_3$) 7.51-7.09 (10H, m), 7.03-6.98 (1H, m), 3.68-3.59 (4H, m), 3.02-2.94 (4H, m), 2.43 (4H, s), 1.01 (6H, s). LCMS (ES+) 476.3 (M+H)$^+$.

Example 235

N-[3-(5,5-Dimethyl-2-(morpholin-4-yl)-7-oxo-4,5,6,7-tetrahydro-1-benzothien-3-yl)phenyl]morpholine-4-carboxamide To a solution of Example 77 (50 mg, 0.14 mmol) in DCM (10 mL) was added 4-morpholinecarbonyl chloride (20 µL, 0.154 mmol) followed by triethylamine (40 µL, 0.31 mmol) and the reaction mixture was stirred at room temperature for 42 h. Further 4-morpholinecarbonyl chloride (40 µL, 0.308 mmol) was added and the reaction mixture was stirred for an additional 96 h. The solvent was removed in vacuo and the residue was purified by preparative HPLC (pH 2.5) to give the title compound (11 mg, 17%) as a cream solid. $\delta_H$ (DMSO-$d_6$) 8.59 (1H, s), 7.52 (1H, s), 7.47-7.40 (1H, m), 7.32 (1H, t, J 7.7 Hz), 6.94 (1H, d, J 7.3 Hz), 3.65-3.53 (8H, m), 3.47-3.39 (4H, m), 2.98-2.89 (4H, m), 2.44 (2H, s), 2.36 (2H, s), 0.96 (6H, s). LCMS (ES+) 470.3 (M+H)$^+$.

Example 236

2-{3-[4-(5,5-Dimethyl-2-(morpholin-4-yl)-7-oxo-4,5,6,7-tetrahydro-1-benzothien-3-yl)pyridin-2-yl]phenoxy}acetamide A mixture of Example 103 (37 mg, 0.085 mmol), 2-chloroacetamide (10 mg, 0.107 mmol) and potassium carbonate (14 mg, 0.101 mmol) in DMF (5.0 mL) was stirred at room temperature for 18 h, then heated in a sealed tube at 100° C., under microwave irradiation, for 1 h. Further 2-chloroacetamide (10 mg, 0.107 mmol) was added and heating was continued for an additional 50 minutes. The solvent was removed in vacuo and the residue was purified by preparative HPLC to give the title compound (21 mg, 50%) as a yellow gum. $\delta_H$ (CDCl$_3$) 8.76 (1H, d, J 5.1 Hz), 7.80 (1H, s), 7.72 (1H, d, J 1.9 Hz), 7.63 (1H m), 7.46 (1H, t, J 7.9 Hz), 7.30-7.26 (2H, m), 7.03 (1H, dd, J 8.3, 2.6 Hz), 6.61 (1H, br s), 5.81 (1H, br s), 4.62 (2H, s), 3.71-3.64 (4H, m), 3.05-2.99 (4H, m), 2.53 (2H, s), 2.46 (2H, s), 1.05 (6H, s). LCMS (ES+) 492.3 (M+H)$^+$.

Example 237

5,5-Dimethyl-2-(morpholin-4-yl)-3-[2'-(morpholin-4-ylcarbonyl)-2,4'-bipyridin-4-yl]-5,6-dihydro-1-benzothiophen-7(4H)-one A mixture of Example 223 (55 mg, 0.12 mmol), morpholine (12 mL, 0.14 mmol), EDC (46 mg, 0.24 mmol) and 1-hydroxybenzotriazole hydrate (3 mg, 0.02 mmol) in DCM (10 mL) was stirred at room temperature for 18 h. The solvent was removed in vacuo and the residue was purified by preparative HPLC (pH 2.5) to give the title compound (31 mg, 49%) as a yellow oil. $\delta_H$ (CDCl$_3$) 8.82 (1H, dd, J 5.1, 0.6 Hz), 8.73 (1H, dd, J 5.1, 0.4 Hz), 8.30 (1H, d, J 1.1 Hz), 8.04 (1H, dd, J 5.1, 1.7 Hz), 7.91 (1H, s), 7.38 (1H, dd, J 4.9, 1.3 Hz), 3.90-3.81 (4H, m), 3.77-3.71 (4H, m), 3.70-3.65 (4H, m), 3.05-2.98 (4H, m), 2.51 (2H, s), 2.47 (2H, s), 1.05 (6H, s). LCMS (ES+) 533.3 (M+H)$^+$.

Example 238

Tert-Butyl N-{3-[4-(5,5-dimethyl-2-(morpholin-4-yl)-7-oxo-4,5,6,7-tetrahydro-1-benzothien-3-yl)pyridin-2-yl]benzyl}-N-methylcarbamate Sodium hydride (60% dispersion in mineral oil, 24 mg, 0.59 mmol) was added to a solution of Example 224 (320 mg, 0.59 mmol) in DMF (10 mL) and the mixture was stirred for 30 minutes at room temperature. Methyl iodide (37 pt, 0.59 mmol) was added and the reaction mixture was stirred for 16.5 h at room temperature. The solvent was removed in vacuo from a 3 mL portion of the reaction mixture and purified by preparative HPLC (pH 2.5) to give the title compound (18 mg, 18%) as an off-white solid. $\delta_H$ (DMSO-$d_6$) 8.74 (1H, d, J 5.1 Hz), 8.09-7.99 (3H, m), 7.51 (1H, t, J 7.9 Hz), 7.40 (1H, dd, J 4.9, 1.1 Hz), 7.34-7.29 (1H, m), 4.47 (2H, s), 3.65-3.53 (4H, m), 3.03-2.94 (4H, m), 2.81 (3H, s), 2.57 (2H, s), 2.39 (2H, s), 1.42 (9H, s), 0.97 (6H, s). LCMS (ES+) 562.5 (M+H)$^+$.

Example 239

5,5-Dimethyl-2-(morpholin-4-yl)-3-{2-[3-(piperazin-1-yl)phenyl]pyridin-4-yl}-5,6-dihydro-1-benzothiophen-7(4H)-one A solution of Example 227 (2.44 g, 4.05 mmol) in DCM (30 mL) was treated dropwise with a solution of HCl in Et$_2$O (2M, 12 mL, 24 mmol) and the reaction mixture stirred for 72 h at room temperature. The precipitate was filtered off, washed with Et$_2$O, then dissolved in dilute sodium bicarbonate solution (30 mL) and extracted with DCM (3×100 mL). The combined organic phases were dried (magnesium sulfate) and the solvent was removed in vacuo. The residue was purified by column chromatography (SiO$_2$, 0-10% MeOH/DCM, containing 1% NH$_4$OH solution) to give the title compound (1.24 g, 61%) as a pale yellow solid. $\delta_H$ (CD$_3$OD) 8.70 (1H, dd, J 5.1, 0.8 Hz), 7.94 (1H, m), 7.65-7.61 (1H, m), 7.49-7.39 (3H, m), 7.16-7.11 (1H, m), 3.73-3.66 (4H, m), 3.35-3.27 (4H, m), 3.14-3.04 (8H, m), 2.65 (2H, s), 2.48 (2H, s), 1.06 (6H, s). LCMS (ES+) 503.4 (M+H)$^+$.

Example 240

5,5-Dimethyl-2-(morpholin-4-yl)-3-{2-[3-(piperazin-1-yl)phenyl]pyridin-4-yl}-5,6-dihydro-1-benzothiophen-7(4H)-one, Acetic Acid Salt A mixture of Example 73 (77 mg, 0.2 mmol), 3-[4-(tert-butoxycarbonyl)-piperazin-1-yl]phenylboronic acid pinacol ester (79 mg, 0.2 mmol), potassium phosphate (70 mg, 0.33 mmol) and Pd(PPh$_3$)$_4$ (30 mg, 0.026 mmol) in DME (4.0 mL) and water (1.0 nit) was heated in a sealed tube at 140° C., under microwave irradiation, for 4 h. The solvent was removed in vacuo, redissolved in MeOH (5.0 mL) and treated with a solution of HCl in Et$_2$O (2M, 2.5 mL, 5.0 mmol), then stirred at room temperature for 18 h. The solvent was removed in vacuo and the residue was purified by preparative HPLC (pH 5.8) to give the title compound (84 mg, 68%) as an off-white solid. $\delta_H$ (DMSO-$d_6$) 8.72 (1H, d, J 5.1 Hz), 8.03 (1H, s), 7.66 (1H, s), 7.57-7.50 (1H, m), 7.42-7.30 (2H, m), 7.03 (1H, dd, J 8.1, 2.1 Hz), 3.65-3.54 (4H, m), 3.19-3.10 (4H, m), 3.02-2.94 (4H, m), 2.91-2.82 (4H, m), 2.59 (2H, s), 2.39 (2H, s), 1.88 (6H, s), 0.97 (6H, s). LCMS (ES+) 503.4 (M+H)$^+$.

Example 241

5,5-Dimethyl-2-(morpholin-4-yl)-3-{2-[3-(piperidin-1-ylcarbonyl)phenyl]pyridin-4-yl}-5,6-dihydro-1-benzothiophen-7(4H)-one The title compound was prepared from Example 73 and 3-(piperidin-1-yl-carbonyl)phenylboronic acid according to Method L and was isolated as a white solid (63%) after purification by preparative HPLC (pH 5.8). $\delta_H$ (DMSO-$d_6$) 8.76 (1H, d, J 5.1 Hz), 8.23 (1H, d, J 8.1 Hz), 8.14 (1H, s), 8.10 (1H, s), 7.59 (1H, t, J 7.7 Hz), 7.47-7.42 (2H, m), 3.67-3.55 (6H, m), 3.37-3.33 (2H, m), 3.01-2.93 (4H, m), 2.59 (2H, s), 2.39 (2H, s), 1.68-1.43 (6H, m), 0.97 (6H, s). LCMS (ES+) 530.5 (M+H)$^+$.

Example 242

N,N-Diethyl-3-[4-(5,5-dimethyl-2-(morpholin-4-yl)-7-oxo-4,5,6,7-tetrahydro-1-benzothien-3-yl)pyridin-2-yl]benzamide The title compound was prepared from Example 73 and 3-(N,N-diethylamino-carbonyl)phenylboronic acid according to Method L and was isolated as an off-white solid (59%) after purification by preparative HPLC (pH 5.8). $\delta_H$ (DMSO-$d_6$) 8.76 (1H, d, J 5.1 Hz), 8.22 (1H, d, J 7.9 Hz), 8.14-8.08 (2H, m), 7.58 (1H, t, J 7.7 Hz), 7.47-7.40 (2H, m), 3.63-3.53 (4H, m), 3.52-3.40 (2H, m), 3.29-3.17 (2H, m), 3.02-2.94 (4H, m), 2.59 (2H, s), 2.39 (2H, s), 1.23-1.02 (6H, m), 0.97 (6H, s). LCMS (ES+) 518.5 (M+H)$^+$.

Example 243

3-[4-(5,5-Dimethyl-2-(morpholin-4-yl)-7-oxo-4,5,6,7-tetrahydro-1-benzothien-3-yl)pyridin-2-yl]-N-ethyl-N-methylbenzamide The title compound was prepared from Example 73 and 3-(N-ethyl-N-methyl-aminocarbonyl)phenylboronic acid according to Method L and was isolated as an off-white solid (55%) after purification by preparative HPLC (pH 5.8). $\delta_H$ (DMSO-$d_6$) 8.76 (1H, d, J 5.1 Hz), 8.22 (1H, d, J 8.1 Hz), 8.15 (1H, s), 8.10 (1H, s), 7.59 (1H, t, J 7.7 Hz), 7.49-7.41 (2H, m), 3.63-3.55 (4H, m), 3.54-3.45 (1H, m), 3.30-3.20 (1H, m), 3.03-2.90 (7H, m), 2.59 (2H, s), 2.39 (2H, s), 1.21-1.04 (3H, m), 0.97 (6H, s). LCMS (ES+) 504.5 (M+H)$^+$.

Example 244

5,5-Dimethyl-3-(2-{3-[(4-methylpiperazin-1-yl)carbonyl]phenyl}pyridin-4-yl)-2-(morpholin-4-yl)-5,6-dihydro-1-benzothiophen-7(4H)-one, Formic Acid Salt The title compound was prepared from Example 73 and 2-{3-[(4-methylpiperazin-1-yl)carbonyl]phenyl}-4,4,5,5-tetramethyl-1,3,2-dioxaborolane according to Method L and was isolated as a yellow glass (80%) after purification by preparative HPLC (pH 2.5). $\delta_H$ (DMSO-$d_6$) 8.76 (1H, d, J 5.1 Hz), 8.24 (1H, d, J 7.9 Hz), 8.15 (2H, m), 8.10 (1H, s), 7.59 (1H, t, J 7.5 Hz), 7.49-7.43 (2H, m), 3.73-3.54 (6H, m), 3.44-3.34 (2H, m), 3.03-2.94 (4H, m), 2.59 (2H, s), 2.44-2.25 (6H, m), 2.21 (3H, s), 0.97 (6H, s). LCMS (ES+) 545.5 (M+H)$^+$.

Example 245

5,5-Dimethyl-2-(morpholin-4-yl)-3-{2-[2-(morpholin-4-ylcarbonyl)phenyl]pyridin-4-yl}-5,6-dihydro-1-benzothiophen-7(4H)-one, Acetic Acid Salt The title compound was prepared from Example 73 and 2-(morpholin-4-yl-carbonyl)phenylboronic acid according to Method L and was isolated as a brown solid (15%) after purification by preparative HPLC (pH 5.8). $\delta_H$ (CD$_3$OD) 8.73 (1H, d, J 5.1 Hz), 7.83-7.75 (2H, m), 7.66-7.55 (2H, m), 7.52-7.42 (2H, m), 3.77-3.50 (8H, m), 3.44-3.33 (4H, m), 3.11-3.02 (4H, m), 2.64 (2H, s), 2.48 (2H, s), 1.95 (6H, s), 1.07 (6H, s). LCMS (ES+) 532.5 (M+H)$^+$.

Example 246

2-[4-(5,5-Dimethyl-2-(morpholin-4-yl)-7-oxo-4,5,6,7-tetrahydro-1-benzothien-3-yl)pyridin-2-yl]benzamide The title compound was prepared from Example 73 and 2-(aminocarbonyl)-phenylboronic acid according to Method L and was isolated as a yellow solid (40%) after purification by preparative HPLC (pH 5.8). $\delta_H$ (DMSO-$d_6$) 8.64 (1H, d, J 4.7 Hz), 8.34 (2H, br s), 7.62-7.53 (3H, m), 7.49-7.38 (2H, m), 7.36-7.32 (1H, m), 3.61-3.52 (4H, m), 3.00-2.90 (4H, m), 2.55 (2H, s), 2.36 (2H, s), 0.98 (6H, s). LCMS (ES+) 462.4 (M+H)$^+$.

Example 247

N-{2-[4-(5,5-Dimethyl-2-(morpholin-4-yl)-7-oxo-4,5,6,7-tetrahydro-1-benzothien-3-yl)pyridin-2-yl]phenyl}acetamide The title compound was prepared from Example 73 and 2-(acetylamino)-phenylboronic acid according to Method L and was isolated as an off-white solid (57%) after purification by preparative HPLC (pH 5.8). $\delta_H$ (DMSO-$d_6$) 11.77 (1H, br s), 8.79 (1H, d, J 5.1 Hz), 8.23 (1H, dd, J 7.7, 0.6 Hz), 7.88 (1H, s), 7.83 (1H, dd, J 7.9, 1.3 Hz), 7.51-7.40 (2H, m), 7.28-7.21 (1H, m), 3.64-3.56 (4H, m), 3.02-2.94 (4H, m), 2.57 (2H, s), 2.39 (2H, s), 2.07 (3H, s), 0.97 (6H, s). LCMS (ES+) 476.4 (M+H)$^+$.

Example 248

(Method AH)

3-(2-{3-[(3-Aminopyrrolidin-1-yl)carbonyl]phenyl}pyridin-4-yl)-5,5-dimethyl-2-(morpholin-4-yl)-5,6-dihydro-1-benzothiophen-7(4H)-one, Formic Acid Salt A mixture of Example 254 (100 mg, 0.22 mmol), 3-(tert-butoxycarbonylamino)-pyrrolidine (48 mg, 0.26 mmol) and EDC (83 mg, 0.43 mmol) in DCM (5.0 mL) was stirred at room temperature for 18 h. The reaction mixture was partitioned between water (20 mL) and DCM (20 mL). The aqueous phase was extracted with further DCM (20 mL). A solution of HCl in Et$_2$O (2M, 0.5 mL, 1.0 mmol) was added to the combined organic phases and the solution was stirred at room temperature for 18 h. The solvent was removed in vacuo and the residue was purified by preparative HPLC (pH 2.5) and then column chromatography (SiO$_2$, 20% MeOH/DCM) to give the title compound (44.2 mg, 35%) as a pale yellow solid. $\delta_H$(CDCl$_3$) 8.73 (1H, d, J 5.1 Hz), 8.39 (1H, s), 8.27-8.16 (1H, m), 8.07-7.99 (1H, m), 7.84-7.78 (1H, m), 7.62-7.47 (2H, m), 7.33-7.27 (1H, m), 4.03-3.73 (4H, m), 3.70-3.52 (5H, m), 3.06-2.96 (4H, m), 2.52 (2H, s), 2.44 (2H, s), 2.34-2.09 (2H, m), 1.03 (6H, s). LCMS (ES+) 531.3 (M+H)$^+$.

Example 249

N-[2-(Dimethylamino)ethyl]-3-[4-(5,5-dimethyl-2-(morpholin-4-yl)-7-oxo-4,5,6,7-tetrahydro-1-benzothien-3-yl)pyridin-2-yl]-N-methylbenzamide, Formic Acid Salt The title compound was prepared from Example 254 and N,N,N'-trimethyl-ethylenediamine according to Method I and was isolated as a clear gum (22%) after purification by preparative HPLC (pH 2.5). $\delta_H$ (CD$_3$OD) 8.75 (1H, d, J 5.1 Hz), 8.48 (1H, s), 8.24-8.13 (2H, m), 8.03 (1H, s), 7.70-7.57 (2H, m), 7.49 (1H, dd, J 5.1, 1.5 Hz), 3.99-3.86 (2H, m), 3.72-3.63 (4H, m), 3.13 (3H, s), 3.11-3.02 (4H, m), 2.90 (6H, s), 2.64 (2H, s), 2.48 (2H, s), 1.05 (6H, s). LCMS (ES+) 547.2 (M+H)$^+$.

Example 250

5,5-Dimethyl-3-[2-(3-{[(3S)-3-hydroxypyrrolidin-1-yl]carbonyl}phenyl)pyridin-4-yl]-2-(morpholin-4-yl)-5,6-dihydro-1-benzothiophen-7(4H)-one The title compound was prepared from Example 254 and (R)-(+)-3-hydroxy-pyrrolidine according to Method I and was isolated as a pale yellow solid (75%) after purification by preparative HPLC (pH 2.5). $\delta_H$ (CDCl$_3$) 8.76 (1H, dd, J 5.1, 1.9 Hz), 8.19 (1H, d, J 12.1 Hz), 8.08 (1H, t, J 7.7 Hz), 7.81 (1H, s), 7.66-7.51 (2H, m), 7.32-7.27 (1H, m), 4.64-4.44 (1H, m), 3.92-3.62 (7H, m), 3.60-3.48 (1H, m), 3.07-2.98 (4H, m), 2.91-2.77 (1H, br s), 2.53 (2H, s), 2.46 (2H, s), 2.17-1.94 (2H, m), 1.05 (6H, s). LCMS (ES+) 532.4 (M+H)$^+$.

Example 251

N-(2,3-Dihydroxypropyl)-3-[4-(5,5-dimethyl-2-(morpholin-4-yl)-7-oxo-4,5,6,7-tetrahydro-1-benzothien-3-yl)pyridin-2-yl]benzamide The title compound was prepared from Example 254 and 3-amino-1,2-propanediol according to Method I and was isolated as a pale yellow solid (20%) after purification by preparative HPLC (pH 2.5). $\delta_H$ (CDCl$_3$) 8.76 (1H, d, J 5.1 Hz), 8.51 (1H, s), 8.13 (1H, d, J 7.9 Hz), 7.93 (1H, d, J 7.9 Hz), 7.87 (1H, s), 7.59 (1H, t, J 7.7 Hz), 7.40-7.30 (2H, m), 3.97-3.89 (1H, m), 3.74-3.59 (8H, m), 3.06-2.98 (4H, m), 2.52 (2H, s), 2.42 (2H, s), 1.04 (6H, s). LCMS (ES+) 536.3 (M+H)$^+$.

Example 252

3'-(5,5-Dimethyl-2-(morpholin-4-yl)-7-oxo-4,5,6,7-tetrahydro-1-benzothien-3-yl)-N,N,5'-trimethylbiphenyl-3-carboxamide A mixture of Example 17 (100 mg, 0.26 mmol), 3-bromo-5-methylphenylboronic acid (60 mg, 0.26 mmol), K$_3$PO$_4$ (70 mg, 0.33 mmol) and Pd(PPh$_3$)$_4$ (50 mg, 0.04 mmol) in DME, (3.0 mL) and water (1.0 mL) was heated in a sealed tube at 120° C., under microwave irradiation, for 50 minutes. The solvent was removed in vacuo and the residue was purified by column chromatography (SiO$_2$, 0-50% EtOAc/heptane). The intermediate so obtained was combined with 3-(N,N-dimethylaminocarbonyl)-phenylboronic acid (30 mg, 0.16 mmol), K$_3$PO$_4$ (35 mg, 0.17 mmol) and Pd(PPh$_3$)$_4$ (20 mg, 0.02 mmol) in DME (1.5 mL) and water (0.5 mL) and was heated in a sealed tube to 120° C., under microwave irradiation, for 1 h. The solvent was removed in vacuo and the residue was purified by preparative HPLC (pH 2.5) to give the title compound (27 mg, 35%) as an off-white solid. $\delta_H$ (CDCl$_3$) 7.69-7.62 (2H, m), 7.52-7.46 (1H, m), 7.42-7.36 (3H, m), 7.16 (1H, s), 3.67-3.60 (4H, m), 3.15 (3H, s), 3.08-2.97 (7H, m), 2.49 (2H, s), 2.46 (3H, s), 2.44 (2H, s), 1.04 (6H, s). LCMS (ES+) 503.4 (M+H)$^+$.

Example 253

5,5-Dimethyl-2-(morpholin-4-yl)-3-{2-[3-(piperazin-1-ylcarbonyl)phenyl]pyridin-4-yl}-5,6-dihydro-1-benzothiophen-7(4H)-one, Formic Acid Salt The title compound was prepared from Example 254 and 1-(tert-butoxycarbonyl)-piperazine according to Method AH and was isolated as a white solid (71%) after purification by preparative HPLC (pH 2.5). $\delta_H$ (CDCl$_3$) 8.77 (1H, d, J 4.9 Hz), 8.38 (1H, s), 8.16-8.06 (2H, m), 7.81 (1H, s), 7.59 (1H, t, J 7.7 Hz), 7.52-7.47 (1H, m), 7.31 (1H, dd, J 4.9, 1.3 Hz), 4.16-3.72 (4H, br m), 3.71-3.62 (4H, m), 3.28-3.07 (4H, br m), 3.06-2.97 (4H, m), 2.53 (2H, s), 2.46 (2H, s), 1.05 (6H, s). LCMS (ES+) 531.3 (M+H)$^+$.

Example 254

3-[4-(5,5-Dimethyl-2-(morpholin-4-yl)-7-oxo-4,5,6,7-tetrahydro-1-benzothien-3-yl)pyridin-2-yl]benzoic Acid A mixture of Example 73 (300 mg, 0.80 mmol), 3-ethoxycarbonylphenylboronic acid (155 mg, 0.80 mmol), K$_3$PO$_4$ (250 mg, 1.18 mmol) and Pd(PPh$_3$)$_4$ (150 mg, 0.13 mmol) in DME (80 mL) and water (20 mL) was heated at reflux for 18 h. Water (50 mL) was added and the organic phase was removed in vacuo. The remaining aqueous phase was basified to pH 10 with dilute sodium hydroxide solution and the mixture was stirred at room temperature for 1 h. The reaction mixture was concentrated in vacuo and purified by column chromatography (SiO$_2$, 0-100% EtOAc/heptane) to give the title compound (67 mg, 18%) as a yellow solid. $\delta_H$ (CDCl$_3$) 8.92 (1H, dd, J 5.1, 0.4 Hz), 8.88 (1H, t, J 1.5 Hz), 8.30-8.20 (2H, m), 7.93 (1H, d, J 0.6 Hz), 7.65 (1H, t, J 7.7 Hz), 7.35 (1H, dd, J 5.1, 1.3 Hz), 3.75-3.66 (4H, m), 3.09-3.01 (4H, m), 2.56 (2H, s), 2.48 (2H, s), 1.07 (6H, s). LCMS (ES+) 463.3 (M+H)$^+$.

Example 255

N,N-Diethyl-2-[4-(5,5-dimethyl-2-(morpholin-4-yl)-7-oxo-4,5,6,7-tetrahydro-1-benzothien-3-yl)pyridin-2-yl]benzamide The title compound was prepared from Example 73 and 2-(N,N-diethylamino-carbonyl)phenylboronic acid according to Method L and was isolated as a pale yellow solid (25%) after purification by preparative HPLC (pH 5.8). $\delta_H$ (DMSO-d$_6$) 8.66 (1H, d, J 5.1 Hz), 7.82 (1H, dd, J 7.7, 1.7 Hz), 7.72 (1H, s), 7.59-7.47 (2H, m), 7.41 (1H, dd, J 5.1, 1.5 Hz), 7.35-7.30 (1H, m), 3.62-3.52 (4H, m), 3.34-3.28 (4H, m), 2.98-2.90 (4H, m), 2.57 (2H, s), 2.39 (2H, s), 1.02-0.83 (12H, m). LCMS (ES+) 518.5 (M+H)$^+$.

Example 256

Ethyl {[3-(5,5-dimethyl-2-(morpholin-4-yl)-7-oxo-4,5,6,7-tetrahydro-1-benzothien-3-yl)phenyl]amino}(oxo)acetate Ethyl oxalyl chloride (0.20 mL, 1.69 mmol) and triethylamine (0.24 mL, 1.69 mmol) were added to a solution of Example 77 (400 mg, 1.12 mmol) in DCM (20 mL) and the reaction mixture was stirred at room temperature for 18 h. Water (20 mL) was added and the mixture was extracted with DCM (100 mL). The organic phase was dried (magnesium sulfate) and the solvent was removed in vacuo. The residue was purified by column chromatography (SiO$_2$, 40-50% EtOAc/heptane) to give the title compound (330 mg, 64%) as a cream solid. δ$_H$ (CDCl$_3$) 8.93 (1H, s), 7.77-7.72 (1H, m), 7.57-7.51 (1H, m), 7.44 (1H, t, J 7.7 Hz), 7.20 (1H, dt, J 7.5, 1.3 Hz), 4.45 (2H, q, J 7.2 Hz), 3.71-3.62 (4H, m), 3.03-2.95 (4H, m), 2.47 (2H, s), 2.43 (2H, s), 1.45 (3H, t, J 7.2 Hz), 1.04 (7H, s). LCMS (ES+) 457.3 (M+H)$^+$.

Example 257

3-(6-Aminobiphenyl-3-yl)-5,5-dimethyl-2-(morpholin-4-yl)-5,6-dihydro-1-benzothiophen-7(4H)-one The title compound was prepared from Example 272 and phenylboronic acid according to Method L, heating at 150° C. for 2 h, and was obtained as an off-white solid (56%) after purification by preparative HPLC (pH 2.5). δ$_H$ (DMSO-d$_6$) 7.52-7.41 (4H, m), 7.40-7.32 (1H, m), 7.07 (1H, d, J 8.5 Hz), 7.00 (1H, s), 6.84 (1H, d, J 8.3 Hz), 5.01-4.92 (1H, m), 3.64-3.51 (4H, m), 3.02-2.89 (4H, m), 2.50 (2H, s), 2.34 (2H, s), 0.97 (6H, s). LCMS (ES+) 433.3 (M+H)$^+$.

Example 258

(Method AI)

N,N-Dimethyl-3-[4-(2-(morpholin-4-yl)-7-oxo-4,5,6,7-tetrahydro-1-benzothien-3-yl)pyridin-2-yl]benzamide A mixture of Intermediate 2 (1.00 g, 2.75 mmol), 2-chloropyridine-4-boronic acid (0.43 g, 2.75 mmol), K$_3$PO$_4$ (0.70 g, 3.30 mmol) and Pd(PPh$_3$)$_4$ (400 mg, 0.35 mmol) in DME (30 mL) and water (10 mL) was heated at 70° C. for 5 h. The solvent was removed in vacuo and the residue was purified by column chromatography (SiO$_2$, 0-100% EtOAc/heptane). A sample (50 mg) of the intermediate so obtained was combined with 3-(N,N-dimethylaminocarbonyl)phenylboronic acid (28 mg, 0.14 mmol), K$_3$PO$_4$ (35 mg, 0.17 mmol) and Pd(PPh$_3$)$_4$ (20 mg, 0.017 mmol) in DME (1.5 mL) and water (0.5 mL) and was heated in a sealed tube at 120° C., under microwave irradiation, for 1 h. The solvent was removed in vacuo and the residue purified by preparative HPLC (pH 2.5) to give the title compound (56 mg, 67%) as a yellow glass. δ$_H$ (CD$_3$OD) 8.73 (1H, dd, J 5.3, 0.8 Hz), 8.19-8.09 (2H, m), 8.01 (1H, dd, J 1.3, 0.8 Hz), 7.63 (1H, td, J 7.5, 0.6 Hz), 7.57-7.52 (1H, m), 7.49 (1H, dd, J 5.1, 1.5 Hz), 3.72-3.63 (4H, m), 3.16 (3H, s), 3.12-3.01 (7H, m), 2.74 (2H, t, J 6.0 Hz), 2.63-2.55 (2H, m), 2.18-2.07 (2H, m). LCMS (ES+) 462.3 (M+H)$^+$.

Example 259

3-(2-{3-[(Dimethylamino)methyl]phenyl}pyridin-4-yl)-2-(morpholin-4-yl)-5,6-dihydro-1-benzothiophen-7(4H)-one, Formic Acid Salt The title compound was prepared from Intermediate 2 and 3-(N,N-dimethylamino-methyl)phenylboronic acid according to Method AI and was obtained as a pale yellow glass (61%) after purification by preparative HPLC (pH 2.5). δ$_H$ (CD$_3$OD) 8.75 (1H, dd, J 5.1, 0.8 Hz), 8.21 (1H, s), 8.15 (1H, dt, J 7.0, 1.7 Hz), 8.00 (1H, d, J 0.6 Hz), 7.70-7.60 (2H, m), 7.51 (1H, dd, J 5.1, 1.5 Hz), 4.39 (2H, s), 3.72-3.63 (4H, m), 3.12-3.03 (4H, m), 2.87 (6H, s), 2.74 (2H, t, J 5.8 Hz), 2.63-2.56 (2H, m), 2.18-2.07 (2H, m). LCMS (ES+) 448.2 (M+H)$^+$.

Example 260

(Method AJ)

3-(6-{3-[(Dimethylamino)methyl]phenyl}pyridin-2-yl)-5,5-dimethyl-2-(morpholin-4-yl)-5,6-dihydro-1-benzothiophen-7(4H)-one A mixture of Example 17 (100 mg, 0.26 mmol), 6-chloropyridine-2-boronic acid (61 mg, 0.26 mmol), K$_3$PO$_4$ (100 mg, 0.47 mmol) and Pd(PPh$_3$)$_4$ (20 mg, 0.017 mmol) in DME (3 mL) and water (1 mL) was heated in a sealed tube at 120° C., under microwave irradiation, for 20 minutes. The solvent was removed in vacuo and the residue was purified by column chromatography (SiO$_2$, 0-60% EtOAc/heptane). A sample of the intermediate so obtained (50 mg) was combined with 3-[(N,N-dimethylamino)methyl]-phenylboronic acid pinacol ester (40 mg, 0.13 mmol), K$_3$PO$_4$ (50 mg, 0.24 mmol) and Pd(PPh$_3$)$_4$ (10 mg, 0.009 mmol) in DME (3 mL) and water (1 mL) and the mixture was heated in a sealed tube at 140° C., under microwave irradiation, for 2 h. The solvent was removed in vacuo and the residue was purified by column chromatography (SiO$_2$, 20-100% EtOAc/heptane then 10% MeOH/EtOAc) to give the title compound (32 mg, 29%) as a beige solid. δ$_H$ (DMSO-d$_6$) 8.15 (1H, s), 8.02-7.88 (3H, m), 7.63 (1H, dd, J 7.2, 0.8 Hz), 7.47 (1H, t, J 7.5 Hz), 7.39-7.34 (1H, m), 3.67-3.59 (4H, m), 3.49 (2H, s), 3.01-2.93 (4H, m), 2.75 (2H, s), 2.41 (2H, s), 2.19 (6H, s), 1.01 (6H, s). LCMS (ES+) 476.5 (M+H)$^+$.

Example 261

3-[6-(5,5-Dimethyl-2-(morpholin-4-yl)-7-oxo-4,5,6,7-tetrahydro-1-benzothien-3-yl)pyridin-2-yl]-N,N-dimethylbenzamide The title compound was prepared from Example 17 and 3-(N,N-dimethyl-aminocarbonyl)phenylboronic acid according to Method AJ and was obtained as a yellow solid (40%) after purification by column chromatography (SiO$_2$, 0-100% EtOAc/heptane). δ$_H$ (DMSO-d$_6$) 8.23-8.16 (2H, m), 8.01-7.96 (2H, m), 7.67 (1H, t, J 4.1 Hz), 7.59 (1H, t, J 7.7 Hz), 7.50-7.46 (1H, m), 3.66-3.59 (4H, m), 3.10-2.85 (10H, m), 2.71 (2H, s), 2.41 (2H, s), 0.98 (6H, s). LCMS (ES+) 476.5 (M+H)$^+$.

Example 262

3-[4-(5,5-Dimethyl-2-(morpholin-4-yl)-7-oxo-4,5,6,7-tetrahydro-1-benzothien-3-yl)pyridin-2-yl]benzyl Methanesulfonate Triethylamine (140 μL, 1.0 mmol) and methanesulfonyl chloride (68 μL, 0.88 mmol) were added to a solution of Example 155 (359 mg, 0.80 mmol) in DCM (40 mL) and the reaction mixture was stirred at room temperature for 1 h. The solvent was removed in vacuo and the residue was purified by column chromatography (SiO$_2$, 20-100% EtOAc/heptane) to give the title compound (288 mg, 68%) as a yellow solid. δ$_H$ (DMSO-d$_6$) 8.77 (1H, d, J 4.9 Hz), 8.26 (1H, d, J 0.4 Hz), 8.21-8.15 (1H, m), 8.07 (1H, s), 7.63-7.52 (2H, m), 7.44 (1H, d, J 4.9 Hz), 5.37 (2H, s), 3.63-3.55 (4H, m), 3.28 (3H, s), 3.02-2.93 (4H, m), 2.59 (2H, s), 2.39 (2H, s), 0.97 (6H, s). LCMS (ES+) 527.2 (M+H)$^+$.

Example 263

(Method AK)

5,5-Dimethyl-3-(2-{3-[(methylamino)methyl] phenyl}pyridin-4-yl)-2-(morpholin-4-yl)-5,6-dihydro-1-benzothiophen-7(4H)-one, Acetic Acid Salt Example 262 (46 mg, 0.087 mmol) was combined with methylamine hydrochloride (67 mg, 1.0 mmol), triethylamine (140 µL, 1.0 mmol) and THF (3 mL) in a sealed tube and the mixture was stirred at room temperature for 16 h. A solution of methylamine in THF (2M, 1.0 mL, 2.0 mmol) was added and the mixture was then heated at 120° C., under microwave irradiation, for 1 h. The solvent was removed in vacuo and the residue was purified by preparative HPLC (pH 5.8) to give the title compound (16 mg, 31%) as a yellow solid. $\delta_H$ (DMSO-$d_6$) 8.74 (1H, d, J 4.9 Hz), 8.12 (1H, s), 8.06-7.96 (2H, m), 7.49-7.36 (3H, m), 3.74 (2H, s), 3.64-3.54 (4H, m), 3.03-2.92 (4H, m), 2.58 (2H, s), 2.39 (2H, s), 2.29 (3H, s), 1.86 (6H, s), 0.97 (6H, s). LCMS (ES+) 462.3 (M+H)$^+$.

Example 264

(Method AL)

N-[3-(5,5-Dimethyl-2-(morpholin-4-yl)-7-oxo-4,5,6, 7-tetrahydro-1-benzothien-3-yl)phenyl]benzamide To a solution of Example 77 (50 mg, 0.14 mmol) in DCM (5.0 mL) was added benzoic acid (21 mg, 0.17 mmol), EDC (54 mg, 0.28 mmol) and 1-hydroxybenzotriazole (3.0 mg, 0.03 mmol) and the reaction mixture was stirred at room temperature for 18 h. The solvent was removed in vacuo and the residue was purified by preparative HPLC (pH 2.5) to give the title compound (32 mg, 50%) as a cream solid. $\delta_H$ (CDCl$_3$) 7.92-7.86 (3H, m), 7.73 (1H, t, J 1.9 Hz), 7.62-7.49 (4H, m), 7.44 (1H, t, J 7.9 Hz), 7.17-7.12 (1H, m), 3.71-3.64 (4H, m), 3.05-2.98 (4H, m), 2.49 (2H, s), 2.43 (2H, s), 1.04 (6H, s). LCMS (ES+) 461.3 (M+H)$^+$.

Example 265

Tert-Butyl N-(1-{3-[4-(5,5-dimethyl-2-(morpholin-4-yl)-7-oxo-4,5,6,7-tetrahydro-1-benzothien-3-yl) pyridin-2-yl]benzoyl}piperidin-4-yl)-N-methylcarbamate The title compound was prepared from Example 254 and 4-[N-(tert-butoxy-carbonyl)-N-methylamino]piperidine according to Method I and was isolated as a white solid (14%) after purification by preparative HPLC (pH 5.8). $\delta_H$ (CD$_3$OD) 8.75 (1H, m), 8.19-8.11 (2H, m), 8.02 (1H, s), 7.65 (1H, t, J 7.5 Hz), 7.58-7.53 (1H, m), 7.48 (1H, dd, J 5.1, 1.5 Hz), 4.87-4.75 (1H, m), 4.25-4.08 (1H, m), 3.97-3.84 (1H, m), 3.72-3.63 (4H, m), 3.30-3.19 (1H, m), 3.14-3.03 (4H, m), 3.00-2.86 (1H, m), 2.80 (3H, m), 2.64 (2H, s), 2.47 (2H, s), 1.91-1.59 (4H, m), 1.48 (9H, s), 1.05 (6H, s). LCMS (ES+) 659.2 (M+H)$^+$.

Example 266

3-[4-(5,5-Dimethyl-2-(morpholin-4-yl)-7-oxo-4,5,6, 7-tetrahydro-1-benzothien-3-yl)pyridin-2-yl]-N-methyl-N-(1-methylpyrrolidin-3-yl)benzamide, Formic Acid Salt The title compound was prepared from Example 254 and N,N'-dimethyl-3-aminopyrrolidine (21 mg, 0.18 mmol) according to Method I and was isolated as a yellow glass (40%) after purification by preparative HPLC (pH 2.5). $\delta_H$ (CD$_3$OD) 8.75 (1H, dd, J 5.1, 0.6 Hz), 8.35 (2H, s), 8.20-8.14 (2H, m), 8.02 (1H, d, J 0.6 Hz), 7.67 (1H, t, J 7.7 Hz), 7.62-7.56 (1H, m), 7.49 (1H, dd, J 5.1, 1.5 Hz), 4.82-4.68 (1H, m), 3.95-3.72 (2H, m), 3.72-3.63 (4H, m), 3.61-3.43 (1H, m), 3.30-3.20 (1H, m), 3.14 (3H, s), 3.10-3.04 (4H, m), 3.03-2.87 (3H, m), 2.67-2.55 (3H, m), 2.52-2.34 (3H, m), 1.05 (6H, s). LCMS (ES+) 559.4 (M+H)$^+$.

Example 267

3-[4-(5,5-Dimethyl-2-(morpholin-4-yl)-7-oxo-4,5,6, 7-tetrahydro-1-benzothien-3-yl)pyridin-2-yl]-N-methyl-N-(1-methylpiperidin-4-yl)benzamide, Formic Acid Salt The title compound was prepared from Example 254 and 1-methyl-4-(methylamino)piperidine (26 µL, 0.18 mmol) according to Method I and was isolated as a white solid (25%) after purification by preparative HPLC (pH 2.5). $\delta_H$ (CD$_3$OD) 8.75 (1H, d, J 5.1 Hz), 8.20-8.11 (2H, m), 8.03 (1H, s), 7.66 (1H, t, J 7.7 Hz), 7.59-7.53 (1H, m), 7.48 (1H, dd, J 5.3, 1.5 Hz), 4.79-4.59 (1H, m), 3.76-3.65 (4H, m), 3.64-3.42 (2H, m), 3.29-3.12 (2H, m), 3.12-3.04 (4H, m), 3.04-2.95 (3H, br s), 2.94-2.72 (3H, br s), 2.64 (2H, s), 2.47 (2H, s), 2.35-2.16 (2H, m), 2.16-1.99 (2H, m), 1.05 (6H, s). LCMS (ES+) 573.3 (M+H)$^+$.

Example 268

(Method AM)

3-(2-{3-[(4-Aminopiperidin-1-yl)carbonyl] phenyl}pyridin-4-yl)-5,5-dimethyl-2-(morpholin-4-yl)-5,6-dihydro-1-benzothiophen-7(4H)-one A solution of HCl in Et$_2$O (2M, 3.3 mL, 6.6 mmol) was added to a solution of Example 273 (0.21 g, 0.33 mmol) in DCM (6 mL) and the reaction mixture was stirred at room temperature for 18 h. The precipitate was filtered off and washed with Et$_2$O. The solid was partitioned between DCM (100 mL) and dilute sodium hydrogencarbonate solution (50 mL). The organic phase was dried (magnesium sulfate) and the solvent was removed in vacuo to give the title compound (104 mg, 59%) as a yellow solid. $\delta_H$ (CD$_3$OD) 8.74 (1H, dd, J 5.1, 0.6 Hz), 8.18-8.13 (1H, m), 8.12-8.09 (1H, m), 8.02 (1H, s), 7.65 (1H, t, J 7.7 Hz), 7.56-7.51 (1H, m), 7.48 (1H, dd, J 5.1, 1.5 Hz), 4.72-4.56 (1H, m), 3.89-3.75 (1H, m), 3.73-3.64 (4H, m), 3.25-3.16 (1H, m), 3.14-3.05 (4H, m), 3.03-2.90 (2H, m), 2.64 (2H, s), 2.48 (2H, s), 2.08-1.93 (1H, m), 1.91-1.77 (1H, m), 1.52-1.30 (2H, m), 1.06 (6H, s). LCMS (ES+) 545.3 (M+H)$^+$.

Example 269

3-(2,6-Dichloropyridin-4-yl)-5,5-dimethyl-2-(morpholin-4-yl)-5,6-dihydro-1-benzothiophen-7(4H)-one The title compound was prepared from Example 17 and 2,6-dichloropyridyl-4-boronic acid pinacol ester according to Method J and was isolated as an off-white solid (45%) after purification by column chromatography (SiO$_2$, 0-50% EtOAc/heptane). $\delta_H$ (CDCl$_3$) 7.35 (2H, s), 3.77-3.70 (4H, m), 3.05-2.96 (4H, m), 2.51 (2H, s), 2.46 (2H, s), 1.07 (6H, s). LCMS (ES+) 411.3, 413.2 (M+H)$^+$.

Example 270

5,5-Dimethyl-3-[2-(3-{[4-(methylamino)piperidin-1-yl]carbonyl}phenyl)pyridin-4-yl]-2-(morpholin-4-yl)-5,6-dihydro-1-benzothiophen-7(4H)-one The title compound was prepared from Example 265 according to Method AM and was isolated as a white solid (51%). $\delta_H$ (CD$_3$OD) 8.74 (1H, dd, J 5.1, 0.6 Hz), 8.18-8.13 (1H, m), 8.12-8.09 (1H, m), 8.01 (1H, s), 7.65 (1H, t, J 7.7 Hz), 7.56-7.51 (1H, m), 7.48 (1H, dd, J 5.3, 1.5 Hz), 4.71-4.60 (1H, m), 3.90-3.78 (1H, m), 3.73-3.64 (4H, m), 3.29-3.17 (1H, m), 3.13-3.05 (4H, m), 3.05-2.93 (1H, m), 2.80-2.67 (1H, m), 2.64 (2H, s), 2.48 (2H, s), 2.42 (3H, s), 2.16-2.04 (1H, m), 1.99-1.86 (1H, m), 1.47-1.26 (2H, m), 1.06 (6H, s). LCMS (ES+) 559.3 (M+H)$^+$.

Example 271

(Method AN)

5,5-Dimethyl-3-(2-{2-[(4-methylpiperazin-1-yl)methyl]phenyl}pyridin-4-yl)-2-(morpholin-4-yl)-5,6-dihydro-1-benzothiophen-7(4H)-one Acetic Acid Salt A mixture of 2-formylphenylboronic acid (100 mg, 0.67 mmol), 1-methyl-piperazine (90 µL, 0.80 mmol) and activated molecular sieves (100 mg) in methanol (3.0 mL) was stirred at room temperature for 4 h. Sodium borohydride (30 mg, 0.79 mmol) was then added and stirring was continued for 1 h. The solvent was removed in vacuo and the residue was taken up in DME (3.0 mL) and water (1.0 mL), to which was added K$_3$PO$_4$ (50 mg, 0.24 mmol), Pd(PPh$_3$)$_4$ (10 mg, 0.009 mmol) and Example 73 (50 mg, 0.13 mmol). The reaction mixture was heated at 140° C., under microwave irradiation, for 2 h. The solvent was removed in vacuo and the residue was purified by preparative HPLC (pH 5.8) to give the title compound (40 mg, 52%) as an off-white solid. $\delta_H$ (DMSO-d$_6$) 8.71 (1H, d, J 5.1 Hz), 7.81 (1H, s), 7.54-7.48 (1H, m), 7.47-7.37 (4H, m), 3.63-3.56 (4H, m), 3.51 (2H, s), 3.02-2.93 (4H, m), 2.56 (2H, s), 2.38 (2H, s), 2.31-1.99 (11H, m), 1.89 (3H, s), 0.97 (6H, s). LCMS (ES+) 531.6 (M+H)$^+$.

Example 272

3-(4-Amino-3-bromophenyl)-5,5-dimethyl-2-(morpholin-4-yl)-5,6-dihydro-1-benzothiophen-7(4H)-one N-Bromosuccinimide (70 mg, 0.39 mmol) was added to a solution of Example 78 (140 mg, 0.39 mmol) in THF (10 mL) and the reaction mixture was stirred at room temperature for 35 minutes. The solvent was removed in vacuo and the residue was purified by column chromatography (SiO$_2$, 10-70% EtOAc/heptane) to give the title compound (136 mg, 79%) as a yellow solid. $\delta_H$ (DMSO-d$_6$) 7.37 (1H, d, J 1.9 Hz), 7.09 (1H, dd, J 8.3, 1.7 Hz), 6.86 (1H, d, J 8.3 Hz), 3.64-3.54 (4H, m), 2.97-2.88 (4H, m), 2.47 (2H, s), 2.34 (2H, s), 0.96 (6H, s). LCMS (ES+) 435.3, 437.2 (M+H)$^+$.

Example 273

Tert-Butyl (1-{3-[4-(5,5-dimethyl-2-(morpholin-4-yl)-7-oxo-4,5,6,7-tetrahydro-1-benzothien-3-yl)pyridin-2-yl]benzoyl}piperidin-4-yl)carbamate The title compound was prepared from Example 254 and 4-(tert-butoxycarbonyl-amino)piperidine according to Method I and was obtained as an off-white solid (14%) after purification by preparative HPLC (pH 2.5). $\delta_H$ (CD$_3$OD) 8.74 (1H, dd, J 5.1, 0.6 Hz), 8.19-8.13 (1H, m), 8.12-8.08 (1H, m), 8.01 (1, d, J 0.6 Hz), 7.64 (1H, t, J 7.5 Hz), 7.56-7.46 (2H, m), 4.63-4.48 (1H, m), 3.85-3.60 (6H, m), 3.29-3.18 (1H, m), 3.17-3.01 (5H, m), 2.64 (2H, s), 2.48 (2H, s), 2.08-1.81 (2H, m), 1.61-1.35 (11H, m), 1.05 (6H, s). LCMS (ES+) 645.2 (M+H)$^+$.

Example 274

N-Benzyl-N-[3-(5,5-dimethyl-2-(morpholin-4-yl)-7-oxo-4,5,6,7-tetrahydro-1-benzothien-3-yl)phenyl]propanamide Sodium hydride (60% dispersion in oil, 2.8 mg, 0.07 mmol) was added to a solution of Example 278 (24 mg, 0.06 mmol) in DMF (1.0 mL) and the reaction mixture was stirred at room temperature for 5 minutes. Benzyl bromide (7 µL, 0.06 mmol) was then added and stirring was continued for 18.5 h. The reaction mixture was filtered and purified by preparative HPLC (pH 2.5) to give the title compound (10 mg, 33%) as a yellow solid. $\delta_H$ (CDCl$_3$) 7.42 (1H, t, J 7.7 Hz), 7.25-7.14 (6H, m), 7.10-7.03 (1H, m), 6.93-6.87 (1H, m), 4.95 (2H, s), 3.59-3.51 (4H, m), 2.92-2.83 (4H, m), 2.41 (2H, s), 2.25 (2H, s), 2.21-2.10 (2H, m), 1.12 (3H, t, J 7.5 Hz), 1.01 (6H, s). LCMS (ES+) 503.6 (M+H)$^+$.

Example 275

Tert-Butyl 4-{[3-(5,5-dimethyl-2-(morpholin-4-yl)-7-oxo-4,5,6,7-tetrahydro-1-benzothien-3-yl)phenyl]carbamoyl}piperidine-1-carboxylate The title compound was prepared from Example 77 and N-(tert-butoxycarbonyl)-isonipecotic acid according to Method AL and was obtained as a cream solid (55%) after purification by preparative HPLC (pH 2.5). $\delta_H$ (CDCl$_3$) 7.59-7.55 (1H, m), 7.49-7.43 (1H, m), 7.42-7.35 (1H, m), 7.31-7.27 (1H, m), 7.12-7.06 (1H, m), 4.30-4.13 (2H, m), 3.70-3.61 (4H, m), 3.03-2.95 (4H, m), 2.88-2.74 (2H, m), 2.45 (2H, s), 2.44-2.35 (3H, m), 1.99-1.87 (2H, m), 1.84-1.68 (2H, m), 1.47 (9H, s), 1.03 (6H, s). LCMS (ES+) 568.2 (M+H)$^+$.

Example 276

N-[3-(5,5-Dimethyl-2-(morpholin-4-yl)-7-oxo-4,5,6,7-tetrahydro-1-benzothien-3-yl)phenyl]-2-phenylacetamide The title compound was prepared from Example 77 and phenylacetic acid according to Method AL and was obtained as a cream solid (65%) after purification by preparative HPLC (pH 2.5). $\delta_H$ (CDCl$_3$) 7.55-7.51 (1H, m), 7.47-7.27 (7H, m), 7.11-7.03 (2H, m), 3.78 (2H, s), 3.66-3.59 (4H, m), 3.00-2.93 (4H, m), 2.45 (2H, s), 2.41 (2H, s), 1.02 (6H, s). LCMS (ES+) 475.3 (M+H)$^+$.

Example 277

N-[3-(5,5-Dimethyl-2-(morpholin-4-yl)-7-oxo-4,5,6,7-tetrahydro-1-benzothien-3-yl)phenyl]-1H-indole-3-carboxamide The title compound was prepared from Example 77 and indole-3-carboxylic acid according to Method AL and was obtained as a cream solid (20%) after purification by preparative HPLC (pH 2.5). $\delta_H$ (CDCl$_3$) 8.76 (1H, br s), 8.10-8.04 (1H, m), 7.93 (1H, d, J 2.8 Hz), 7.79 (1H, s), 7.74 (1H, t, J 1.7 Hz), 7.64-7.58 (1H, m), 7.53-7.47 (1H, m), 7.44 (1H, t, J 7.9 Hz), 7.36-7.30 (2H, m), 7.14-7.09 (1H, m), 3.72-3.64 (4H, m), 3.06-2.98 (4H, m), 2.51 (2H, s), 2.43 (2H, s), 1.04 (6H, s). LCMS (ES+) 500.3 (M+H)$^+$.

Example 278

N-[3-(5,5-Dimethyl-2-(morpholin-4-yl)-7-oxo-4,5,6,7-tetrahydro-1-benzothien-3-yl)phenyl]propanamide The title compound was prepared from Example 77 and propionic acid according to Method AL and was obtained as a cream solid (76%) after purification by preparative HPLC (pH 2.5). $\delta_H$ (CDCl$_3$) 7.59 (1H, br s), 7.47-7.34 (2H, m), 7.17 (1H, s), 7.08 (1H, d, J 7.3 Hz), 3.70-3.62 (4H, m), 3.03-2.95 (4H, m), 2.50-2.38 (6H, m), 1.27 (3H, t, J 7.5 Hz), 1.03 (6H, s). LCMS (ES+) 413.3 (M+H)$^+$.

Example 279

N-[3-(5,5-dimethyl-2-(morpholin-4-yl)-7-oxo-4,5,6,7-tetrahydro-1-benzothien-3-yl)phenyl]isonicotinamide The title compound was prepared from Example 77 and isonicotinic acid according to Method AL and was obtained as a cream solid (37%) after purification by preparative HPLC (pH 2.5). $\delta_H$ (CDCl$_3$) 8.86-8.81 (2H, m), 8.05 (1H, br s), 7.78-7.71 (3H, m), 7.62-7.57 (1H, m), 7.47 (1H, t, J 7.9 Hz), 7.19 (1H, d, J 7.7 Hz), 3.72-3.64 (4H, m), 3.05-2.97 (4H, m), 2.49 (2H, s), 2.42 (2H, s), 1.03 (6H, s). LCMS (ES+) 462.3 (M+H)$^+$.

Example 280

N-[3-(5,5-dimethyl-2-(morpholin-4-yl)-7-oxo-4,5,6,7-tetrahydro-1-benzothien-3-yl)phenyl]cyclopentanecarboxamide The title compound was prepared from Example 77 and cyclopentanecarboxylic acid according to Method AL and was obtained as a cream solid (63%) after purification by preparative HPLC (pH 2.5). $\delta_H$ (CDCl$_3$) 7.58 (1H, br s), 7.50-7.45 (1H, m), 7.37 (1H, t, J 7.7 Hz), 7.23 (1H, br s), 7.07 (1H, d, J 7.5 Hz), 3.70-3.62 (4H, m), 3.03-2.96 (4H, m), 2.78-2.65 (1H, m), 2.48 (2H, s), 2.42 (2H, s), 2.04-1.58 (8H, m), 1.03 (6H, s). LCMS (ES+) 453.4 (M+H)$^+$.

Example 281

3-{3-[(Dimethylamino)methyl]phenyl}-5,5-dimethyl-2-morpholin-4-yl-5,6-dihydro-1-benzothiophen-7(4H)-one, Formic Acid Salt The title compound was prepared from Example 17 and 3-[(N,N-dimethylamino)-methyl]phenylboronic acid according to Method J and was obtained as an off-white solid (60%) after purification by preparative HPLC (pH 2.5). $\delta_H$ (CD$_3$OD) 8.45 (1H, s), 7.62-7.55 (1H, m), 7.53-7.46 (3H, m), 4.25 (2H, s), 3.67-3.59 (4H, m), 3.05-2.95 (4H, m), 2.78 (6H, s), 2.49 (2H, s), 2.42 (2H, s), 1.01 (6H, s). LCMS (ES+) 399.3 (M+H)$^+$.

Example 282

5,5-Dimethyl-2-(morpholin-4-yl)-3-(2-phenylpyrimidin-4-yl)-5,6-dihydro-1-benzothiophen-7(4H)-one A mixture of Example 344 (70 mg, 0.19 mmol), benzamidine hydrochloride (61 mg, 0.39 mmol) and sodium ethoxide (53 mg, 0.77 mmol) in EtOH (3.0 mL) was heated at 100° C., under microwave irradiation, for 80 minutes. The solvent was removed in vacuo and the residue was purified by column chromatography (SiO$_2$, 0-100% EtOAc/heptane) and preparative HPLC (pH 2.5) to give the title compound (13 mg, 16%) as an off-white solid. $\delta_H$ (DMSO-d$_6$) 8.94 (1H, d, J 5.2 Hz), 8.47-8.41 (2H, m), 7.73 (1H, d, J 5.2 Hz), 7.59-7.53 (3H, m), 3.71-3.63 (4H, m), 3.07-3.00 (4H, m), 2.82 (2H, s), 2.43 (2H, s), 1.00 (6H, s). LCMS (ES+) 420.3 (M+H)$^+$.

Example 283

5,5-Dimethyl-2-(morpholin-4-yl)-3-(6-phenylpyridin-2-yl)-5,6-dihydro-1-benzothiophen-7(4R)-one The title compound was prepared from Example 17, 6-chloropyridine-2-boronic acid and phenylboronic acid according to Method AJ and was obtained as an off-white solid (30%) after purification by preparative HPLC (pH 2.5). $\delta_H$ (DMSO-d$_6$) 8.18-8.12 (2H, m), 8.01-7.91 (2H, m), 7.62 (1H, dd, J 7.2, 1.3 Hz), 7.56-7.43 (3H, m), 3.67-3.57 (4H, m), 3.02-2.94 (4H, m), 2.69 (2H, s), 2.40 (2H, s), 0.98 (6H, s). LCMS (ES+) 419.3 (M+H)$^+$.

Example 284

(Method AO)

3-Acetyl-5,5-dimethyl-2-(morpholin-4-yl)-5,6-dihydro-1-benzothiophen-7(4R)-one

A solution of Intermediate 57 (365 mg, 1.00 mmol) in aqueous hydrochloric acid (1M, 4.0 mL) and acetonitrile (10.0 mL) was stirred at room temperature for 3 h. The solvent was removed in vacuo and the residue was purified by column chromatography (SiO$_2$, 0-100% EtOAc/heptane) to give the title compound (270 mg, 88%) as a pale yellow solid. $\delta_H$ (CD$_3$OD) 3.91-3.85 (4H, m), 3.25-3.19 (4H, m), 2.78 (2H, s), 2.55 (3H, s), 2.43 (2H, s), 1.08 (6H, s). LCMS (ES+) 308.2 (M+H)$^+$.

Example 285

(Method AP)

Tert-Butyl (1-{[3-(5,5-dimethyl-2-(morpholin-4-yl)-7-oxo-4,5,6,7-tetrahydro-1-benzothien-3-yl)phenyl]carbamoyl}pyrrolidin-3-yl)carbamate Triphosgene (42 mg, 0.14 mmol) and triethylamine (0.2 mL, 1.40 mmol) were added to a cooled solution of Example 77 (10 mg, 0.28 mmol) in THF (15 mL) at −78° C. The mixture was then allowed to warm to 0° C. and stirred at this temperature for 30 minutes. The reaction mixture was then recooled to −78° C., 3-(tert-butoxycarbonyl-amino)pyrrolidine (78 mg, 0.42 mmol) was added, and then it was allowed to warm to 0° C. and stirred for 1 h. Water (20 mL) was added and the mixture was extracted with EtOAc (75 mL). The combined organic phase was washed with brine (20 mL), dried (magnesium sulfate) and the solvent was removed in vacuo. A sample (40 mg) of the residue was purified by preparative HPLC (pH 2.5) to give the title compound (21 mg) as an off-white solid. $\delta_H$ (CDCl$_3$) 7.44-7.41 (1H, m), 7.37-7.33 (2H, m), 7.03-6.98 (1H, m), 6.20 (1H, s), 4.75-4.65 (1H, m), 4.34-4.25 (1H, m), 3.82-3.73 (1H, m), 3.69-3.54 (6H, m), 3.41-3.32 (1H, m), 3.04-2.96 (4H, m), 2.47 (2H, s), 2.41 (2H, s), 2.32-2.20 (1H, m), 2.01-1.89 (1H, m), 1.46 (9H, s), 1.03 (6H, s). LCMS (ES+) 569.2 (M+H)$^+$.

Example 286

Tert-Butyl 4-{[3-(5,5-dimethyl-2-(morpholin-4-yl)-7-oxo-4,5,6,7-tetrahydro-1-benzothien-3-1)phenyl] carbamoyl}piperazine-1-carboxylate The title compound was prepared from Example 77 and 1-(tert-butoxycarbonyl)-piperazine according to Method AP and was obtained as an off-white solid (19 mg) after purification by preparative HPLC (pH 2.5). $\delta_H$ (CDCl$_3$) 7.39-7.29 (3H, m), 7.02 (1H, dt, J 7.0, 1.7 Hz), 6.43 (1H, s), 3.69-3.62 (4H, m), 3.52 (8H, s), 3.03-2.96 (4H, m), 2.46 (2H, s), 2.41 (2H, s), 1.49 (9H, s), 1.02 (6H, s). LCMS (ES+) 569.2 (M+H)$^+$.

Example 287

(3R)—N-[3-(5,5-Dimethyl-2-(morpholin-4-yl)-7-oxo-4,5,6,7-tetrahydro-1-benzothien-3-yl)phenyl]-3-hydroxypyrrolidine-1-carboxamide The title compound was prepared from Example 77 and (R)-(+)-3-hydroxy-pyrrolidine according to Method AP and was obtained as a pale yellow solid (58%) after purification of the entire sample by preparative HPLC (pH 2.5). $\delta_H$ (CDCl$_3$) 7.46-7.42 (1H, m), 7.38-7.33 (2H, m), 7.03-6.97 (1H, m), 6.23 (1H, s), 4.63-4.57 (1H, m), 3.72-3.49 (8H, m), 3.04-2.97 (4H, m), 2.46 (2H, s), 2.41 (2H, s), 2.18-2.06 (2H, m), 1.85-1.75 (1H, m), 1.02 (6H, s). LCMS (ES+) 470.3 (M+H)$^+$.

Example 288

3-(Biphenyl-3-yl)-2-(morpholin-4-yl)-5,6-dihydro-1-benzothiophen-7(4H)-one

The title compound was prepared from Intermediate 2 and 3-biphenylboronic acid according to Method J and was obtained as an off-white solid (77%) after purification by preparative HPLC (pH 2.5). $\delta_H$ (DMSO-d$_6$) 6.87-6.79 (4H, m), 6.79-6.72 (1H, m), 6.70-6.63 (2H, m), 6.60-6.53 (2H, m), 2.86-2.78 (4H, m), 2.28-2.20 (4H, m), 1.91-1.83 (2H, m), 1.80-1.72 (2H, m), 1.34-1.25 (2H, m). LCMS (ES+) 390.3 (M+H)$^+$.

Example 289

3-Acetyl-5,5-dimethyl-2-(morpholin-4-yl)-5,6-dihydrothieno[2,3-c]pyridin-7(4H)-one The title compound was prepared from Intermediate 58 according to Method AO and was obtained as a yellow solid (60%) after purification by column chromatography (SiO$_2$, 0-100% EtOAc/heptane). $\delta_H$ (CD$_3$OD) 3.94-3.86 (4H, m), 3.21-3.13 (4H, m), 2.95 (2H, s), 2.60 (3H, s), 1.33 (6H, s). LCMS (ES+) 309.2 (M+H)$^+$.

Example 290

Ethyl 3-[4-(5,5-dimethyl-2-(morpholin-4-yl)-7-oxo-4,5,6,7-tetrahydro-1-benzothien-3-yl)pyridin-2-yl] benzoate The title compound was prepared from Example 73 and 3-ethoxycarbonylphenyl-boronic acid according to Method L and was isolated as an off-white solid (5%) after purification by column chromatography (SiO$_2$, 0-100% EtOAc/heptane). $\delta_H$ (CDCl$_3$) 8.79 (1H, dd, J 5.1, 0.8 Hz), 8.66-8.64 (1H, m), 8.32-8.24 (1H, m), 8.17-8.12 (1H, m), 7.89 (1H, d, J 0.8 Hz), 7.60 (1H, t, J 7.9 Hz), 7.30-7.25 (1H, m), 4.43 (2H, q, J 7.2 Hz), 3.73-3.65 (4H, m), 3.06-2.99 (4H, m), 2.55 (2H, s), 2.47 (2H, s), 1.43 (3H, t, J 7.2 Hz), 1.06 (6H, s). LCMS (ES+) 491.3 (M+H)$^+$.

Example 291

2-(Morpholin-4-yl)-7-oxo-4,5,6,7-tetrahydro-1-benzothiophene-3-carbonitrile

Tert-butyl nitrite (4.6 mL, 4.3 mmol) was added to a cooled mixture of copper(II) bromide (10.5 g, 46.9 mmol) in acetonitrile (50 mL). 2-Amino-7-oxo-4,5,6,7-tetrahydro-1-benzothiophene-3-carbonitrile (6.0 g, 31.3 mmol) was then added over a period of 1 h and the reaction mixture was then allowed to warm to room temperature. The solvent was removed in vacuo and the residue was partitioned between DCM and 1M aqueous HCl. The organic phase was dried (magnesium sulfate) and concentrated in vacuo. The residue was purified by column chromatography (SiO$_2$, 0-100% EtOAc/heptane) and the isolated product was combined with morpholine (4.5 mL) in DMSO (80 mL). The reaction mixture was heated at 100° C. for 1.5 h, then water (300 mL) was immediately added with rapid stirring and the mixture was allowed to cool to room temperature overnight. The precipitate was filtered off, washed with water and dried in vacuo to give the title compound (5.65 g, 69%) as a pale brown solid. $\delta_H$ (DMSO-d$_6$) 3.80-3.72 (4H, m), 3.67-3.59 (4H, m), 2.73 (2H, t, J 6.0 Hz), 2.49-2.42 (2H, m), 2.13-2.03 (2H, m). LCMS (ES+) 263.2 (M+H)$^+$.

Example 292

{[3-(5,5-Dimethyl-2-(morpholin-4-yl)-7-oxo-4,5,6, 7-tetrahydro-1-benzothien-3-yl)phenyl]amino}(oxo) acetic Acid Sodium hydroxide (53 mg, 1.32 mmol) was added to a mixture of Example 256 (300 mg, 0.66 mmol) in THF (10 mL) and water (10 mL) and the reaction mixture was stirred at room temperature for 3 h. The THF was removed in vacuo and the aqueous phase was diluted with water (10 mL), washed with EtOAc (20 mL) and acidified to pH 2 with 2M aqueous HCl. The aqueous phase was extracted with EtOAc (50 mL) and the organic phase was dried (magnesium sulfate) and the solvent was removed in vacuo to give the title compound (204 mg, 72%) as a yellow solid. $\delta_H$ (CDCl$_3$) 9.04 (1H, br s), 7.77-7.74 (1H, m), 7.59-7.47 (2H, m), 7.28-7.25 (1H, m), 3.72-3.66 (4H, m), 3.04-2.98 (4H, m), 2.51 (2H, s), 2.47 (2H, s), 1.06 (6H, s). LCMS (ES+) 429.0 (M+H)$^+$.

Example 293

N-[3-(5,5-Dimethyl-2-(morpholin-4-yl)-7-oxo-4,5,6,7-tetrahydro-1-benzothien-3-yl)phenyl]-5-methylisoxazole-3-carboxamide The title compound was prepared from Example 77 and 5-methylisoxazole-3-carboxylic acid according to Method AL and was isolated as a cream solid (57%) after purification by preparative HPLC (pH 2.5). $\delta_H$ (CDCl$_3$) 8.57 (1H, br s), 7.73 (1H, t, J 1.7 Hz), 7.61-7.55 (1H, m), 7.44 (1H, t, J 7.7 Hz), 7.18-7.14 (1H, m), 6.55 (1H, d, J 0.8 Hz), 3.70-3.63 (4H, m), 3.04-2.96 (4H, m), 2.55 (3H, d, J 0.9 Hz), 2.48 (2H, s), 2.43 (2H, s), 1.04 (6H, s). LCMS (ES+) 466.3 (M+H)$^+$.

Example 294

N-[3-(5,5-Dimethyl-2-(morpholin-4-yl)-7-oxo-4,5,6,7-tetrahydro-1-benzothien-3-yl)phenyl]-N'-methylethanediamide The title compound was prepared from Example 292 and ethylamine (2M in THF) according to Method AL and was isolated as an off-white solid (5%) after purification by preparative HPLC (pH 2.5). $\delta_H$ (CDCl$_3$) 9.33 (1H, s), 7.70 (1H, t, J 1.7 Hz), 7.60-7.50 (2H, m), 7.44 (1H, t, J 7.7 Hz), 7.20-7.15 (1H, m), 3.70-3.63 (4H, m), 3.50-3.39 (2H, m), 3.03-2.96 (4H, m), 2.48 (2H, s), 2.43 (2H, s), 1.26 (311, t, J 7.3 Hz), 1.04 (6H, s). LCMS (ES+) 456.3 (M+H)$^+$.

Example 295

3-{2-[3-(2,3-Dihydroxypropoxy)phenyl]pyridin-4-yl}-5,5-dimethyl-2-(morpholin-4-yl)-5,6-dihydro-1-benzothiophen-7(4H)-one A mixture of Example 103 (30 mg, 0.069 mmol), 2,2-dimethyl-1,3-dioxolan-4-yl-methyl p-toluenesulfonate (30 mg, 0.104 mmol) and potassium carbonate (29 mg, 0.207 mmol) in DMF (5.0 mL) was heated at 80° C. for 18 h. The solvent was removed in vacuo and the residue was purified by column chromatography (SiO$_2$, 0-100% EtOAc/heptane). The resulting intermediate was combined with p-toluenesulfonic acid monohydrate (1.0 mg, 0.004 mmol) in MeOH (1.5 mL) and water (0.5 mL) and the reaction mixture was stirred at room temperature for 18 h, then in a sealed tube at 80° C. for 1 h. The solvent was removed in vacuo and the residue was purified by preparative HPLC (pH 2.5) to give the title compound (10 mg, 47%) as a clear oil. $\delta_H$ (CD$_3$OD) 8.71 (1H, d, J 5.3 Hz), 7.95 (1H, d, J 0.6 Hz), 7.65-7.56 (2H, m), 7.49-7.41 (2H, m), 7.13-7.07 (1H, m), 4.23-4.16 (1H, m), 4.14-3.99 (2H, m), 3.76-3.66 (6H, m), 3.12-3.04 (4H, m), 2.64 (2H, s), 2.48 (2H, s), 1.06 (6H, s). LCMS (ES+) 509.3 (M+H)$^+$.

Example 296

N-[3-(5,5-Dimethyl-2-(morpholin-4-yl)-7-oxo-4,5,6,7-tetrahydro-1-benzothien-3-yl)phenyl]-2-(morpholin-4-yl)-2-oxoacetamide The title compound was prepared from Example 292 and morpholine according to Method AL and was isolated as a cream solid (10%) after purification by preparative HPLC (pH 2.5). $\delta_H$ (CDCl$_3$) 9.30 (1H, s), 7.66 (1H, t, J 1.7 Hz), 7.57-7.51 (1H, m), 7.43 (1H, t, J 7.7 Hz), 7.16 (1H, d, J 7.5 Hz), 4.38-4.31 (2H, m), 3.84-3.72 (6H, m), 3.70-3.61 (4H, m), 3.04-2.95 (4H, m), 2.48 (2H, s), 2.43 (2H, s), 1.04 (6H, s). LCMS (ES+) 498.3 (M+H)$^+$.

Example 297

(Method AQ)

5,5-Dimethyl-2-(morpholin-4-yl)-3-[3-(morpholin-4-ylcarbonyl)phenyl]-5,6-dihydro-1-benzothiophen-7(4H)-one A mixture of Example 66 (1.40 g, 3.39 mmol) and lithium hydroxide monohydrate (0.43 g, 10.17 mmol) in THF (12 mL), MeOH (8 mL) and water (4 mL) was stirred at room temperature for 1 h. Water (30 mL) was added and the resulting precipitate was filtered off and dried in vacuo to give a beige solid (1.15 g). A sample of this intermediate lithium salt (50 mg, 0.13 mmol) was dissolved in DMF (2 mL) and stirred with morpholine (10 µL, 0.13 mmol), HBTU (52 mg, 0.13 mmol) and diisopropylethyl-amine (70 µL, 0.39 mmol) at room temperature for 72 h. The solvent was removed in vacuo and the residue was purified by preparative HPLC (pH 2.5) to give the title compound (44 mg, 64%) as a white solid. $\delta_H$ (CDCl$_3$) 7.54-7.36 (4H, m), 3.91-3.42 (12H, m), 3.00-2.92 (4H, m), 2.48 (2H, s), 2.44 (2H, s), 1.04 (6H, s). LCMS (ES+) 455.4 (M+H)$^+$.

Example 298

N-Benzyl-3-(5,5-dimethyl-2-(morpholin-4-yl)-7-oxo-4,5,6,7-tetrahydro-1-benzothien-3-yl)benzamide The title compound was prepared from Example 66 and benzylamine according to Method AQ and was isolated as a white solid (25%) after purification by preparative HPLC (pH 2.5). $\delta_H$ (CDCl$_3$) 7.89-7.85 (1H, m), 7.75-7.70 (1H, m), 7.53-7.48 (2H, m), 7.41-7.29 (5H, m), 6.44-6.37 (1H, m), 4.68 (2H, d, J 5.7 Hz), 3.66-3.58 (4H, m), 2.99-2.91 (4H, m), 2.48 (2H, s), 2.43 (2H, s), 1.03 (6H, s). LCMS (ES+) 475.4 (M+H)$^+$.

Example 299

3-(5,5-Dimethyl-2-(morpholin-4-yl)-7-oxo-4,5,6,7-tetrahydro-1-benzothien-3-yl)-N-isopropylbenzamide The title compound was prepared from Example 66 and isopropylamine according to Method AQ and was isolated as a white solid (52%) after purification by preparative HPLC (pH 2.5). $\delta_H$ (CDCl$_3$) 7.83 (1H, d, J 0.6 Hz), 7.71-7.64 (1H, m), 7.54-7.46 (2H, m), 5.92 (1H, d, J 7.7 Hz), 4.38-4.26 (1H, m), 3.68-3.60 (4H, m), 3.00-2.91 (4H, m), 2.48 (2H, s), 2.43 (2H, s), 1.31 (3H, s), 1.28 (3H, s), 1.03 (6H, s). LCMS (ES+) 427.3 (M+H)$^+$.

Example 300

3-(5,5-Dimethyl-2-(morpholin-4-yl)-7-oxo-4,5,6,7-tetrahydro-1-benzothien-3-yl)-N-(1H-imidazol-2-yl)benzamide The title compound was prepared from Example 66 and 2-aminoimidazole sulfate according to Method AQ and was isolated as a white solid (12%) after purification by preparative HPLC (pH 2.5). $\delta_H$ (CDCl$_3$) 8.10 (1H, s), 8.03-7.97 (1H, m), 7.63-7.58 (2H, m), 6.66 (2H, s), 3.66-3.58 (4H, m), 2.99-2.91 (4H, m), 2.51 (2H, s), 2.45 (2H, s), 1.04 (6H, s). LCMS (ES+) 451.3 (M+H)$^+$.

Example 301

3-(5,5-Dimethyl-2-(morpholin-4-yl)-7-oxo-4,5,6,7-tetrahydro-1-benzothien-3-yl)-N-ethylbenzamide The title compound was prepared from Example 66 and ethylamine (2M in THF) according to Method AQ and was isolated as a white solid (33%) after purification by preparative HPLC (pH 5.8). $\delta_H$ (CDCl$_3$) 7.83 (1H, s), 7.72-7.67 (1H, m), 7.55-7.47 (2H, m), 6.16-6.07 (1H, m), 3.68-3.61 (4H, m), 3.54 (2H, dq, J 7.2, 5.7 Hz), 3.00-2.93 (4H, m), 2.48 (1H, s), 2.43 (2H, s), 1.29 (3H, t, J 7.2 Hz), 1.03 (6H, s). LCMS (ES+) 413.3 (M+H)$^+$.

Example 302

3-(5,5-Dimethyl-2-(morpholin-4-yl)-7-oxo-4,5,6,7-tetrahydro-1-benzothien-3-yl)-N,N-dimethylbenzamide The title compound was prepared from Example 66 and dimethylamine hydrochloride according to Method AQ and was isolated as a white solid (32%) after purification by preparative HPLC (pH 5.8). $\delta_H$ (CDCl$_3$) 7.51-7.38 (4H, m), 3.68-3.61 (4H, m), 3.15 (3H, s), 3.04 (3H, s), 3.00-2.94 (4H, m), 2.48 (2H, s), 2.43 (2H, s), 1.03 (6H, s). LCMS (ES+) 413.4 (M+H)$^+$.

Example 303

N-[3-(5,5-Dimethyl-2-(morpholin-4-yl)-7-oxo-4,5,6,7-tetrahydro-1-benzothien-3-yl)phenyl]-4-methylpiperazine-1-carboxamide The title compound was prepared from Example 77 and 1-methylpiperazine according to Method AP and was isolated as a yellow solid (32%) after purification by preparative HPLC (pH 2.5). $\delta_H$ (CDCl$_3$) 7.39-7.29 (3H, m), 7.03-6.98 (1H, m), 6.49 (1H, s), 3.69-3.63 (4H, m), 3.62-3.55 (4H, m), 3.04-2.96 (4H, m), 2.59-2.52 (4H, m), 2.45 (2H, s), 2.41 (2H, s), 2.39 (3H, s), 1.02 (6H, s). LCMS (ES+) 483.2 (M+H)$^+$.

Example 304

5,5-Dimethyl-2-(morpholin-4-yl)-3-{2-[2-(piperazin-1-ylmethyl)phenyl]pyridin-4-yl}-5,6-dihydro-1-benzothiophen-7(4H)-one, Acetic Acid Salt The title compound was prepared from piperazine and Example 73 according to Method AN and was isolated as a brown solid (38%) after purification by preparative HPLC (pH 5.8). $\delta_H$ (DMSO-d$_6$) 8.71 (1H, d, J 5.1 Hz), 7.74 (1H, s), 7.51-7.38 (5H, m), 3.62-3.56 (4H, m), 3.50 (2H, s), 3.02-2.95 (4H, m), 2.56 (2H, s), 2.52-2.45 (4H, m), 2.38 (2H, s), 2.18-2.09 (4H, m), 1.90 (3H, s), 0.97 (6H, s). LCMS (ES+) 517.5 (M+H)$^+$.

Example 305

5,5-Dimethyl-2-(morpholin-4-yl)-3-{2-[3-(pyrrolidin-1-ylmethyl)phenyl]pyridin-4-yl}-5,6-dihydro-1-benzothiophen-7(4H)-one The title compound was prepared from pyrrolidine and Example 262 according to Method AK and was isolated as a brown solid (41%) after purification by preparative HPLC (pH 5.8). $\delta_H$ (DMSO-d$_6$) 8.75 (1H, d, J 4.9 Hz), 8.17-8.11 (1H, m), 8.08-7.99 (2H, m), 7.51-7.37 (3H, m), 3.76 (2H, s), 3.65-3.55 (4H, m), 3.37-3.25 (4H, m, obscured), 3.03-2.94 (4H, m), 2.61 (2H, s), 2.39 (2H, s), 1.79-1.68 (4H, m), 0.97 (6H, s). LCMS (ES+) 502.5 (M+H)$^+$.

Example 306

5,5-Dimethyl-3-(2-{3-[(4-methylpiperazin-1-yl)methyl]phenyl}pyridin-4-yl)-2-(morpholin-4-yl)-5,6-dihydro-1-benzothiophen-7(4H)-one, Acetic Acid Salt The title compound was prepared from 1-methylpiperazine and Example 262 according to Method AK and was isolated as a brown solid (3%) after purification by preparative HPLC (pH 5.8). $\delta_H$ (DMSO-d$_6$) 8.75 (1H, d, J 5.1 Hz), 8.11-8.00 (3H, m), 7.46 (1H, t, J 8.1 Hz), 7.42-7.35 (2H, m), 3.65-3.57 (4H, m), 3.54 (2H, s), 3.03-2.95 (4H, m), 2.60 (2H, s), 2.46-2.26 (10H, m), 2.14 (3H, s), 1.90 (6H, s), 0.98 (6H, s). LCMS (ES+) 531.6 (M+H)$^+$.

Example 307

5,5-Dimethyl-2-(morpholin-4-yl)-3-{2-[3-(piperazin-1-ylmethyl)phenyl]pyridin-4-yl}5,6-dihydro-1-benzothiophen-7(4H)-one, Acetic Acid Salt The title compound was prepared from piperazine and Example 262 according to Method AK and was isolated as a brown glass (49%) after purification by preparative HPLC (pH 5.8). $\delta_H$(DMSO-d$_6$) 8.75 (1H, d, J 4.9 Hz), 8.11-7.99 (3H, m), 7.46 (1H, t, J 7.5 Hz), 7.42-7.35 (2H, m), 3.64-3.58 (4H, m), 3.52 (2H, s), 3.03-2.95 (4H, m), 2.75-2.68 (4H, m), 2.60 (2H, s), 2.40 (2H, s), 2.38-2.30 (4H, m), 1.90 (6H, s), 0.97 (6H, s). LCMS (ES+) 517.5 (M+H)$^+$.

Example 308

5,5-Dimethyl-3-[2-(3-{[(3S)-3-Hydroxypyrrolidin-1-yl]methyl}phenyl)pyridin-4-yl]-2-(morpholin-4-yl)-5,6-dihydro-1-benzothiophen-7(4H)-one, Acetic Acid Salt The title compound was prepared from (R)-(+)-3-hydroxypyrrolidine and Example 262 according to Method AK and was isolated as a brown glass (64%) after purification by preparative HPLC (pH 5.8). $\delta_H$(DMSO-d$_6$) 8.75 (1H, d, J 4.9 Hz), 8.10 (1H, s), 8.05-7.98 (2H, m), 7.46 (1H, t, J 7.5 Hz), 7.42-7.36 (2H, m), 4.26-4.16 (1H, m), 3.72-3.57 (6H, m), 3.03-2.95 (4H, m), 2.76-2.69 (1H, m), 2.59 (2H, s), 2.58-2.53 (1H, m), 2.49-2.41 (1H, m), 2.39 (2H, s), 2.37-2.29 (1H, m), 2.07-1.94 (1H, m), 1.91 (6H, s), 1.60-1.49 (1H, m), 0.97 (6H, s). LCMS (ES+) 518.6 (M+H)$^+$.

Example 309

N-(2-Aminoethyl)-3-[4-(5,5-dimethyl-2-(morpholin-4-yl)-7-oxo-4,5,6,7-tetrahydro-1-benzothien-3-yl)pyridin-2-yl]-N-methylbenzamide, Acetic Acid Salt The title compound was prepared from Example 254 and N-(tert-butoxycarbonyl)-2-(methylamino)ethylamine hydrochloride according to Method AH and was isolated as a yellow glass (20%) after purification by preparative HPLC (pH 5.8). $\delta_H$(DMSO-d$_6$) 8.78 (1H, d, J 5.1 Hz), 8.58 (1H, s), 8.30

(1H, d, J 7.9 Hz), 8.14 (1H, s), 7.94 (1H, d, J 7.7 Hz), 7.61 (1H, t, J 7.9 Hz), 7.44 (1H, dd, J 4.7, 0.9 Hz), 3.63-3.55 (4H, m), 3.45-3.37 (2H, m), 3.03-2.95 (4H, m), 2.74-2.66 (2H, m), 2.61 (2H, s), 2.39 (2H, s), 2.32 (3H, s), 1.88 (9H, s), 0.98 (6H, s). LCMS (ES+) 519.6 (M+H)$^+$.

Example 310

(Method AR)

N-[3-(5,5-Dimethyl-2-(morpholin-4-yl)-7-oxo-4,5,6,7-tetrahydro-1-benzothien-3-yl)phenyl]piperazine-1-carboxamide, Acetic Acid Salt A solution of HCl in Et$_2$O (2M, 2.0 mL, 4.0 mmol) was added to a solution of Example 286 (100 mg, 0.18 mmol) in DCM (8 mL) and the reaction mixture was stirred at room temperature for 3 h. Methanol (4 mL) was added followed by an additional solution of HCl in Et$_2$O (2M, 2.0 mL, 4.0 mmol) and stirring was continued for 18 h. The solvent was removed in vacuo and the residue was purified by preparative HPLC (pH 5.8) to give the title compound (85 mg, 86%) as a yellow solid (20%) after purification by preparative HPLC (pH 5.8). $\delta_H$ (CDCl$_3$) 7.41-7.32 (3H, m), 7.07-6.99 (1H, m), 6.70-6.64 (1H, m), 3.74-3.55 (8H, m), 3.13-2.97 (8H, m), 2.46 (2H, s), 2.42 (2H, s), 2.08 (3H, s), 1.03 (6H, s). LCMS (ES+) 469.2 (M+H)$^+$.

Example 311

3-Amino-N-[3-(5,5-dimethyl-2-(morpholin-4-yl)-7-oxo-4,5,6,7-tetrahydro-1-benzothien-3-yl)phenyl]pyrrolidine-1-carboxamide, Acetic Acid Salt The title compound was prepared from Example 285 according to Method AR and was isolated as a yellow glass (78%) after purification by preparative HPLC (pH 5.8). $\delta_H$ (CDCl$_3$) 7.47-7.43 (1H, m), 7.40-7.32 (2H, m), 7.03-6.98 (1H, m), 6.35 (1H, br s), 3.82-3.51 (8H, m), 3.40-3.32 (1H, m), 3.05-2.97 (4H, m), 2.48 (2H, s), 2.43 (2H, s), 2.28-2.17 (1H, m), 1.94-1.85 (1H, m), 1.04 (6H, s). LCMS (ES+) 469.3 (M+H)$^+$.

Example 312

3-(5,5-Dimethyl-2-(morpholin-4-yl)-7-oxo-4,5,6,7-tetrahydro-1-benzothien-3-yl)-N-[(1-methyl-1H-imidazol-4-yl)methyl]benzamide The title compound was prepared from Example 66 and (1-methyl-1H-imidazol-4-yl)methylamine according to Method AQ and was isolated as a yellow solid (39%) after purification by preparative HPLC (pH 2.5). $\delta_H$ (CDCl$_3$) 7.85 (1H, s), 7.81-7.75 (1H, m), 7.63-7.56 (1H, m), 7.53-7.45 (3H, m), 6.97 (1H, s), 4.57 (2H, d, J 5.7 Hz), 3.73 (3H, s), 3.67-3.57 (4H, m), 3.00-2.91 (4H, m), 2.47 (2H, s), 2.43 (2H, s), 1.02 (6H, s). LCMS (ES+) 479.2 (M+H)$^+$.

Example 313

3-(5,5-Dimethyl-2-(morpholin-4-yl)-7-oxo-4,5,6,7-tetrahydro-1-benzothien-3-yl)-N-[2-(morpholin-4-yl)ethyl]benzamide The title compound was prepared from Example 66 and 4-(2-aminoethyl)-morpholine according to Method AQ and was isolated as a yellow solid (15%) after purification by preparative HPLC (pH 2.5). $\delta_H$ (CDCl$_3$) 7.87 (1H, s), 7.80-7.75 (1H, m), 7.57-7.51 (2H, m), 3.85-3.77 (3H, m), 3.68-3.59 (5H, m), 3.43-3.38 (1H, m), 3.01-2.94 (3H, m), 2.85-2.78 (1H m), 2.77-2.69 (3H, m), 2.47 (2H, s), 2.44 (2H, s), 1.03 (6H, s). LCMS (ES+) 498.2 (M+H)$^+$.

Example 314

N-(Cyanomethyl)-3-(5,5-dimethyl-2-(morpholin-4-yl)-7-oxo-4,5,6,7-tetrahydro-1-benzothien-3-yl)benzamide The title compound was prepared from Example 66 and aminoacetonitrile hydrochloride according to Method AQ and was isolated as a white solid (49%) after purification by preparative HPLC (pH 2.5). $\delta_H$ (CDCl$_3$) 7.86-7.80 (1H, m), 7.79-7.76 (1H, m), 7.61-7.53 (2H, m), 7.20-7.13 (1H, m), 4.44 (2H, d, J 5.8 Hz), 3.69-3.59 (4H, m), 3.00-2.90 (4H, m), 2.40 (2H, s), 2.33 (2H, s), 1.01 (6H, s). LCMS (ES+) 424.3 (M+H)$^+$.

Example 315

3-(5,5-Dimethyl-2-(morpholin-4-yl)-7-oxo-4,5,6,7-tetrahydro-1-benzothien-3-yl)-N-(pyridin-2-ylmethyl)benzamide The title compound was prepared from Example 66 and 2-(aminomethyl)pyridine according to Method AQ and was isolated as a yellow solid (44%) after purification by preparative HPLC (pH 2.5). $\delta_H$ (CDCl$_3$) 8.60-8.56 (1H, m), 7.93 (1H, s), 7.87-7.77 (3H, m), 7.57-7.46 (3H, m), 7.38-7.32 (1H, m), 4.83 (2H, d, J 4.7 Hz), 3.70-3.62 (4H, m), 3.02-2.94 (4H, m), 2.50 (2H, s), 2.44 (2H, s), 1.04 (6H, s). LCMS (ES+) 476.3 (M+H)$^+$.

Example 316

3-(5,5-Dimethyl-2-(morpholin-4-yl)-7-oxo-4,5,6,7-tetrahydro-1-benzothien-3-yl)-N-(pyridin-4-ylmethyl)benzamide The title compound was prepared from Example 66 and 4-(aminomethyl)pyridine according to Method AQ and was isolated as a yellow solid (46%) after purification by preparative HPLC (pH 2.5). $\delta_H$ (CDCl$_3$) 8.64-8.57 (2H, m), 7.90 (1H, s), 7.79-7.73 (1H, m), 7.57-7.52 (2H, m), 7.33-7.29 (2H, m), 6.67-6.60 (1H, m), 4.71 (2H, d, J 6.0 Hz), 3.67-3.60 (4H, m), 3.00-2.92 (4H, m), 2.46 (2H, s), 2.42 (2H, s), 1.03 (6H, s). LCMS (ES+) 476.3 (M+H)$^+$.

Example 317

3-[4-Amino-3-(6-chloropyridin-2-yl)phenyl]-5,5-dimethyl-2-(morpholin-4-yl)-5,6-dihydro-1-benzothiophen-7(4H)-one The title compound was prepared from Example 272 and 6-chloropyridine-2-boronic acid pinacol ester according to Method L, heating at 150° C., and was isolated as a brown solid (14%) after purification by preparative HPLC (pH 2.5). $\delta_H$ (DMSO-d$_6$) 7.95 (1H, t, J 7.9 Hz), 7.86-7.81 (1H, m), 7.58 (1H, d, J 1.9 Hz), 7.44 (1H, d, J 7.7 Hz), 7.17 (1H, dd, J 8.3, 1.7 Hz), 6.88 (1H, d, J 8.3 Hz), 6.57-6.52 (1H, m), 3.65-3.54 (4H, m), 3.03-2.93 (4H, m), 2.50 (2H, s, obscured), 2.35 (2H, s), 0.97 (6H, s). LCMS (ES+) 468.3, 470.3 (M+H)$^+$.

Example 318

(Method AS)

3-[4-(5,5-Dimethyl-2-(morpholin-4-yl)-7-oxo-4,5,6,7-tetrahydrothieno[2,3-c]pyridin-3-yl)pyridin-2-yl]benzoic Acid, Trifluoroacetic Acid Salt Trifluoroacetic acid (3 mL) was added to a solution of Example 333 (180 mg, 0.35 mmol) in DCM (10 mL) and the reaction mixture was stirred at room temperature for 90 minutes. The solvent was removed in vacuo and the residue was triturated with $Et_2O$ to give the title compound (170 mg, 85%) as a bright yellow solid. $\delta_H$ (DMSO-$d_6$) 8.77 (1H, d, J 5.1 Hz), 8.74-8.71 (1H, m), 8.39-8.33 (1H, m), 8.16 (1H, s), 8.06-8.01 (1H, m), 7.67 (1H, t, J 7.7 Hz), 7.57 (1H, s), 7.52-7.48 (1H, m), 3.66-3.58 (4H, m), 2.97-2.87 (4H, m), 2.73 (2H, s), 1.20 (6H, s). LCMS (ES+) 464.3 (M+H)$^+$.

Example 319

3-(5,5-Dimethyl-2-(morpholin-4-yl)-7-oxo-4,5,6,7-tetrahydro-1-benzothien-3-yl)-N-(pyridin-3-ylmethyl)benzamide The title compound was prepared from Example 66 and pyridin-3-ylmethylamine according to Method AQ and was isolated as a yellow solid (32%) after purification by preparative HPLC (pH 2.5). $\delta_H$ (CDCl$_3$) 8.56 (1H, d, J 1.7 Hz), 8.49 (1H, dd, J 4.9, 1.3 Hz), 7.88 (1H, s), 7.84-7.70 (3H, m), 7.56-7.49 (2H, m), 7.37-7.33 (1H, m), 4.66 (2H, d, J 6.0 Hz), 3.67-3.60 (4H, m), 3.01-2.94 (4H, m), 2.46 (2H, s), 2.43 (2H, s), 1.03 (6H, s). LCMS (ES+) 476.3 (M+H)$^+$.

Example 320

N-(2,3-Dihydroxypropyl)-3-(5,5-dimethyl-2-(morpholin-4-yl)-7-oxo-4,5,6,7-tetrahydro-1-benzothien-3-yl)benzamide The title compound was prepared from Example 66 and 3-amino-1,2-propanediol according to Method AQ and was isolated as a white solid (9%) after purification by preparative HPLC (pH 2.5). $\delta_H$ (CDCl$_3$) 7.86-7.82 (1H, m), 7.79-7.74 (1H, m), 7.57-7.50 (2H, m), 6.87-6.79 (1H, m), 3.99-3.91 (1H, m), 3.77-3.59 (7H, m), 3.05-2.93 (5H, m), 2.45 (2H, s), 2.40 (2H, s), 1.02 (6H, s). LCMS (ES+) 459.3 (M+H)$^+$.

Example 321

5,5-Dimethyl-3-{2-[3-(methylsulfonyl)phenyl]pyridin-4-yl}-2-(morpholin-4-yl)-5,6-dihydro-1-benzothiophen-7(4H)-one The title compound was prepared from Example 73 and 3-(methanesulfonyl)-phenylboronic acid according to Method L and was isolated as a white solid (60%) after purification by preparative HPLC (pH 2.5). $\delta_H$ (DMSO-$d_6$) 8.81 (1H, d, J 4.9 Hz), 8.69 (1H, s), 8.50 (1H, d, J 7.9 Hz), 8.23 (1H, s), 8.02 (1H, d, J 8.1 Hz), 7.81 (1H, t, J 7.9 Hz), 7.49 (1H, dd, J 5.1, 1.1 Hz), 3.63-3.56 (4H, m), 3.02-2.95 (4H, m), 2.59 (2H, s), 2.40 (2H, s), 2.09 (3H, s), 0.97 (6H, s). LCMS (ES+) 497.4 (M+H)$^+$.

Example 322

Tert-Butyl 4-{3-[4-(5,5-dimethyl-2-(morpholin-4-yl)-7-oxo-4,5,6,7-tetrahydrothieno[2,3-c]pyridin-3-yl)pyridin-2-yl]benzoyl}piperazine-1-carboxylate The title compound was prepared from Example 318 and 1-(tert-butoxycarbonyl)-piperazine according to Method T and was isolated as an off-white solid (51%) after purification by column chromatography (SiO$_2$, 0-4.5% MeOH/DCM) and trituration with $Et_2O$. $\delta_H$ (DMSO-$d_6$) 8.74 (1H, d, J 5.1 Hz), 8.25 (1H, d, J 7.9 Hz), 8.17 (1H, s), 8.10 (1H, s), 7.64-7.54 (2H, m), 7.51-7.46 (2H, m), 3.66-3.56 (4H, m), 3.40-3.32 (8H, m, obscured), 2.95-2.87 (4H, m), 2.72 (2H, s), 1.41 (9H, s), 1.19 (6H, s). LCMS (ES+) 632.2 (M+H)$^+$.

Example 323

(Method AT)

5,5-Dimethyl-2-(morpholin-4-yl)-3-{2-[3-(piperazin-1-ylcarbonyl)phenyl]pyridin-4-yl}-5,6-dihydrothieno[2,3-c]pyridin-7(4H)-one Trifluoroacetic acid (1 mL) was added to a solution of Example 322 (40 mg, 0.06 mmol) in DCM (5 mL) and the reaction mixture was stirred at room temperature for 75 minutes. The solvent was removed in vacuo and the residue was triturated with $Et_2O$ to give the title compound (48 mg, 100%) as a yellow-orange solid. $\delta_H$ (DMSO-$d_6$) 8.97-8.83 (1H, m), 8.75 (1H, d, J 4.9 Hz), 8.29-8.21 (2H, m), 8.10 (1H, s), 7.67-7.47 (4H, m), 3.87-3.66 (4H, m), 3.64-3.55 (4H, m), 3.28-3.10 (4H, m), 2.96-2.85 (4H, m), 2.71 (2H, s), 1.19 (6H, s). LCMS (ES+) 532.6 (M+H)$^+$.

Example 324

(Method AU)

5,5-Dimethyl-2-(morpholin-4-yl)-3-{6-[3-(piperazin-1-ylcarbonyl)phenyl]pyridin-2-yl}-5,6-dihydro-1-benzothiophen-7(4H)-one A mixture of Example 17 (1.00 g, 2.56 mmol), 6-chloropyridine-2-boronic acid pinacol ester (613 mg, 2.56 mmol), K$_3$PO$_4$ (1.63 g, 7.67 mmol) and Pd(PPh$_3$)$_4$ (148 mg, 0.128 mmol) in DME (6 mL) and water (2 mL) was heated in a sealed tube at 120° C., under microwave irradiation, for 20 minutes. The solvent was removed in vacuo and the residue was purified by column chromatography (SiO$_2$, 0-100% EtOAc/heptane). A sample of this intermediate (100 mg, 0.27 mmol) was combined with 3-(tert-butoxy-carbonyl)phenylboronic acid (65 mg, 0.29 mmol), K$_3$PO$_4$ (170 mg, 0.80 mmol) and Pd(PPh$_3$)$_4$ (31 mg, 0.03 mmol) in DME (3 mL) and water (1 mL) and the mixture was heated in a sealed tube at 140° C., under microwave irradiation, for 2 h. The solvent was removed in vacuo and the residue was purified by column chromatography (SiO$_2$, 0-50% EtOAc/heptane). Trifluoroacetic acid (1 mL) was added to a solution of the product in DCM (5 mL) and the reaction mixture was stirred at room temperature for 18 h. The solvent was removed in vacuo and the residue was combined with EDC.HCl (61 mg, 0.32 mmol), triethylamine (0.15 mL, 1.06 mmol) and piperazine (28 mg, 0.32 mmol) in DCM (10 mL) and the mixture was stirred at room temperature for 48 h. The solvent was removed in vacuo and the residue was purified by preparative HPLC (pH 5.8) to give the title compound (20 mg, 5%) as a yellow solid. $\delta_H$ (CD$_3$OD) 8.24-8.17 (2H, m), 8.04-7.97 (1H, m), 7.94-7.89 (1H, m), 7.70-7.61 (2H, m), 7.56-7.52 (1H, m), 3.97-3.75 (2H, m), 3.74-3.67 (4H, m), 3.66-3.54 (2H, m), 3.12-3.06 (4H, m), 3.05-2.93 (4H, m), 2.74 (2H, s), 2.48 (2H, s), 1.98 (3H, s), 1.07 (6H, s). LCMS (ES+) 531.5 (M+H)$^+$.

Example 325

3-[2-(3-{[(3S)-3-Aminopyrrolidin-1-yl]carbonyl}phenyl)pyridin-4-yl]-5,5-dimethyl-2-(morpholin-4-yl)-5,6-dihydro-1-benzothiophen-7(4H)-one, Hydrochloride Salt The title compound was prepared from Example 254 and (3S)-(−)-3-(tert-butoxycarbonylamino)pyrrolidine according to Method AH and was isolated as a clear glass (46%) after purification by column chromatography (SiO$_2$, 0-20% MeOH/DCM). $\delta_H$ (CD$_3$OD) 8.63 (1H, d, J 5.3 Hz), 8.13 (1H, d, J 9.6 Hz), 8.09-8.02 (1H, m), 7.93-7.88 (1H, m), 7.60-7.50 (2H, m), 7.37 (1H, dd, J 5.1, 1.5 Hz), 3.83-3.61 (3H, m), 3.60-3.41 (6H, m), 3.00-2.92 (4H, m), 2.53 (2H, s), 2.36 (2H, s), 2.25-2.07 (1H, m), 1.91-1.76 (1H, m), 0.94 (6H, s). LCMS (ES+) 531.3 (M+H)$^+$.

Example 326

3-[2-(3-{[(3R)-3-Aminopyrrolidin-1-yl]carbonyl}phenyl)pyridin-4-yl]-5,5-dimethyl-2-(morpholin-4-yl)-5,6-dihydro-1-benzothiophen-7(4H)-one The title compound was prepared from Example 254 and (3R)-(+)-3-(tert-butoxycarbonylamino)pyrrolidine according to Method AH. The reaction mixture was basified with saturated sodium hydrogencarbonate solution and extracted into DCM. The title compound was isolated as an off-white solid (55%) after purification by column chromatography (SiO$_2$, 0-20% MeOH/DCM). $\delta_H$ (CDCl$_3$) 8.76 (1H, d, J 5.1 Hz), 8.21 (1H, d, J 1.3 Hz), 8.13-8.07 (1H, m), 7.81 (1H, s), 7.65-7.51 (2H, m), 7.30-7.28 (1H, m), 3.93-3.22 (10H, m), 3.06-2.99 (4H, m), 2.53 (2H, s), 2.46 (2H, s), 2.27-2.01 (1H, m), 1.87-1.67 (1H, m), 1.66-1.45 (2H, m), 1.05 (6H, s). LCMS (ES+) 531.2 (M+H)$^+$.

Example 327

3-[2-(3-{[(3R)-3-Aminopyrrolidin-1-yl]carbonyl}phenyl)pyridin-4-yl]-5,5-dimethyl-2-(morpholin-4-yl)-5,6-dihydro-1-benzothiophen-7(4H)-one, Hydrochloride Salt The title compound was prepared from Example 254 and (3R)-(+)-3-(tert-butoxycarbonylamino)pyrrolidine according to Method AH and was isolated as a clear glass (46%) after purification by column chromatography (SiO$_2$, 0-20% MeOH/DCM). $\delta_H$ (CD$_3$OD) 8.84 (1H, d, J 6.0 Hz), 8.43-8.35 (1H, m), 8.26-8.19 (1H, m), 8.17-8.11 (1H, m), 8.08-7.99 (1H, m), 7.93-7.78 (2H, m), 4.11-3.96 (2H, m), 3.93-3.68 (7H, m), 3.19-3.11 (4H, m), 2.75 (2H, s), 2.51 (2H, s), 2.51-2.39 (1H, m), 2.25-2.10 (1H, m), 1.07 (6H, s). LCMS (ES+) 531.3 (M+H)$^+$.

Example 328

2-(Morpholin-4-yl)-3-{2-[3-(piperazin-1-ylcarbonyl)phenyl]pyridin-4-yl}-5,6-dihydro-1-benzothiophen-7(4H)-one, Acetic Acid Salt The title compound was prepared from Intermediate 2,2-chloropyridine-4-boronic acid and 3-(tert-butoxycarbonyl)phenylboronic acid according to Method AU and was isolated as a clear glass (13%) after purification by preparative HPLC (pH 5.8). $\delta_H$ (CDCl$_3$) 8.98 (1H, d, J 5.7 Hz), 8.61 (1H, t, J 1.5 Hz), 8.28-8.21 (2H, m), 8.03 (1H, d, J 0.9 Hz), 7.71 (1H, t, J 7.9 Hz), 7.65 (1H, dd, J 5.7, 1.7 Hz), 3.78-3.71 (4H, m), 3.12-3.05 (4H, m), 2.78-2.71 (2H, m), 2.68-2.62 (2H, m), 2.22-2.12 (2H, m). LCMS (ES+) 503.3 (M+H)$^+$.

Example 329

N-[2-(Dimethylamino)ethyl]-N'-[3-(5,5-dimethyl-2-(morpholin-4-yl)-7-oxo-4,5,6,7-tetrahydro-1-benzothien-3-yl)phenyl]ethanediamide Isobutyl chloroformate (30 μL, 0.23 mmol) and triethylamine (30 μL, 0.23 mmol) were added to a solution of Example 292 (50 mg, 0.12 mmol) in DCM (5.0 mL) and the reaction mixture was stirred at room temperature for 1 h. N,N-Dimethylethylenediamine (60 μL, 0.58 mmol) was then added and the reaction mixture was stirred at room temperature for 72 h. The solvent was removed in vacuo and the residue was purified by preparative HPLC (pH 5.8) to give the title compound (4 mg, 6%) as a yellow solid. $\delta_H$ (CDCl$_3$) 9.12 (1H, s), 8.41 (1H, br s), 7.55-7.46 (2H, m), 7.29 (1H, t, J 7.9 Hz), 7.05-7.00 (1H, m), 3.61-3.49 (6H, m), 2.90-2.77 (6H, m), 2.49 (6H, s), 2.33 (2H, s), 2.29 (2H, s), 0.90 (6H, s). LCMS (ES+) 499.3 (M+H)$^+$.

Example 330

N-[3-(5,5-Dimethyl-2-(morpholin-4-yl)-7-oxo-4,5,6,7-tetrahydro-1-benzothien-3-yl)phenyl]-N'-[2-{pyrrolidin-1-yl}ethyl]ethanediamide Benzotriazol-1-yloxytris(dimethylamino)phosphonium hexafluorophosphate (145 mg, 0.33 mmol) and 1-(2-aminoethyl)pyrrolidine (60 μL, 0.49 mmol) were added to a solution of Example 292 (70 mg, 0.16 mmol) in DCM (10 mL) and the reaction mixture was stirred at room temperature for 18 h. A further portion of 1-(2-aminoethyl)-pyrrolidine (60 μL, 0.49 mmol) was added and stirring was continued for 72 h. The solvent was removed in vacuo and the residue was purified by preparative HPLC (pH 2.5) to give the title compound (16 mg, 19%) as an off-white solid. $\delta_H$ (CDCl$_3$) 9.26 (1H, s), 8.43 (1H, br s), 7.74-7.69 (1H, m), 7.65-7.59 (1H, m), 7.45 (1H, t, J 7.7 Hz), 7.23-7.16 (1H, m), 3.78-3.64 (6H, m), 3.11-2.92 (10H, m), 2.49 (2H, s), 2.45 (2H, s), 2.07-1.96 (4H, m), 1.05 (6H, s). LCMS (ES+) 525.3 (M+H)$^+$.

Example 331

(Method AV)

3-(2-Amino-6-phenylpyridin-4-yl)-5,5-dimethyl-2-(morpholin-4-yl)-5,6-dihydro-1-benzothiophen-7(4H)-one A mixture of Example 332 (40 mg, 0.07 mmol) in trifluoroacetic acid (10 mL) was heated under reflux for 1 h. The solvent was removed in vacuo and the residue was purified by column chromatography (SiO$_2$, 0-100% EtOAc/heptane) to give the title compound (17 mg, 54%) as a white solid. $\delta_H$ (CD$_3$OD) 7.88-7.82 (2H, m), 7.68-7.62 (3H, m), 7.34 (1H, d, J 1.5 Hz), 7.01 (1H, d, J 1.5 Hz), 3.78-3.70 (4H, m), 3.21-3.13 (4H, m), 2.72 (2H, s), 2.49 (2H, s), 1.08 (6H, s). LCMS (ES+) 434.3 (M+H)$^+$.

Example 332

(METHOD AW)

3-{2-[(4-Methoxybenzyl)amino]-6-phenylpyridin-4-yl}-5,5-dimethyl-2-(morpholin-4-yl)-5,6-dihydro-1-benzothiophen-7(4H)one A mixture of Example 269 (100 mg, 0.24 mmol), 4-methoxybenzylamine (158 μL, 1.21 mmol) and triethylamine (168 mL, 1.21 mmol) in NMP (2.0 mL) was heated at 230° C., under microwave irradiation, for 1 h. The reaction mixture was purified by column chromatography (SiO$_2$, 0-50% EtOAc/heptane) and triturated with water to give a pale yellow solid after drying in vacuo. The solid was combined with phenylboronic acid (9 mg, 0.07 mmol), K$_3$PO$_4$ (30 mg, 0.14 mmol) and Pd(PPh$_3$)$_4$ (20 mg, 0.02 mmol) in DME (1.5 mL) and water (0.5 mL) and was heated in a sealed tube at 120° C., under microwave irradiation, for 1 h. The solvent was removed in vacuo and the residue was purified by column chromatography (SiO$_2$, 0-100% EtOAc/heptane) to give the title compound (44 mg, 39%) as a white solid. δ$_H$ (CDCl$_3$) 8.04-8.00 (2H, m), 7.51-7.33 (5H, m), 7.12 (1H, d, J 0.8 Hz), 6.93-6.85 (2H, m), 6.24 (1H, d, J 0.8 Hz), 5.15-5.08 (1H, m), 4.54 (2H, d, J 5.7 Hz), 3.82 (3H, s), 3.66-3.58 (4H, m), 3.08-2.99 (4H, m), 2.41 (2H, s), 2.38 (2H, s), 0.99 (6H, s). LCMS (ES+) 554.3 (M+H)$^+$.

Example 333

Tert-Butyl 3-[4-(5,5-dimethyl-2-(morpholin-4-yl)-7-oxo-4,5,6,7-tetrahydrothieno[2,3-c]pyridin-3-yl)pyridin-2-yl]benzoate The title compound was prepared from Intermediate 19, 2-chloropyridine-4-boronic acid and 3-(tent-butoxycarbonyl)phenylboronic acid according to Method AF and was isolated as an off-white solid (30%) after purification by column chromatography (SiO$_2$, 0-100% EtOAc/heptane). δ$_H$ (DMSO-d$_6$) 8.77 (1H, d, J 5.1 Hz), 8.64 (1H, s), 8.35 (1H, d, J 7.9 Hz), 8.10 (1H, s), 7.99 (1H, d, J 7.7 Hz), 7.65 (1H, t, J 7.7 Hz), 7.57 (1H, s), 7.48 (1H, dd, J 5.1, 1.1 Hz), 3.67-3.57 (4H, m), 2.96-2.87 (4H, m), 2.72 (2H, s), 1.59 (9H, s), 1.20 (6H, s). LCMS (ES+) 520.2 (M+H)$^+$.

Example 334

3-[2-(3-Acetylphenyl)pyridin-4-yl]-5,5-dimethyl-2-(morpholin-4-yl)-5,6-dihydrothieno[2,3-c]pyridin-7(4H)-one The title compound was prepared from Intermediate 19, 2-chloropyridine-4-boronic acid and 3-acetylphenylboronic acid according to Method AF and was isolated as a beige solid (30%) after purification by column chromatography (SiO$_2$, 0-100% EtOAc/heptane) and preparative HPLC (pH 2.5). δ$_H$ (DMSO-d$_6$) 8.77 (1H, d, J 5.1 Hz), 8.68 (1H, s), 8.42-8.37 (1H, m), 8.19 (1H, s), 8.07-8.02 (1H, m), 7.68 (1H, t, J 7.7 Hz), 7.57 (1H, s), 7.50-7.47 (1H, m), 3.66-3.58 (4H, m), 2.95-2.88 (4H, m), 2.75 (2H, s), 2.68 (3H, s), 1.20 (6H, s). LCMS (ES+) 462.3 (M+H)$^+$.

Example 335

3-[2-(3-{[(3-exo)-3-Amino-8-azabicyclo[3.2.1]oct-8-yl]carbonyl}phenyl)pyridin-4-yl]-5,5-dimethyl-2-(morpholin-4-yl)-5,6-dihydro-1-benzothiophen-7(4H)-one A mixture of Example 254 (105 mg, 0.23 mmol), Intermediate 63 (70 mg, 0.27 mmol), and EDC (87 mg, 0.45 mmol) in DCM (5.0 mL) was stirred at room temperature for 18 h. The solvent was removed in vacuo and the residue was purified by column chromatography (SiO$_2$, 0-100% EtOAc/heptane). The resulting white solid was combined with hydrazine monohydrate (11 μL, 0.23 mmol) and EtOH (2.0 mL) and heated in a sealed tube at 100° C., under microwave irradiation, for 70 minutes. The reaction mixture was filtered and the filtrate was purified by column chromatography (SiO$_2$, 0-20% MeOH/DCM) to give the title compound (23 mg, 17%) as an off-white solid. δ$_H$ (CD$_3$OD) 1.05 (6H, s), 1.59-1.47 (1H, m), 1.79-1.66 (1H, m), 1.95-1.79 (3H, m), 2.17-1.98 (3H, m), 2.48 (2H, s), 2.64 (2H, s), 3.12-3.04 (4H, m), 3.34-3.25 (1H, m), 3.73-3.64 (4H, m), 4.24-4.17 (1H, m), 4.85-4.78 (1H, m), 7.48 (1H, dd, J 5.1, 1.5 Hz), 7.69-7.59 (2H, m), 8.03 (1H, s), 8.21-8.15 (2H, m), 8.75 (1H, d, J 5.1 Hz). LCMS (ES+) 571 (M+H)$^+$.

Example 336

3-(3-Benzoylphenyl)-5,5-dimethyl-2-(morpholin-4-yl)-5,6-dihydro-1-benzothiophen-7(4H)-one A mixture of Example 66 (1.40 g, 3.39 mmol) and lithium hydroxide monohydrate (0.43 g, 10.17 mmol) in THF (12 mL), MeOH (8 mL) and water (4 mL) was stirred at room temperature for 1 h. Water (30 mL) was added and the resulting precipitate was filtered off and dried in vacuo to give a beige solid (1.15 g). A sample of this intermediate lithium salt (177 mg, 0.45 mmol) was combined with HBTU (179 mg, 0.45 mmol), N,O-dimethylhydroxylamine hydrochloride (44 mg, 0.45 mmol) and diisopropylethylamine (0.24 mL, 1.35 mmol) in DMF (3.0 mL) and stirred at room temperature for 40 h. The solvent was removed in vacuo and the residue was partitioned between EtOAc (150 mL) and water (50 mL). The organic phase was washed with water (2×50 mL), dried (magnesium sulfate) and the solvent was removed in vacuo. The residue was purified by column chromatography (SiO$_2$, 0-100% EtOAc/heptane) and the resulting yellow solid was dissolved in THF (5.0 mL). This solution was added dropwise to a cooled (−78° C.) solution of phenyllithium (1.9M in butyl ether, 0.76 mL, 1.44 mmol) in THF (8.0 mL) and the reaction mixture was allowed to stir at −78° C. for 1 h, then at room temperature for 18 h. The reaction was quenched with aqueous ammonium chloride solution (1.0 mL), diluted with water (15 mL) and extracted with EtOAc (2×70 ml). The combined organic layers were dried (magnesium sulfate) and the solvent was removed in vacuo. The residue was purified by column chromatography (SiO$_2$, 0-100% EtOAc/heptane) and preparative HPLC (pH 2.5) to give the title compound (15 mg, 7%) as a yellow solid. δ$_H$ (CDCl$_3$) 7.79-7.89 (4H, m), 7.69-7.50 (5H, m), 3.72-3.64 (4H, m), 3.04-2.96 (4H, m), 2.53 (2H, s), 2.47 (2H, s), 1.08 (6H, s). LCMS (ES+) 446.3 (M+H)$^+$.

Example 337

3-[4-(5,5-Dimethyl-2-(morpholin-4-yl)-7-oxo-4,5,6,7-tetrahydro-1-benzothien-3-yl)pyridin-2-yl]-N-(piperidin-4-ylmethyl)benzamide, Acetic Acid Salt A solution of HCl in Et$_2$O (2M, 1.6 mL, 3.2 mmol) was added to a solution of Example 338 (105 mg, 0.16 mmol) in DCM (5.0 mL) and the reaction mixture was stirred at room temperature for 72 h. The precipitate was filtered off and purified by preparative HPLC (pH 5.8) to give the title compound (99 mg, 78%) as a yellow gum. δ$_H$ (CD$_3$OD) 8.79-8.74 (1H, m), 8.51 (1H, t, J 1.7 Hz), 8.25-8.19 (1H, m), 8.03 (1H, d, J 0.6 Hz), 7.98-7.92 (1H, m), 7.66 (1H, t, J 7.7 Hz), 7.49

(1H, dd, J 5.1, 1.5 Hz), 3.73-3.64 (4H, m), 3.49-3.37 (4H, m), 3.13-2.93 (6H, m), 2.64 (2H, s), 2.48 (2H, s), 2.10-1.99 (3H, m), 1.94 (6H, m), 1.61-1.44 (2H, m), 1.06 (6H, s). LCMS (ES+) 559.3 (M+H)+.

Example 338

Tert-Butyl 4-[({3-[4-(5,5-dimethyl-2-(morpholin-4-yl)-7-oxo-4,5,6,7-tetrahydro-1-benzothien-3-yl)pyridin-2-yl]benzoyl}amino)methyl]piperidine-1-carboxylate The title compound was prepared from Example 254 and 4-(aminomethyl)-1-(tert-butoxycarbonyppiperidine according to Method I and was obtained as a yellow solid (47%) after purification by column chromatography (SiO$_2$, 75-100% EtOAc/heptane). $\delta_H$ (CDCl$_3$) 8.80 (1H, d, J 5.3 Hz), 8.56 (1H, br m), 8.17-8.11 (1H, m), 7.98-7.90 (2H, m), 7.62 (1H, t, J 7.7 Hz), 7.41-7.35 (1H, m), 6.75-6.43 (1H, br m), 4.25-4.07 (2H, m), 3.77-3.66 (4H, m), 3.51-3.35 (2H, m), 3.12-3.00 (4H, m), 2.83-2.64 (2H, m), 2.57 (2H, s), 2.48 (2H, s), 1.95-1.74 (3H, m), 1.72-1.52 (2H, m), 1.47 (9H, s), 1.06 (6H, s). LCMS (ES+) 659.2 (M+H)+.

Example 339

5,5-Dimethyl-3-{2-[(4-Methoxybenzyl)oxy]-6-phenylpyridin-4-yl}-2-(morpholin-4-yl)-5,6-dihydro-1-benzothiophen-7(4H)-one A mixture of Example 269 (100 mg, 0.24 mmol), 4-methoxybenzyl alcohol (138 mg, 1.0 mmol) and triethylamine (168 mL, 1.2 mmol) in NMP (2.0 mL) was heated in a sealed tube at 230° C., under microwave irradiation, for 20 minutes. Sodium hydride (60% dispersion in mineral oil, 15 mg, 0.38 mmol) was then added and the reaction mixture was stirred at room temperature for 20 h. The solvent was removed in vacuo and the residue was purified by column chromatography (SiO$_2$, 0-100% EtOAc/heptane). The resulting white solid was combined with phenylboronic acid (19 mg, 0.16 mmol), K$_3$PO$_4$ (60 mg, 0.28 mmol) and Pd(PPh$_3$)$_4$ (40 mg, 0.035 mmol) in DME (3.0 mL) and water (1.0 mL) and was heated in a sealed tube at 120° C., under microwave irradiation, for 1 h. The solvent was removed in vacuo and the residue was purified by column chromatography (SiO$_2$, 0-50% EtOAc/heptane) and preparative HPLC (pH 2.5) to give the title compound (26 mg, 19%) as a white solid. $\delta_H$ (CDCl$_3$) 8.13-8.07 (2H, m), 7.55-7.44 (6H, m), 6.99-6.92 (2H, m), 6.67 (1H, d, J 0.9 Hz), 5.49 (2H, s), 3.83 (3H, s), 3.72-3.64 (4H, m), 3.10-3.00 (4H, m), 2.53 (2H, s), 2.43 (2H, s), 1.04 (6H, s). LCMS (ES+) 555.4 (M+H)+.

Example 340

3-[2-(3-Aminophenyl)pyridin-4-yl]-5,5-dimethyl-2-(morpholin-4-yl)-5,6-dihydro-1-benzothiophen-7(4H)-one The title compound was prepared from Example 73 and 3-aminophenylboronic acid according to Method L and was obtained as an off-white solid (19%) after purification by column chromatography (SiO$_2$, 0-100% EtOAc/heptane) and preparative HPLC (pH 2.5). $\delta_H$ (CD$_3$OD) 8.67 (1H, d, J 4.9 Hz), 7.86 (1H, s), 7.42 (1H, dd, J 5.1, 1.5 Hz), 7.36-7.32 (1H, m), 7.30-7.23 (2H, m), 6.88-6.82 (1H, m), 3.74-3.65 (4H, m), 3.13-3.04 (4H, m), 2.63 (2H, s), 2.48 (2H, s), 1.06 (6H, s). LCMS (ES+) 434.3 (M+H)+.

Example 341

4-(5,5-Dimethyl-2-(morpholin-4-yl)-7-oxo-4,5,6,7-tetrahydro-1-benzothien-3-yl)-6-phenylpyridin-2(1H)-one A solution of Example 339 (36 mg, 0.065 mmol) in trifluoroacetic acid (10 mL) was heated at reflux for 4 h. The solvent was removed in vacuo and the residue was purified by column chromatography (SiO$_2$, 0-100% EtOAc/heptane) to give the title compound (12 mg, 42%) as an off-white solid. $\delta_H$ (CDCl$_3$) 7.70-7.64 (2H, m), 7.58-7.52 (3H, m), 6.70 (1H, d, J 1.3 Hz), 6.46 (1H, d, J 1.3 Hz), 3.77-3.70 (4H, m), 3.17-3.11 (4H, m), 2.61 (2H, s), 2.45 (2H, s), 1.07 (6H, s). LCMS (ES+) 435.3 (M+H)+.

Example 342

5,5-Dimethyl-3-[2-(3-methylphenyl)pyridin-4-yl]-2-(morpholin-4-yl)-5,6-dihydro-1-benzothiophen-7(4H)-one The title compound was prepared from Example 73 and m-tolylboronic acid according to Method L and was obtained as an off-white solid (81%) after purification by column chromatography (SiO$_2$, 10-90% EtOAc/heptane). $\delta_H$ (DMSO-d$_6$) 8.73 (1H, d, J 5.1 Hz), 7.99 (2H, d, J 6.4 Hz), 7.93 (1H, dd, J 7.7, 0.6 Hz), 7.45-7.37 (2H, m), 7.28 (1H, d, J 7.7 Hz), 3.63-3.54 (4H, m), 3.02-2.94 (4H, m), 2.58 (2H, s), 2.41 (3H, s) 2.39 (2H, s), 0.97 (6H, s). LCMS (ES+) 433.3 (M+H)+.

Example 343

3-[2-(3-Bromo-5-methylphenyl)pyridin-4-yl]-5,5-dimethyl-2-(morpholin-4-yl)-5,6-dihydro-1-benzothiophen-7(4H)-one The title compound was prepared from Example 73 and 3-bromo-5-methylboronic acid according to Method L and was obtained as a white solid (6%) after purification by column chromatography (SiO$_2$, 0-100% EtOAc/heptane) and preparative HPLC (pH 2.5). $\delta_H$ (DMSO-d$_6$) 8.74 (1H, d, J 5.1 Hz), 8.13 (1H, s), 8.08 (1H, s), 7.99 (1H, d, J 0.4 Hz), 7.51 (1H, s), 7.43 (1H, dd, J 5.1, 1.5 Hz), 3.62-3.54 (4H, m), 3.02-2.94 (4H, m), 2.56 (2H, s), 2.41 (3H, s), 2.39 (2H, s), 0.97 (6H, s). LCMS (ES+) 511.3, 513.2 (M+H)+.

Example 344

(Method AX)

3-[(2E)-3-(Dimethylamino)prop-2-enoyl]-5,5-dimethyl-2-(morpholin-4-yl)-5,6-dihydro-1-benzothiophen-7(4R)-one A mixture of Example 284 (418 mg, 1.36 mmol) and DMF-dimethyl acetal (10 mL, 45 mmol) was heated in a sealed tube at 140° C., under microwave irradiation, for 2 h. The solvent was removed in vacuo and the residue was triturated with Et$_2$O to give the title compound (322 mg, 65%) as a yellow solid. $\delta_H$ (CDCl$_3$) 7.90-7.58 (1H, br m), 5.65-5.41 (1H, br m), 3.85-3.76 (4H, m), 3.30-3.26 (4H, m), 3.20-3.11 (3H, m), 2.98-2.90 (3H, m), 2.79-2.67 (2H, m), 2.41 (2H, s),1.08 (6H, s). LCMS (ES+) 363.1 (M+H)+.

Example 345

N-[4-(5,5-Dimethyl-2-(morpholin-4-yl)-7-oxo-4,5,6, 7-tetrahydro-1-benzothien-3-yl)phenyl]methanesulfonamide The title compound was prepared from Example 17 and 4-(methanesulfonyl-amino)phenylboronic acid according to Method L and was obtained as an off-white solid (63%) after purification by column chromatography (SiO$_2$, 10-100% EtOAc/heptane). $\delta_H$ (DMSO-d$_6$) 9.92 (1H, s), 7.39-7.25 (4H, m), 3.62-3.53 (4H, m), 3.06 (3H, s), 2.95-2.87 (4H, m), 2.47, (2H, s), 2.36 (2H, s), 0.96 (6H, s). LCMS (ES+) 435.2 (M+H)+.

Example 346

1-{3-[4-(5,5-Dimethyl-2-(morpholin-4-yl)-7-oxo-4, 5,6,7-tetrahydro-1-benzothien-3-yl)pyridin-2-yl] phenyl}-3-(piperidin-4-yl)urea, Formic Acid Salt Triethylamine (0.2 mL, 1.15 mmol) and triphosgene (42 mg, 0.12 mmol) were added to a solution of Example 340 (100 mg, 0.23 mmol) in THF (15 mL) and the reaction mixture was stirred at 0° C. for 30 minutes. The reaction mixture was then cooled to −78° C. and 4-amino-1-(tert-butoxycarbonyl)piperidine (56 mg, 0.27 mmol) was added. The reaction mixture was then stirred at room temperature for 18 h. The solvent was removed in vacuo and the residue was purified by column chromatography (SiO$_2$, 0-100% EtOAc/heptane). The resulting off-white solid was taken up in methanol (3.0 mL) and a solution of HCl in Et$_2$O (2M, 3.0 mL, 6.0 mmol) was added. The reaction mixture was stirred at room temperature for 1 h then the solvent was removed in vacuo. The residue was purified by preparative HPLC (pH 2.5) to give the title compound (39 mg, 54%) as an off-white solid. $\delta_H$ (CD$_3$OD) 8.70 (1H, d, J 5.3 Hz), 8.15 (1H, d, J 0.9 Hz), 8.44 (1H, s), 7.94 (1H, d, J 0.6 Hz), 7.66-7.62 (1H, m), 7.48-7.40 (3H, m), 3.96-3.84 (1H, m), 3.75-3.67 (4H, m), 3.50-3.39 (2H, m), 3.20-3.13 (2H, m), 3.12-3.06 (4H, m), 2.64 (2H, s), 2.48 (2H, s), 2.20 (2H, m), 1.74 (2H, m), 1.06 (6H, s). LCMS (ES+) 560.2 (M+H)+.

Example 347

(Method AY)

3-[2-(3-{[(3R)-3-Aminopyrrolidin-1-yl] carbonyl}phenyl)pyridin-4-yl]-5,5-dimethyl-2-(morpholin-4-yl)-5,6-dihydrothieno[2,3-c]pyridin-7(4H)-one, Trifluoroacetic Acid Salt A mixture of Example 318 (37 mg, 0.064 mmol), EDC (26 mg, 0.136 mmol), Et$_3$N (30 µL, 0.215 mmol), 3R-(+)-(tert-butoxycarbonylamino)pyrrolidine (26 mg, 0.140 mmol) and 1-hydroxybenzotriazole (ca 1 mg) in DCM (4.0 mL) was stirred at room temperature for 18 h. Further EDC (13 mg, 0.064 mmol), Et$_3$N (10 µL, 0.072 mmol), 3R-(+)-(tert-butoxycarbonylamino)pyrrolidine (13 mg, 0.070 mmol) and HOBT (ca 1 mg) were added and stirring was continued for 48 h. The reaction mixture was diluted with DCM (10 mL), then washed with water (15 mL) and saturated aqueous sodium hydrogencarbonate solution (15 mL). The organic phase was dried (magnesium sulfate) and the solvent was removed in vacuo. The residue was purified by column chromatography (SiO$_2$, 0-5% MeOH/DCM) to give a pale yellow solid, which was dissolved in DCM (5.0 mL) and treated with trifluoroacetic acid (1.0 mL). The reaction mixture was stirred at room temperature for 75 minutes, the solvent was then removed in vacuo and the residue was treated with toluene (5 mL) and concentrated in vacuo. The residue was triturated with Et$_2$O and dried in vacuo to give the title compound (27 mg, 56%) as a yellow solid. $\delta_H$ (DMSO-d$_6$) 8.77-8.74 (1H, m), 8.30 (1H, s), 8.23-8.19 (1H, m), 8.00 (1H, s), 7.64-7.59 (2H, m), 7.42-7.40 (1H, m), 3.94-3.87 (1H, m), 3.87-3.80 (1H, m), 3.80-3.70 (1H, m), 3.63-3.57 (6H, m), 2.98-2.92 (4H, m), 2.70 (2H, s), 2.36-2.25 (1H, m), 2.09-1.98 (1H, m), 1.25 (6H, s). LCMS (ES+) 532.3 (M+H)+.

Example 348

3-[2-(3-{[(3S)-3-Aminopyrrolidin-1-yl] carbonyl}phenyl)pyridin-4-yl]-5,5-dimethyl-2-(morpholin-4-yl)-5,6-dihydrothieno[2,3-c]pyridin-7(4H)-one, Trifluoroacetic Acid Salt The title compound was prepared from Example 318 and 3S-(−)-(tert-butoxycarbonylamino)pyrrolidine according to Method AY and was obtained as a yellow solid (39%). $\delta_H$ (DMSO-d$_6$) 8.74 (1H, d, J 5.3 Hz), 8.36-8.30 (1H, m), 8.26-8.22 (1H, m), 8.09 (1H, s), 8.07-8.03 (1H, m), 7.98-7.90 (1H, m), 7.66-7.56 (3H, m), 7.48 (1H, dd, J 4.9, 1.1 Hz), 3.97-3.87 (1H, m), 3.87-3.61 (2H, m), 3.60-3.50 (6H, m), 3.01-2.88 (4H, m), 2.71 (2H, s), 2.33-2.17 (1H, m), 2.09-1.93 (1H, m), 1.19 (6H, s), LCMS (ES+) 532.3 (M+H)+.

Example 349

Tert-Butyl [(3S)-1-{3-[4-(2-(morpholin-4-yl)-7-oxo-4,5,6,7-tetrahydro-1-benzothien-3-yl)pyridin-2-yl] benzoyl}pyrrolidin-3-yl]carbamate The title compound was prepared from Intermediate 2,2-chloropyridine-4-boronic acid and Intermediate 59 according to Method AI and was obtained as a clear glass (84%) after purification by column chromatography (SiO$_2$, 0-100% EtOAc/heptane). $\delta_H$ (CDCl$_3$) 8.79-8.72 (1H, m), 8.24-8.17 (1H, m), 8.13-8.06 (1H, m), 7.83-7.76 (1H, m), 7.63-7.49 (2H, m), 7.32 (1H, dd, J 4.9, 1.3 Hz), 4.76-4.55 (1H, m), 4.40-4.12 (1H, m), 3.99-3.74 (2H, m), 3.72-3.65 (4H, m), 3.64-3.32 (1H, m), 3.09-2.98 (4H, m), 2.71-2.64 (2H, m), 2.64-2.58 (2H, m), 2.35-2.06 (3H, m), 1.99-1.82 (1H, m), 1.47 (4H, s), 1.39 (5H, s). LCMS (ES+) 603.2 (M+H)+.

Example 350

Tert-Butyl [(3R)-1-{3-[4-(2-(morpholin-4-yl)-7-oxo-4,5,6,7-tetrahydro-1-benzothien-3-yl)pyridin-2-yl] benzoyl}pyrrolidin-3-yl]carbamate The title compound was prepared from Intermediate 2,2-chloropyridine-4-boronic acid and Intermediate 60 according to Method AI and was obtained as a white solid (81%) after purification by column chromatography (SiO$_2$, 0-100% EtOAc/heptane). $\delta_H$ (CDCl$_3$) 8.75 (1H, d, J 5.1 Hz), 8.23-8.17 (1H, m), 8.09 (1H, dt, J 7.3, 1.7 Hz), 7.79 (1H, s), 7.63-7.50 (2H, m), 7.32 (1H, dd, J 4.9, 1.3 Hz), 4.75-4.57 (1H, m), 4.40-4.13 (1H, m), 3.98-3.73 (2H, m), 3.72-3.64 (4H, m), 3.63-3.32 (2H, m), 3.08-2.98 (4H, m), 2.67 (2H, t, J 5.8 Hz), 2.64-2.58 (2H, m), 2.35-2.19 (1H, m), 2.19-2.06 (2H, m), 1.98-1.83 (1H, m), 1.47 (4H, s), 1.39 (5H, s). LCMS (ES+) 603.2 (M+H)$^+$.

Example 351

3-[4-(5,5-Dimethyl-2-(morpholin-4-yl)-7-oxo-4,5,6, 7-tetrahydro-1-benzothien-3-yl)pyridin-2-yl]-N,N-dimethyl-5-nitrobenzamide The title compound was prepared from Example 73 and 5-(N,N-dimethylamino-carbonyl)-3-nitrophenylboronic acid according to Method L and was obtained as a yellow solid (83%) after purification by column chromatography (SiO$_2$, 10-100% EtOAc/heptane, then 15% MeOH/EtOAc). $\delta_H$ (DMSO-d$_6$) 9.03 (1H, t, J 1.7 Hz), 8.83 (1H, d, J 4.9 Hz), 8.67-8.62 (1H, m), 8.33 (1H, s), 8.30-8.27 (1H, m), 7.53 (1H, dd, J 4.9, 1.1 Hz), 3.58 (4H, m), 3.05 (3H, s), 3.02-2.95 (7H, m), 2.59 (2H, s), 2.39 (2H, s), 0.97 (6H, s). LCMS (ES+) 535.3 (M+H)$^+$.

Example 352

5,5-Dimethyl-3-[2-(2-methylphenyl)pyridin-4-yl]-2-(morpholin-4-yl)-5,6-dihydro-1-benzothiophen-7 (4H)-one The title compound was prepared from Example 73 and 2-methylphenylboronic acid according to Method L and was obtained as a white solid (94%) after purification by column chromatography (SiO$_2$, 10-90% EtOAc/heptane). $\delta_H$ (DMSO-d$_6$) 8.77-8.71 (1H, m), 7.50 (1H, s), 7.44 (2H, dd, J 5.1, 1.5 Hz), 7.37-7.28 (3H, m), 3.55-3.64 (4H, m), 2.91-3.02 (4H, m), 2.58 (2H, s), 2.47-2.55 (2H, m), 2.38 (3H, s), 0.98 (6H, s). LCMS (ES+) 433.3 (M+H)$^+$.

Example 353

5,5-Dimethyl-2-(morpholin-4-yl)-3-{2-[3-(morpholin-4-ylacetyl)phenyl]pyridin-4-yl}-5,6-dihydrothieno[2,3-c]pyridin-7(4H)-one, Formic Acid Salt Morpholine (30 μL, 0.344 mmol), potassium carbonate (16 mg, 0.116 mmol) and potassium iodide (20 mg, 0.120 mmol) were added to a solution of Intermediate 56 (56 mg, 0.113 mmol) in DME (3.0 mL) and the reaction mixture was stirred at reflux for 18 h. The solvent was removed in vacuo and the residue was purified by preparative HPLC (pH 2.5) and triturated with Et$_2$O to give the title compound (9 mg, 13%) as a yellow solid. $\delta_H$ (DMSO-d$_6$) 8.77 (1H, d, J 5.0 Hz), 8.68 (1H, s), 8.39 (1H, d, J 8.0 Hz), 8.17 (1H, s), 8.14 (1H, s), 8.07 (1H, d, J 7.5 Hz), 7.68 (1H, t, J 7.5 Hz), 7.58 (1H, s), 7.50-7.46 (1H, m), 3.98 (2H, s), 3.67-3.57 (8H, m), 2.96-2.87 (4H, m), 2.73 (2H, s), 2.55 (4H, s), 1.20 (6H, s). LCMS (ES+) 547.3 (M+H)$^+$.

Example 354

N-[3-(5,5-Dimethyl-2-(morpholin-4-yl)-7-oxo-4,5,6, 7-tetrahydro-1-benzothien-3-yl)phenyl]-2-oxo-1,2-dihydropyridine-3-carboxamide The title compound was prepared from Example 77 and 2-hydroxynicotinic acid according to Method AL and was obtained as a pale yellow solid (24%) after purification by preparative HPLC (pH 2.5). $\delta_H$ (CDCl$_3$) 11.81 (1H, br s), 10.58-10.43 (1H, m), 8.73 (1H, d, J 7.3 Hz), 7.83 (1H, d, J 1.7 Hz), 7.63-7.55 (1H, m), 7.44 (1H, t, J 7.7 Hz), 7.22-7.17 (1H, m), 7.14-7.08 (1H, m), 6.66-6.59 (1H, m), 3.74-3.65 (4H, m), 3.11-3.01 (4H, m), 2.51 (2H, s), 2.47 (2H, s), 1.06 (6H, s). LCMS (ES+) 478.3 (M+H)$^+$.

Example 355

N-[3-(5,5-Dimethyl-2-(morpholin-4-yl)-7-oxo-4,5,6, 7-tetrahydro-1-benzothien-3-yl)phenyl]-2-oxo-1-phenylpyrrolidine-3-carboxamide The title compound was prepared from Example 77 and 1-phenyl-2-oxo-3-pyrrolidinecarboxylic acid according to Method AL and was obtained as an off-white solid (51%) after purification by preparative HPLC (pH 2.5). $\delta_H$ (CDCl$_3$) 9.78 (1H, br s), 7.71-7.68 (1H, m), 7.64-7.58 (2H, m), 7.57-7.52 (1H, m), 7.49-7.37 (3H, m), 7.31-7.23 (1H, m), 7.13-7.07 (1H, m), 3.99-3.90 (2H, m), 3.77-3.63 (5H, m), 3.08-2.99 (4H, m), 2.80-2.52 (2H, m), 2.47 (2H, s), 2.46 (2H, s), 1.05 (6H, d, J 1.7 Hz). LCMS (ES+) 544.4 (M+H)$^+$.

Example 356

N-[3-(5,5-Dimethyl-2-(morpholin-4-yl)-7-oxo-4,5,6, 7-tetrahydro-1-benzothien-3-yl)phenyl]-1-isopropyl-5-oxopyrrolidine-3-carboxamide The title compound was prepared from Example 77 and 1-isopropyl-5-oxo-3-pyrrolidinecarboxylic acid according to Method AL and was obtained as an off-white solid (46%) after purification by preparative HPLC (pH 2.5). $\delta_H$ (CDCl$_3$) 7.74-7.46 (3H, m), 7.46-7.38 (1H, m), 7.17-7.11 (1H, m), 4.49-4.36 (1H, m), 3.79-3.56 (6H, m), 3.33-3.18 (1H, m), 3.05-2.96 (4H, m), 2.90-2.70 (2H, m), 2.46 (2H, s), 2.44 (2H, s), 1.20 (6H, t, J 6.4 Hz), 1.04 (6H, s). LCMS (ES+) 510.3 (M+H)$^+$.

Example 357

Ethyl 3-{[3-(5,5-dimethyl-2-(morpholin-4-yl)-7-oxo-4,5,6,7-tetrahydro-1-benzothien-3-yl)phenyl] amino}-3-oxopropanoate The title compound was prepared from Example 77 and ethyl malonate potassium salt according to Method AL and was obtained as a pale yellow solid (70%) after purification by column chromatography (SiO$_2$, 50-60% EtOAc/heptane). $\delta_H$ (CDCl$_3$) 9.46-9.35 (1H, br s), 7.70-7.65 (1H, m), 7.53-7.47 (1H, m), 7.41 (1H, t, J 7.7 Hz), 7.16-7.10 (1H, m), 4.36-4.24 (2H, m), 3.73-3.63 (4H, m), 3.52 (2H, s), 3.08-2.96 (4H, m), 2.48 (2H, s), 2.45 (2H, s), 1.36 (3H, t, J 7.2 Hz), 1.05 (6H, s). LCMS (ES+) 471.3 (M+H)$^+$.

Example 358

Methyl 4-{[3-(5,5-dimethyl-2-(morpholin-4-yl)-7-oxo-4,5,6,7-tetrahydro-1-benzothien-3-yl)phenyl] amino}-4-oxobutanoate The title compound was prepared from Example 77 and mono-methyl succinate according to Method AL, with stirring for 90 h, and was obtained as a pale yellow solid (70%) after purification by column chromatography (SiO$_2$, 60-65% EtOAc/heptane). $\delta_H$ (CDCl$_3$) 7.71-7.65 (1H, m), 7.59 (1H, s), 7.51-7.44 (1H, m), 7.39 (1H, t, J 7.7 Hz), 7.13-7.07 (1H, m), 3.74 (3H, s), 3.71-3.65 (4H, m), 3.04-2.97 (4H, m), 2.85-2.76

(2H, m), 2.76-2.68 (2H, m), 2.48 (2H, s), 2.44 (2H, s), 1.05 (6H, s). LCMS (ES+) 471.4 (M+H)$^+$.

Example 359

5,5-Dimethyl-3-[2-(2-ethylphenyl)pyridin-4-yl]-2-(morpholin-4-yl)-5,6-dihydro-1-benzothiophen-7(4H)-one The title compound was prepared from Example 73 and 2-ethylphenylboronic acid according to Method L and was isolated as a white solid (84%) after purification by column chromatography (SiO$_2$, 10-90% EtOAc/heptane). δ$_H$ (DMSO-d$_6$) 8.73 (1H, dd, J 4.9, 0.6 Hz), 7.48-7.41 (2H, m), 7.40-7.27 (4H, m), 3.63-3.54 (4H, m), 3.01-2.93 (4H, m), 2.80-2.69 (2H, m), 2.56 (2H, s), 2.38 (2H, s), 1.08-1.01 (3H, m), 0.98 (6H, s). LCMS (ES+) 447.4 (M+H)$^+$.

Example 360

3-[4-(5,5-Dimethyl-2-(morpholin-4-yl)-7-oxo-4,5,6,7-tetrahydro-1-benzothien-3-yl)pyridin-2-yl]phenyl Trifluoromethanesulfonate N-Phenyltrifluoromethanesulfonimide (171 mg, 0.48 mmol) and Et$_3$N (122 μL, 0.87 mmol) were added to a solution of Example 103 (190 mg, 0.44 mmol) in DCM (10 mL) and the mixture was stirred at room temperature for 17 h. The solvent was removed in vacuo and the residue was purified by column chromatography (SiO$_2$, 0-80% EtOAc/heptane) to give the title compound (219 mg, 89%) as a white solid. δ$_H$ (DMSO-d$_6$) 8.79 (1H, d, J 5.1 Hz), 8.33 (1H, d, J 7.9 Hz), 8.29 (1H, d, J 2.3 Hz), 8.21 (1H, s), 7.73 (1H, t, J 8.1 Hz), 7.61 (1H, dd, J 8.1, 2.3 Hz), 7.49 (1H, dd, J 5.1, 1.1 Hz), 3.63-3.54 (4H, m), 3.03-2.93 (4H, m), 2.59 (2H, s), 2.39 (2H, s), 0.97 (6H, s). LCMS (ES+) 567.2 (M+H)$^+$.

Example 361

3-{3-[4-(5,5-Dimethyl-2-(morpholin-4-yl)-7-oxo-4,5,6,7-tetrahydro-1-benzothien-3-yl)pyridin-2-yl]phenyl}-1-methyl-1-(piperidin-4-yl)urea, Formic Acid Salt Triphosgene (24 mg, 0.08 mmol) and triethylamine (50 μL, 0.36 mmol) were added to a cooled solution of Example 340 (82 mg, 0.19 mmol) in THF (10 mL) at −78° C. The mixture was then allowed to warm to 0° C. and stirred at this temperature for 30 minutes. The reaction mixture was then recooled to −78° C. and 1-(tert-butoxycarbonyl)-4-(methylamino)piperidine (45 mg, 0.21 mmol) was added, then allowed to warm to 0° C. and stirred for 1 h. A further portion of 1-(tert-butoxycarbonyl)-4-(methylamino)-piperidine (45 mg, 0.21 mmol) was added and the mixture was stirred for a further 1 h at 0° C. The solvent was removed in vacuo and the residue was purified by column chromatography (SiO$_2$, 0-80% EtOAc/heptane). The solid obtained was taken up in MeOH (2.0 mL) and a solution of HCl in Et$_2$O (2M, 2.0 mL, 4.0 mmol) was added and the reaction mixture was stirred at room temperature for 5 h. The solvent was removed in vacuo and the residue was purified by preparative HPLC (pH 2.5) to give the title compound (51 mg, 43%) as an off-white solid. δ$_H$ (CD$_3$OD) 8.71 (1H, dd, J 5.1, 0.6 Hz), 8.50 (1H, s), 8.12 (1H, d, J 0.9 Hz), 7.95 (1H, d, J 0.6 Hz), 7.73-7.66 (1H, m), 7.51-7.43 (3H, m), 4.51-4.38 (1H, m), 3.77-3.67 (4H, m), 3.59-3.48 (2H, m), 3.20-3.06 (6H, m), 3.01 (3H, s), 2.65 (2H, s), 2.48 (2H, s), 2.14-1.91 (4H, m), 1.06 (6H, s). LCMS (ES+) 574.2 (M+H)$^+$.

Example 362

(Method AZ)

3-[6-(3-{[(3R)-3-Aminopyrrolidin-1-yl]carbonyl}phenyl)pyridin-2-yl]-5,5-dimethyl-2-(morpholin-4-yl)-5,6-dihydrothieno[2,3-c]pyridin-7-(4H)-one, Acetic Acid Salt A mixture of Intermediate 19 (146 mg, 0.38 mmol), 6-chloropyridine-2-boronic acid pinacol ester (98 mg, 0.41 mmol), K$_3$PO$_4$ (238 mg, 1.12 mmol) and Pd(PPh$_3$)$_4$ (22 mg, 0.02 mmol) in DME (3 mL) and water (1 mL) was heated in a sealed tube at 120° C., under microwave irradiation, for 20 minutes. The solvent was removed in vacuo and the residue was purified by column chromatography (SiO$_2$, 0-100% EtOAc/heptane). The solid obtained was combined with Intermediate 60 (72 mg, 0.22 mmol), K$_3$PO$_4$ (115 mg, 0.54 mmol) and Pd(PPh$_3$)$_4$ (10 mg, 0.009 mmol) in DME (3 mL) and water (1 mL) and the mixture was heated in a sealed tube at 140° C., under microwave irradiation, for 2 h. The solvent was removed in vacuo and the residue was purified by column chromatography (SiO$_2$, 0-100% EtOAc/heptane). The solid obtained was dissolved in MeOH (2 mL), treated with a solution of HCl in Et$_2$O (2M, 2.0 mL, 4.0 mmol) and the reaction mixture was stirred at room temperature for 5 h. The solvent was removed in vacuo and the residue was purified by preparative HPLC (pH 5.8) to give the title compound (20 mg, 8%) as a white solid. δ$_H$ (CD$_3$OD) 8.33-8.27 (1H, m), 8.26-8.20 (1H, m), 7.99 (1H, m), 7.91-7.87 (1H, m), 7.84-7.80 (1H, m), 7.68-7.61 (2H, m), 4.01-3.60 (9H, m), 3.04-3.00 (4H, m), 2.96 (2H, s), 2.45-2.27 (1H, m), 2.12-1.91 (10H, m), 1.33 (6H, s). LCMS (ES+) 532.3 (M+H)$^+$.

Example 363

3-[6-(3-{[(3S)-3-Aminopyrrolidin-1-yl]carbonyl}phenyl)pyridin-2-yl]-5,5-dimethyl-2-(morpholin-4-yl)-5,6-dihydrothieno[2,3-c]pyridin-7(4H)-one, Acetic Acid Salt The title compound was prepared from Intermediate 19, 6-chloropyridine-2-boronic acid pinacol ester and Intermediate 59 according to Method AZ and was isolated as a white solid (6%) after purification by preparative HPLC (pH 5.8). δ$_H$ (CD$_3$OD) 8.34-8.27 (1H, m), 8.27-8.19 (1H, m), 7.99 (1H, m), 7.92-7.86 (1H, m), 7.85-7.80 (1H, m), 7.69-7.60 (2H, m), 4.00-3.54 (9H, m), 3.07-3.00 (4H, m), 2.96 (2H, s), 2.43-2.25 (1H, m), 2.10-1.92 (7H, m), 1.33 (6H, s). LCMS (ES+) 532.3 (M+H)$^+$.

Example 364

(Method BA)

3-{2-[3-(3-Aminopyrrolidin-1-yl)phenyl]pyridin-4-yl}-5,5-dimethyl-2-(morpholin-4-yl)-5,6-dihydro-1-benzothiophen-7(4H)-one, Hydrochloride Salt A mixture of Example 360 (100 mg, 0.18 mmol), 3-(tert-butoxycarbonylamino)-pyrrolidine (66 mg, 0.35 mmol), potassium tert-butoxide (28 mg, 0.25 mmol) and acetato(2'-di-tert-butylphosphino-1,1'-biphenyl-2-yl)palladium(II) (20 mg, 0.043 mmol) in 1,4-dioxane (2.0 mL) was heated in a sealed tube at 100° C., under microwave irradiation, for 2 h. The solvent was removed in vacuo and the residue was purified by column chromatography (SiO$_2$, 0-100% EtOAc/heptane). The obtained solid was taken up in DCM (10 mL), treated with a solution of HCl in Et$_2$O (2M, 1.0 mL, 2.0 mmol) and stirred at room temperature for 18 h. The solvent was removed in vacuo and the residue was purified by column chromatography (0-20% MeOH/DCM) to give the title compound (36 mg, 38%) as an orange solid. $\delta_H$ (CD$_3$OD) 8.89-8.77 (1H, m), 8.57-8.44 (1H, m), 8.22-8.09 (1H, m), 7.62-7.51 (1H, m), 7.38-7.20 (2H, m), 7.02 (1H, d, J 7.7 Hz), 4.22-4.08 (1H, m), 3.93-3.48 (8H, m), 3.27-3.05 (4H, m), 2.81 (2H, s), 2.68-2.45 (3H, m), 2.38-2.21 (1H, m), 1.08 (6H, s). LCMS (ES+) 503.4 (M+H)$^+$.

Example 365

3-Amino-5-[4-(5,5-dimethyl-2-(morpholin-4-yl)-7-oxo-4,5,6,7-tetrahydro-1-benzothien-3-yl)pyridin-2-yl]-N,N-dimethylbenzamide A mixture of Example 351 (203 mg, 0.38 mmol) and 20% palladium on carbon (10 mg) in EtOAc (20 mL) and MeOH (5 mL) was stirred at room temperature under an atmosphere of hydrogen for 12 days. The reaction mixture was filtered and the solvent was removed in vacuo to give the title compound (177 mg, 92%) as a pale yellow glass. $\delta_H$ (DMSO-d$_6$) 8.71 (1H, d, J 5.1 Hz), 7.90 (1H, s), 7.43 (1H, s), 7.40-7.36 (1H, m), 7.23 (1H, s), 6.63 (1H, m), 5.48-5.41 (2H, m), 3.63-3.54 (4H, m), 2.97 (10H, s), 2.56 (2H, s), 2.39 (2H, s), 0.97 (6H, s). LCMS (ES+) 505.3 (M+H)$^+$.

Example 366

5,5-Dimethyl-2-(morpholin-4-yl)-3-[3-(piperazin-1-yl)phenyl]-5,6-dihydrothieno[2,3-c]pyridin-7(4H)-one, Acetic Acid Salt A mixture of Intermediate 19 (106 mg, 0.28 mmol), 3-[4-(tert-butoxycarbonyl)-piperazin-1-yl]phenylboronic acid pinacol ester (109 mg, 0.28 mmol), K$_3$PO$_4$ (179 mg, 0.84 mmol) and Pd(PPh$_3$)$_4$ (16 mg, 0.014 mmol) in DME (3 mL) and water (1 mL) was heated in a sealed tube at 140° C., under microwave irradiation, for 2 h. The solvent was removed in vacuo and the residue taken up in MeOH. A solution of HCl in Et$_2$O (2M, 2.0 mL, 4.0 mmol) was added and the reaction mixture was stirred at room temperature for 20 h. The solvent was removed in vacuo and the residue was purified by preparative HPLC (pH 5.8) to give the title compound (34 mg, 22%) as an off-white solid (34 mg). $\delta_H$ (DMSO-d$_6$) 7.43 (1H, s), 7.27 (1H, t, J 7.9 Hz), 6.95 (1H, s), 6.92-6.86 (1H, m), 6.76 (1H, d, J 7.5 Hz), 3.60-3.53 (4H, m), 3.13-3.04 (4H, m), 2.90-2.79 (8H, m), 2.58 (2H, s), 1.18 (6H, s), 1.90 (6H, s). LCMS (ES+) 427.4 (M+H)$^+$.

Example 367

5,5-Dimethyl-2-(morpholin-4-yl)-3-{6-[3-(piperazin-1-yl)phenyl]pyridin-2-yl}-5,6-dihydro-1-benzothiophen-7(4H)-one, Acetic Acid Salt The title compound was prepared from Example 17, 6-chloropyridine-2-boronic acid pinacol ester and 3-[4-(tert-butoxycarbonyl)piperazin-1-yl]phenylboronic acid pinacol ester according to Method AZ and was isolated as a white solid (11%) after purification by preparative HPLC (pH 5.8). $\delta_H$ (CD$_3$OD) 8.56 (1H, s), 7.97 (1H, t, J 7.7 Hz), 7.84 (1H, dd, J 7.9, 0.8 Hz), 7.76-7.72 (1H, m), 7.63 (1H, dd, J 7.5, 0.8 Hz), 7.60-7.55 (1H, m), 7.44 (1H, t, J 8.1 Hz), 7.18-7.12 (1H, m), 3.75-3.67 (4H, m), 3.50-3.41 (4H, m), 3.38-3.28 (4H, m), 3.12-3.04 (4H, m), 2.75 (2H, s), 2.48 (2H, s), 1.94 (3H, s), 1.08 (6H, s). LCMS (ES+) 503.4 (M+H)$^+$.

Example 368

(Method BB)

Tert-Butyl 3-({3-[4-(5,5-dimethyl-2-(morpholin-4-yl)-7-oxo-4,5,6,7-tetrahydro-1-benzothien-3-yl)pyridin-2-yl]phenyl}amino)pyrrolidine-1-carboxylate A mixture of Example 360 (115 mg, 0.20 mmol), 3-amino-1-(tert-butoxy-carbonyl)pyrrolidine (76 mg, 0.41 mmol), potassium tert-butoxide (32 mg, 0.28 mmol) and acetato(2'-di-tert-butylphosphino-1,1'-biphenyl-2-yl)palladium(II) (20 mg, 0.043 mmol) in 1,4-dioxane (2.0 mL) was heated in a sealed tube at 100° C., under microwave irradiation, for 2 h. The solvent was removed in vacuo and the residue was purified by column chromatography (SiO$_2$, 0-100% EtOAc/heptane) to give the title compound (79 mg, 65%) as an off-white solid. $\delta_H$ (CDCl$_3$) 8.73 (1H, d, J 5.1 Hz), 7.75 (1H, s), 7.38 (1H, s), 7.35-7.23 (3H, m), 6.74-6.68 (1H, m), 4.25-4.12 (1H, m), 4.00-3.88 (1H, m), 3.84-3.73 (1H, m), 3.72-3.64 (4H, m), 3.58-3.43 (2H, m), 3.37-3.20 (1H, m), 3.07-2.99 (4H, m), 2.53 (2H, s), 2.45 (2H, s), 2.31-2.17 (1H, m), 2.01-1.89 (1H, m), 1.47 (9H, s), 1.05 (6H, s). LCMS (ES+) 603.2 (M+H)$^+$.

Example 369

Tert-Butyl [(3R)-1-(3-{4-(5,5-dimethyl-2-(morpholin-4-yl)-7-oxo-4,5,6,7-tetrahydro-1-benzothien-3-yl)-6-[(4-methoxybenzyl)amino]pyridin-2-yl}benzoyl)pyrrolidin-3-yl]carbamate The title compound was prepared from Example 269, 4-methoxybenzylamine and Intermediate 60 according to Method AW and was isolated as a clear oil (38%) after purification by column chromatography (SiO$_2$, 0-100% EtOAc/heptane). $\delta_H$ (CDCl$_3$) 8.22-8.16 (1H, m), 8.10-8.03 (1H, m), 7.58-7.45 (2H, m), 7.36 (1H, s), 7.33 (1H, s), 7.14-7.10 (1H, m), 6.92 (1H, s), 6.89 (1H, s), 6.26 (1H, s), 5.22-5.13 (1H, m), 4.78-4.60 (1H, m), 4.58-4.51 (2H, m), 4.39-4.11 (1H, m), 3.99-3.67 (5H, m), 3.64-3.58 (4H, m), 3.57-3.27 (2H, m), 3.07-2.99 (4H, m), 2.40 (2H, s), 2.37 (2H, s), 2.33-2.09 (1H, m), 1.96-1.81 (1H, m), 1.47 (4H, s), 1.39 (5H, s), 1.00 (6H, s). LCMS (ES+) 766.3 (M+H)$^+$.

Example 370

Tert-Butyl [(3S)-1-(3-{4-(5,5-dimethyl-2-(morpholin-4-yl)-7-oxo-4,5,6,7-tetrahydro-1-benzothien-3-yl)-6-[(4-methoxybenzyl)amino]pyridin-2-yl}benzoyl)pyrrolidin-3-yl]carbamate The title compound was prepared from Example 269, 4-methoxybenzylamine and Intermediate 59 according to Method AW and was isolated as a clear oil (40%) after purification by column chromatography (SiO$_2$, 0-100% EtOAc/heptane). $\delta_H$ (CDCl$_3$) 8.23-8.15 (1H, m), 8.11-8.02 (1H, m), 7.59-7.44 (2H, m), 7.36 (1H, s), 7.33 (1H, s), 7.15-7.10 (1H, m), 6.92 (1H, s), 6.89 (1H, s), 6.27 (1H, d, J 0.6 Hz), 5.26-5.14 (1H, m), 4.83-4.62 (1H, m), 4.54 (2H, d, J 5.7 Hz), 4.39-4.10 (1H, m), 4.00-3.68 (5H, m), 3.67-3.25 (6H, m), 3.10-2.97

(4H, m), 2.47-2.33 (4H, m), 1.75-2.32 (2H, m), 1.47 (4H, s), 1.39 (5H, s), 1.00 (6H, s). LCMS (ES+) 766.3 (M+H)+.

Example 371

(Method BC)

5,5-Dimethyl-2-(morpholin-4-yl)-3-{2-[3-(pyrrolidin-3-ylamino)phenyl]pyridin-4-yl}-5,6-dihydro-1-benzothiophen-7(4H)-one, Acetic Acid Salt A solution of HCl in Et$_2$O (2M, 1.0 mL, 2.0 mmol) was added to a solution of Example 368 (70 mg, 0.12 mmol) in DCM (10 mL) and the mixture was stirred at room temperature for 1 h. The solvent was removed in vacuo and the residue was purified by preparative HPLC (pH 5.8) to give the title compound (36 mg, 44%) as a yellow solid. $\delta_H$ (CD$_3$OD) 8.69 (1H, dd, J 5.1, 0.6 Hz), 7.89 (1H, d, J 0.6 Hz), 7.45 (1H, dd, J 5.1, 1.5 Hz), 7.38-7.25 (3H, m), 6.85-6.78 (1H, m), 4.39-4.28 (1H, m), 3.75-3.64 (4H, m), 3.59-3.29 (4H, m), 3.13-3.04 (4H, m), 2.63 (2H, s), 2.48 (2H, s), 2.45-2.34 (1H, m), 2.19-2.05 (1H, m), 1.94 (9H, s), 1.06 (6H, s). LCMS (ES+) 503.3 (M+H)+.

Example 372

3-[2-Amino-6-(3-{[(3S)-3-aminopyrrolidin-1-yl]carbonyl}phenyl)pyridin-4-yl]-5,5-dimethyl-2-(morpholin-4-yl)-5,6-dihydro-1-benzothiophen-7(4H)-one, Acetic Acid Salt The title compound was prepared from Example 370 according to Method AV and was isolated as a white solid (44%) after purification by preparative HPLC (pH 5.8). $\delta_H$ (CD$_3$OD) 8.20-8.13 (1H, m), 8.12-8.05 (1H, m), 7.65-7.56 (2H, m), 7.15 (1H, s), 6.59 (1H, d, J 1.1 Hz), 3.99-3.42 (9H, m), 3.18-3.09 (4H, m), 2.62 (2H, s) 2.46 (2H, s), 2.42-2.24 (1H, m), 2.08-1.98 (1H, m), 1.96 (4.5H, s), 1.06 (6H, s). LCMS (ES+) 546.3 (M+H)+.

Example 373

3-[2-Amino-6-(3-{[(3R)-3-aminopyrrolidin-1-yl]carbonyl}phenyl)pyridin-4-yl]-5,5-dimethyl-2-(morpholin-4-yl)-5,6-dihydro-1-benzothiophen-7(4H)-one, Acetic Acid Salt The title compound was prepared from Example 369 according to Method AV and was isolated as a white solid (28%) after purification by preparative HPLC (pH 5.8). $\delta_H$ (CD$_3$OD) 7.42-7.36 (1H, m), 7.35-7.27 (1H, m), 6.87-6.81 (2H, m), 6.38 (1H, s), 5.81 (1H, d, J 0.9 Hz), 2.22-3.64 (9H, m), 2.40-2.32 (4H, m), 1.85 (2H, s), 1.68 (2H, s), 1.64-1.20 (2H, m), 1.18 (3H, s), 0.29 (6H, s). LCMS (ES+) 546.3 (M+H)+.

Example 374

1-[2-(Dimethylamino)ethyl]-3-[3-(5,5-dimethyl-2-(morpholin-4-yl)-7-oxo-4,5,6,7-tetrahydro-1-benzothien-3-yl)phenyl]urea, Formic Acid Salt The title compound was prepared from Example 77 and N,N-dimethylethylene-diamine according to Method AP and was isolated as a pale yellow solid (36%) after purification by preparative HPLC (pH 2.5). $\delta_H$ (CDCl$_3$) 8.43 (1H, s), 7.85-7.67 (2H, m), 7.46 (1H, d, J 1.7 Hz), 7.44-7.39 (1H, m), 7.36-7.29 (1H, m), 6.99-6.93 (1H, m), 3.75-3.64 (6H, m), 3.23-3.18 (2H, m), 3.05-2.99 (4H, m), 2.87 (6H, s), 2.48 (2H, s), 2.43 (2H, s), 1.04 (6H, s). LCMS (ES+) 471.2 (M+H)+.

Example 375

1-[2-(Dimethylamino)ethyl]-3-[3-(5,5-dimethyl-2-(morpholin-4-yl)-7-oxo-4,5,6,7-tetrahydro-1-benzothien-3-yl)phenyl]-1-methylurea, Formic Acid Salt The title compound was prepared from Example 77 and N,N,N'-trimethylethylene-diamine according to Method AP and was isolated as a pale yellow solid (28%) after purification by preparative HPLC (pH 2.5). $\delta_H$ (CDCl$_3$) 8.50-8.37 (1H, m), 8.30 (1H, s), 7.44 (1H, s), 7.41-7.31 (2H, m), 7.04-6.98 (1H, m), 3.75 (2H, t, J 6.0 Hz), 3.68 (4H, m), 3.12 (3H, s), 3.08-3.00 (6H, m), 2.73 (6H, s), 2.50 (2H, s), 2.43 (2H, s), 1.04 (6H, s). LCMS (ES+) 485.2 (M+H)+.

Example 376

1-[3-(5,5-Dimethyl-2-(morpholin-4-yl)-7-oxo-4,5,6,7-tetrahydro-1-benzothien-3-yl)phenyl]-3-[2-(morpholin-4-yl)ethyl]urea, Formic Acid Salt The title compound was prepared from Example 77 and 4-(2-aminoethyl)-morpholine according to Method AP and was isolated as a pale yellow solid (29%) after purification by preparative HPLC (pH 2.5). $\delta_H$ (CDCl$_3$) 8.40 (1H, s), 7.54-7.48 (1H, m), 7.46-7.43 (1H, m), 7.42-7.31 (2H, m), 7.01-6.89 (2H, m), 4.05-3.97 (4H, m), 3.74-3.61 (6H, m), 3.09-2.97 (10H, m), 2.48 (2H, s), 2.43 (2H, s), 1.04 (6H, s). LCMS (ES+) 513.2 (M+H)+.

Example 377

1-[3-(5,5-Dimethyl-2-(morpholin-4-yl)-7-oxo-4,5,6,7-tetrahydro-1-benzothien-3-yl)phenyl]-3-(1-methylazetidin-3-yl)urea The title compound was prepared from Example 77 and 1-methyl-3-amino-azetidine hydrochloride according to Method AP and was isolated as a pale yellow solid (27%) after purification by preparative HPLC (pH 2.5). $\delta_H$ (CDCl$_3$) 8.37-8.28 (1H, m) 7.98-7.90 (1H, m), 7.49-7.45 (1H, m), 7.43-7.30 (2H, m), 7.01-6.97 (1H, m), 4.99-4.83 (1H, m), 4.59-4.43 (2H, m), 4.28-4.08 (2H, m), 3.72-3.64 (4H, m), 3.03-2.98 (4H, m), 2.96 (3H, s), 2.48 (2H, s), 2.43 (2H s), 1.04 (6H, s). LCMS (ES+) 469.3 (M+H)+.

Example 378

1-[3-(5,5-Dimethyl-2-(morpholin-4-yl)-7-oxo-4,5,6,7-tetrahydro-1-benzothien-3-yl)phenyl]-3-[(1-methyl-1H-imidazol-4-yl)methyl]urea, Formic Acid Salt The title compound was prepared from Example 77 and (1-methyl-1H-imidazol-4-yl)methylamine according to Method AP and was isolated as a pale yellow solid (52%) after purification by preparative HPLC (pH 2.5). $\delta_H$(CDCl$_3$) 8.31 (1H, s), 8.00-7.89 (1H, m), 7.76 (1H, s), 7.46 (1H, s), 7.40-7.35 (1H, m), 7.27-7.03 (1H, m), 7.17-7.02 (1H, m), 6.96-6.90 (2H, m), 4.41 (2H, s), 3.70-3.55 (4H, m), 3.05-2.96 (4H, m), 2.48 (2H, s), 2.43 (2H, s), 1.04 (6H, s). LCMS (ES+) 494.2 (M+H)+.

Example 379

3-(2-{3-[(Dimethylamino)acetyl]phenyl}pyridin-4-yl)-5,5-dimethyl-2-(morpholin-4-yl)-5,6-dihydrothieno[2,3-c]pyridin-7(4B)-one, Formic Acid Salt A suspension of Intermediate 56 (71 mg, 0.143 mmol) in MeOH (5.0 mL) was added dropwise to a methanolic solution of dimethylamine (2M, 2.5 mL, 5.0 mmol) and the reaction mixture was stirred at 40° C. for 10 minutes. A further portion of methanolic dimethylamine (2M, 2.5 mL, 5.0 mmol) was added and stirring was continued at 40° C. for 20 minutes. The solvent was removed in vacuo and the residue was purified by preparative HPLC (pH 2.5) to give the title compound (7 mg, 9%) as an off-white solid. $\delta_H$ (DMSO-$d_6$) 8.81-8.72 (1H, m), 8.67 (1H, d, J 0.8 Hz), 8.45-8.33 (1H, m), 8.16 (1H, s), 8.11-8.01 (1H, m), 7.72-7.62 (1H, m), 7.58 (1H, s), 7.53-7.43 (1H, m), 3.88 (2H, s), 3.65-3.56 (4H, m), 2.97-2.87 (4H, m), 2.73 (2H, s), 2.50 (3H, s), 2.28 (3H, s), 1.20 (6H, s). LCMS (ES+) 505.3 (M+H)+.

Example 380

(Method BD)

3-[2-(3-{[(3R)-3-Aminopyrrolidin-1-yl]methyl}phenyl)pyridin-4-yl]-5,5-dimethyl-2-(morpholin-4-yl)-5,6-dihydro-1-benzothiophen-7(4H)-one Example 262 (400 mg, 0.76 mmol) was combined with (3R)-(+)-3-(tert-butoxy-carbonylamino)pyrrolidine (150 mg, 0.81 mmol) and THF (5.0 mL) in a sealed tube and the mixture was heated at 120° C., under microwave irradiation, for 1 h. Further (3R)-(+)-3-(tert-butoxycarbonylamino)pyrrolidine (100 mg, 0.54 mmol) and triethylamine (0.5 mL, 3.6 mmol) were added and heating was continued at 120° C. for a further 1 h. The solvent was removed in vacuo and the residue was purified by column chromatography (SiO$_2$, 0-20% MeOH/DCM). The obtained solid was taken up in MeOH (5 mL) and was treated with a solution of HCl in Et$_2$O (2M, 2 mL, 4 mmol). The reaction mixture was stirred at room temperature for 20 h. The solvent was removed in vacuo and the residue was purified by column chromatography (SiO$_2$, 0-20% MeOH/DCM containing 1% NH$_4$OH) to give the title compound (56 mg, 14%) as a yellow glass. $\delta_H$ (DMSO-$d_6$) 8.74 (1H, d, J 5.1 Hz), 8.09 (1H, s), 8.05-7.99 (2H, m), 8.05-7.99 (2H, m), 7.46 (1H, t, J 7.5 Hz), 7.42-7.36 (2H, m), 3.64 (2H, d, J 4.7 Hz), 3.62-3.57 (4H, m), 3.41-3.27 (1H, m), 3.03-2.94 (4H, m), 2.76-2.67 (1H, m), 2.59 (2H, s), 2.57-2.43 (1H, m), 2.39 (2H, s), 2.19-2.12 (1H, m), 2.09-1.83 (2H, m), 1.43-1.30 (1H, m), 0.97 (6H, s). LCMS (ES+) 517.3 (M+H)+.

Example 381

3-[2-(3-{[(3R)-3-Aminopyrrolidin-1-yl]methyl}phenyl)pyridin-4-yl]-5,5-dimethyl-2-(morpholin-5,6-dihydro-1-benzothiophen-7(4H)-one, Acetic Acid Salt The title compound was prepared from Example 262 and (3R)-(+)-3-(tert-butoxy-carbonylamino)pyrrolidine according to Method BD and was isolated as an off-white solid (27%) after purification by preparative HPLC (pH 5.8). $\delta_H$ (DMSO-$d_6$) 8.74 (1H, d, J 5.1 Hz), 8.09 (1H, s), 7.46 (1H, t, J 7.5 Hz), 7.43-7.37 (2H, m), 3.65 (2H, d, J 3.8 Hz), 3.63-3.57 (4H, m), 3.44-3.33 (1H, m), 3.04-2.94 (4H, m), 2.77-2.67 (1H, m), 2.59 (2H, s), 2.54-2.43 (2H, m), 2.39 (2H, s), 2.25-2.17 (1H, m), 2.11-1.98 (1H, m), 1.87 (6H, s), 1.49-1.35 (1H, m), 0.97 (6H, s). LCMS (ES+) 517.3 (M+H)+.

Example 382

3-[2-(3-{[(3S)-3-Aminopyrrolidin-1-yl]methyl}phenyl)pyridin-4-yl]-5,5-dimethyl-2-(morpholin-4-yl)-5,6-dihydro-1-benzothiophen-7(4H)-one, Acetic Acid Salt The title compound was prepared from Example 262 and (3S)-(−)-3-(tert-butoxy-carbonylamino)pyrrolidine according to Method BD and was isolated as an off-white solid (27%) after purification by preparative HPLC (pH 5.8). $\delta_H$ (DMSO-$d_6$) 8.74 (1H, d, J 5.1 Hz), 8.09 (1H, s), 8.04 (1H, s), 8.03-7.98 (2H, m), 7.46 (1H, t, J 7.5 Hz), 7.42-7.36 (2H, m), 3.65 (2H, d, J 4.1 Hz), 3.63-3.56 (4H, m), 3.51-3.19 (1H, m), 3.03-2.94 (4H, m), 2.76-2.67 (1H, m), 2.59 (2H, s), 2.54-2.45 (2H, m), 2.39 (2H, s), 2.24-2.16 (1H, m), 2.11-1.97 (1H, m), 1.88 (3H, s), 1.47-1.35 (1H, m), 0.97 (6H, s). LCMS (ES+) 517.3 (M+H)+.

Example 383

5,5-Dimethyl-3-[2-(3-{[4-(methylamino)piperidin-1-yl]methyl}phenyl)pyridin-4-yl]-2-(morpholin-4-yl)-5,6-dihydro-1-benzothiophen-7(4H)-one, Acetic Acid Salt The title compound was prepared from Example 262 and 4-[N-(tert-butoxy-carbonyl)-N-methylamino]piperidine according to Method BD and was isolated as a beige glass (55%) after purification by preparative HPLC (pH 5.8). $\delta_H$ (DMSO-$d_6$) 8.75 (1H, d, J 5.1 Hz), 8.10-7.98 (3H, m), 7.46 (1H, t, J 7.7 Hz), 7.42-7.34 (2H, m), 3.64-3.56 (4H, m), 3.53 (2H, s), 3.02-2.94 (4H, m), 2.84-2.71 (2H, m), 2.59 (2H, s), 2.39 (2H, s), 2.26 (3H, s), 2.05-1.94 (2H, m), 1.86 (6H, s), 1.82-1.73 (2H, m), 1.33-1.17 (2H, m), 0.97 (6H, s). LCMS (ES+) 545.5 (M+H)+.

Example 384

N-{3-[4-(5,5-Dimethyl-2-(morpholin-4-yl)-7-oxo-4,5,6,7-tetrahydro-1-benzothien-3-yl)pyridin-2-yl]phenyl}piperazine-1-carboxamide, Acetic Acid Salt Triphosgene (24 mg, 0.07 mmol) and triethylamine (50 μL, 0.38 mmol) were added to a cooled solution of Example 340 (83 mg, 0.19 mmol) in THF (10 mL) at −78° C. The mixture was then allowed to warm to 0° C. and stirred at this temperature for 30 minutes. The reaction mixture was then recooled to −78° C., tert-butyl 1-piperazine-carboxylate (39 mg, 0.21 mmol) was added, and then it was allowed to warm to 0° C. and stirred for 1 h. The solvent was removed in vacuo and the residue was purified by column chromatography (SiO$_2$, 0-100% EtOAc/heptane). The obtained solid was taken up in MeOH (2.0 mL) and a solution of HCl in Et$_2$O (2 m, 2.0 mL, 4.0 mmol) was added. The reaction mixture was stirred at room temperature for 3.5 h. The solvent was removed in vacuo and the residue was purified by preparative HPLC (pH 5.8) to give the title compound (44 mg, 35%) as a yellow solid. $\delta_H$(CD$_3$OD) 8.71 (1H, d, J 5.1 Hz), 8.17-8.10 (1H, m), 7.98-7.93 (1H, m), 7.74-7.65 (1H, m), 7.51-7.43 (3H, m) 3.78-3.66 (8H, m), 3.20-3.03 (8H, m), 2.65 (2H, s), 2.48 (2H, s), 1.97 (6H, s), 1.06 (6H, s). LCMS (ES+) 546.2 (M+H)+.

Example 385

3-(2-{3-[(4-Aminopiperidin-1-yl)methyl]phenyl}pyridin-4-yl)-5,5-dimethyl-2-(morpholin-4-yl)-5,6-dihydro-1-benzothiophen-7(4H)-one, Acetic Acid Salt The title compound was prepared from Example 262 and 4-[N-(tert-butoxy-carbonyl)amino]piperidine according to Method BD and was isolated as a beige gum (24%) after purification by preparative HPLC (pH 5.8). $\delta_H$ (DMSO-$d_6$) 8.75 (1H, d, J 4.9 Hz), 8.15-7.95 (3H, m), 7.46 (1H, t, J 7.5 Hz), 7.43-7.32 (2H, m), 3.66-3.57 (4H, m), 3.53 (2H, s), 3.03-2.94 (4H, m), 2.91-2.71 (2H, m), 2.59 (2H, s), 2.39 (2H, s), 2.06-1.94 (2H, m), 1.88 (6H, s), 1.81-1.66 (2H, m), 1.43-1.22 (2H, m), 0.97 (6H, s). LCMS (ES+) 531.3 (M+H)+.

Example 386

(Method BE)

5,5-Dimethyl-3-[2-(3-{[4-(methylamino)piperidin-1-yl]carbonyl}phenyl)pyrimidin-4-yl]-(morpholin-4-yl)-5,6-dihydro-1-benzothiophen-7(4H)-one, Acetic Acid Salt Sodium hydride (60% dispersion in oil, 66 mg, 1.68 mmol) was slowly added to a solution of 3-methoxycarbonylbenzamidine (180 mg, 0.84 mmol) in DMF (6.0 mL) at 30° C. Stirring was continued for 5 minutes, then Example 344 (152 mg, 0.42 mmol) was added. The reaction mixture was heated to 100° C. for 7 days, then cooled to room temperature and the solvent was removed in vacuo. The residue was partitioned between EtOAc (100 mL) and water (60 mL), and the aqueous phase was extracted with further EtOAc (2×100 mL). The combined organic phases were washed with water (100 mL), dried (magnesium sulfate) and the solvent was removed in vacuo. The obtained solid was taken up in a mixture of MeOH (4.0 mL), THF (6.0 mL) and water (2.0 mL) and lithium hydroxide monohydrate (70 mg, 1.62 mmol) was added. The reaction mixture was stirred at room temperature for 22 h then concentrated in vacuo. The residue was diluted with water (7 mL) and acidified with concentrated HCl. The precipitate was filtered off, washed with a little ice water and dried in vacuo. The obtained solid was combined with HBTU (64 mg, 0.16 mmol), DIPEA (0.08 mL, 0.48 mmol) and 4-[N-(tert-butoxycarbonyl)-N-methylamino]piperidine (51 mg, 0.24 mmol) in DMF (2.0 mL) and the reaction mixture was stirred at room temperature for 4 h. The solvent was removed in vacuo and the residue was partitioned between EtOAc (100 mL) and water (40 mL). The organic layer was washed with water (3×40 mL), dried (magnesium sulfate) and the solvent was removed in vacuo. The residue was purified by column chromatography (SiO$_2$, 0-100% EtOAc/heptane). The obtained solid was taken up in DCM (5.0 mL) and treated with a solution of HCl in Et$_2$O (2M, 2.0 mL, 4.0 mmol). The reaction mixture was stirred at room temperature for 72 h. A further portion of HCl in Et$_2$O (2M, 1.0 mL, 2.0 mmol) was added and stirring was continued for a further 5 h. The solvent was removed in vacuo and purified by preparative HPLC (pH 5.8) to give the title compound (29 mg, 10%) as a yellow solid. $\delta_H$ (CDCl$_3$) 8.85 (1H, d, J 5.1 Hz), 8.61-8.50 (2H, m), 7.65 (1H, d, J 5.1 Hz), 7.61-7.52 (2H, m), 4.93-4.68 (1H, m), 4.01-3.84 (1H, m), 3.83-3.72 (4H, m), 3.17-3.07 (4H, m), 3.05-2.90 (2H, m), 2.86 (2H, s), 2.56 (3H, s), 2.50 (2H, s), 2.24-1.87 (10H, m), 1.74-1.47 (2H, m), 1.09 (6H, s). LCMS (ES+) 560.3 (M+H)+.

Example 387

5,5-Dimethyl-3-[2-(3-{[4-(methylamino)piperidin-1-yl]carbonyl}phenyl)pyrimidin-4-yl]-2-(morpholin-4-yl)-5,6-dihydrothieno[2,3-c]pyridin-7(4H)-one, Acetic Acid Salt The title compound was prepared from Intermediate 55, 3-methoxycarbonyl-benzamidine and 4-[N-(tert-butoxycarbonyl)-N-methylamino]piperidine according to Method BE and was obtained as a yellow solid (13%) after purification by preparative HPLC (pH 5.8). $\delta_H$ (CDCl$_3$) 8.84 (1H, d, J 5.3 Hz), 8.54 (1H, s), 8.52-8.49 (1H, m), 7.82 (1H, d, J 5.3 Hz), 7.60-7.53 (2H, m), 5.87 (1H, s), 4.79-4.61 (1H, m), 3.76-3.87 (4H, m), 3.38-3.17 (4H, m), 3.11 (2H, s), 3.10-3.03 (4H, m), 2.88-2.75 (1H, m), 2.51 (3H, s), 2.09 (6H, s), 1.60-1.42 (2H, m), 1.37 (6H, s). LCMS (ES+) 561.3 (M+H)+.

Example 388

Methyl[3-(5,5-dimethyl-2-(morpholin-4-yl)-7-oxo-4,5,6,7-tetrahydro-1-benzothien-3-yl)phenyl]acetate A mixture of Example 17 (1.0 g, 2.56 mmol), [3-(4,4,5,5-tetramethyl-[1,3,2]dioxa-borolan-2-yl)phenyl]acetic acid methyl ester (0.85 g, 3.08 mmol), K$_3$PO$_4$ (0.55 g, 2.59 mmol) and Pd(PPh$_3$)$_4$ (0.35 g, 0.30 mmol) in DME (0.3 mL) and water (10 mL) was heated at 90° C. for 17 h. A further portion of [3-(4,4,5,5-tetramethyl-[1,3,2]dioxaborolan-2-yl)phenyl] acetic acid methyl ester (0.40 g, 1.45 mmol) was added and heating was continued for a further 24 h. A saturated solution of sodium hydrogencarbonate (50 mL) was added and the mixture was extracted into EtOAc (3×100 mL). The combined organic phases were dried (magnesium sulfate) and the solvent was removed in vacuo. The residue was purified by column chromatography (SiO$_2$, 0-80% EtOAc/heptane) to give the title compound (0.44 g, 42%) as a pale brown foam. $\delta_H$ (DMSO-$d_6$) 7.42 (1H, t, J 7.7 Hz), 7.33 (1H, s), 7.29-7.21 (2H, m), 3.74 (2H, s), 3.64 (3H, s), 3.60-3.52 (4H, m), 2.96-2.84 (4H, m), 2.47 (2H, s), 2.36 (2H, s), 0.96 (6H, s). LCMS (ES+) 414.3 (M+H)+.

Example 389

3-(2-{3-[(3S)-3-Aminopyrrolidin-1-yl]phenyl}pyridin-4-yl)-5,5-dimethyl-2-(morpholin-4-yl)-5,6-dihydro-1-benzothiophen-7(4H)-one, Acetic Acid Salt The title compound was prepared from Example 360 and (3S)-(+3-(tert-butoxy-carbonylamino)pyrrolidine according to Method BA and was obtained as a clear glass (18%) after purification by column chromatography (SiO$_2$, 0-20% MeOH/DCM). $\delta_H$ (CD$_3$OD) 8.73-8.68 (1H, m), 7.93 (1H, d, J 0.8 Hz), 7.45 (1H, dd, J 5.1, 1.5 Hz), 7.43-7.36 (1H, m), 7.32-7.26 (2H, m), 6.80 (1H, dd, J 7.3, 1.5 Hz), 4.12-4.01 (1H, m), 3.79-3.63 (6H, m), 3.58-3.43 (2H, m), 3.15-3.04 (4H, m), 2.64 (2H, s), 2.59-2.42 (3H, m), 2.28-2.13 (1H, m), 1.95 (6H, s), 1.06 (6H, s). LCMS (ES+) 503.4 (M+H)+.

Example 390

3-(2-{3-[(3R)-3-Aminopyrrolidin-1-yl] phenyl}pyridin-4-yl)-5,5-dimethyl-2-(morpholin-4-yl)-5,6-dihydro-1-benzothiophen-7(4H)-one The title compound was prepared from Example 360 and (3R)-(+)-3-(tert-butoxy-carbonylamino)pyrrolidine according to Method BA and was obtained as a white solid (17%) after partitioning between saturated sodium hydrogencarbonate solution and DCM, and subsequent purification by column chromatography (SiO$_2$, 0-20% MeOH/DCM). $\delta_H$ (CD$_3$OD) 8.68 (1H, dd, J 5.1, 0.6 Hz), 7.90 (1H, d, J 0.6 Hz), 7.43 (1H, dd, J 5.3, 1.5 Hz), 7.35 (1H, t, J 7.9 Hz), 7.28-7.18 (2H, m), 6.77-6.69 (1H, m), 3.87-3.76 (1H, m), 3.75-3.66 (4H, m), 3.64-3.54 (2H, m), 3.50-3.38 (1H, m), 3.30-3.22 (1H, m), 3.13-3.01 (4H, m), 2.63 (2H, s), 2.46 (2H, s), 2.43-2.28 (1H, m), 2.08-1.90 (1H, m), 1.05 (6H, s). LCMS (ES+) 503.4 (M+H)$^+$.

Example 391

3-(2-{3-[(3R)-3-Aminopyrrolidin-1-yl] phenyl}pyridin-4-yl)-5,5-dimethyl-2-(morpholin-4-yl)-5,6-dihydro-1-benzothiophen-7(4H)-one, Acetic Acid Salt The title compound was prepared from Example 360 and (3R)-(+)-3-(tert-butoxy-carbonylamino)pyrrolidine according to Method BA and was obtained as a clear glass (15%) after purification by column chromatography (SiO$_2$, 0-20% MeOH/DCM). $\delta_H$ (CD$_3$OD) 8.70 (1H, d, J 5.1 Hz), 7.98-7.89 (1H, m), 7.45 (1H, dd, J 5.1, 1.5 Hz), 7.39 (1H, t, J 8.1 Hz), 7.33-7.26 (2H, m), 6.85-6.75 (1H, m), 4.14-4.00 (1H, m), 3.80-3.63 (6H, m), 3.60-3.42 (2H, m), 3.14-3.02 (4H, m), 2.63 (2H, s), 2.59-2.44 (3H, m), 2.30-2.13 (1H, m), 1.95 (9H, s), 1.05 (6H, s). LCMS (ES+) 503.4 (M+H)$^+$.

Example 392

Tert-Butyl (3R)-3-({3-[4-(5,5-dimethyl-2-(morpholin-4-yl)-7-oxo-4,5,6,7-tetrahydro-1-benzothien-3-yl)pyridin-2-yl]phenyl}amino)pyrrolidine-1-carboxylate The title compound was prepared from Example 360 and (R)-(+)-3-amino-1-(tert-butoxycarbonyl)pyrrolidine according to Method BB and was obtained as a clear glass (60%) after purification by column chromatography (SiO$_2$, 0-100% EtOAc/heptane). $\delta_H$ (CDCl$_3$) 8.73 (1H, d, J 5.1 Hz), 7.80-7.71 (1H, m), 7.41-7.36 (1H, m), 7.34-7.22 (3H, m), 6.74-6.66 (1H, m), 4.28-4.04 (1H, m), 3.97-3.84 (1H, m), 3.83-3.62 (5H, m), 3.59-3.39 (2H, m), 3.38-3.17 (1H, m), 3.08-2.96 (4H, m), 2.53 (2H, s), 2.46 (2H, s), 2.33-2.15 (1H, m), 2.02-1.87 (1H, m), 1.47 (9H, s), 1.05 (6H, s). LCMS (ES+) 603.6 (M+H)$^+$.

Example 393

Tert-Butyl (3S)-3-({3-[4-(5,5-dimethyl-2-(morpholin-4-yl)-7-oxo-4,5,6,7-tetrahydro-1-benzothien-3-yl)pyridin-2-yl]phenyl}amino)pyrrolidine-1-carboxylate The title compound was prepared from Example 360 and (S)-(−)-3-amino-1-(tert-butoxycarbonyl)pyrrolidine according to Method BB and was obtained as a clear glass (44%) after purification by column chromatography (SiO$_2$, 0-100% EtOAc/heptane). $\delta_H$ (CDCl$_3$) 8.73 (1H, d, J 4.9 Hz), 7.76-7.71 (1H, m), 7.40-7.35 (1H, m), 7.33-7.28 (2H, m), 7.27-7.21 (1H, m), 6.74-6.66 (1H, m), 4.24-4.11 (1H, m), 3.93-3.84 (1H, m), 3.84-3.63 (5H, m), 3.58-3.40 (2H, m), 3.36-3.19 (1H, m), 3.07-2.98 (4H, m), 2.54 (2H, s), 2.45 (2H, s), 2.32-2.14 (1H, m), 2.04-1.84 (1H, m), 1.46 (9H, s), 1.04 (6H, s). LCMS (ES+) 603.6 (M+H)$^+$.

Example 394

5,5-Dimethyl-2-(morpholin-4-yl)-3-(2-{3-[(3S)-pyrrolidin-3-ylamino]phenyl}pyridin-4-yl)-5,6-dihydro-1-benzothiophen-7(4H)-one The title compound was prepared from Example 393 according to Method AM and was obtained as a clear glass (42%) after purification by column chromatography (SiO$_2$, 0-20% MeOH/DCM, 1% NH$_4$OH). $\delta_H$ (CDCl$_3$) 8.72 (1H, t, J 7.7 Hz), 7.75 (1H, s), 7.40-7.32 (1H, m), 7.32-7.21 (3H, m), 6.77-6.64 (1H, m), 6.39-5.72 (1H, br m), 4.93-4.07 (2H, m), 3.72-3.62 (4H, m), 3.53-3.27 (2H, m), 3.06-2.98 (4H, m), 2.97-2.55 (2H, m), 2.52 (2H, s), 2.45 (2H, s), 2.39-1.68 (2H, m), 1.04 (6H, s). LCMS (ES+) 503.4 (M+H)$^+$.

Example 395

5,5-Dimethyl-2-(morpholin-4-yl)-3-(2-{3-[(3R)-pyrrolidin-3-ylamino]phenyl}pyridin-4-yl)-5,6-dihydro-1-benzothiophen-7(4H)-one The title compound was prepared from Example 392 according to Method AM and was obtained as a clear glass (63%). $\delta_H$ (CDCl$_3$) 8.74-8.69 (1H, m), 7.78-7.72 (1H, m), 7.42-7.20 (4H, m), 6.77-6.64 (1H, m), 4.90-4.75 (1H, m), 4.37-4.28 (1H, m), 3.74-3.62 (4H, m), 3.54-3.25 (2H, m), 3.07-2.96 (4H, m), 2.96-2.88 (1H, m), 2.80-2.72 (1H, m), 2.52 (2H, s), 2.45 (2H, s), 2.39-1.70 (2H, m), 1.04 (6H, s). LCMS (ES+) 503.4 (M+H)$^+$.

Example 396

3-[2-(3-{[4-(Dimethylamino)piperidin-1-yl] carbonyl}phenyl)pyrimidin-4-yl]-5,5-dimethyl-2-(morpholin-4-yl)-5,6-dihydrothieno[2,3-c]pyridin-7(4H)-one, Formic Acid Solvate The title compound was prepared from Intermediate 55, 3-methoxycarbonyl-benzamidine and 4-(dimethylamino)piperidine according to Method BE, omitting the final acidic deprotection step, and was obtained as a beige solid (14%). $\delta_H$ (CDCl$_3$) 8.84 (1H, d, J 5.3 Hz), 8.57-8.50 (2H, m), 8.39 (0.5H, s), 7.82 (1H, d, J 5.3 Hz), 7.61-7.55 (2H, m), 5.39 (1H, br s), 4.99-4.75 (1H, m), 4.00-3.89 (1H, m), 3.83-3.76 (4H, m), 3.11 (2H, s), 3.10-3.04 (4H, m), 2.89-2.75 (3H, m), 2.48 (6H, s), 2.09-1.43 (1H, m), 1.37 (6H, s). LCMS (ES+) 575.3 (M+H)$^+$.

Example 397

Tert-Butyl (1-{[3-(5,5-dimethyl-2-(morpholin-4-yl)-7-oxo-4,5,6,7-tetrahydro-1-benzothien-3-yl)phenyl] acetyl}piperidin-4-yl)carbamate The title compound was prepared from Example 71 and 4-(tert-butoxycarbonyl-amino)piperidine according to Method I and was obtained as an off-white solid (100%). $\delta_H$ (DMSO-d$_6$) 7.40 (1H, t, J 7.5 Hz), 7.28-7.17 (3H, m), 6.88-6.81 (1H, m), 4.28-4.18 (1H, m), 3.94-3.84 (1H, m), 3.77-3.72 (2H, m), 3.59-3.52 (4H, m), 3.49-3.42 (1H, m), 3.12-2.99 (1H, m), 2.94-2.86 (4H, m), 2.77-2.63 (1H, m), 2.44 (2H, s), 2.35 (2H, s), 1.75-1.61 (2H, m), 1.36 (9H, s), 1.26-1.13 (2H, m), 0.95 (6H, s). LCMS (ES+) 582.2 (M+H)$^+$.

Example 398

2-[3-(5,5-Dimethyl-2-(morpholin-4-yl)-7-oxo-4,5,6,7-tetrahydro-1-benzothien-3-yl)phenyl]-N-(pyridin-4-ylmethyl)acetamide The title compound was prepared from Example 71 and 4-(aminomethyl)pyridine according to Method I and was obtained as an off-white solid (100%). δ$_H$ (DMSO-d$_6$) 8.74-8.66 (1H, m), 8.47-8.40 (2H, m), 7.45-7.33 (2H, m), 7.30-7.21 (2H, m), 7.20 (2H, d, J 5.8 Hz), 4.31 (2H, d, J 5.8 Hz), 3.56 (2H, s), 3.55-3.49 (4H, m), 2.92-2.84 (4H, m), 2.46 (2H, s), 2.35 (2H, s), 0.93 (6H, s). LCMS (ES+) 490.3 (M+H)$^+$.

Example 399

Tert-Butyl [(3S)-1-{[3-(5,5-dimethyl-2-(morpholin-4-yl)-7-oxo-4,5,6,7-tetrahydro-1-benzothien-3-yl)phenyl]acetyl}pyrrolidin-3-yl]carbamate The title compound was prepared from Example 71 and (3S)-(+3-(tert-butoxy-carbonylamino)pyrrolidine according to Method I and was obtained as an off-white solid (100%). δ$_H$ (DMSO-d$_6$) 7.44-7.34 (1H, m), 7.31-7.13 (4H, m), 4.08-3.90 (1H, m), 3.74-3.29 (8H, m), 2.94-2.85 (4H, m), 2.46 (2H, s), 2.35 (2H, s), 2.12-1.63 (4H, m), 1.38 (9H, d, J 2.5 Hz), 0.95 (6H, s). LCMS (ES+) 568.2 (M+H)$^+$.

Example 400

Tert-Butyl 3-({[3-(5,5-dimethyl-2-(morpholin-4-yl)-7-oxo-4,5,6,7-tetrahydro-1-benzothien-3-yl)phenyl]acetyl}amino)azetidine-1-carboxylate The title compound was prepared from Example 71 and 3-amino-1-(tert-butoxy-carbonyl)azetidine according to Method I and was obtained as an off-white solid (96%). δ$_H$ (DMSO-d$_6$) 8.74 (1H, br d, J 7.2 Hz), 7.40 (1H, t, J 7.2 Hz), 7.33-7.31 (1H, m), 7.25-7.19 (2H, m), 4.44-4.31 (1H, m), 4.13-4.00 (2H, m), 3.71-3.61 (2H, m), 3.57-3.51 (4H, m), 3.45 (2H, s), 2.93-2.82 (4H, m), 2.46 (2H, s), 2.36 (2H, s), 1.36 (9H, s), 0.95 (6H, s). (LCMS (ES+) 554.1 (M+H)$^+$.

Example 401

2-[3-(5,5-Dimethyl-2-(morpholin-4-yl)-7-oxo-4,5,6,7-tetrahydro-1-benzothien-3-yl)phenyl]-N,N-dimethylacetamide The title compound was prepared from Example 71 and dimethylamine hydrochloride according to Method I and was obtained as a white solid (92%). δ$_H$ (DMSO-d$_6$) 7.40 (1H, t, J 7.5 Hz), 7.27-7.17 (3H, m), 3.73 (2H, s), 3.60-3.51 (4H, m), 3.02 (3H, s), 2.92-2.87 (4H, m), 2.84 (3H, s), 2.45 (2H, s), 2.35 (2H, s), 0.95 (6H, s). LCMS (ES+) 427.3 (M+H)$^+$.

Example 402

2-[3-(5,5-Dimethyl-2-(morpholin-4-yl)-7-oxo-4,5,6,7-tetrahydro-1-benzothien-3-yl)phenyl]-N-(pyridin-4-yl)acetamide The title compound was prepared from Example 71 and 4-aminopyridine according to Method I and was obtained as a yellow solid (42%) after trituration with Et$_2$O. δ$_H$ (DMSO-d$_6$) 10.60 (1H, br s), 8.44-8.40 (2H, m), 7.60-7.55 (2H, m), 7.47-7.39 (2H, m), 7.32-7.19 (2H, m), 3.74 (2H, s), 3.59-3.47 (4H, m), 2.94-2.82 (4H, m), 2.46 (2H, s), 2.34 (2H, s), 0.92 (6H, s). LCMS (ES+) 476.3 (M+H)$^+$.

Example 403

N-[2-(Diethylamino)ethyl]-2-[3-(5,5-dimethyl-2-(morpholin-4-yl)-7-oxo-4,5,6,7-tetrahydro-1-benzothien-3-yl)phenyl]-N-methylacetamide The title compound was prepared from Example 71 and N,N-diethyl-N'-methyl-ethylenediamine according to Method I and was obtained as a white foam (93%). δ$_H$ (DMSO-d$_6$) 7.40 (1H, t, J 7.5 Hz), 7.28-7.16 (3H, m), 3.78 (1H, s), 3.72 (1H, s), 3.60-3.51 (4H, m), 3.41-3.30 (4H, m), 3.03 (1.5H, s), 2.93-2.87 (4H, m), 2.85 (1.5H, s), 2.50-2.45 (4H, m), 2.42 (2H, s), 2.35 (2H, s), 0.98-0.85 (12H, m). LCMS (ES+) 512.2 (M+H)$^+$.

Example 404

Tert-Butyl 3-[({[3-(5,5-dimethyl-2-(morpholin-4-yl)-7-oxo-4,5,6,7-tetrahydro-1-benzothien-3-yl)phenyl]acetyl}amino)methyl]pyrrolidine-1-carboxylate The title compound was prepared from Example 71 and 3-(aminomethyl)-1-(tert-butoxycarbonyl)pyrrolidine according to Method I and was obtained as an off-white solid (86%). δ$_H$ (DMSO-d$_6$) 8.25-8.16 (1H, m), 7.39 (1H, t, J 7.7 Hz), 7.35-7.32 (1H, m), 7.26-7.19 (2H, m), 3.59-3.52 (4H, m), 3.45 (2H, s), 3.42-3.23 (3H, m), 3.21-2.97 (3H, m), 2.94-2.83 (4H, m), 2.46 (2H, s), 2.35 (2H, m), 2.30-2.18 (1H, m), 1.92-1.75 (1H, m), 1.55-1.44 (1H, m), 1.37 (9H, s), 0.95 (6H, s). LCMS (ES+) 582.1 (M+H)$^+$.

Example 405

Tert-Butyl (1-{3-[4-(5,5-dimethyl-2-(morpholin-4-yl)-7-oxo-4,5,6,7-tetrahydro-1-benzothien-3-yl)pyridin-2-yl]benzoyl}azetidin-3-yl)carbamate The title compound was prepared from Example 254 and azetidin-3-ylcarbamic acid tent-butyl ester according to Method AL and was obtained as a yellow solid (42%) after purification by column chromatography (SiO$_2$, 75-100% EtOAc/heptane). δ$_H$ (CDCl$_3$) 8.85-8.79 (1H, m), 8.39-8.35 (1H, m), 8.23-8.17 (1H, m), 7.95-7.90 (1H, m), 7.77-7.71 (1H, m), 7.61 (1H, t, J 7.7 Hz), 7.44-7.38 (1H, m), 5.17-5.05 (1H, m), 4.69-4.50 (3H, m), 4.34-4.23 (1H, m), 4.12-4.00 (1H, m), 3.77-3.65 (4H, m), 3.10-3.00 (4H, m), 2.56 (2H, s), 2.48 (2H, s), 1.46 (9H, s), 1.07 (6H, s). LCMS (ES+) 617.2 (M+H)$^+$.

Example 406

Tert-Butyl 3-({3-[4-(5,5-dimethyl-2-(morpholin-4-yl)-7-oxo-4,5,6,7-tetrahydro-1-benzothien-3-yl)pyridin-2-yl]benzoyl}amino)azetidine-1-carboxylate The title compound was prepared from Example 254 and 3-amino-1-(tert-butoxycarbonyl)azetidine according to Method AL and was obtained as a cream solid (66%) after purification by column chromatography (SiO$_2$, 75-100% EtOAc/heptane). $\delta_H$ (CDCl$_3$) 8.82-8.78 (1H, m), 8.67-8.59 (1H, m); 8.23-8.15 (1H, m), 8.04-7.97 (1H, m), 7.95-7.90 (1H, m), 7.65 (1H, t, J 7.7 Hz), 7.44-7.37 (1H, m), 4.95-4.82 (1H, m), 4.41-4.32 (2H, m), 3.99-3.90 (2H, m), 3.73-3.66 (4H, m), 3.09-3.00 (4H, m), 2.54 (2H, s), 2.42 (2H, s), 1.46 (9H, s), 1.06 (6H, s). LCMS (ES+) 617.1 (M+H)$^+$.

Example 407

Tert-Butyl N-(1-{[3-(5,5-dimethyl-2-(morpholin-4-yl)-7-oxo-4,5,6,7-tetrahydro-1-benzothien-3-yl)phenyl]acetyl}piperidin-4-yl)-N-methylcarbamate The title compound was prepared from Example 71 and 4-[N-(tert-butoxy-carbonyl)-N-methylamino]piperidine according to Method I and was obtained as a white solid (56%) after purification by column chromatography (SiO$_2$, 0-100% EtOAc/heptane). $\delta_H$ (DMSO-d$_6$) 7.41 (1H, t, J 7.5 Hz), 7.31-7.28 (1H, m), 7.26-7.19 (2H, m), 4.56-4.45 (1H, m), 4.09-3.97 (2H, m), 3.77 (2H, s), 3.59-3.51 (4H, m), 3.07-2.95 (1H, m), 2.93-2.86 (4H, m), 2.56 (3H, s), 2.44 (2H, s), 2.36 (2H, s), 1.56-1.44 (4H, m), 1.38 (9H, s), 0.95 (6H, s). LCMS (ES+) 596.2 (M+H)$^+$.

Example 408

3-{3-[2-(4-Aminopiperidin-1-yl)-2-oxoethyl]phenyl}-5,5-dimethyl-2-(morpholin-4-yl)-5,6-dihydro-1-benzothiophen-7(4H)-one, Trifluoroacetic Acid Salt The title compound was prepared from Example 397 according to Method AT and was obtained as a white solid (100%) after trituration with Et$_2$O. $\delta_H$ (DMSO-d$_6$) 7.93-7.76 (3H, br m), 7.41 (1H, t, J 7.7 Hz), 7.29-7.17 (3H, m), 4.48-4.34 (1H, m), 4.11-3.98 (1H, m), 3.88-3.68 (2H, m), 3.57-3.54 (4H, m), 3.31-3.17 (1H, m), 3.12-2.96 (1H, m), 2.95-2.86 (4H, m), 2.70-2.58 (1H, m), 2.45 (2H, s), 2.36 (2H, s), 1.97-1.77 (2H, m), 1.39-1.21 (2H, m), 0.96 (6H, s). LCMS (ES+) 482.3 (M+H)$^+$.

Example 409

3-(3-{2-[(3S)-3-Aminopyrrolidin-1-yl]-2-oxoethyl}phenyl)-5,5-dimethyl-2-(morpholin-4-yl)-5,6-dihydro-1-benzothiophen-7(4H)-one, Trifluoroacetic Acid Salt The title compound was prepared from Example 399 according to Method AT and was obtained as a white solid (96%) after trituration with Et$_2$O, $\delta_H$ (DMSO-d$_6$) 8.14-7.91 (3H, m), 7.41 (1H, t, J 7.7 Hz), 7.34-7.17 (3H, m), 3.98-3.51 (8H, m), 2.97-2.86 (4H, m), 2.46 (2H, s), 2.36 (2H, s), 0.96 (6H, s). LCMS (ES+) 468.3 (M+H)$^+$.

Example 410

N-(Azetidin-3-yl)-2-[3-(5,5-dimethyl-2-(morpholin-4-yl)-7-oxo-4,5,6,7-tetrahydro-1-benzothien-3-yl)phenyl]acetamide, Trifluoroacetic Acid Salt The title compound was prepared from Example 400 according to Method AT and was obtained as a grey-brown solid (56%) after trituration with Et$_2$O. $\delta_H$ (DMSO-d$_6$) 8.91-8.80 (1H, m), 8.74-8.54 (2H, m), 7.41 (1H, t, J 7.5 Hz), 7.33 (1H, s), 7.29-7.18 (2H, m), 4.69-4.53 (1H, m), 4.20-4.01 (4H, m), 3.99-3.84 (2H, m), 3.60-3.52 (4H, m), 2.97-2.83 (4H, m), 2.46 (2H, s), 2.36 (2H, s), 0.95 (6H, s). LCMS (ES+) 454.3 (M+H)$^+$.

Example 411

2-[3-(5,5-Dimethyl-2-(morpholin-4-yl)-7-oxo-4,5,6,7-tetrahydro-1-benzothien-3-yl)phenyl]-N-(pyrrolidin-3-ylmethyl)acetamide, Trifluoroacetic Acid Salt The title compound was prepared from Example 404 according to Method AT and was obtained as a grey-brown solid (68%) after trituration with Et$_2$O. $\delta_H$ (DMSO-d$_6$) 8.74-8.49 (2H, m), 8.33-8.21 (1H, m), 7.40 (1H, t, J 7.5 Hz), 7.35-7.31 (1H, m), 7.25-7.19 (2H, m), 3.61-3.52 (4H, m), 3.47 (2H, s), 3.26-3.00 (3H, m), 2.94-2.86 (4H, m), 2.85-2.71 (2H, m), 2.46 (2H, s), 2.43-2.32 (4H, m), 2.01-1.88 (1H, m), 1.64-1.50 (1H, m), 0.95 (6H, s). LCMS (ES+) 482.4 (M+H)$^+$.

Example 412

5,5-Dimethyl-3-(3-{2-[4-(methylamino)piperidin-1-yl]-2-oxoethyl}phenyl)-2-(morpholin-4-yl)-5,6-dihydro-1-benzothiophen-7(4H)-one, Trifluoroacetic Acid Salt The title compound was prepared from Example 407 according to Method AT and was obtained as a yellow solid (94%) after trituration with Et$_2$O. $\delta_H$ (DMSO-d$_6$) 8.62-8.44 (2H, m), 4.71 (1H, t, J 7.9 Hz), 7.30-7.16 (3H, m), 4.52-4.41 (1H, m), 4.16-4.02 (1H, m), 3.91-3.66 (2H, m), 3.63-3.53 (4H, m), 3.28-3.12 (1H, m), 3.09-2.95 (1H, m), 2.94-2.86 (4H, m), 2.62-2.53 (4H, m), 2.45 (2H, s), 2.36 (2H, s), 2.09-1.88 (2H, m), 1.47-1.42 (2H, m), 0.96 (6H, s). LCMS (ES+) 496.3 (M+H)$^+$.

Example 413

N-(Azetidin-3-yl)-3-[4-(5,5-dimethyl-2-(morpholin-4-yl)-7-oxo-4,5,6,7-tetrahydro-1-benzothien-3-yl)pyridin-2-yl]benzamide The title compound was prepared from Example 406 according to Method AM and was obtained as a yellow solid (46%) after trituration with Et$_2$O. $\delta_H$ (CD$_3$OD) 8.76 (1H, d, J 5.5 Hz), 8.56-8.48 (1H, m), 8.29-8.18 (1H, m), 8.04 (1H, s), 7.99-7.93 (1H, m), 7.66 (1H, t, J 7.7 Hz), 7.49 (1H, dd, J 5.1, 1.3 Hz), 5.01-4.84 (1H, m), 4.06-3.75 (4H, m), 3.72-3.64 (4H, m), 3.13-3.03 (4H, m), 2.64 (2H, s), 2.48 (2H, s), 1.05 (6H, s). LCMS (ES+) 517.3 (M+H)$^+$.

Example 414

3-{2-[3-(3-Aminoazetidin-1-yl)phenyl]pyridin-4-yl}-5,5-dimethyl-2-(morpholin-4-yl)-5,6-dihydro-1-benzothiophen-7(4H)-one The title compound was prepared from Example 360 and azetidin-3-ylcarbamic acid tert-butyl ester according to Method BA and was obtained as a white solid (13%) after washing with saturated aqueous sodium hydrogencarbonate solution and purification by column chromatography (SiO$_2$, 0-20% MeOH/DCM, 1% NH$_4$OH). $\delta_H$ (CD$_3$OD) 8.56 (1H, dd, J 5.1, 0.8 Hz), 7.79 (1H, d, J 0.8 Hz), 7.34-7.30 (1H, m), 7.27-7.13 (2H, m), 7.02-6.97 (1H, m), 6.54-6.48 (1H, m), 4.17-4.07 (2H, m), 3.90-3.77 (1H, m), 3.64-3.44 (6H, m), 3.01-2.89 (4H, m), 2.56 (2H, s), 2.36 (2H, s), 0.94 (6H, s). LCMS (ES+) 489.3 (M+H)$^+$.

Example 415

3-{2-[3-(Azetidin-3-ylamino)phenyl]pyridin-4-yl}-5,5-dimethyl-2-(morpholin-4-yl)-5,6-dihydro-1-benzothiophen-7(4H)-one The title compound was prepared from Example 360 and 3-amino-1-(tert-butoxy-carbonyl)azetidine according to Method BA and was obtained as a yellow solid (24%) after washing with saturated aqueous sodium hydrogencarbonate solution and purification by column chromatography (SiO$_2$, 0-20% MeOH/DCM, 1% NH$_4$OH). $\delta_H$ (CD$_3$OD) 8.70 (1H, d, J 5.1 Hz), 7.89 (1H, s), 7.49-7.42 (1H, m), 7.38-7.28 (2H, m), 7.25-7.20 (1H, m), 6.79-6.70 (1H, m), 4.71-4.58 (1H, m), 4.53-4.40 (2H, m), 4.12-3.98 (2H, m), 3.77-3.59 (4H, m), 3.15-2.98 (4H, m), 2.62 (2H, s), 2.47 (2H, s), 1.05 (6H, s). LCMS (ES+) 489.2 (M+H)$^+$.

Example 416

(Method BF)

3-{2-[3-(1,4-Diazepan-1-ylmethyl)phenyl]pyridin-4-yl}-5,5-dimethyl-2-(morpholin-4-yl)-5,6-dihydro-1-benzothiophen-7(4H)-one A mixture of 3-(bromomethyl)phenylboronic acid (246 mg, 1.14 mmol), 1-(tert-butoxycarbonyl)homopiperazine (229 mg, 1.14 mmol) and triethylamine (280 µL, 2.0 mmol) in DCM (20 mL) was stirred at room temperature for 21 h. The solvent was removed in vacuo and the resulting boronic acid was combined with Example 73 (177 mg, 0.47 mmol), K$_3$PO$_4$ (80 mg, 0.38 mmol) and Pd(PPh$_3$)$_4$ (10 mg, 0.01 mmol) in DME (4.0 mL) and water (1.0 mL) and the reaction mixture was heated in a sealed tube at 140° C., under microwave irradiation, for 3 h. The reaction mixture was partitioned between EtOAc (25 mL) and aqueous sodium hydroxide solution (2N, 25 mL). The organic phase was concentrated in vacuo and purified by column chromatography (SiO$_2$, 0-20% MeOH/DCM, 1% NH$_4$OH). The obtained solid was taken up in MeOH (5.0 mL) and was treated with a solution of HCl in Et$_2$O (2N, 2.0 mL, 4.0 mmol). The reaction mixture was stirred at room temperature for 3 h and the solvent was removed in vacuo. The residue was partitioned between EtOAc (25 mL) and aqueous sodium hydroxide solution (2N, 25 mL). The organic phase was concentrated in vacuo and purified by column chromatography (SiO$_2$, 0-20% MeOH/DCM, 1% NH$_4$OH) to give the title compound (68 mg, 27%) as a clear glass. $\delta_H$ (DMSO-d$_6$) 8.75 (1H, d, J 5.1 Hz), 8.10 (1H, s), 8.04-7.97 (2H, m), 7.51-7.36 (3H, m), 3.71 (2H, s), 3.63-3.54 (4H, m), 3.40-3.27 (2H, m), 3.02-2.93 (4H, m), 2.83 (2H, t, J 6.2 Hz), 2.78-2.73 (2H, m), 2.69-2.63 (2H, m), 2.59 (2H, s), 2.39 (2H, s), 1.73-1.61 (2H, m), 0.97 (6H, s). LCMS (ES+) 531.3 (M+H)$^+$.

Example 417

Tert-Butyl 4-{3-[4-(5,5-dimethyl-2-(morpholin-4-yl)-7-oxo-4,5,6,7-tetrahydrothieno[2,3-c]pyridin-3-yl)pyridin-2-yl]phenyl}piperazine-1-carboxylate A mixture of Intermediate 19 (2.00 g, 5.10 mmol), 2-chloropyridine-4-boronic acid (0.81 g, 5.16 mmol), K$_3$PO$_4$ (1.1 g, 5.19 mmol) and Pd(PPh$_3$)$_4$ (0.59 g, 0.51 mmol) in DME (65 mL) and water (18 mL) was heated at 90° C. for 22 h. The reaction mixture was quenched with saturated aqueous sodium hydrogencarbonate solution (100 mL) and extracted into EtOAc (3×150 mL). The combined organic phases were washed with brine (100 mL) and dried (magnesium sulfate). The solvent was removed in vacuo and the residue was purified by column chromatography (SiO$_2$, 0-100% EtOAc/heptane). A sample of the solid obtained (100 mg) was combined with 3-[4-(tert-butoxycarbonyl)-piperazin-1-yl]phenylboronic acid pinacol ester (120 mg, 0.31 mmol), K$_3$PO$_4$ (85 mg, 0.40 mmol) and Pd(PPh$_3$)$_4$ (15 mg, 0.013 mmol) in DME (4 mL) and water (1 mL) and the mixture was heated in a sealed tube at 130° C., under microwave irradiation, for 1.5 h. The reaction mixture was partitioned between saturated aqueous sodium hydrogen-carbonate solution (30 mL) and EtOAc (30 mL) and the aqueous phase was extracted with further EtOAc (30 mL). The combined organic phases were dried (magnesium sulfate); the solvent was removed in vacuo and the residue was purified by column chromatography (SiO$_2$, 0-4% MeOH/DCM) to give the title compound (127 mg, 41%) as a white solid. $\delta_H$ (DMSO-d$_6$) 8.70 (1H, d, J 5.9 Hz), 8.07-8.03 (1H, m), 7.71-7.66 (1H, m), 7.60-7.52 (2H, m), 7.42 (1H, dd, J 4.9, 1.1 Hz), 7.37 (1H, t, J 8.1 Hz), 7.06 (1H, dd, 7.9, 1.9 Hz), 3.64-3.55 (4H, m), 3.55-3.44 (4H, m), 3.24-3.16 (4H, m), 2.94-2.86 (4H, m), 2.71 (2H, s), 1.42 (9H, s), 1.07 (6H, s). LCMS (ES+) 604.2 (M+H)$^+$.

Example 418

5,5-Dimethyl-2-(morpholin-4-yl)-3-{2-[3-(piperazin-1-yl)phenyl]pyridin-4-yl}-5,6-dihydrothieno[2,3-c]pyridin-7(4H)-one, Trifluoroacetic Acid Salt The title compound was prepared from Example 417 according to Method AT and was obtained as a yellow solid (88%) after trituration with Et$_2$O. $\delta_H$ (DMSO-d$_6$) 8.81-8.68 (3H, m), 8.08 (1H, s), 7.75-7.70 (1H, m), 7.66-7.61 (1H, m), 7.57 (1H, s), 7.48-7.37 (2H, m), 7.14-7.08 (1H, m), 3.65-3.56 (4H, m), 3.48-3.40 (4H, m), 3.35-3.21 (4H, m), 2.94-2.86 (4H, m), 2.71 (2H, s), 1.19 (6H, s). LCMS (ES+) 504.4 (M+H)$^+$.

Example 419

(Method BG)

5,5-Dimethyl-2-(morpholin-4-yl)-3-{6-[3-(piperazin-1-ylmethyl)phenyl]pyridin-2-yl}-5,6-dihydro-1-benzothiophen-7(4H)-one A mixture of Example 17 (1.00 g, 2.56 mmol), 6-chloropyridine-2-boronic acid pinacol ester (613 mg, 2.56 mmol), $K_3PO_4$ (1.63 g, 7.67 mmol) and $Pd(PPh_3)_4$ (148 mg, 0.128 mmol) in DME (6 mL) and water (2 mL) was heated in a sealed tube at 120° C., under microwave irradiation, for 20 minutes. The solvent was removed in vacuo and the residue was purified by column chromatography ($SiO_2$, 0-100% EtOAc/heptane). A sample of this intermediate (100 mg, 0.27 mmol), $K_3PO_4$ (85 mg, 0.40 mmol) and $Pd(PPh_3)_4$ (15 mg, 0.013 mmol) in DME (3 mL) and water (1 mL) was combined with the boronic acid (200 mg, 0.92 mmol) [formed from the reaction between 3-(bromomethyl)-phenylboronic acid (300 mg, 1.40 mmol), 1-(tert-butoxycarbonyl)piperazine (373 mg, 2.00 mmol) and triethylamine (280 μL, 2.00 mmol) in DCM (20 mL) and stirred at room temperature for 2 h before removal of the solvent in vacuo]. The mixture was heated in a sealed tube at 140° C., under microwave irradiation, for 2 h. The solvent was removed in vacuo and the residue was purified by column chromatography ($SiO_2$, 0-20% MeOH/EtOAc). The obtained solid was taken up in DCM (2.0 mL), MeOH (2.0 mL) and treated with a solution of HCl in $Et_2O$ (2N, 4.0 mL, 8.0 mmol) and stirred at room temperature for 18 h. The solvent was removed in vacuo and the residue was purified by column chromatography ($SiO_2$, 0-20% MeOH/DCM, 1% $NH_4OH$) to give the title compound (69 mg, 16%) as a yellow solid. $\delta_H$ ($CD_3OD$) 8.29-8.22 (1H, m), 8.17-8.04 (2H, m), 8.01-7.95 (1H, m), 7.68 (1H, dd, J 7.5, 0.8 Hz), 7.65-7.61 (2H, m), 4.30-4.16 (2H, m), 3.77-3.65 (4H, m), 3.35-3.42 (4H, m), 3.29-3.16 (4H, m), 3.14-3.04 (4H, m), 2.71 (2H, s), 2.48 (2H, s), 1.07 (6H, s). LCMS (ES+) 517.3 $(M+H)^+$.

Example 420

1-{3-[4-(5,5-Dimethyl-2-(morpholin-4-yl)-7-oxo-4,5,6,7-tetrahydro-1-benzothien-3-yl)pyridin-2-yl]benzyl}pyrrolidine-2,5-dione A mixture of Example 155 (100 mg, 0.22 mmol), diethyl azodicarboxylate (40 pt, 0.22 mmol), triphenylphosphine (59 mg, 0.22 mmol) and succinimide (22 mg, 0.22 mmol) in THF (5.0 mL) was stirred at room temperature for 18 h. The solvent was removed in vacuo and the residue was purified by column chromatography ($SiO_2$, 0-100% EtOAc/heptane) to give the title compound (51 mg, 44%) as a white solid. $\delta_H$ (DMSO-$d_6$) 8.75 (1H, d, J 5.1 Hz), 8.08-7.96 (3H, m), 7.47 (1H, t, J 7.7 Hz), 7.42 (1H, dd, J 5.1, 1.3 Hz), 7.37-7.32 (1H, m), 4.64 (2H, s), 3.66-3.55 (4H, m), 3.02-2.93 (4H, m), 2.70 (2H, s), 2.58 (2H, s), 2.38 (4H, s), 0.97 (6H, s). LCMS (ES+) 530.3 $(M+H)^+$.

Example 421

3-(3-Bromophenyl)-5,5-dimethyl-2-(morpholin-4-yl)-5,6-dihydrothieno[2,3-c]pyridin-7(4H)-one The title compound was prepared from Intermediate 19 and 3-bromophenyl-boronic acid according to Method J and was obtained as a white solid (40%) after purification by column chromatography ($SiO_2$, 0-80% EtOAc/heptane). $\delta_H$ (DMSO-$d_6$) 7.66 (1H, s), 7.56-7.47 (2H, m), 7.46-7.40 (2H, m), 3.62-3.53 (4H, m), 2.90-2.78 (4H, m), 2.60 (2H, s), 1.18 (6H, s). LCMS (ES+) 421.2, 423.2 $(M+H)^+$.

Example 422

Tert-Butyl (1-{3-[4-(5,5-dimethyl-2-(morpholin-4-yl)-7-oxo-4,5,6,7-tetrahydrothieno[2,3-c]pyridin-3-yl)pyridin-2-yl]benzoyl}piperidin-4-yl)carbamate The title compound was prepared from Example 318 and 4-(tert-butoxycarbonyl-amino)piperidine according to Method I and was obtained as a white solid (88%) after trituration with $Et_2O$. $\delta_H$ (DMSO-$d_6$) 8.74 (1H, d J 4.9 Hz), 8.23-8.18 (1H, m), 8.15-8.12 (1H, m), 8.10-8.07 (1H, m), 7.62-7.53 (2H, m), 7.49-7.39 (2H, m), 6.94-6.84 (1H, m), 4.45-4.27 (1H, m), 3.64-3.54 (4H, m), 3.54-3.43 (1H, m), 3.26-3.06 (1H, m), 2.93-2.86 (4H, m), 2.71 (2H, s), 1.91-1.64 (4H, m), 1.38 (9H, s), 1.18 (6H, s). LCMS (ES+) 646.2 $(M+H)^+$.

Example 423

Tert-Butyl N-(1-{3-[4-(5,5-dimethyl-2-(morpholin-4-yl)-7-oxo-4,5,6,7-tetrahydro-thieno[2,3-c]pyridin-3-yl)pyridin-2-yl]benzoyl}piperidin-4-yl)-N-methyl-carbamate The title compound was prepared from Example 318 and 4-[N-(tert-butoxy-carbonyl)-N-methylamino]piperidine according to Method I and was obtained as a white solid (87%) after trituration with $Et_2O$. $\delta_H$ (DMSO-$d_6$) 8.74 (1H, d, J 4.7 Hz), 8.26-8.20 (1H, m), 8.19-8.16 (1H, m), 8.12-8.10 (1H, m), 7.62-7.54 (2H, m), 7.50-7.44 (2H, m), 4.70-4.52 (1H, m), 4.16-3.85 (1H, m), 3.76-3.53 (5H, m), 3.31 (3H, s), 3.23-3.06 (1H, m), 2.94-2.86 (4H, m), 2.74-2.70 (1H, m), 2.69 (2H, s), 1.78-1.54 (4H, m), 1.40 (9H, s), 1.18 (6H, s). LCMS (ES+) 660.2 $(M+H)^+$.

Example 424

3-[2-(3-{[4-(Dimethylamino)piperidin-1-yl]carbonyl}phenyl)pyridin-4-yl]-5,5-dimethyl-2-(morpholin-4-yl)-5,6-dihydrothieno[2,3-c]pyridin-7(4H)-one The title compound was prepared from Example 318 and 4-(dimethylamino)-piperidine according to Method I and was obtained as an off-white solid (92%) after trituration with $Et_2O$. $\delta_H$ (DMSO-$d_6$) 8.74 (1H, d, J 5.3 Hz), 8.24-8.19 (1H, m), 8.16-8.14 (1H, m), 8.12-8.08 (1H, m), 7.62-7.54 (2H, m), 7.48-7.43 (2H, m), 4.56-4.38 (1H, m), 3.76-3.53 (5H, m), 3.18-2.98 (1H, m), 2.94-2.80 (4H, m), 2.71 (2H, s), 2.44-2.30 (1H, m), 2.23-2.13 (6H, s), 1.91-1.77 (1H, m), 1.77-1.63 (1H, m), 1.46-1.28 (2H, m), 1.19 (6H, s). LCMS (ES+) 574.3 $(M+H)^+$.

Example 425

5,5-Dimethyl-3-(2-{3-[(4-methylpiperazin-1-yl)carbonyl]phenyl}pyridin-4-yl)-2-(morpholin-4-yl)-5,6-dihydrothieno[2,3-c]pyridin-7(4H)-one The title compound was prepared from Example 318 and N-methylpiperazine according to Method I and was obtained as a pale yellow solid (90%) after trituration with $Et_2O$. $\delta_H$ (DMSO-$d_6$) 8.74 (1H, d, J 5.1 Hz), 8.25-8.19 (1H, m), 8.15-8.08 (2H, m), 7.62-7.53 (2H, m), 7.49-7.42 (2H, m), 3.75-3.54 (6H, m), 3.43-3.26 (2H, m), 2.95-2.85 (4H, m), 2.71 (2H, s), 2.43-2.23 (4H, m), 2.19 (3H, s), 1.19 (6H, s). LCMS (ES+) 546.3 $(M+H)^+$.

Example 426

5,5-Dimethyl-3-(2-morpholin-4-yl)-3-{2-[3-(pyrrolidin-1-ylcarbonyl)phenyl]pyridin-4-yl}-5,6-dihydrothieno[2,3-c]pyridin-7(4H)-one The title compound was prepared from Example 318 and pyrrolidine according to Method I and was obtained as a pale yellow solid (85%) after trituration with Et₂O. δ$_H$ (DMSO-d₆) 8.74 (1H, d, J 5.1 Hz), 8.27 (1H, s), 8.24-8.19 (1H, m), 8.10 (1H, s), 7.63-7.54 (3H, m), 7.47 (1H, dd, J 5.1, 1.3 Hz), 3.62-3.56 (4H, m), 3.53-3.37 (4H, m), 2.93-2.84 (4H, m), 2.71 (2H, s), 1.95-1.76 (4H, m), 1.19 (6H, s). LCMS (ES+) 517.3 (M+H)⁺.

Example 427

3-(2-{3-[(4-Aminopiperidin-1-yl)carbonyl] phenyl}pyridin-4-yl)-5,5-dimethyl-2-(morpholin-4-yl)-5,6-dihydrothieno[2,3-c]pyridin-7(4R)-one, Trifluoroacetic Acid Salt The title compound was prepared from Example 422 according to Method AT and was obtained as a yellow solid (100%) after trituration with Et₂O, δ$_H$ (DMSO-d₆) 8.74 (1H, d, J 5.1 Hz), 8.25-8.19 (1H, m), 8.17 (1H, s), 8.10 (1H, s), 7.93-7.84 (3H, m), 7.62 (1H, t, J 7.7 Hz), 7.57 (1H, s), 7.50-7.42 (2H, m), 4.60-4.40 (1H, m), 4.27-3.78 (1H, m), 3.68-3.64 (1H, m), 3.64-3.55 (4H, m), 3.34-3.24 (1H, m), 3.23-3.07 (1H, m), 2.93-2.87 (4H, m), 2.71 (2H, s), 2.06-1.77 (2H, m), 1.59-1.31 (2H, m), 1.19 (6H, s). LCMS (ES+) 546.3 (M+H)⁺.

Example 428

5,5-Dimethyl-3-[2-(3-{[4-(methylamino)piperidin-1-yl]carbonyl}phenyl)pyridin-4-yl]-2-(morpholin-4-yl)-5,6-dihydrothieno[2,3-c]pyridin-7(4H)-one, Trifluoroacetic Acid Salt The title compound was prepared from Example 423 according to Method AT and was obtained as a yellow solid (100%) after trituration with Et₂O. δ$_H$ (DMSO-d₆) 8.74 (1H, d, J 5.1 Hz), 8.57-8.46 (2H, m), 8.25-8.20 (1H, m), 8.17 (1H, s), 8.11 (1H, s), 7.62 (1H, t, J 7.7 Hz), 7.57 (1H, s), 7.50-7.43 (2H, m), 4.97-4.00 (2H, m), 3.79-3.64 (1H, m), 3.63-3.55 (4H, m), 3.33-3.19 (1H, m), 3.19-3.08 (1H, m), 2.94-2.83 (4H, m), 2.71 (2H, s), 2.62-2.55 (3H, m), 2.18-1.86 (2H, m), 1.58-1.32 (2H, m), 1.19 (6H, s). LCMS (ES+) 560.3 (M+H)⁺.

Example 429

(Method BH)

Tert-Butyl 3-[N-{3-[4-(5,5-dimethyl-2-(morpholin-4-0)-7-oxo-4,5,6,7-tetrahydro-1-benzothien-3-yl) pyridin-2-yl]benzoyl}-N-(ethyl)amino]azetidine-1-carboxylate Sodium hydride (60% dispersion in oil, 20 mg, 0.49 mmol) was added to a solution of Example 406 (120 mg, 0.33 mmol) in DMF (7.0 mL) and the reaction mixture was stirred at room temperature for 30 minutes. Bromoethane (40 μL, 0.49 mmol) was added and stirring was continued at room temperature for 1.5 h. Water (20 mL) was added and the mixture was extracted with EtOAc (75 mL). The organic phase was washed with water (7×20 mL), then with brine (20 mL), and was then dried (magnesium sulfate) and the solvent was removed in vacuo. The residue was purified by column chromatography (SiO₂, 75-100% EtOAc/heptane) to give the title compound (60 mg, 48%) as a yellow solid. δ$_H$ (CD₃OD) 8.75 (1H, d, J 5.1 Hz), 8.20-8.14 (1H, m), 8.11-8.06 (1H, m), 8.04-8.01 (1H, m), 7.66 (1H, t, J 7.7 Hz), 7.56-7.46 (2H, m), 4.80-4.60 (1H, m), 4.27-4.15 (4H, m), 3.74-3.62 (6H, m), 3.14-3.04 (4H, m), 2.64 (2H, s), 2.48 (2H, s), 1.46 (9H, s), 1.35-1.15 (3H, m), 1.05 (6H, s). LCMS (ES+) 645.1 (M+H)⁺.

Example 430

Methyl {3-[4-(5,5-dimethyl-2-(morpholin-4-yl)-7-oxo-4,5,6,7-tetrahydro-1-benzothien-3-yl)pyridin-2-yl]phenyl}acetate The title compound was prepared from Example 73 and [3-(4,4,5,5-tetramethyl-[1,3,2]dioxaborolan-2-yl)phenyl] acetic acid methyl ester according to Method J and was obtained as a white solid (50%) after purification by column chromatography (SiO₂, 0-3% MeOH/DCM and subsequently 0-100% EtOAc/heptane). δ$_H$ (DMSO-d₆) 8.75 (1H, d, J 4.9 Hz), 8.10-8.00 (3H, m), 7.47 (1H, t, J 7.7 Hz), 7.41 (1H, dd, J 4.9, 1.3 Hz), 7.38-7.33 (1H, m), 3.80 (2H, s), 3.63 (3H, s), 3.61-3.56 (4H, m), 3.01-2.92 (4H, m), 2.58 (2H, s), 2.38 (2H, s), 0.97 (6H, s). LCMS (ES+) 491.3 (M+H)⁺.

Example 431

Tert-Butyl 4-[3'-(5,5-dimethyl-2-(morpholin-4-yl)-7-oxo-4,5,6,7-tetrahydrothieno[2,3-c]pyridin-3-yl) biphenyl-3-yl]piperazine-1-carboxylate The title compound was prepared from Example 421 and 3-[4-(tert-butoxy-carbonyl)piperazin-1-yl]phenylboronic acid pinacol ester according to Method L, stirring at 130° C. under microwave irradiation for 1.5 h, and was obtained as a white solid (43%) after purification by column chromatography (SiO₂, 0-80% EtOAc/heptane and subsequently 0-3% MeOH/DCM). δ$_H$ (DMSO-d₆) 7.71 (1H, s), 7.65-7.58 (1H, m), 7.52 (1H, t, J 7.7 Hz), 7.49 (1H, s), 7.44-7.42 (1H, m), 7.41-7.39 (1H, m), 7.36-7.30 (1H, m), 7.22-7.19 (1H, m), 7.16-7.11 (1H, m), 7.01-6.95 (1H, m), 3.62-3.53 (4H, m), 3.53-3.44 (4H, m), 3.24-3.15 (4H, m), 2.92-2.83 (4H, m), 2.65 (2H, s), 1.42 (9H, s), 1.19 (6H, s). LCMS (ES+) 603.1 (M+H)⁺.

Example 432

(Method BI)

5,5-Dimethyl-3-(2-{3-[3-(methylamino)azetidin-1-yl]phenyl}pyridin-4-yl)-2-(morpholin-4-yl)-5,6-dihydro-1-benzothiophen-7(4H)-one A mixture of Example 360 (200 mg, 0.35 mmol), azetidin-3-ylcarbamic acid tert-butyl ester (125 mg, 0.71 mmol), potassium tert-butoxide (60 mg, 0.49 mmol) and acetato(2'-di-tert-butylphosphino-1,1'-biphenyl-2-yl)palladium(II) (10 mg, 0.02 mmol) in 1,4-dioxane (3.0 mL) was heated in a sealed tube at 100° C., under microwave irradiation, for 30 minutes. The solvent was removed in vacuo and the residue was purified by column chromatography (SiO₂, 0-100% EtOAc/heptane). To a solution of the obtained solid in DMF (10 mL) was added sodium hydride (60% dispersion in oil, 10 mg, 0.24 mmol) and the reaction was stirred at room temperature for 30 minutes. Methyl iodide (18 μL, 0.29 mmol) was added and stirring was continued at room temperature for 18 h. Further sodium hydride (60% dispersion in oil, 10 mg, 0.24 mmol) was added and stirring was continued for 2 h at room temperature. The solvent was removed in vacuo and the residue was purified by column chromatography (SiO₂, 0-100% EtOAc/heptane). To a solution of the obtained solid in DCM (8 mL) was added TFA (2 mL) and the reaction mixture was stirred at room temperature for 2 h. The solvent was removed in vacuo and the residue was partitioned between DCM (20 mL) and saturated aqueous sodium hydrogencarbonate solution (20 mL). The organic phase was concentrated in vacuo and was purified by column chromatography (SiO$_2$, 0-20% MeOH/DCM) to give the title compound (5 mg, 31%) as a clear glass. δ$_H$(CD$_3$OD) 8.68 (1H, d, J 5.1 Hz), 7.91 (1H, s), 7.44 (1H, dd, J 5.3, 1.7 Hz), 7.39-7.29 (2H, m), 7.14-7.08 (1H, m), 6.68-6.60 (1H, m), 4.29-4.17 (2H, m), 4.02-3.91 (1H, m), 3.74-3.56 (6H, m), 3.15-3.01 (4H, m), 2.64 (2H, s), 2.47 (2H, m), 1.05 (6H, s). LCMS (ES+) 503.3 (M+H)$^+$.

Example 433

5,5-Dimethyl-2-(morpholin-4-yl)-3-[3'-(piperazin-1-yl)biphenyl-3-yl]-5,6-dihydrothieno[2,3-c]pyridin-7(4H)-one, Trifluoroacetic Acid Salt The title compound was prepared from Example 431 according to Method AT and was obtained as a white solid (98%) after trituration with Et$_2$O. δ$_H$ (DMSO-d$_6$) 8.79-8.68 (2H, m), 7.73 (1H, s), 7.68-7.62 (1H, m), 7.58-7.48 (2H, m), 7.47-7.34 (2H, m), 7.26 (1H, d, J 0.6 Hz), 7.23-7.18 (1H, m), 7.07-7.00 (1H, m), 3.61-3.54 (4H, m), 3.52-3.30 (4H, m), 3.31-323 (4H, m), 2.91-2.84 (4H, m), 2.65 (2H, s), 1.19 (6H, s). LCMS (ES+) 503.3 (M+H)$^+$.

Example 434

3-[2-(3-{[(3R)-3-Aminopyrrolidin-1-yl]carbonyl}phenyl)pyridin-4-yl]-2-(morpholin-4-yl)-5,5,6-trimethyl-5,6-dihydrothieno[2,3-c]pyridin-7(4H)-one Sodium hydride (60% dispersion in oil, 32 mg, 0.80 mmol) was slowly added to a mixture of 3-(2-chloropyridin-4-yl)-5,5-dimethyl-2-(morpholin-4-yl)-5,6-dihydro-thieno[2,3-c]pyridin-7(4H)-one (300 mg, 0.79 mmol) and methyl iodide (107 mg, 0.75 mmol) in DMF (7.0 mL) and the reaction mixture was stirred at room temperature for 2 h. The solvent was removed in vacuo and the residue was purified by column chromatography (SiO$_2$, 0-100% EtOAc/heptane). A sample of the obtained solid (100 mg) was combined with Intermediate 60 (105 mg, 0.31 mmol), K$_3$PO$_4$ (43 mg, 0.20 mmol), tetrabutylammonium bromide (80 mg, 0.25 mmol) and Pd(PPh$_3$)$_4$ (240 mg, 0.208 mmol) in DME (2.0 mL) and water (0.5 mL) and the mixture was heated in a sealed tube at 140° C., under microwave irradiation, for 3 h. The reaction mixture was partitioned between aqueous sodium hydroxide solution (2M, 15 mL) and EtOAc (15 mL). The organic phase was concentrated in vacuo and the residue was purified by column chromatography (SiO$_2$, 0-10% MeOH/DCM). The obtained solid was taken up in MeOH (5.0 mL) and a solution of HCl in Et$_2$O (2N, 2.0 mL, 4.0 mmol) was added. The reaction mixture was stirred at room temperature for 3 h and the solvent was removed in vacuo. The residue was purified by column chromatography (SiO$_2$, 0-15% MeOH/DCM, 0.75% NH$_4$OH) to give the title compound (68 mg, 33%) as a clear oil. δ$_H$ (CD$_3$OD) 8.73 (1H, d, J 5.1 Hz), 8.31-8.24 (1H, m), 8.20-8.14 (1H, m), 8.05 (1H, s), 7.73-7.60 (2H, m), 7.53-7.47 (1H, m), 4.07-3.56 (9H, m), 3.04 (3H, s), 3.00-2.94 (4H, m), 2.86 (2H, s), 2.49-2.31 (1H, m), 2.19-2.04 (1H, m), 1.32 (6H, s). LCMS (ES+) 546.1 (M+H)$^+$.

Example 435

(Method BJ)

4-{3-[4-(5,5-Dimethyl-2-(morpholin-4-yl)-7-oxo-4,5,6,7-tetrahydro-1-benzothien-3-yl)pyridin-2-yl]benzyl}piperazin-2-one, Acetic Acid Salt A mixture of 3-(bromomethyl)phenylboronic acid (246 mg, 1.14 mmol), piperazinone (114 mg, 1.14 mmol) and triethylamine (280 µL, 2.0 mmol) in DCM (20 mL) was stirred at room temperature for 21 h. The solvent was removed in vacuo and the resulting boronic acid was combined with Example 73 (285 mg, 0.76 mmol), K$_3$PO$_4$ (80 mg, 0.38 mmol) and Pd(PPh$_3$)$_4$ (10 mg, 0.01 mmol) in DME (5.0 mL) and water (1.0 mL) and the reaction mixture was heated in a sealed tube at 140° C., under microwave irradiation, for 3 h. The organic phase was concentrated in vacuo and purified by preparative HPLC (pH 5.8) to give the title compound (70 mg, 16%) as an off-white solid. δ$_H$ (DMSO-d$_6$) 8.75 (1H, d, J 4.9 Hz), 8.13 (1H, s), 8.08-8.02 (2H, m), 7.76 (1H, s), 7.49 (1H, t, J 7.7 Hz), 7.44-7.38 (2H, m), 3.67 (2H, s), 3.63-3.56 (4H, m), 3.21-3.13 (2H, m), 3.03-2.96 (4H, m), 2.94 (2H, s), 2.65-2.56 (4H, m), 2.39 (2H, s), 1.88 (3H, s), 0.97 (6H, s). LCMS (ES+) 531.3 (M+H)$^+$.

Example 436

5,5-Dimethyl-2-(morpholin-4-yl)-3-(6-{3-[(3S)-pyrrolidin-3-ylamino]phenyl}pyridin-2-yl)-5,6-dihydro-1-benzothiophen-7(4H)-one A mixture of Example 17 (8.16 g, 20.9 mmol), 6-chloropyridine-2-boronic acid pinacol ester (5.0 mg, 20.9 mmol), K$_3$PO$_4$ (6.64 g, 31.3 mmol) and Pd(PPh$_3$)$_4$ (1.20 g, 1.04 mmol) in DME (350 mL) and water (35 mL) was heated at reflux for 50 h. The solvent was removed in vacuo and the residue was purified by column chromatography (SiO$_2$, 20-60% EtOAc/heptane). A sample of the intermediate so obtained (400 mg) was combined with 3-hydroxyphenylboronic acid (148 mg, 1.07 mmol), K$_3$PO$_4$ (340 mg, 1.60 mmol) and Pd(PPh$_3$)$_4$ (60 mg, 0.052 mmol) in DME (9 mL) and water (3 mL) and the mixture was heated in a sealed tube at 120° C., under microwave irradiation, for 2 h. The solvent was removed in vacuo and the residue was purified by column chromatography (SiO$_2$, 0-100% EtOAc/heptane). The obtained solid was combined with N-phenyl-trifluoromethanesulfonimide (228 mg, 0.61 mmol), and triethylamine (0.15 mL, 1.11 mmol) in DCM (10 mL) and the reaction mixture was stirred at room temperature for 1.5 h. The solvent was removed in vacuo and the residue was purified by column chromatography (SiO$_2$, 0-100% EtOAc/heptane). A sample of the obtained solid (100 mg) was combined with (S)-3-amino-1-(tert-butoxycarbonyl)pyrrolidine (0.06 mL, 0.35 mmol), potassium tert-butoxide (28 mg, 0.25 mmol) and acetato(2'-di-tert-butyl-phosphino-1,1'-biphenyl-2-yl)palladium(II) (42 mg, 0.09 mmol) in 1,4-dioxane (2.0 mL) and the mixture was heated in a sealed tube at 100° C., under microwave irradiation, for 1 h. The solvent was removed in vacuo and the residue was purified by column chromatography (SiO$_2$, 0-100% EtOAc/heptane). A sample of the obtained solid (20 mg) was taken up in DCM (1.0 mL) and MeOH (1.0 mL) and was treated with a solution of HCl in Et$_2$O (2M, 0.5 mL, 1.0 mmol). The reaction mixture was stirred at room temperature for 18 h. The solvent was removed in vacuo and the residue was purified by column chromatography (0-20% MeOH/DCM, 1% NH$_4$OH) to give the title compound (11 mg, 4%) as a yellow solid. $\delta_H$ (CD$_3$OD) 7.98-7.91 (1H, m), 7.78 (1H, dd, J 7.7, 0.6 Hz), 7.56 (1H, dd, J 7.7, 0.8 Hz), 7.36-7.23 (3H, m), 6.77 (1H, dt, J 7.3, 1.9 Hz), 4.19-4.08 (1H, m), 3.74-3.64 (4H, m), 3.31-3.15 (2H, m), 3.12-2.94 (6H, m), 2.70 (2H, s), 2.47 (2H, s), 2.33-2.17 (1H, m), 1.94-1.80 (1H, m), 1.06 (6H, s). LCMS (ES+) 503.4 (M+H)$^+$.

Example 437

3-[2-(3-Bromophenyl)pyrimidin-4-yl]-5,5-dimethyl-2-(morpholin-4-yl)-5,6-dihydro-1-benzothiophen-7(4H)-one A mixture of Example 344 (1.60 g, 4.42 mmol), 3-bromobenzamidine hydrochloride (1.04 g, 4.42 mmol) and sodium methoxide solution (25% w/w in MeOH, 3 mL, 15 mmol) in MeOH was heated at reflux for 21 h. The reaction mixture was evaporated in vacuo and the residue was purified by column chromatography (SiO$_2$, 0-100% EtOAc/heptane) to give the title compound (477 mg, 22%) as a pale yellow solid. $\delta_H$ (CDCl$_3$) 8.83 (1H, d, J 5.3 Hz), 8.66 (1H, d, J 1.5 Hz), 8.41 (1H, dd, J 7.7, 0.9 Hz), 7.69-7.62 (2H, m), 7.40 (1H, t, J 7.7 Hz), 3.82-3.73 (4H, m), 3.13-3.05 (4H, m), 2.90 (2H, s), 2.49 (2H, s), 1.10 (6H, s). LCMS (ES+) 500.2 (M+H)$^+$.

Example 438

(Method BK)

5,5-Dimethyl-3-[2-(4-methylphenyl)pyridin-4-yl]-2-(morpholin-4-yl)-5,6-dihydro-1-benzothiophen-7(4H)-one A mixture of Example 73 (100 mg, 0.27 mmol), 4-methylphenylboronic acid (37 mg, 0.27 mmol), K$_3$PO$_4$ (65 mg, 0.31 mmol) and Pd(PPh$_3$)$_4$ (11 mg, 0.01 mmol) in DME (4 mL) and water (1 mL) was heated in a sealed tube at 150° C., under microwave irradiation, for 10 minutes. The reaction mixture was concentrated in vacuo and purified by preparative HPLC (pH 2.5) to give the title compound (12 mg, 10%) as a yellow solid. $\delta_H$ (CDCl$_3$) 8.76 (1H, d, J 5.3 Hz), 7.98-7.92 (2H, m), 7.78 (1H, s), 7.36-7.31 (2H, m), 7.24 (1H, dd, J 5.1, 1.5 Hz), 3.74-3.65 (4H, m), 3.09-3.00 (4H, m), 2.55 (2H, s), 2.47 (2H, s), 2.45 (3H, s), 1.06 (6H, s). LCMS (ES+) 433.3 (M+H)$^+$.

Example 439

5,5-Dimethyl-3-[2-(4-fluorophenyl)pyridin-4-yl]-2-(morpholin-4-yl)-5,6-dihydro-1-benzothiophen-7(4H)-one The title compound was prepared from Example 73 and 4-fluorophenylboronic acid according to Method BK and was obtained as a beige solid (21%) after purification by preparative HPLC (pH 2.5). $\delta_H$ (CDCl$_3$) 8.76 (1H, d, J 4.1 Hz), 8.08-8.00 (2H, m), 7.76 (1H, s), 7.31-7.16 (3H, m), 3.74-3.65 (4H, m), 3.08-2.99 (4H, m), 2.55 (2H, s), 2.48 (2H, s), 1.07 (6H, s). LCMS (ES+) 437.0 (M+H)$^+$.

Example 440

3-[2-(4-Chlorophenyl)pyridin-4-yl]-5,5-dimethyl-2-(morpholin-4-yl)-5,6-dihydro-1-benzothiophen-7(4H)-one The title compound was prepared from Example 73 and 4-chlorophenylboronic acid according to Method BK and was obtained as a yellow solid (21%) after purification by preparative HPLC (pH 2.5). $\delta_H$ (CDCl$_3$) 8.77 (1H, d, J 5.1 Hz), 8.03-7.97 (2H, m), 7.79 (1H, s), 7.53-7.46 (2H, m), 7.30-7.26 (1H, m), 3.73-3.64 (4H, m), 3.09-2.99 (4H, m), 2.54 (2H, s), 2.47 (2H, s), 1.07 (6H, s). LCMS (ES+) 453.3, 455.3 (M+H)$^+$.

Example 441

(Method BL)

2-{3-[4-(5,5-Dimethyl-2-(morpholin-4-yl)-7-oxo-4,5,6,7-tetrahydro-1-benzothien-3-yl)pyridin-2-yl]phenyl}-N,N-dimethylacetamide A solution of lithium hydroxide monohydrate (58 mg, 1.38 mmol) in water (7.5 mL) was added to a solution of Example 430 (340 mg, 0.69 mmol) in THF (30 mL) and the reaction mixture was stirred at room temperature for 23 h. Dilute aqueous HCl (1N) was added dropwise until a yellow coloration just persisted and the mixture was extracted into EtOAc (2×50 mL). The combined organic extracts were washed with brine (40 mL), dried (magnesium sulfate) and evaporated in vacuo. A sample of the obtained solid (40 mg) was combined with dimethylamine hydrochloride (8.0 mg, 0.1 mmol), triethylamine (38 μL, 0.27 mmol), EDC (17 mg, 0.09 mmol) and 1-hydroxybenzotriazole (catalytic amount) in DCM (3.0 mL) and the reaction mixture was stirred at room temperature for 72 h. The reaction mixture was diluted with DCM (5 mL), then washed with water (10 mL) and saturated aqueous sodium hydrogencarbonate solution (10 mL). The organic phase was dried (magnesium sulfate) and the solvent was removed in vacuo. The residue was triturated with Et$_2$O to give the title compound (25 mg, 64%) as a white powder. $\delta_H$ (DMSO-d$_6$) 8.74 (1H, d, J 4.9 Hz), 8.05-7.97 (3H, m), 7.45 (1H, t, J 7.7 Hz), 7.39 (1H, dd, J 4.9, 1.1 Hz), 7.34-7.29 (1H, m), 3.79 (2H, s), 3.64-3.55 (4H, m), 3.04 (3H, s), 3.00-2.94 (4H, m), 2.84 (3H, s), 2.57 (2H, s), 2.38 (2H, s), 0.97 (6H, s). LCMS (ES+) 504.3 (M+H)$^+$.

Example 442

5,5-Dimethyl-2-(morpholin-4-yl)-3-{2-[3-(2-oxo-2-(pyrrolidin-1-yl)ethyl)phenyl]pyridin-4-yl}-5,6-dihydro-1-benzothiophen-7(4H)-one The title compound was prepared from Example 430 and pyrrolidine according to Method BL and was obtained as an off-white solid (97%). $\delta_H$ (DMSO-d$_6$) 8.74 (1H, d, J 4.9 Hz), 8.06-7.94 (3H, m), 7.45 (1H, t, J 7.7 Hz), 7.40 (1H, dd, J 4.9, 1.1 Hz), 7.35-7.29 (1H, m), 3.72 (2H, s), 3.63-3.55 (4H, m), 3.56-3.47 (2H, m), 3.37-3.26 (2H, m), 3.01-2.92 (4H, m), 2.56 (2H, s), 2.38 (2H, s), 1.93-1.82 (2H, m), 1.82-1.70 (2H, m), 0.97 (6H, s). LCMS (ES+) 530.3 (M+H)$^+$.

Example 443

5,5-Dimethyl-2-(morpholin-4-yl)-3-{2-[3-(piperazin-1-ylmethyl)phenyl]pyridin-4-yl}-5,6-dihydrothieno[2,3-c]pyridin-7(4H)-one A mixture of Intermediate 19 (700 mg, 1.79 mmol), 2-chloropyridine-4-boronic acid (284 mg, 1.81 mmol), K$_3$PO$_4$ (456 mg, 2.15 mmol) and Pd(PPh$_3$)$_4$ (240 mg, 0.208 mmol) in DME (22 mL) and water (6.8 mL) was heated in a sealed tube at 120° C., under microwave irradiation, for 40 minutes. The reaction was quenched with saturated aqueous NaHCO$_3$ solution and extracted into EtOAc (4×85 mL). The combined organic phases were dried (magnesium sulfate) and the solvent was removed in vacuo. The residue was purified by column chromatography (SiO₂, 0-100% EtOAc/heptane) to give a pale orange solid (235 mg). A portion of this intermediate (100 mg) was combined with the boronic acid (105 mg, 0.48 mmol) [formed from the reaction between 3-(bromomethyl)phenylboronic acid (300 mg, 1.40 mmol), 1-(tert-butoxycarbonyl)piperazine (373 mg, 2.00 mmol) and triethylamine (280 µL, 2.00 mmol) in DCM (20 mL) and stirred at room temperature for 2 h before removal of the solvent in vacuo], $K_3PO_4$ (43 mg, 0.20 mmol), tetrabutylammonium bromide (80 mg, 0.25 mmol) and $Pd(PPh_3)_4$ (5 mg, 0.004 mmol) in DME (2.0 mL) and water (0.5 mL) and was heated in a sealed tube at 140° C., under microwave irradiation, for 3 h. The reaction mixture was partitioned between aqueous sodium hydroxide solution (2M, 15 mL) and EtOAc (15 mL). The organic phase was concentrated in vacuo and the residue was taken up in MeOH (4.0 mL) and a solution of HCl in $Et_2O$ (2N, 4.0 mL, 8.0 mmol) was added. The reaction mixture was stirred at room temperature for 4 h and the solvent was removed in vacuo. The residue was purified by column chromatography (SiO₂, 0-20% MeOH/DCM, 1% $NH_4OH$) to give the title compound (16 mg, 4%) as a yellow solid. $\delta_H$ (CD₃OD) 8.75 (1H, d, J 4.9 Hz), 8.13 (1H, s), 8.07-8.01 (2H, m), 7.79-7.74 (1H, m), 7.49 (1H, t, J 7.7 Hz), 7.43-7.38 (2H, m), 3.64 (2H, s), 3.62-3.56 (4H, m), 3.00-2.95 (4H, m), 2.93 (2H, s), 2.59 (2H, s), 2.39 (2H, s), 1.88 (3H, s), 0.97 (6H, s). LCMS (ES+) 518.1 (M+H)⁺.

Example 444

5,5-Dimethyl-3-(2-{3-[2-(4-methylpiperazin-1-yl)-2-oxoethyl]phenyl}pyridin-4-yl)-2-(morpholin-4-yl)-5,6-dihydro-1-benzothiophen-7(4H)-one The title compound was prepared from Example 430 and 1-methylpiperazine according to Method BL and was obtained as a white solid (62%). $\delta_H$ (DMSO-d₆) 8.74 (1H, d, J 5.1 Hz), 8.05-7.97 (3H, m), 7.45 (1H, t, J 7.5 Hz), 7.39 (1H, dd, J 5.1, 1.3 Hz), 7.34-7.29 (1H, m), 3.81 (2H, s), 3.62-3.55 (4H, m), 3.53-3.44 (4H, m), 3.02-2.91 (4H, m), 2.57 (2H, s), 2.38 (2H, s), 2.27-2.17 (4H, m), 2.12 (3H, s), 0.97 (6H, s). LCMS (ES+) 559.3 (M+H)⁺.

Example 445

N-[2-(Diethylamino)ethyl]-2-{3-[4-(5,5-dimethyl-2-(morpholin-4-yl)-7-oxo-4,5,6,7-tetrahydro-1-benzothien-3-yl)pyridin-2-yl]phenyl}-N-methylacetamide The title compound was prepared from Example 430 and N,N-diethyl-N'-methyl-ethylenediamine according to Method BL and was obtained as a white solid (89%). $\delta_H$ (DMSO-d₆) 8.74 (1H, d, J 4.9 Hz), 8.04-7.96 (3H, m), 7.49-7.36 (2H, m), 7.35-7.27 (1H, m), 3.83 (1H, s), 3.77 (1H, s), 3.64-3.56 (4H, m), 3.44-3.36 (2H, m), 3.01-2.94 (4H, m), 2.85 (3H, s), 2.57 (2H, s), 2.48-2.36 (14H, m), 0.96 (6H, s), 0.93-0.84 (6H, m). LCMS (ES+) 589.2 (M+H)⁺.

Example 446

Tert-Butyl 3-[({3-[4-(5,5-dimethyl-2-(morpholin-4-yl)-7-oxo-4,5,6,7-tetrahydro-1-benzothien-3-yl)pyridin-2-yl]phenyl}acetyl)amino]azetidine-1-carboxylate The title compound was prepared from Example 430 and 3-amino-1-(tert-butoxy-carbonyl)azetidine according to Method BL and was obtained as a white solid (100%). $\delta_H$ (DMSO-d₆) 8.78-8.72 (2H, m), 8.09-8.05 (1H, m), 8.02-7.96 (2H, m), 7.45 (1H, t, J 7.7 Hz), 7.40 (1H, dd, J 4.9, 1.3 Hz), 7.36-7.31 (1H, m), 4.43-4.31 (1H, m), 4.10-4.00 (2H, m), 3.71-3.63 (2H, m), 3.62-3.55 (4H, m), 3.01-2.92 (4H, m), 2.57 (2H, m), 2.38 (2H, m), 1.37 (9H, s), 0.97 (6H, s). LCMS (ES+) 631.1 (M+H)⁺.

Example 447

(Method BM)

3-(2-{3-[(3-Aminoazetidin-1-yl)carbonyl]phenyl}pyridin-4-yl)-5,5-dimethyl-2-(morpholin-4-yl)-5,6-dihydro-1-benzothiophen-7(4H)-one Trifluoroacetic acid (1.0 mL) was added to a solution of Example 405 (75 mg, 0.122 mmol) in DCM (5.0 mL) and the reaction mixture was stirred at room temperature for 30 minutes. The solvent was removed in vacuo and the residue was purified by preparative HPLC (pH 5.8). The obtained product was partitioned between saturated sodium hydrogencarbonate solution (50 mL) and DCM (75 mL) and the aqueous phase was extracted with further DCM (75 mL). The combined organic phases were dried (magnesium sulfate) and the solvent was removed in vacuo to give the title compound as an off-white solid (26 mg, 41%). $\delta_H$ (CD₃OD) 8.75 (1H, dd, J 5.1, 0.6 Hz), 8.35-8.31 (1H, m), 8.22-8.16 (1H, m), 8.00 (1H, s), 7.80-7.82 (1H, m), 7.65 (1H, t, J 7.9 Hz), 7.51-7.45 (1H, m), 4.65-4.56 (1H, m), 4.50-4.38 (1H, m), 4.19-4.09 (1H, m), 3.99-3.84 (2H, m), 3.73-3.64 (4H, m), 3.12-3.04 (4H, m), 2.65 (2H, m), 2.48 (2H, m), 1.05 (6H, s). LCMS (ES+) 517.3 (M+H)⁺.

Example 448

Tert-Butyl[1-({3-[4-(5,5-dimethyl-2-(morpholin-4-yl)-7-oxo-4,5,6,7-tetrahydro-1-benzothien-3-yl)pyridin-2-yl]phenyl}acetyl)azetidin-3-yl]carbamate The title compound was prepared from Example 430 and azetidin-3-ylcarbamic acid tert-butyl ester according to Method BL and was obtained as a white solid (47%) after purification by column chromatography (SiO₂, 0-100% EtOAc/heptane). $\delta_H$ (DMSO-d₆) 8.74 (1H, d J 5.1 Hz), 8.04-7.94 (3H, m), 7.60-7.52 (1H, m), 7.60-7.52 (1H, m), 7.47-7.36 (2H, m), 7.34-7.30 (1H, m), 4.47-4.36 (1H, m), 4.31-4.21 (1H, m), 4.12-3.95 (2H, m), 3.72-3.63 (1H, m), 3.62-3.56 (4H, m), 3.51 (2H, s), 3.03-2.92 (4H, m), 2.58 (2H, s), 2.38 (1H, s), 1.37 (9H, s), 0.97 (6H, s). LCMS (ES+) 631.2 (M+H)⁺.

Example 449

Tert-Butyl [(3S)-1-({3-[4-(5,5-dimethyl-2-(morpholin-4-yl)-7-oxo-4,5,6,7-tetrahydro-1-benzothien-3-yl)pyridin-2-yl]phenyl}acetyl)pyrrolidin-3-yl]carbamate The title compound was prepared from Example 430 and (3S)-(+3-(tert-butoxy-carbonylamino)pyrrolidine according to Method BL and was obtained as a white solid (78%) after purification by column chromatography (SiO₂, 0-100% EtOAc/heptane). $\delta_H$ (DMSO-d₆) 8.74 (1H, d, J 4.9 Hz), 8.04 (1H, s), 8.02-7.96 (2H, m), 7.48-7.37 (2H, m), 7.34-7.29 (1H, m), 7.21-7.11 (1H, m), 4.09-3.89 (1H, m), 3.77-3.09 (10H, m), 3.01-2.94 (4H, m), 2.57 (2H, s), 2.38 (2H, s), 2.11-1.65 (2H, m), 1.37 (9H, d, J 4.5 Hz), 0.97 (6H, s). LCMS (ES+) 645.2 (M+H)$^+$.

Example 450

Tert-Butyl N-[1-({3-[4-(5,5-dimethyl-2-(morpholin-4-yl)-7-oxo-4,5,6,7-tetrahydro-1-benzothien-3-yl) pyridin-2-yl]phenyl}acetyl)piperidin-4-yl]-N-methylcarbamate The title compound was prepared from Example 430 and 4-[N-(tert-butoxy-carbonyl)-N-methylamino]piperidine according to Method BL and was obtained as a white solid (100%). $\delta_H$ (DMSO-d$_6$) 8.74 (1H, d, J 5.1 Hz), 8.04 (1H, s), 8.02-7.97 (2H, m), 7.46 (1H, t, J 7.7 Hz), 7.39 (1H, dd, J 4.9, 1.3 Hz), 7.36-7.31 (1H, m), 4.58-4.47 (1H, m), 4.09-3.96 (2H, m), 3.86-3.81 (2H, m), 3.63-3.55 (4H, m), 3.08-2.92 (6H, m), 2.57 (2H, s), 2.53-2.46 (3H, m), 2.38 (2H, s), 1.63-1.43 (4H, m), 0.97 (6H, s). LCMS (ES+) 673.2 (M+H)$^+$.

Example 451

N-(Azetidin-3-yl)-2-{3-[4-(5,5-dimethyl-2-(morpholin-4-yl)-7-oxo-4,5,6,7-tetrahydro-1-benzothien-3-yl)pyridin-2-yl]phenyl}acetamide, Trifluoroacetic Acid Salt The title compound was prepared from Example 446 according to Method AT and was obtained as a yellow solid (83%). $\delta_H$ (DMSO-d$_6$) 8.85 (1H, d, J 7.0 Hz), 8.75 (1H, d, J 5.1 Hz), 8.68-8.58 (2H, br 8.45-8.30 (1H, br m), 8.07 (1H, s), 8.02-7.97 (2H, m), 7.50-7.30 (3H, m), 4.64-4.46 (1H, m), 4.28-3.83 (6H, m), 3.64-3.50 (4H, m), 3.03-2.90 (4H, m), 2.57 (2H, s), 2.39 (2H, s), 0.97 (6H, s). LCMS (ES+) 531.3 (M+H)$^+$.

Example 452

3-(2-{3-[2-(3-Aminoazetidin-1-yl)-2-oxoethyl] phenyl}pyridin-4-yl)-5,5-dimethyl-2-(morpholin-4-yl)-5,6-dihydro-1-benzothiophen-7(4H)-one, Trifluoroacetic Acid Salt The title compound was prepared from Example 448 according to Method AT and was obtained as a yellow solid (100%). $\delta_H$ (DMSO-d$_6$) 8.75 (1H, d, J 7.9 Hz), 8.32-8.20 (3H, m), 8.05 (1H, s), 8.02-7.97 (2H, m), 7.47 (1H, t, J 7.7 Hz), 7.42 (1H, dd, J 4.9, 1.3 Hz), 7.37-7.32 (1H, m), 4.53-4.43 (1H, m), 4.22-3.78 (4H, m), 3.63-3.53 (6H, m), 3.03-2.92 (4H, m), 2.57 (2H, s), 2.39 (2H, s), 0.97 (6H, s). LCMS (ES+) 531.3 (M+H)$^+$.

Example 453

3-[2-(3-{2-[(3S)-3-Aminopyrrolidin-1-yl]-2-oxo ethyl}phenyl)pyridin-4-yl]-5,5-dimethyl-2-(morpholin-4-yl)-5,6-dihydro-1-benzothiophen-7(4H)-one, Trifluoroacetic Acid Salt The title compound was prepared from Example 449 according to Method AT and was obtained as a yellow solid (95%). $\delta_H$ (DMSO-d$_6$) 8.74 (1H, d, J 4.9 Hz), 8.11-7.92 (6H, m), 7.50-7.38 (2H, m), 7.37-7.29 (1H, m), 4.02-3.32 (9H, m), 3.04-2.91 (4H, m), 2.57 (2H, s), 2.38 (2H, s), 2.32-1.86 (2H, m), 0.96 (6H, s). LCMS (ES+) 545.3 (M+H)$^+$.

Example 454

5,5-Dimethyl-3-[2-(3-{2-[4-(methylamino)piperidin-1-yl]-2-oxoethyl}phenyl)pyridin-4-yl]-2-(morpholin-4-yl)-5,6-dihydro-1-benzothiophen-7(4H)-one, Trifluoroacetic Acid Salt The title compound was prepared from Example 450 according to Method AT and was obtained as a yellow solid (86%). $\delta_H$ (DMSO-d$_6$) 8.75 (1H, d, J 4.9 Hz), 8.56-8.41 (2H, br m), 8.08-7.96 (3H, m), 7.46 (1H, t, J 7.5 Hz), 7.41 (1H, dd, J 4.9, 1.1 Hz), 7.33 (1H, m), 4.52-4.40 (1H, m), 4.18-4.08 (1H, m), 4.00-3.65 (2H, m), 3.65-3.54 (2H, m), 3.28-3.14 (1H, m), 3.09-2.90 (5H, m), 2.65-2.52 (6H, m), 2.39 (2H, s), 2.05-1.91 (2H, m), 1.37-1.20 (2H, m), 0.97 (6H, s). LCMS (ES+) 573.3 (M+H)$^+$.

Example 455

3-{2-[3-(3,8-Diazabicyclo[3.2.1]oct-3-ylmethyl) phenyl]pyridin-4-yl}-5,5-dimethyl-2-(morpholin-4-yl)-5,6-dihydro-1-benzothiophen-7(4H)-one The title compound was prepared from 3-(bromomethyl) phenylboronic acid, 8-(tert-butoxycarbonyl)-3,8-diazabicyclo[3.2.1]octane and Example 73 according to Method BF and was obtained as an off-white solid (50%) after purification by column chromatography (SiO$_2$, 0-20% MeOH/DCM, 1% NH$_4$OH). $\delta_H$ (DMSO-d$_6$) 8.75 (1H, d, J 4.9 Hz), 8.10-7.93 (3H, m), 7.46 (1H, t, J 7.5 Hz), 7.42-7.33 (2H, m), 3.66-3.55 (4H, m), 3.52 (2H, s), 3.04-2.90 (4H, m), 2.59-2.48 (6H, m), 2.17 (2H, d, J 10.2 Hz), 2.39 (2H, s), 1.79 (2H, d, J 6.4 Hz), 1.64-1.55 (2H, m), 0.97 (6H, s). LCMS (ES+) 543.3 (M+H)$^+$.

Example 456

3-[6-(3-{[(3R)-3-Aminopyrrolidin-1-yl] methyl}phenyl)pyridin-2-yl]-5,5-dimethyl-2-(morpholin-4-yl)-5,6-dihydro-1-benzothiophen-7(4H)-one The title compound was prepared from Example 17, 6-chloropyridine-2-boronic acid pinacol ester, 3-(bromomethyl)phenylboronic acid and (3S)-(−)-3-(tert-butoxy-carbonylamino)pyrrolidine according to Method BG and was obtained as a yellow solid (8%) after purification by column chromatography (SiO$_2$, 0-20% MeOH/DCM, 1% NH$_4$OH). $\delta_H$ (DMSO-d$_6$) 8.13 (1H, s), 8.01-7.88 (3H, m), 7.62 (1H, dd, J 7.4, 7.2 Hz), 7.40-7.36 (2H, m), 3.70-3.56 (6H, m), 3.40-3.24 (1H, m), 3.01-2.92 (4H, m), 2.73 (3H, s), 2.70-2.66 (1H, m), 2.62-2.53 (1H, m), 2.53-2.47 (1H, m), 2.40 (2H, s), 2.21-2.15 (1H, m), 2.09-1.96 (1H, m), 1.46-1.31 (1H, m), 1.00 (6H, s). LCMS (ES+) 517.3 (M+H)$^+$.

Example 457

Tert-Butyl N-(1-{3-[4-(5,5-dimethyl-2-(morpholin-4-yl)-7-oxo-4,5,6,7-tetrahydro-1-benzothien-3-yl) pyridin-2-yl]benzoyl}azetidin-3-yl)-N-methylcarbamate The title compound was prepared from Example 405 and iodomethane according to Method BH and was obtained as an off-white solid (55%) after purification by column chromatography (SiO$_2$, 75-100% EtOAc/heptane). $\delta_H$ (CD$_3$OD) 8.75 (1H, d, J 4.5 Hz), 8.36-8.33 (1H, m), 8.23-8.18 (1H, m), 8.02 (1H, s), 7.81-7.76 (1H, m), 7.66 (1H, t, J 7.7 Hz), 7.49 (1H, dd, J 5.1, 1.5 Hz), 4.88-4.87 (1H, m), 4.64-4.55 (2H, m), 4.47-4.28 (2H, m), 3.72-3.63 (4H, m), 3.10-3.05 (4H, m), 2.98 (3H, s), 2.65 (2H, s), 2.48 (2H, s), 1.48 (9H, s), 1.05 (6H, s). LCMS (ES+) 631.2 (M+H)$^+$.

Example 458

5,5-Dimethyl-3-[2-(3-{[3-(methylamino)azetidin-1-yl]carbonyl}phenyl)pyridin-4-yl]-2-(morpholin-4-yl)-5,6-dihydro-1-benzothiophen-7(4H)-one The title compound was prepared from Example 457 according to Method BM and was obtained as an off-white solid (59%). $\delta_H$ (CD$_3$OD) 8.75 (1H, d, J 5.1 Hz), 8.35-8.32 (1H, m), 8.22-8.17 (1H, m), 8.01 (1H, s), 7.78-7.73 (1H, m), 7.65 (1H, t, J 7.7 Hz), 7.48 (1H, dd, J 5.1, 1.5 Hz), 4.65-4.54 (1H, m), 4.44-4.33 (1H, m), 4.22-4.12 (1H, m), 4.01-3.92 (1H, m), 3.75-3.63 (5H, m), 3.13-3.04 (4H, m), 2.64 (2H, s), 2.48 (2H, s), 2.36 (3H, s), 1.05 (6H, s). LCMS (ES+) 531.2 (M+H)$^+$.

Example 459

5,5-Dimethyl-2-(morpholin-4-yl)-3-{2-[3-(piperazin-1-yl)phenyl]pyrimidin-4-yl}-5,6-dihydro-1-benzothiophen-7(4H)-one The title compound was prepared from Example 437 and 1-tert-butoxycarbonyl-piperazine according to Method BA and was obtained as a brown solid (16%) after purification by column chromatography (SiO$_2$, 0-20% MeOH/DCM, 1% NH$_4$OH). $\delta_H$ (DMSO-d$_6$) 8.92 (1H, d, J 5.1 Hz), 8.06-8.02 (1H, m), 7.95 (1H, d, J 7.9 Hz), 7.70 (1H, d, J 5.3 Hz), 7.45 (1H, t, J 8.1 Hz), 7.21 (1H, dd, J 7.9, 2.3 Hz), 3.74-3.62 (4H, m), 3.46-3.38 (4H, m), 3.26-3.19 (4H, m), 3.07-2.99 (4H, m), 2.91-2.85 (2H, m), 2.46-2.41 (2H, m), 1.00 (6H, s). LCMS (ES+) 504.1 (M+H)$^+$.

Example 460

5,5-Dimethyl-3-[2-(3-{[(3R)-3-(methylamino)pyrrolidin-1-yl]carbonyl}phenyl)pyridin-4-yl]-2-(morpholin-4-yl)-5,6-dihydro-1-benzothiophen-7(4H)-one To a solution of Example 254 (300 mg, 0.44 mmol) in DCM (20 mL) was added triethylamine (0.6 mL, 4.35 mmol), EDC (334 mg, 1.74 mmol) and 1-hydroxybenzo-triazole (10 mg, 0.09 mmol) and the reaction mixture was stirred at room temperature for 2 h. (3R)-(+)-3-(tert-Butoxycarbonylamino) pyrrolidine (323 mg, 1.74 mmol) was then added and stirring was continued at room temperature for 18 h. Water (30 mL) was added and the mixture was extracted into DCM (100 mL). The organic phase was washed with saturated aqueous sodium hydrogencarbonate solution (30 mL) and dried (magnesium sulfate). The solvent was removed in vacuo and the residue was purified by column chromatography (SiO$_2$, 75-100% EtOAc/heptane). The obtained solid was taken up in DMF (5.0 mL) and sodium hydride (60% dispersion in oil, 14 mg, 0.36 mmol) was added. The reaction mixture was stirred at room temperature for 30 minutes, then iodomethane (20 µL, 0.36 mmol) was added and stirring was continued for 1 h. Water (20 mL) was added and the reaction mixture was extracted with EtOAc (80 mL). The organic phase was washed with water (6×20 mL) and brine (20 mL), then dried (magnesium sulfate). The solvent was removed in vacuo and the residue was purified by column chromatography (SiO$_2$, 75-100% EtOAc/heptane). The obtained solid was taken up in DCM (5.0 mL) and trifluoroacetic acid (1.0 mL) was added. The reaction mixture was stirred at room temperature for 30 minutes and the solvent was removed in vacuo. The residue was purified by preparative HPLC (pH 5.8) and the obtained product was partitioned between sodium hydrogencarbonate solution (20 mL) and DCM (2×75 mL). The combined organic phases were dried (magnesium sulfate) and the solvent was removed in vacuo to give the title compound (25 mg, 8%) as an off-white solid. $\delta_H$ (CD$_3$OD) 8.75 (1H, d, J 5.1 Hz), 8.28-8.13 (2H, m), 8.01 (1H, s), 7.69-7.60 (2H, m), 7.51-7.45 (1H, m), 3.88-3.50 (7H, m), 3.41-3.22 (2H, m), 3.14-3.02 (4H, m), 2.64 (2H, s), 2.46 (3H, 2×s), 2.33 (2H, s), 2.30-2.06 (1H, m), 1.98-1.80 (1H, m), 1.05 (6H, s). LCMS (ES+) 545.3 (M+H)$^+$.

Example 461

3-{2-[3-(3,8-Di azabicyclo[3.2.1]oct-8-ylmethyl) phenyl]pyridin-4-yl}-5,5-dimethyl-2-(morpholin-4-yl)-5,6-dihydro-1-benzothiophen-7(4H)-one, Acetic Acid Salt A mixture of 3-(bromomethyl)phenylboronic acid (208 mg, 0.97 mmol), Intermediate 62 (238 mg, 0.97 mmol) and triethylamine (280 µL, 2.0 mmol) in DCM (20 mL) was stirred at room temperature for 19 h. The solvent was removed in vacuo and the resulting boronic acid (150 mg) was combined with Example 73 (125 mg, 0.33 mmol), K$_3$PO$_4$ (40 mg, 0.19 mmol) and Pd(PPh$_3$)$_4$ (10 mg, 0.01 mmol) in DME (5.0 mL) and water (1.0 mL) and the reaction mixture was heated in a sealed tube at 140° C., under microwave irradiation, for 3 h. The reaction mixture was partitioned between EtOAc (50 mL) and 2N aqueous sodium hydroxide solution (50 mL). The organic phase was concentrated in vacuo and the residue was purified by column chromatography (SiO$_2$, 0-20% MeOH/DCM, 1% NH$_4$OH). The residue was taken up in MeOH (15 mL) and 10% palladium on carbon was added. The reaction mixture was stirred under an atmosphere of hydrogen at room temperature for 23 h and the solvent was removed in vacuo. The residue was purified by column chromatography (SiO$_2$, 0-20% MeOH/DCM, 1% NH$_4$OH) and preparative HPLC (pH 5.8) to give the title compound (14 mg, 7%) as a white solid. $\delta_H$ (DMSO-d$_6$) 8.75 (1H, d, J 5.1 Hz), 8.14 (1H, s), 8.02-8.01 (1H, m), 8.01-7.97 (1H, m), 7.46 (2H, d, J 4.9 Hz), 7.40 (1H, d, J 5.1 Hz), 3.65-3.57 (4H, m), 3.49 (2H, s), 3.42-3.17 (2H, m), 3.02-2.92 (4H, m), 2.77 (2H, d, J 11.7 Hz), 2.59 (2H, s), 2.48-2.41 (2H, m), 2.39 (2H, s), 1.98-1.90 (2H, m), 1.89 (3H, s), 1.75-1.65 (2H, m), 0.97 (6H, s). LCMS (ES+) 543.3 (M+H)$^+$.

Example 462

3-{2-[3-(4-Aminopiperidin-1-yl)phenyl]pyridin-4-yl}-5,5-dimethyl-2-(morpholin-4-yl)-5,6-dihydro-1-benzothiophen-7(4H)-one A mixture of Example 360 (150 mg, 0.27 mmol), 4-(tert-butoxycarbonylamino)-piperidine (105 mg, 0.52 mmol), potassium tert-butoxide (45 mg, 0.37 mmol) and acetato(2'-di-tert-butylphosphino-1,1'-biphenyl-2-yl)palladium(II) (20 mg, 0.043 mmol) in 1,4-dioxane (6.0 mL) was heated in a sealed tube at 100° C., under microwave irradiation, for 30 minutes. The solvent was removed in vacuo and the residue was purified by column chromatography (SiO$_2$, 0-100% EtOAc/heptane). A sample of the obtained solid (43 mg) was taken up in DCM (8.0 mL), treated with trifluoroacetic acid (2.0 mL) and stirred at room temperature for 4 h. The reaction mixture was partitioned between DCM (20 mL) and saturated aqueous sodium hydrogencarbonate solution (20 mL). The organic phase was dried (magnesium sulfate), the solvent was removed in vacuo and the residue was purified by column chromatography (0-20% MeOH/DCM, 1% NH$_4$OH) to give the title compound (23 mg, 33%) as a clear glass. $\delta_H$ (CD$_3$OD) 8.68 (1H, d, J 5.1 Hz), 7.91 (1H, s), 7.64-7.59 (1H, m), 7.46-7.33 (3H, m), 7.15-7.06 (1H, m), 3.87-3.77 (2H, m), 3.72-3.64 (4H, m), 3.10-3.00 (4H, m), 2.92-2.75 (3H, m), 2.63 (2H, s), 2.46 (2H, s), 2.01-1.90 (2H, m), 1.63-1.47 (2H, m), 1.04 (6H, s). LCMS (ES+) 517.3 (M+H)$^+$.

Examples 463 & 464

Tert-Butyl 1-{3-[4-(5,5-dimethyl-2-(morpholin-4-yl)-7-oxo-4,5,6,7-tetrahydro-1-benzothien-3-yl)pyridin-2-yl]benzyl}-L-prolinate, Formic Acid Salt and 1-{3-[4-(5,5-dimethyl-2-(morpholin-4-yl)-7-oxo-4,5,6,7-tetrahydro-1-benzothien-3-yl)pyridin-2-yl]benzyl}-L-proline, Formic Acid Salt The title compounds were prepared from 3-(bromomethyl)phenylboronic acid, L-proline tert-butyl ester hydrochloride and Example 73 according to Method BJ and were obtained as yellow glasses (2% and 11% respectively) after purification by preparative HPLC (pH 2.5). Example 463: $\delta_H$ (DMSO-d$_6$) 8.74 (1H, d, J 5.1 Hz), 8.27 (2H, s), 8.10 (1H, s), 8.03-7.97 (2H, m), 7.46 (1H, t, J 7.5 Hz), 7.41-7.38 (2H, m), 3.98-3.54 (7H, m), 3.20-3.12 (1H, m), 3.02-2.95 (4H, m), 2.92-2.84 (1H, m), 2.58 (2H, s), 2.38 (2H, s), 2.10-1.96 (1H, m), 1.85-1.64 (3H, m), 1.36 (9H, s), 0.96 (6H, s). LCMS (ES+) 602.1 (M+H)$^+$. Example 464: $\delta_H$ (DMSO-d$_6$) 8.76 (1H, d, J 5.1 Hz), 8.23-8.18 (2H, m), 8.11-8.01 (2H, m), 7.50-7.44 (2H, m), 7.41 (1H, d, J 5.3 Hz), 4.16 (1H, d, J 13.0 Hz), 3.83 (1H, d, J 12.6 Hz), 3.65 (1H, s), 3.61-3.55 (4H, m), 3.40-3.32 (1H, m), 3.14-3.05 (1H, m), 3.01-2.94 (4H, m), 2.59 (2H, s), 2.38 (2H, s), 2.19-2.04 (1H, m), 1.95-1.67 (3H, m), 0.97 (6H, s). LCMS (ES+) 546.3 (M+H)$^+$.

Example 465

5,5-Dimethyl-3-(2-{3-[4-(methylamino)piperidin-1-yl]phenyl}pyridin-4-yl)-2-(morpholin-4-yl)-5,6-dihydro-1-benzothiophen-7(41-1)-one, Acetic Acid Salt The title compound was prepared from Example 360, 4-(tert-butoxycarbonyl-amino)piperidine and iodomethane according to Method BI and was obtained as a clear glass (3 mg, 3%). $\delta_H$(CD$_3$OD) 8.70 (1H, d, J 5.3 Hz), 7.94 (1H, s), 7.65 (1H, d, J 0.9 Hz), 7.50-7.38 (3H, m), 7.19-7.12 (1H, m), 4.04-3.90 (2H, m), 3.75-3.65 (4H, m), 3.29-3.16 (1H, m), 3.15-3.04 (4H, m), 3.01-2.86 (2H, m), 2.74 (3H, s), 2.65 (2H, s), 2.48 (2H, s), 2.28-2.08 (2H, m), 1.89-1.71 (2H, m), 1.06 (6H s). LCMS (ES+) 531 (M+H)$^+$.

Example 466

Tert-Butyl (3S)-3-({3-[4-(5,5-dimethyl-2-(morpholin-4-yl)-7-oxo-4,5,6,7-tetrahydro-1-benzothien-3-yl)pyridin-2-yl]benzoyl}amino)pyrrolidine-1-carboxylate To a solution of (S)-(−)-3-amino-1-(tert-butoxycarbonyl) pyrrolidine (323 mg, 1.74 mmol) in DCM (20 mL) was added Example 254 (300 mg, 0.65 mmol), triethylamine (0.6 mL, 4.35 mmol), EDC (334 mg, 1.74 mmol) and 1-hydroxybenzotriazole (12 mg, 0.09 mmol). The reaction mixture was stirred at room temperature for 18 h. Water (30 mL) was added and the mixture was extracted with DCM (100 mL). The organic phase was washed with sodium hydrogencarbonate solution (30 mL), then dried (magnesium sulfate) and the solvent was removed in vacuo. The residue was purified by column chromatography (SiO$_2$, 100% EtOAc) to give the title compound (106 mg, 26%) as a yellow solid. $\delta_H$ (CD$_3$OD) 8.76 (1H, d, J 5.1 Hz), 8.49-8.45 (1H, m), 8.24-8.18 (1H, m), 8.03 (1H, s), 7.97-7.91 (1H, m), 7.68-7.61 (1H, m), 7.45 (1H, dd, J 5.1, 1.5 Hz), 4.65-4.54 (1H, m), 3.79-3.25 (8H, m), 3.12-3.03 (4H, m), 2.64 (2H, s), 2.48 (2H, s), 2.34-2.20 (1H, m), 2.14-2.03 (1H, m), 1.48 (9H, s), 1.05 (6H, s). LCMS (ES+) 631.1 (M+H)$^+$.

Example 467

5,5-Dimethyl-3-[2-(3-{[N-isopropyl-N-(methyl)amino]methyl}phenyl)pyridin-4-yl]-2-(morpholin-4-yl)-5,6-dihydro-1-benzothiophen-7(4H)-one, Formic Acid Salt The title compound was prepared from 3-(bromomethyl)phenylboronic acid, N-methylisopropylamine and Example 73 according to Method BJ and was obtained as an off-white solid (16%) after purification by preparative HPLC (pH 2.5). $\delta_H$ (DMSO-d$_6$) 8.75 (1H, d, J 5.1 Hz), 8.17 (0.5H, s), 8.10 (1H, s), 8.02 (1H, s), 8.00 (1H, d, J 7.5 Hz), 7.48-7.35 (3H, m), 3.63-3.59 (4H, m), 3.58 (2H, s), 3.02-2.93 (4H, m), 2.93-2.82 (1H, m), 2.59 (2H, s), 2.39 (2H, s), 2.09 (3H, s), 1.05 (3H, s), 1.03 (3H, s), 0.97 (6H, s). LCMS (ES+) 504.2 (M+H)$^+$.

Example 468

1-{3-[4-(5,5-Dimethyl-2-(morpholin-4-yl)-7-oxo-4,5,6,7-tetrahydro-1-benzothien-3-yl)pyridin-2-yl]benzyl}piperazin-2-one Sodium hydride (60% dispersion in oil, 56 mg, 1.40 mmol) was added to a solution of 1-(tert-butoxycarbonyl)-3-oxopiperazine (280 mg, 1.40 mmol) in DMF (10 mL) and the reaction mixture was stirred at room temperature for 15 minutes. 3-(Bromo-methyl)phenylboronic acid neopentyl glycol ester (396 mg, 1.40 mmol) was then added and stirring was continued at room temperature for 16 h. The solvent was removed in vacuo and the resulting boronic acid was combined with Example 73 (250 mg, 0.66 mmol), K$_3$PO$_4$ (80 mg, 0.38 mmol) and Pd(PPh$_3$)$_4$ (10 mg, 0.01 mmol) in DME (5.0 mL) and water (1.0 mL) and the reaction mixture was heated in a sealed tube at 140° C., under microwave irradiation, for 3 h. The reaction mixture was concentrated in vacuo and purified by column chromatography (SiO$_2$, 20-100% EtOAc/heptane, then 15% MeOH/DCM). The obtained solid was taken up in MeOH (5.0 mL) and was treated with a solution of HCl in Et$_2$O (2N, 2.0 mL, 4.0 mmol). The reaction mixture was stirred at room temperature for 19 h and the solvent was removed in vacuo. The residue was partitioned between EtOAc (25 mL) and aqueous sodium hydroxide solution (2N, 25 mL). The organic phase was concentrated in vacuo and purified by column chromatography (SiO$_2$, 0-20% MeOH/DCM, 1% NH$_4$OH) to give the title compound (61 mg, 17%) as a yellow glass. $\delta_H$ (DMSO-d$_6$) 8.74 (1H, d, J 5.1 Hz), 8.04 (1H, s), 8.00 (1H, s), 7.66-7.31 (4H, m), 4.63 (2H, s), 4.01-3.98 (2H, m), 3.64-3.57 (4H, m), 3.57-3.50 (2H, m), 3.30-

3.27 (2H, m), 3.02-2.93 (4H, m), 2.57 (2H, s), 2.38 (2H, s), 1.38 (9H, s), 0.96 (6H, s). LCMS (ES+) 531.3 (M+H)+.

Example 469

3-[2-(3-{[(3-exo)-3-Amino-8-azabicyclo[3.2.1]oct-8-yl]methyl}phenyl)pyridin-4-yl]-5,5-dimethyl-2-(morpholin-4-yl)-5,6-dihydro-1-benzothiophen-7(4H)-one A mixture of 3-(bromomethyl)phenylboronic acid (204 mg, 0.95 mmol), Intermediate 63 (243 mg, 0.95 mmol) and triethylamine (280 μL, 2.0 mmol) in DCM (20 mL) was stirred at room temperature for 17 h. The solvent was removed in vacuo and the resulting boronic acid was combined with Example 73 (250 mg, 0.66 mmol), $K_3PO_4$ (80 mg, 0.38 mmol) and Pd(PPh$_3$)$_4$ (10 mg, 0.01 mmol) in DME (5.0 mL) and water (1.0 mL) and the reaction mixture was heated in a sealed tube at 140° C., under microwave irradiation, for 3 h. The reaction mixture was concentrated in vacuo and was purified by column chromatography (SiO$_2$, 0-20% MeOH/DCM, 1% NH$_4$OH). The residue was taken up in EtOH (5.0 mL) and treated with hydrazine hydrate (105 μL, 2.16 mmol). The reaction mixture was stirred at room temperature for 21 h and then concentrated in vacuo. The residue was purified by column chromatography (SiO$_2$, 0-20% MeOH/DCM, 1% NH$_4$OH) to give the title compound (124 mg, 23%) as a pale yellow solid. $\delta_H$ (DMSO-d$_6$) 8.75 (1H, d, J 5.1 Hz), 8.13 (1H, s), 8.02 (2H, s), 7.48-7.39 (3H, m), 3.64-3.57 (4H, m), 3.18-3.10 (2H, m), 3.01-2.94 (4H, m), 2.91-2.78 (1H, m), 2.59 (2H, s), 2.39 (2H, s), 2.00-1.88 (2H, m), 1.62-1.47 (4H, m), 1.43-1.31 (2H, m), 0.97 (6H, s). LCMS (ES+) 557.3 (M+H)+.

Example 470

3-[2-(3-{[(2R,6S)-2,6-Dimethylmorpholin-4-yl]methyl}phenyl)pyridin-4-yl]-5,5-dimethyl-2-(morpholin-4-yl)-5,6-dihydro-1-benzothiophen-7(4H)-one, Formic Acid Salt The title compound was prepared from 3-(bromomethyl)phenylboronic acid, cis-2,6-dimethylmorpholine and Example 73 according to Method BJ and was obtained as a clear glass (46%) after purification by preparative HPLC (pH 2.5). $\delta_H$ (DMSO-d$_6$) 8.75 (1H, d, J 4.9 Hz), 8.14 (0.5H, s), 8.11-8.01 (3H, m), 7.47 (3H, t, J 7.4 Hz), 7.41-7.36 (3H, m), 3.65-3.57 (6H, m), 3.53 (2H, s), 3.02-2.94 (4H, m), 2.70 (2H, d, J 11.3 Hz), 2.59 (2H, s), 2.39 (2H, s), 1.68 (2H, t, J 10.6 Hz), 1.03 (3H, s), 1.01 (3H, s), 0.97 (6H, s). LCMS (ES+) 546.3 (M+H)+.

Example 471

Tert-Butyl (4-{3-[4-(5,5-Dimethyl-2-(morpholin-4-yl)-7-oxo-4,5,6,7-tetrahydrothieno[2,3-e]pyridin-3-yl)pyridin-2-yl]phenyl}piperazin-1-yl)acetate A mixture of Example 418 (41 mg, 0.056 mmol) and triethylamine (25 μL, 0.179 mmol) was added dropwise to a solution of tert-butyl bromoacetate (10 μL, 0.068 mmol) in THF (4.0 mL) and the reaction mixture was heated at reflux for 2 h. Further tert-butyl bromoacetate (4 μL, 0.068 mmol) was added and reflux was continued for a further 0.5 h. The reaction mixture was cooled to room temperature, concentrated in vacuo and partitioned between EtOAc (15 mL) and water (15 mL). The organic phase was washed with water (15 mL), dried (magnesium sulfate) and the solvent was removed in vacuo to give the title compound (35 mg, 100%) as a white powder. $\delta_H$ (DMSO-d$_6$) 8.70 (1H, d, J 5.1 Hz), 8.04 (1H, s), 7.65 (1H, br s), 7.55-7.52 (2H, m), 7.42-7.40 (1H, m), 7.34 (1H, t, J 8.1 Hz), 7.03 (1H, dd, J 8.1, 1.9 Hz), 3.65-3.56 (4H, m), 3.27-3.21 (4H, m), 2.95-2.86 (4H, m), 2.71 (1H, s), 2.69-2.62 (4H, m), 1.42 (9H, s), 1.18 (6H, s). LCMS (ES+) 618.2 (M+H)+.

The invention claimed is:
1. A compound of formula (I), or a pharmaceutically acceptable salt or solvate thereof:

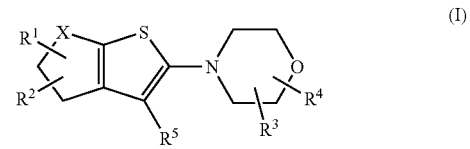

wherein
—X— represents a group of formula (a), (b), (c), (d), (e), (f) or (g):

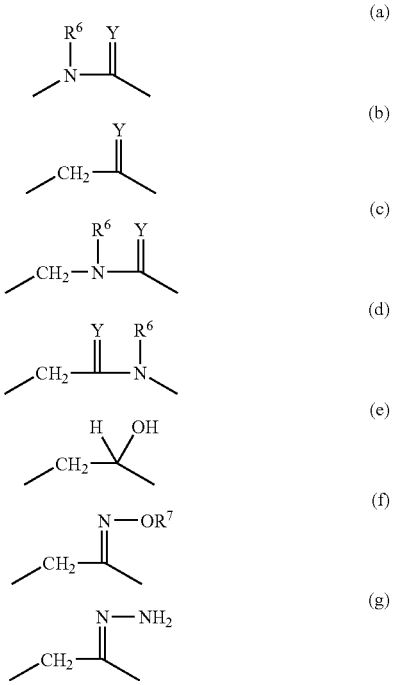

Y represents oxygen or sulphur;
$R^1$ and $R^2$ independently represent hydrogen; or $C_{1-6}$ alkyl, $C_{3-7}$ cycloalkyl, $C_{3-7}$ cycloalkyl($C_{1-6}$)alkyl, aryl, aryl ($C_{1-6}$)alkyl, $C_{3-7}$ heterocycloalkyl, $C_{3-7}$ heterocycloalkyl-($C_{1-6}$)alkyl, heteroaryl or heteroaryl($C_{1-6}$) alkyl, any of which groups may be optionally substituted by one or more substituents; or
$R^1$ and $R^2$, when both are attached to the same carbon atom, represent, when taken together with the carbon atom to which they are both attached, $C_{3-7}$ cycloalkyl or $C_{3-7}$ heterocycloalkyl, either of which groups may be optionally substituted by one or more substituents; or
$R^1$ and $R^2$, when attached to adjacent carbon atoms, represent, when taken together with the carbon atoms to which they are attached, $C_{5-7}$ cycloalkyl, phenyl or heteroaryl, any of which groups may be optionally benzo-fused and/or substituted by one or more substituents;

$R^3$ and $R^4$ independently represent hydrogen; or $C_{1-6}$ alkyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl, aryl($C_{2-6}$)alkynyl, biaryl ($C_{1-6}$)alkyl, $C_{3-7}$ heterocycloalkyl, $C_{3-7}$ heterocycloalkyl($C_{1-6}$)alkyl, $C_{3-7}$ heterocycloalkylcarbonyl, heteroaryl, heteroaryl($C_{1-6}$)alkyl, heteroaryl-aryl($C_{1-6}$)alkyl or aryl-heteroaryl($C_{1-6}$)alkyl, any of which groups may be optionally substituted by one or more substituents; or $R^3$ and $R^4$, when both are attached to the same carbon atom, represent, when taken together with the carbon atom to which they are both attached, $C_{3-7}$ cycloalkyl or $C_{3-7}$ heterocycloalkyl, either of which groups may be optionally substituted by one or more substituents; or $R^3$ and $R^4$, when attached to adjacent carbon atoms, represent, when taken together with the carbon atoms to which they are attached, $C_{5-7}$ cycloalkyl, phenyl or heteroaryl, any of which groups may be optionally benzo-fused and/or substituted by one or more substituents;

$R^5$ represents hydrogen, halogen, cyano, —$SR^a$, —$COR^e$, —$CO_2R^b$ or —$CONR^cR^d$; or $R^5$ represents $C_{1-6}$ alkyl, $C_{2-6}$ alkenyl, $C_{2-6}$ alkenylcarbonyl, $C_{2-6}$ alkynyl, $C_{3-7}$ cycloalkyl, $C_{3-7}$ cycloalkyl($C_{1-6}$)alkyl, $C_{3-7}$ cycloalkyl($C_{2-6}$)alkenyl, $C_{3-7}$ cycloalkyl($C_{2-6}$)alkynyl, aryl, aryl($C_{1-6}$)alkyl, aryl($C_{2-6}$)alkenyl, aryl($C_{2-6}$)alkynyl, biaryl, $C_{3-7}$ heterocycloalkyl, $C_{3-7}$ heterocycloalkyl($C_{1-6}$)alkyl, $C_{3-7}$ heterocycloalkyl($C_{2-6}$)alkenyl, $C_{3-7}$ heterocycloalkyl-($C_{2-6}$)alkynyl, $C_{3-7}$ heterocycloalkylcarbonyl ($C_{2-6}$)alkynyl, $C_{5-9}$ heterobicycloalkyl-($C_{2-6}$)alkynyl, $C_{3-7}$ heterocycloalkyl-aryl, $C_{3-7}$ heterocycloalkyl($C_{1-6}$) alkyl-aryl, $C_{3-7}$ heterocycloalkyl-biaryl, heteroaryl, heteroaryl($C_{1-6}$)alkyl, heteroaryl($C_{1-6}$)alkylcarbonyl, heteroaryl($C_{2-6}$)alkenyl, heteroaryl($C_{2-6}$)alkynyl, heteroaroylcarbonyl, $C_{3-7}$ heterocycloalkyl-heteroaryl, $C_{3-7}$ heterocycloalkyl-heteroaryl($C_{2-6}$)alkynyl, heteroaryl-aryl, heteroaryl-aryl($C_{1-6}$)alkyl, aryl-heteroaryl, aryl-heteroaryl($C_{1-6}$)alkyl, $C_{3-7}$ heterocycloalkyl-aryl-heteroaryl, $C_{3-7}$ heterocycloalkyl($C_{1-6}$)alkyl-aryl-heteroaryl, $C_{5-9}$ heterobicycloalkyl($C_{1-6}$)alkyl-aryl-heteroaryl, heteroaryl-aryl-heteroaryl, bi(heteroaryl), $C_{3-7}$ heterocycloalkylcarbonyl-bi(heteroaryl), aryloxyaryl, aryl($C_{1-6}$)alkoxyaryl, heteroaryl($C_{1-6}$)alkoxyaryl, aryl ($C_{1-6}$)alkylaminoaryl, heteroaryl($C_{1-6}$)alkylaminoaryl, $C_{3-7}$ cycloalkylcarbonylaminoaryl, arylcarbonylaminoaryl, aryl($C_{1-6}$)alkylcarbonylaminoaryl, $C_{3-7}$ heterocycloalkylcarbonylaminoaryl, heteroarylcarbonylaminoaryl, aryl($C_{3-7}$)heterocycloalkylcarbonylaminoaryl, arylsulphonylaminoaryl, aryl($C_{1-6}$)alkyl-sulphonylaminoaryl, heteroaryl($C_{1-6}$)alkylsulphonylaminoaryl, $C_{3-7}$ cycloalkylamino-carbonylaminoaryl, arylaminocarbonylaminoaryl, $C_{3-7}$ heterocycloalkylaminocarbonyl-aminoaryl, $C_{3-7}$ heterocycloalkylaminocarbonylaminoaryl, heteroaryl($C_{1-6}$)alkyl-aminocarbonylaminoaryl, $C_{3-7}$ heterocycloalkylcarbonylcarbonylaminoaryl, $C_{3-7}$ heterocycloalkyl($C_{1-6}$)alkylaminocarbonylcarbonylaminoaryl, arylcarbonylaryl, $C_{3-7}$ heterocycloalkylcarbonylaryl, $C_{3-7}$ heterocycloalkylcarbonyl($C_{1-6}$) alkylaryl, aryl($C_{1-6}$)-alkylaminocarbonylaryl, $C_{3-7}$ heterocycloalkyl($C_{1-6}$)alkylaminocarbonylaryl, heteroaryl-aminocarbonylaryl, heteroaryl($C_{1-6}$)alkylaminocarbonylaryl, $C_{3-7}$ heterocycloalkylamino-carbonyl ($C_{1-6}$)alkylaryl, $C_{3-7}$ heterocycloalkyl($C_{1-6}$) alkylaminocarbonyl($C_{1-6}$)alkylaryl, heteroarylaminocarbonyl($C_{1-6}$)alkylaryl, heteroaryl ($C_{1-6}$)alkylaminocarbonyl($C_{1-6}$)alkyl-aryl, arylaminoheteroaryl, $C_{3-7}$ heterocycloalkylamino-aryl-heteroaryl, $C_{3-7}$ heterocycloalkylcarbonylamino-aryl-heteroaryl, $C_{3-7}$ heterocycloalkylaminocarbonyl-amino-aryl-heteroaryl, $C_{3-7}$ heterocycloalkylcarbonyl-aryl-heteroaryl, $C_{3-7}$ heterocycloalkyl($C_{1-6}$)alkylcarbonyl-aryl-heteroaryl, $C_{5-9}$ heterobicycloalkylcarbonyl-aryl-heteroaryl, $C_{3-7}$ heterocycloalkylcarbonyl($C_{1-6}$)alkyl-aryl-heteroaryl, $C_{3-7}$ heterocycloalkyl-aminocarbonyl-aryl-heteroaryl, $C_{3-7}$ heterocycloalkyl($C_{1-6}$) alkylaminocarbonyl-aryl-heteroaryl or $C_{3-7}$ heterocycloalkylaminocarbonyl($C_{1-6}$)alkyl-aryl-heteroaryl, any of which groups may be optionally substituted by one or more substituents;

$R^a$ represents $C_{1-6}$ alkyl, aryl or heteroaryl, any of which groups may be optionally substituted by one or more substituents;

$R^b$ represents hydrogen; or optionally substituted $C_{1-6}$ alkyl;

$R^c$ represents hydrogen; or $C_{1-6}$ alkyl, aryl, aryl($C_{1-6}$)alkyl, heteroaryl, heteroaryl($C_{1-6}$)alkyl or (aryl)(heteroaryl) ($C_{1-6}$)alkyl, any of which groups may be optionally substituted by one or more substituents;

$R^d$ represents hydrogen or $C_{1-6}$ alkyl;

$R^e$ represents $C_{1-6}$ alkyl; and $R^6$ and $R^7$ independently represent hydrogen or $C_{1-6}$ alkyl.

2. A compound of formula (IA), (IB) or (IC), or a pharmaceutically acceptable salt or solvate thereof:

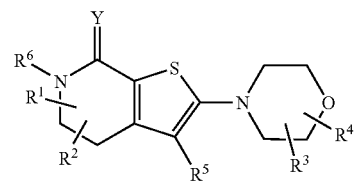

(IA)

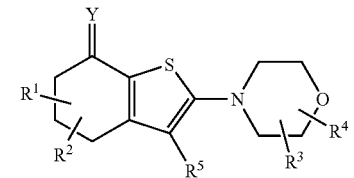

(IB)

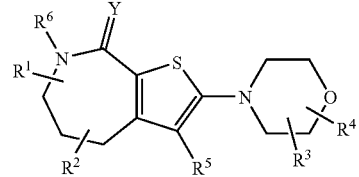

(IC)

wherein

Y represents oxygen or sulphur;

$R^1$ and $R^2$ independently represent hydrogen; or $C_{1-6}$ alkyl, $C_{3-7}$ cycloalkyl, $C_{3-7}$ cycloalkyl($C_{1-6}$)alkyl, aryl, aryl ($C_{1-6}$)alkyl, $C_{3-7}$ heterocycloalkyl, $C_{3-7}$ heterocycloalkyl-($C_{1-6}$)alkyl, heteroaryl or heteroaryl($C_{1-6}$) alkyl, any of which groups may be optionally substituted by one or more substituents; or $R^1$ and $R^2$, when both are attached to the same carbon atom, represent, when taken together with the carbon atom to which they are both attached, $C_{3-7}$ cycloalkyl or $C_{3-7}$ heterocycloalkyl, either of which groups may be optionally substituted by one or more substituents; or R¹ and R², when attached to adjacent carbon atoms, represent, when taken together with the carbon atoms to which they are attached, $C_{5-7}$ cycloalkyl, phenyl or heteroaryl, any of which groups may be optionally benzo-fused and/or substituted by one or more substituents;

R³ and R⁴ independently represent hydrogen; or $C_{1-6}$ alkyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl, aryl($C_{2-6}$)alkynyl, biaryl($C_{1-6}$)alkyl, $C_{3-7}$ heterocycloalkyl, $C_{3-7}$ heterocycloalkyl($C_{1-6}$)alkyl, $C_{3-7}$ heterocycloalkylcarbonyl, heteroaryl, heteroaryl($C_{1-6}$)alkyl, heteroaryl-aryl($C_{1-6}$)alkyl or aryl-heteroaryl($C_{1-6}$)alkyl, any of which groups may be optionally substituted by one or more substituents; or R³ and R⁴, when both are attached to the same carbon atom, represent, when taken together with the carbon atom to which they are both attached, $C_{3-7}$ cycloalkyl or $C_{3-7}$ heterocycloalkyl, either of which groups may be optionally substituted by one or more substituents; or R³ and R⁴, when attached to adjacent carbon atoms, represent, when taken together with the carbon atoms to which they are attached, $C_{5-7}$ cycloalkyl, phenyl or heteroaryl, any of which groups may be optionally benzo-fused and/or substituted by one or more substituents;

R⁵ represents hydrogen, halogen, cyano, —SR$^a$, —COR$^e$, —CO₂R$^b$ or —CONR$^c$R$^d$; or R⁵ represents $C_{1-6}$ alkyl, $C_{2-6}$ alkenyl, $C_{2-6}$ alkenylcarbonyl, $C_{2-6}$ alkynyl, $C_{3-7}$ cycloalkyl, $C_{3-7}$ cycloalkyl($C_{1-6}$)alkyl, $C_{3-7}$ cycloalkyl($C_{2-6}$)alkenyl, $C_{3-7}$ cycloalkyl($C_{2-6}$)alkynyl, aryl, aryl($C_{1-6}$)alkyl, aryl($C_{2-6}$)alkenyl, aryl($C_{2-6}$)alkynyl, biaryl, $C_{3-7}$ heterocycloalkyl, $C_{3-7}$ heterocycloalkyl($C_{1-6}$)alkyl, $C_{3-7}$ heterocycloalkyl($C_{2-6}$)alkenyl, $C_{3-7}$ heterocycloalkyl-($C_{2-6}$)alkynyl, $C_{3-7}$ heterocycloalkylcarbonyl($C_{2-6}$)alkynyl, $C_{5-9}$ heterobicycloalkyl-($C_{2-6}$)alkynyl, $C_{3-7}$ heterocycloalkyl-aryl, $C_{3-7}$ heterocycloalkyl($C_{1-6}$)alkyl-aryl, $C_{3-7}$ heterocycloalkyl-biaryl, heteroaryl, heteroaryl($C_{1-6}$)alkyl, heteroaryl($C_{1-6}$)alkylcarbonyl, heteroaryl($C_{2-6}$)alkenyl, heteroaryl($C_{2-6}$)alkynyl, heteroaroylcarbonyl, $C_{3-7}$ heterocycloalkyl-heteroaryl, $C_{3-7}$ heterocycloalkyl-heteroaryl($C_{2-6}$)alkynyl, heteroaryl-aryl, heteroaryl-aryl($C_{1-6}$)alkyl, aryl-heteroaryl, aryl-heteroaryl($C_{1-6}$)alkyl, $C_{3-7}$ heterocycloalkyl-aryl-heteroaryl, $C_{3-7}$ heterocycloalkyl($C_{1-6}$)alkyl-aryl-heteroaryl, $C_{5-9}$ heterobicycloalkyl($C_{1-6}$)alkyl-aryl-heteroaryl, heteroaryl-aryl-heteroaryl, bi(heteroaryl), $C_{3-7}$ heterocycloalkylcarbonyl-bi(heteroaryl), aryloxyaryl, aryl($C_{1-6}$)alkoxyaryl, heteroaryl($C_{1-6}$)alkoxyaryl, aryl($C_{1-6}$)alkylaminoaryl, heteroaryl($C_{1-6}$)alkylaminoaryl, $C_{3-7}$ cycloalkylcarbonylaminoaryl, arylcarbonylaminoaryl, aryl($C_{1-6}$)alkylcarbonylaminoaryl, $C_{3-7}$ heterocycloalkylcarbonylaminoaryl, heteroarylcarbonylaminoaryl, aryl-($C_{3-7}$)heterocycloalkylcarbonylaminoaryl, arylsulphonylaminoaryl, aryl($C_{1-6}$)alkyl-sulphonylaminoaryl, heteroaryl($C_{1-6}$)alkylsulphonylaminoaryl, $C_{3-7}$ cycloalkylamino-carbonylaminoaryl, arylaminocarbonylaminoaryl, $C_{3-7}$ heterocycloalkylaminocarbonyl-aminoaryl, $C_{3-7}$ heterocycloalkylaminocarbonylaminoaryl, heteroaryl($C_{1-6}$)alkyl-aminocarbonylaminoaryl, $C_{3-7}$ heterocycloalkylcarbonylcarbonylaminoaryl, $C_{3-7}$ heterocycloalkyl($C_{1-6}$)alkylaminocarbonylcarbonylaminoaryl, arylcarbonylaryl, $C_{3-7}$ heterocycloalkylcarbonylaryl, $C_{3-7}$ heterocycloalkylcarbonyl($C_{1-6}$)alkylaryl, aryl($C_{1-6}$)-alkylaminocarbonylaryl, $C_{3-7}$ heterocycloalkyl($C_{1-6}$)alkylaminocarbonylaryl, heteroaryl-aminocarbonylaryl, heteroaryl($C_{1-6}$)alkylaminocarbonylaryl, $C_{3-7}$ heterocycloalkylamino-carbonyl($C_{1-6}$)alkylaryl, $C_{3-7}$ heterocycloalkyl($C_{1-6}$)alkylaminocarbonyl($C_{1-6}$)alkylaryl, heteroarylaminocarbonyl($C_{1-6}$)alkylaryl, heteroaryl($C_{1-6}$)alkylaminocarbonyl($C_{1-6}$)alkyl-aryl, arylamino-heteroaryl, $C_{3-7}$ heterocycloalkylamino-aryl-heteroaryl, $C_{3-7}$ heterocycloalkylcarbonylamino-aryl-heteroaryl, $C_{3-7}$ heterocycloalkylaminocarbonyl-amino-aryl-heteroaryl, $C_{3-7}$ heterocycloalkylcarbonyl-aryl-heteroaryl, $C_{3-7}$ heterocycloalkyl($C_{1-6}$)alkylcarbonyl-aryl-heteroaryl, $C_{5-9}$ heterobicycloalkylcarbonyl-aryl-heteroaryl, $C_{3-7}$ heterocycloalkylcarbonyl($C_{1-6}$)alkyl-aryl-heteroaryl, $C_{3-7}$ heterocycloalkyl-aminocarbonyl-aryl-heteroaryl, $C_{3-7}$ heterocycloalkyl($C_{1-6}$)alkylaminocarbonyl-aryl-heteroaryl or $C_{3-7}$ heterocycloalkylaminocarbonyl($C_{1-6}$)alkyl-aryl-heteroaryl, any of which groups may be optionally substituted by one or more substituents;

R$^a$ represents $C_{1-6}$ alkyl, aryl or heteroaryl, any of which groups may be optionally substituted by one or more substituents;

R$^b$ represents hydrogen; or optionally substituted $C_{1-6}$ alkyl;

R$^c$ represents hydrogen; or $C_{1-6}$ alkyl, aryl, aryl($C_{1-6}$)alkyl, heteroaryl, heteroaryl($C_{1-6}$)alkyl or (aryl)(heteroaryl)($C_{1-6}$)alkyl, any of which groups may be optionally substituted by one or more substituents;

R$^d$ represents hydrogen or $C_{1-6}$ alkyl;

R$^e$ represents $C_{1-6}$ alkyl; and

R⁶ and R⁷ independently represent hydrogen or $C_{1-6}$ alkyl.

3. A compound of formula (IIA), or a pharmaceutically acceptable salt or solvate thereof:

(IIA)

wherein

—X¹— represents a group of formula (a), (b) or (c):

(a)

(b)

(c)

R⁵ represents hydrogen, halogen, cyano, —SR$^a$, —COR$^e$, —CO₂R$^b$ or —CONR$^c$R$^d$; or R⁵ represents $C_{1-6}$ alkyl, $C_{2-6}$ alkenyl, $C_{2-6}$ alkenylcarbonyl, $C_{2-6}$ alkynyl, $C_{3-7}$ cycloalkyl, $C_{3-7}$ cycloalkyl($C_{1-6}$)alkyl, $C_{3-7}$ cycloalkyl($C_{2-6}$)alkenyl, $C_{3-7}$ cycloalkyl($C_{2-6}$)alkynyl, aryl, aryl($C_{1-6}$)alkyl, aryl($C_{2-6}$)alkenyl, aryl($C_{2-6}$)alkynyl, biaryl, $C_{3-7}$ heterocycloalkyl, $C_{3-7}$ heterocycloalkyl($C_{1-6}$)alkyl, $C_{3-7}$ heterocycloalkyl($C_{2-6}$)alkenyl, $C_{3-7}$ heterocycloalkyl-($C_{2-6}$)alkynyl, $C_{3-7}$ heterocycloalkylcarbonyl($C_{2-6}$)alkynyl, $C_{5-9}$ heterobicycloalkyl-($C_{2-6}$)alkynyl, $C_{3-7}$ heterocycloalkyl-aryl, $C_{3-7}$ heterocycloalkyl($C_{1-6}$) alkyl-aryl, $C_{3-7}$ heterocycloalkyl-biaryl, heteroaryl, heteroaryl($C_{1-6}$)alkyl, heteroaryl($C_{1-6}$)alkylcarbonyl, heteroaryl($C_{2-6}$)alkenyl, heteroaryl($C_{2-6}$)alkynyl, heteroaroylcarbonyl, $C_{3-7}$ heterocycloalkyl-heteroaryl, $C_{3-7}$ heterocycloalkyl-heteroaryl($C_{2-6}$)alkynyl, heteroaryl-aryl, heteroaryl-aryl($C_{1-6}$)alkyl, aryl-heteroaryl, aryl-heteroaryl($C_{1-6}$)alkyl, $C_{3-7}$ heterocycloalkyl-aryl-heteroaryl, $C_{3-7}$ heterocycloalkyl($C_{1-6}$)alkyl-aryl-heteroaryl, $C_{5-9}$ heterobicycloalkyl($C_{1-6}$)alkyl-aryl-heteroaryl, heteroaryl-aryl-heteroaryl, bi(heteroaryl), $C_{3-7}$ heterocycloalkylcarbonyl-bi(heteroaryl), aryloxyaryl, aryl($C_{1-6}$)alkoxyaryl, heteroaryl($C_{1-6}$)alkoxyaryl, aryl($C_{1-6}$)alkylaminoaryl, heteroaryl($C_{1-6}$)alkylaminoaryl, $C_{3-7}$ cycloalkylcarbonylaminoaryl, arylcarbonylaminoaryl, aryl($C_{1-6}$)alkylcarbonylaminoaryl, $C_{3-7}$ heterocycloalkylcarbonylaminoaryl, heteroarylcarbonylaminoaryl, aryl-($C_{3-7}$)heterocycloalkylcarbonylaminoaryl, arylsulphonylaminoaryl, aryl($C_{1-6}$)alkyl-sulphonylaminoaryl, heteroaryl($C_{1-6}$)alkylsulphonylaminoaryl, $C_{3-7}$ cycloalkylamino-carbonylaminoaryl, arylaminocarbonylaminoaryl, $C_{3-7}$ heterocycloalkylaminocarbonyl-aminoaryl, $C_{3-7}$ heterocycloalkylaminocarbonylaminoaryl, heteroaryl($C_{1-6}$)alkyl-aminocarbonylaminoaryl, $C_{3-7}$ heterocycloalkylcarbonylcarbonylaminoaryl, $C_{3-7}$ heterocycloalkyl($C_{1-6}$)alkylaminocarbonylcarbonylaminoaryl, arylcarbonylaryl, $C_{3-7}$ heterocycloalkylcarbonylaryl, $C_{3-7}$ heterocycloalkylcarbonyl($C_{1-6}$)alkylaryl, aryl($C_{1-6}$)-alkylaminocarbonylaryl, $C_{3-7}$ heterocycloalkyl($C_{1-6}$)alkylaminocarbonylaryl, heteroaryl-aminocarbonylaryl, heteroaryl($C_{1-6}$)alkylaminocarbonylaryl, $C_{3-7}$ heterocycloalkylamino-carbonyl($C_{1-6}$)alkylaryl, $C_{3-7}$ heterocycloalkyl($C_{1-6}$)alkylaminocarbonyl($C_{1-6}$)alkylaryl, heteroarylaminocarbonyl($C_{1-6}$)alkylaryl, heteroaryl($C_{1-6}$)alkylaminocarbonyl($C_{1-6}$)alkyl-aryl, arylaminoheteroaryl, $C_{3-7}$ heterocycloalkylamino-aryl-heteroaryl, $C_{3-7}$ heterocycloalkylcarbonylamino-aryl-heteroaryl, $C_{3-7}$ heterocycloalkylaminocarbonyl-amino-aryl-heteroaryl, $C_{3-7}$ heterocycloalkylcarbonyl-aryl-heteroaryl, $C_{3-7}$ heterocycloalkyl($C_{1-6}$)alkylcarbonyl-aryl-heteroaryl, $C_{5-9}$ heterobicycloalkylcarbonyl-aryl-heteroaryl, $C_{3-7}$ heterocycloalkylcarbonyl($C_{1-6}$)alkyl-aryl-heteroaryl, $C_{3-7}$ heterocycloalkyl-aminocarbonyl-aryl-heteroaryl, $C_{3-7}$ heterocycloalkyl($C_{1-6}$)alkylaminocarbonyl-aryl-heteroaryl or $C_{3-7}$ heterocycloalkylaminocarbonyl($C_{1-6}$)alkyl-aryl-heteroaryl, any of which groups may be optionally substituted by one or more substituents;

$R^a$ represents $C_{1-6}$ alkyl, aryl or heteroaryl, any of which groups may be optionally substituted by one or more substituents;

$R^b$ represents hydrogen; or optionally substituted $C_{1-6}$ alkyl;

$R^c$ represents hydrogen; or $C_{1-6}$ alkyl, aryl, aryl($C_{1-6}$)alkyl, heteroaryl, heteroaryl($C_{1-6}$)alkyl or (aryl)(heteroaryl)($C_{1-6}$)alkyl, any of which groups may be optionally substituted by one or more substituents;

$R^d$ represents hydrogen or $C_{1-6}$ alkyl;

$R^e$ represents $C_{1-6}$ alkyl;

$R^{11}$ represents hydrogen or optionally substituted $C_{1-6}$ alkyl; and $R^{12}$ represents hydrogen; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or $R^{11}$ and $R^{12}$, when taken together with the carbon atom to which they are both attached, represent $C_{3-7}$ cycloalkyl or $C_{3-7}$ heterocycloalkyl, either of which groups may be optionally substituted by one or more substituents.

4. A compound of formula (IIB), or a pharmaceutically acceptable salt or solvate thereof:

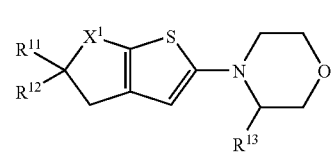

(IIB)

wherein

—$X^1$— represents a group of formula (a), (b) or (c):

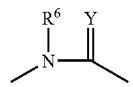

(a)

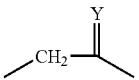

(b)

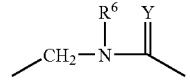

(c)

$R^{11}$ represents hydrogen or optionally substituted $C_{1-6}$ alkyl; and $R^{12}$ represents hydrogen; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or $R^{11}$ and $R^{12}$, when taken together with the carbon atom to which they are both attached, represent $C_{3-7}$ cycloalkyl or $C_{3-7}$ heterocycloalkyl, either of which groups may be optionally substituted by one or more substituents; and $R^{13}$ represents hydrogen; or $C_{1-6}$ alkyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl, aryl($C_{2-6}$)alkynyl, biaryl($C_{1-6}$)alkyl, $C_{3-7}$ heterocycloalkyl, $C_{3-7}$ heterocycloalkyl($C_{1-6}$)alkyl, $C_{3-7}$ heterocycloalkylcarbonyl, heteroaryl, heteroaryl($C_{1-6}$)alkyl, heteroaryl-aryl($C_{1-6}$)alkyl or aryl-heteroaryl($C_{1-6}$)alkyl, any of which groups may be optionally substituted by one or more substituents.

5. A compound as claimed in claim 4 of formula (IIC), or a pharmaceutically acceptable salt or solvate thereof:

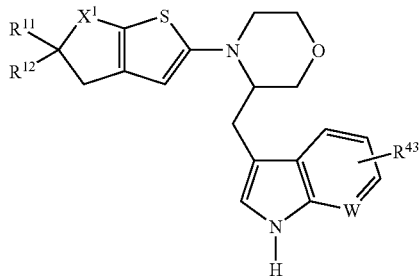

(IIC)

wherein

—$X^1$— represents a group of formula (a), (b) or (c):

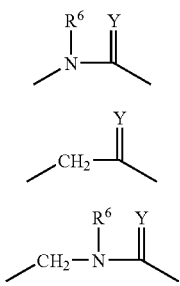

$R^{11}$ represents hydrogen or optionally substituted $C_{1-6}$ alkyl; and $R^{12}$ represents hydrogen; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or $R^{11}$ and $R^{12}$, when taken together with the carbon atom to which they are both attached, represent $C_{3-7}$ cycloalkyl or $C_{3-7}$ heterocycloalkyl, either of which groups may be optionally substituted by one or more substituents;

W represents CH or N; and $R^{43}$ represents hydrogen, halogen, cyano, $C_{1-6}$ alkyl, hydroxy($C_{1-6}$)alkyl, trifluoromethyl, aryl($C_{1-6}$)alkyl, hydroxy, $C_{1-6}$ alkoxy, trifluoromethoxy, aryloxy, aryl($C_{1-6}$)alkoxy, $C_{1-6}$ alkylthio, arylsulphonyl, $C_{1-6}$ alkylsulphonyloxy, amino, $C_{2-6}$ alkylcarbonylamino, $C_{1-6}$ alkylsulphonylamino, $C_{2-6}$ alkylcarbonyl or aminocarbonyl.

6. A pharmaceutical composition comprising a compound of formula (I) as defined in claim 1, or a pharmaceutically acceptable salt or solvate thereof, in association with a pharmaceutically acceptable carrier.

* * * * *